(12) United States Patent
Granger et al.

(10) Patent No.: US 11,345,699 B2
(45) Date of Patent: *May 31, 2022

(54) APOPTOSIS SIGNAL-REGULATING KINASE 1 INHIBITORS AND METHODS OF USE THEREOF

(71) Applicant: Enanta Pharmaceuticals, Inc., Watertown, MA (US)

(72) Inventors: Brett Granger, Sudbury, MA (US); Guoqiang Wang, Belmont, MA (US); Ruichao Shen, Belmont, MA (US); Jing He, Somerville, MA (US); Yong He, Lexington, MA (US); Xuechao Xing, Wilmington, MA (US); Jun Ma, Belmont, MA (US); Jiang Long, Wayland, MA (US); Bin Wang, Newton, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 113 days.

This patent is subject to a terminal disclaimer.

(21) Appl. No.: 16/688,429

(22) Filed: Nov. 19, 2019

(65) Prior Publication Data

US 2020/0157095 A1 May 21, 2020

Related U.S. Application Data

(60) Provisional application No. 62/769,192, filed on Nov. 19, 2018.

(51) Int. Cl.
| | | |
|---|---|---|
| *C07D 471/04* | (2006.01) |
| *C07D 401/14* | (2006.01) |
| *C07D 417/14* | (2006.01) |
| *C07D 405/14* | (2006.01) |
| *C07D 413/14* | (2006.01) |

(52) U.S. Cl.
CPC ......... *C07D 471/04* (2013.01); *C07D 401/14* (2013.01); *C07D 405/14* (2013.01); *C07D 413/14* (2013.01); *C07D 417/14* (2013.01)

(58) Field of Classification Search
CPC combination set(s) only.
See application file for complete search history.

(56) References Cited

U.S. PATENT DOCUMENTS

| | | |
|---|---|---|
| 6,140,347 A | 10/2000 | Castro et al. |
| 6,534,651 B2 | 3/2003 | Jagtap et al. |
| 7,678,792 B2 | 3/2010 | Chianelli et al. |
| 8,378,108 B2 | 2/2013 | Corkey et al. |
| 8,653,075 B2 | 2/2014 | Grundl et al. |
| 8,895,745 B2 | 11/2014 | Berdini et al. |
| 9,067,933 B2 | 6/2015 | Corkey et al. |
| 9,132,140 B2 | 9/2015 | Reddy et al. |
| 9,254,284 B2 | 2/2016 | Notte |
| 9,751,885 B2 | 9/2017 | Tomita et al. |
| 10,246,439 B2 | 4/2019 | Granger et al. |
| 10,253,018 B2 | 4/2019 | Wang et al. |
| 10,450,301 B2 | 10/2019 | Granger et al. |
| 10,597,382 B2 | 3/2020 | Wang et al. |
| 10,683,279 B2 | 6/2020 | Wang et al. |

(Continued)

FOREIGN PATENT DOCUMENTS

| | | |
|---|---|---|
| CN | 107793400 A | 3/2018 |
| WO | 2004018428 A1 | 3/2004 |

(Continued)

OTHER PUBLICATIONS

Pubmed Compound Summary for CID 53276841, '2-Methyl-1,1,3-trioxo-N-pyridin-2-yl-1,2-benzolhiazole-6-carboxamide', U.S. National library of Medicine, Aug. 1, 2011 (Aug. 1, 2011), p. 1-7; p. 2 (https:/lpubchem.ncbi.nlm.nih.gov/compound/53276841).
Gibson, et al., "Structure-based drug design of novel ASK1 inhibitors using an integrated lead optimization strategy", Bioorganic & Medicinal Chemistry Letters, 2017, 1-5.
Kawarazaki, et al., "Apoptosis signal-regulating kinase 1 as a therapeutic target", Expert Opinion on Therapeutic Targets, 18(6), 2014, 651-664.

(Continued)

*Primary Examiner* — Heidi Reese
(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts and esters thereof:

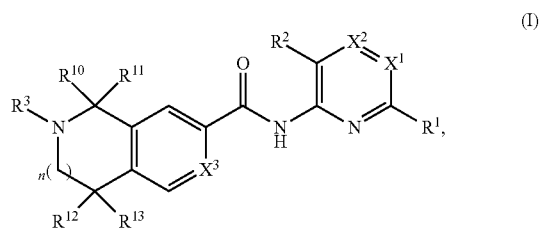

which inhibit the Apoptosis signal-regulating kinase 1 (ASK-1), which associated with autoimmune disorders, neurodegenerative disorders, inflammatory diseases, chronic kidney disease, cardiovascular disease. The present invention further relates to pharmaceutical compositions comprising the aforementioned compounds for administration to a subject suffering from ASK-1 related disease. The invention also relates to methods of treating an ASK-1 related disease in a subject by administering a pharmaceutical composition comprising the compounds of the present invention. The present invention specifically relates to methods of treating ASK-1 associated with hepatic steatosis, including non-alcoholic fatty liver disease (NAFLD) and non-alcohol steatohepatitis disease (NASH).

13 Claims, No Drawings

(56) References Cited

U.S. PATENT DOCUMENTS

| | | | |
|---|---|---|---|
| 10,683,289 | B2 | 6/2020 | Granger et al. |
| 2005/0113450 | A1 | 5/2005 | Thorarensen et al. |
| 2007/0027156 | A1 | 2/2007 | Nakai et al. |
| 2009/0318425 | A1 | 12/2009 | Chang et al. |
| 2010/0029619 | A1 | 2/2010 | Uchikawa et al. |
| 2011/0009410 | A1 | 1/2011 | Corkey et al. |
| 2012/0004267 | A1 | 1/2012 | Corkey et al. |
| 2013/0203731 | A1 | 8/2013 | Chang et al. |
| 2013/0210810 | A1 | 8/2013 | Singh et al. |
| 2014/0018370 | A1 | 1/2014 | Corkey et al. |
| 2014/0179663 | A1 | 6/2014 | Notte |
| 2014/0249135 | A1 | 9/2014 | Burger et al. |
| 2014/0329850 | A1 | 11/2014 | Chang |
| 2015/0005280 | A1 | 1/2015 | Sasmal et al. |
| 2015/0175597 | A1 | 6/2015 | Notte |
| 2016/0166556 | A1 | 6/2016 | Budas et al. |
| 2017/0210748 | A1 | 7/2017 | Witty et al. |
| 2018/0327388 | A1 | 11/2018 | Wang et al. |
| 2018/0362501 | A1 | 12/2018 | Wang et al. |
| 2018/0362502 | A1 | 12/2018 | Granger et al. |
| 2018/0362503 | A1 | 12/2018 | Granger et al. |
| 2019/0062310 | A1 | 2/2019 | Wang et al. |
| 2019/0337923 | A1 | 11/2019 | Wang et al. |
| 2019/0337935 | A1 | 11/2019 | Granger et al. |
| 2020/0062727 | A1 | 2/2020 | He et al. |
| 2020/0157095 | A1 | 5/2020 | Granger et al. |
| 2020/0308193 | A1 | 10/2020 | Granger et al. |
| 2020/0331890 | A1 | 10/2020 | Wang et al. |

FOREIGN PATENT DOCUMENTS

| | | | |
|---|---|---|---|
| WO | 2005009470 | A1 | 2/2005 |
| WO | 2005103288 | A1 | 11/2005 |
| WO | 2007000339 | A1 | 1/2007 |
| WO | 2008082579 | A1 | 7/2008 |
| WO | 2009011850 | A2 | 1/2009 |
| WO | 2009027283 | A1 | 3/2009 |
| WO | 2009123986 | A1 | 10/2009 |
| WO | 2010008843 | A1 | 1/2010 |
| WO | 2011008709 | A1 | 1/2011 |
| WO | 2011041293 | A1 | 4/2011 |
| WO | 2011097079 | A1 | 8/2011 |
| WO | 2012003387 | A1 | 1/2012 |
| WO | 2012011548 | A1 | 1/2012 |
| WO | 2012080735 | A1 | 6/2012 |
| WO | 2013112741 | A1 | 8/2013 |
| WO | 2014100541 | A1 | 6/2014 |
| WO | 2014106019 | A2 | 7/2014 |
| WO | 2014137728 | A1 | 9/2014 |
| WO | 2015095059 | A1 | 6/2015 |
| WO | 2015187499 | A1 | 12/2015 |
| WO | 2016049069 | A1 | 3/2016 |
| WO | 2016049070 | A1 | 3/2016 |
| WO | 2016105453 | A1 | 6/2016 |
| WO | 2016106384 | A1 | 6/2016 |
| WO | 2018090869 | A1 | 5/2018 |
| WO | 2018133856 | A1 | 7/2018 |
| WO | 2018133865 | A1 | 7/2018 |
| WO | 2018133866 | A1 | 7/2018 |
| WO | 2018148204 | A1 | 8/2018 |
| WO | 2018149284 | A1 | 8/2018 |
| WO | 2018151830 | A1 | 8/2018 |
| WO | 2018157277 | A1 | 9/2018 |
| WO | 2018157856 | A1 | 9/2018 |
| WO | 2018157857 | A1 | 9/2018 |
| WO | 2018160406 | A1 | 9/2018 |
| WO | 2018169742 | A1 | 9/2018 |
| WO | 2018183122 | A1 | 10/2018 |
| WO | 2018187506 | A1 | 10/2018 |
| WO | 2018218051 | A1 | 11/2018 |
| WO | 2018233553 | A1 | 12/2018 |
| WO | 2019034096 | A1 | 2/2019 |
| WO | 2019050794 | A1 | 3/2019 |
| WO | 2019051265 | A1 | 3/2019 |
| WO | 2019070742 | A1 | 4/2019 |

OTHER PUBLICATIONS

Lanier, Marion et al., "Structure-Based Design of ASK1 Inhibitors as Potential Agents for Heart Failure", ACS Medicinal Chemistry Letters, vol. 8, 2017, 316-320.

Loomba, et al., "The ASK1 Inhibitor Selonsertib in Patients with Nonalcoholic Steatohepatitis: A Randomized, Phase 2 Trial", Hepatology 67(2), 2018, 549-559.

Lovering, et al., "Rational approach to highly potent and selective apoptosis signal regulating kinase 1 (ASK1) inhibitors", European Journal of Medicinal Chemistry, 145, 2018, 606-621.

Monastyrsky, et al., "Discovery of 2-arylquinazoline derivatives as a new class of ASK1 inhibitors", Bioorganic & Medicinal Chemistry Letters, 28, 2018, 400-404.

Patani, George A. et al., "Bioisosterism: A Rational Approach in Drug Design", Chem. Rev., 96, 1996, 3147-3176.

Sheridan, Robert P, "The Most Common Chemical Replacements in Drug-Like Compounds", J. Chem. Info. Comput. Sci. 2002, vol. 42, 2002, 103-108.

Starosyla, S. et al., "ASK1 Pharmacophore Model Derived from Diverse Classes of Inhibitors", Bioorganic & Medicinal Chemistry Letters, 24, 2014, 4418-4423.

Terao, et al., "Design and biological evaluation of imidazo[1,2-a]pyridines as novel and potent ASK1 inhibitors", Bioorganic & Medicinal Chemistry Letters, 22, 2012, 7326-7329.

Volynets, et al., "Identification of 3H-Naphtho[1,2,3-de]quinoline-2,7-diones as Inhibitors of Apoptosis Signal-Regulating Kinase 1 (ASK1)", Journal of Medicinal Chemistry, 54, 2011, 2680-2686.

Volynets, et al., "Rational design of apoptosis signal-regulating kinase 1 inhibitors Discovering novel structural scaffold", European Journal of Medicinal Chemistry 61, 2013, 104-115.

Wermuth, C. G., "Molecular Variations Based on Isosteric Replacements", in "The Practice of Medicinal Chemistry", Academic Press Limited, 1996, 203-237.

U.S. Appl. No. 16/546,736, filed Aug. 21, 2019.

Ali, et al., "Recent advances in the development of farnesoid X receptor agonists", Ann Transl Med, 3(1), 2015, 1-16.

Burger, A. et al., "Isosteric Compounds. I. Acyl Derivatives of Dibenzothiophene", J. Am. Chem. Soc., vol. 60, 11, 1938, 2628-2630.

Dudkin, V. Y., "Bioisosteric Equivalence of Five-Membered Heterocycles", Chemistry of Heterocyclic Compounds, vol. 48, No. 1, 2012, 27-32.

Silverman, R. B., "The Organic Chemistry of Drug Design and Drug Action", ELSEVIER Academic Press, 2004, 29-32.

Okamoto, M., "Identification of novel ASK1 inhibitors using virtual screening", Bioorganic & Medicinal Chemistry, 19 (2011) 486-489.

Starosyla, S., et al., "Identification of apoptosis signal-regulating kinase 1 (ASK1) inhibitors among the derivatives of benzothiazol-2-yl-3-hydroxy-5-phenyl-1,5-dihydro-pyrrol-2-one", Bioorganic & Medicinal Chemistry 23 (2015) 2489-2497.

APOPTOSIS SIGNAL-REGULATING KINASE 1 INHIBITORS AND METHODS OF USE THEREOF

RELATED APPLICATION

This application claims the benefit of U.S. Provisional Application No. 62/769,192, filed on Nov. 19, 2018. The entire teachings of the above application are incorporated herein by reference.

TECHNICAL FIELD

The present invention relates generally to compounds and pharmaceutical compositions useful as ASK-1 inhibitors. Specifically, the present invention relates to compounds useful as inhibitors of ASK-1 and methods for their preparation and use.

BACKGROUND OF THE INVENTION

Apoptosis signal-regulating kinase 1 (ASK-1) is a member of the mitogen-activated protein kinase kinase kinase (MAPKKK, MAP3K) family, which when activated phosphorylates downstream MAP kinase kinases (MAPKK, MAP2K), which in turn activate MAP kinases (MAPK). MAPKs elicit a response by phosphorylating cellular substrates, thus regulating the activity of transcription factors that ultimately control gene expression. Specifically ASK-1, also known as MAPKKK5, phosphorylates MAPKK4/MAPKK7 or MAPKK3/MAPKK6, which subsequently phosphorylates and activates the c-Jun N-terminal protein kinase (JNK) and p38 MAPKs, respectively (H. Ichijo, et al., *Cell Comm. Signal* 2009, 7, 1-10; K. Takeda, et al., *Annu. Rev. Pharmacol. Toxicol.* 2008, 48, 199-225; H. Nagai, et al., *J. Biochem. Mol. Biol.* 2007, 40, 1-6). Activation of the JNK and p38 pathways triggers a downstream stress response such as apoptosis, inflammation, or differentiation (H. Ichijo, et al., *Science* 1997, 275, 90-94; K. Takeda, et al., *J. Biol. Chem.* 2000, 275, 9805-9813; K. Tobiume, et al., *EMBO Rep.* 2001, 2, 222-228; K. Sayama et al., *J. Biol. Chem.* 2001, 276, 999-1004).

The activity of ASK-1 is regulated by thioredoxin (Trx), which binds to the N-terminal end of ASK-1 (M. Saitoh, et al., *EMBO J.* 1998, 17, 2596-2606). ASK-1 is activated succeeding autophosphorylation at Thr838 in response to environmental stimuli including oxidative stress, lipopolysaccharides (LPS), reactive oxygen species (ROS), endoplasmic reticulum (ER) stress, an increase in cellular calcium ion concentrations, Fas ligand, and various cytokines such as tumor necrosis factor (TNF) (H. Nishitoh, et al., *Genes Dev.* 2002, 16, 1345-1355; K. Takeda, et al., *EMBO Rep.* 2004, 5, 161-166; A. Matsuzawa, et al., *Nat. Immunol.* 2005, 6, 587-592).

ASK-1 has been associated with autoimmune disorders, neurodegenerative disorders, inflammatory diseases, chronic kidney disease, cardiovascular disease, metabolic disorders, and acute and chronic liver diseases (R. Hayakawa, et al., *Proc. Jpn. Acad., Ser. B* 2012, 88, 434-453).

More specifically, ASK-1 has been associated with hepatic steatosis, including non-alcoholic fatty liver disease (NAFLD) and non-alcohol steatohepatitis (NASH). In a mouse model, high fat diets have caused induction of hepatic steatosis, ultimately causing fat accumulation and fatty acid oxidation. This led to the generation of ROS which caused hepatocyte dysfunction and death (S. K. Mantena, et al., *Free Radic. Biol. Med.* 2008, 44, 1259-1272; S. K. Mantena, et al., *Biochem. J.* 2009, 417, 183-193). Moreover, TNF was shown to be critical for apoptosis of hepatocytes through the ASK-1-JNK pathway, and TNF deficient mice showed reduced hepatic steatosis and fibrosis (W. Zhang, et al., *Biochem. Biophys. Res. Commun.* 2010, 391, 1731-1736).

Small molecule compounds which act as ASK-1 inhibitors have been disclosed in the following publications: WO 2008/016131, WO 2009/027283, WO 2009/0318425, WO 2009/123986, US 2009/0318425, WO 2011/041293, WO 2011/097079, US 2011/0009410, *J. Med. Chem.* 2011, 54, 2680-2686, *Bioorg. Med. Chem.* 2011, 19, 486-489, WO 2012/003387, WO 2012/011548, WO 2012/080735, Y. Terao, et al., *Bioorg. Med. Chem. Lett.* 2012, 22, 7326-7329, WO 2013/112741, *Eur. J. Med. Chem.* 2013, 16, 104-115, US 2014/0018370, WO 2014/100541, WO 2015/095059, *Bioorg. Med. Chem. Lett.* 2015, 23, 2489-2497, WO 2016/049069, WO 2016/049070, WO 2016/106384, *ACS Med. Chem. Lett.* 2017, 8, 316-320, WO 2018/090869, WO 2018/133865, WO 2018/133866, WO 2018/148204, WO 2018/149284, WO 2018/151830, WO 2018/157277, WO 2018/157856, WO 2018/157857, WO 2018/160406, WO 2018/169742, WO 2018/183122, WO 2018/187506, *Bioorg. Med. Chem. Lett.* 2018, 28, 400-404, *Eur. J. Med. Chem.* 2018, 145, 606-621.

There is a need for the development of ASK-1 inhibitors for the treatment and prevention of disease. The present invention has identified compounds which inhibit ASK-1 as well as methods of using these compounds to treat disease.

SUMMARY OF THE INVENTION

In one aspect, the invention provides compounds represented by Formula I, or a pharmaceutically acceptable salt or ester thereof:

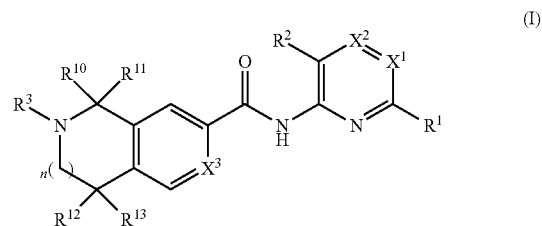

(I)

wherein:

$X^1$ and $X^2$ are each independently $C(R^8)$ or N;
$X^3$ is $C(R^9)$ or N, wherein $R^9$ is selected from the group consisting of hydrogen, optionally substituted —$C_1$-$C_8$ alkyl, optionally substituted —$C_1$-$C_8$ alkoxy and halo;
$R^1$ is selected from

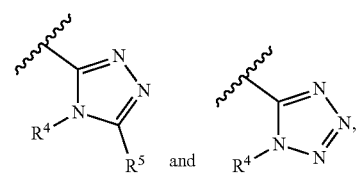

$R^4$ is selected from the group consisting of:
1) Hydrogen;
2) Substituted or unsubstituted —$C_1$-$C_8$ alkyl;
3) Substituted or unsubstituted —$C_2$-$C_8$ alkenyl;
4) Substituted or unsubstituted —$C_2$-$C_8$ alkynyl;

5) Substituted or unsubstituted —$C_3$-$C_8$ cycloalkyl;
6) Substituted or unsubstituted aryl;
7) Substituted or unsubstituted arylalkyl;
8) Substituted or unsubstituted 3- to 8-membered heterocycloalkyl;
9) Substituted or unsubstituted heteroaryl; and
10) Substituted or unsubstituted heteroarylalkyl;

$R^2$, $R^5$ and $R^8$ are each independently selected from the group consisting of:
1) Hydrogen;
2) Halogen;
3) —$NO_2$;
4) Cyano;
5) Substituted or unsubstituted —$C_1$-$C_8$ alkyl;
6) Substituted or unsubstituted —$C_2$-$C_8$ alkenyl;
7) Substituted or unsubstituted —$C_2$-$C_8$ alkynyl;
8) Substituted or unsubstituted —$C_3$-$C_8$ cycloalkyl;
9) Substituted or unsubstituted aryl;
10) Substituted or unsubstituted arylalkyl;
11) Substituted or unsubstituted 3- to 8-membered heterocycloalkyl;
12) Substituted or unsubstituted heteroaryl;
13) Substituted or unsubstituted heteroarylalkyl;
14) —$N(R^6)(R^7)$;
15) —$S(O)_2N(R^6)(R^7)$;
16) —$N(R^6)C(O)R^7$; and
17) —$N(R^6)S(O)_2R^6$;

wherein $R^6$ and $R^7$ are independently hydrogen, —$C_1$-$C_8$ alkyl, —$C_1$-$C_8$ alkenyl, —$C_1$-$C_8$ alkynyl, —$C_3$-$C_8$ cycloalkyl, aryl, arylalkyl, heterocycloalkyl, heteroaryl, and heteroarylalkyl, wherein the —$C_1$-$C_8$ alkyl, —$C_1$-$C_8$ alkenyl, —$C_1$-$C_8$ alkynyl, —$C_3$-$C_8$ cycloalkyl, aryl, arylalkyl, heterocycloalkyl, heteroaryl, and heteroarylalkyl is optionally substituted with 1-3 substituents independently selected from halo, alkyl, —$C_3$-$C_8$ cycloalkyl, alkylamino, dialkylamino, alkyl-C(O)—NH—, aryl-C(O)NH—, heteroaryl-C(O)NH—, —CN, alkoxy, —$CF_3$, aryl, and heteroaryl; or $R^6$ and $R^7$ are taken together with the nitrogen atom to which they are attached to form an optionally substituted heterocycloalkyl;

$R^3$ is selected from the group consisting of:
1) Hydrogen;
2) Substituted or unsubstituted —$C_1$-$C_8$ alkyl;
3) Substituted or unsubstituted —$C_2$-$C_8$ alkenyl;
4) Substituted or unsubstituted —$C_2$-$C_8$ alkynyl;
5) Substituted or unsubstituted —$C_3$-$C_8$ cycloalkyl;
6) Substituted or unsubstituted aryl;
7) Substituted or unsubstituted arylalkyl;
8) Substituted or unsubstituted 3- to 8-membered heterocycloalkyl;
9) Substituted or unsubstituted heteroaryl;
10) Substituted or unsubstituted heteroarylalkyl;
11) —$C(O)R^6$;
12) —$C(O)OR^6$;
13) —$C(O)N(R^6)(R^7)$; and
14) —$SO_2R^6$;

wherein $R^6$ and $R^7$ are as previously defined;

$R^{10}$ and $R^{11}$ are each independently selected from the group consisting of hydrogen, hydroxyl, and optionally substituted —$C_1$-$C_8$ alkyl; alternatively, $R^{10}$ and $R^{11}$ are taken together with the carbon atom to which they are attached to form C(O), spiro-$C_3$-$C_8$ cycloalkyl, or spiro-3- to 8-membered heterocycloalkyl;

$R^{12}$ and $R^{13}$ are each independently selected from the group consisting of hydrogen, halo, and optionally substituted —$C_1$-$C_8$ alkyl; and n is 0, 1 or 2; preferably n is 0 or 1.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, the present invention provides a method for the prevention or treatment of an ASK-1 mediated disease or condition. The method comprises administering a therapeutically effective amount of a compound of Formula (I) to a subject in need thereof. The present invention also provides the use of a compound of Formula (I) for the preparation of a medicament for the prevention or treatment of an ASK-1 mediated disease or condition. Such diseases include autoimmune disorders, neurodegenerative disorders, inflammatory diseases, chronic kidney disease, cardiovascular disease, metabolic disorders, and acute and chronic liver diseases.

DETAILED DESCRIPTION OF THE INVENTION

A first embodiment of the invention is a compound represented by Formula I as described above, or a pharmaceutically acceptable salt or ester thereof.

In a certain embodiment, the present invention relates to compounds of Formula I, or a pharmaceutically acceptable salt or ester thereof, wherein $R^4$ is selected from the groups below:

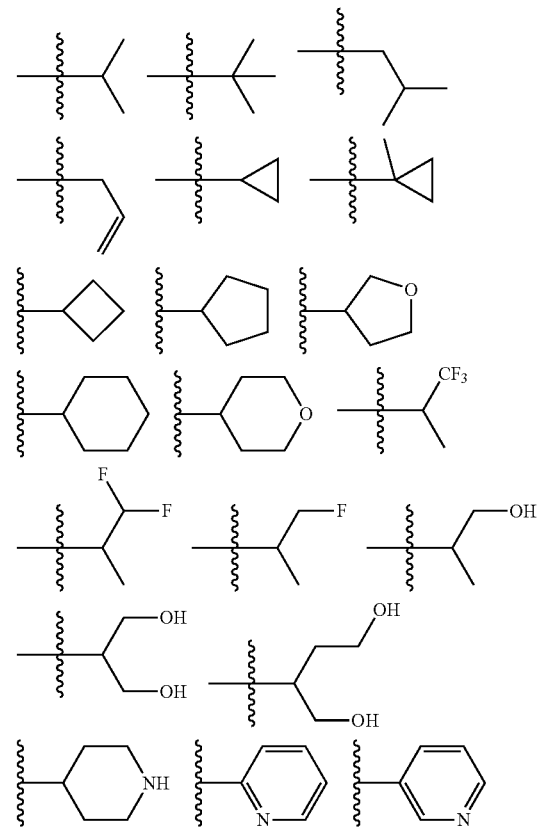

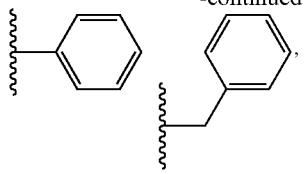

wherein each of the above shown groups is optionally substituted. Preferably, $R^4$ is selected from

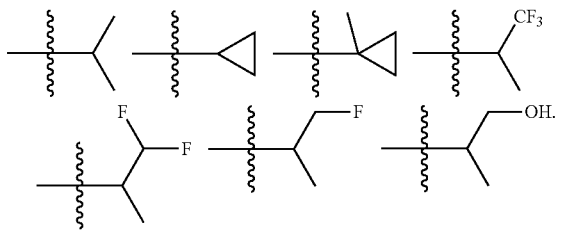

In certain embodiments, the present invention relates to compounds of Formula I, or a pharmaceutically acceptable salt or ester thereof, wherein $R^2$ is hydrogen or halogen.

In certain embodiments, the present invention relates to compounds of Formula I, or a pharmaceutically acceptable salt or ester thereof, wherein $R^5$ is hydrogen.

In certain embodiments, the present invention relates to compounds of Formula I, or a pharmaceutically acceptable salt or ester thereof, wherein $R^2$ is hydrogen, $R^5$ is hydrogen, and n is 0 or 1.

In certain embodiments, the present invention relates to compounds of Formula I, or a pharmaceutically acceptable salt or ester thereof, wherein $R^3$ is

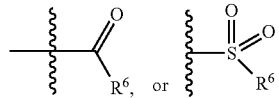

wherein $R^6$ is selected from the groups below:

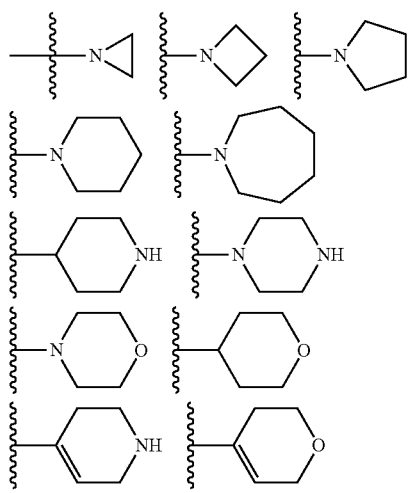
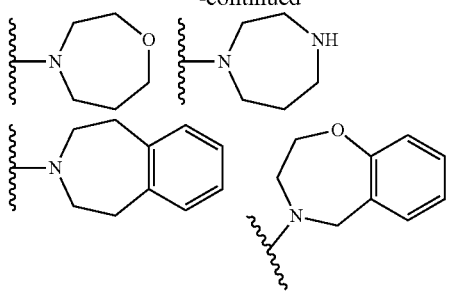
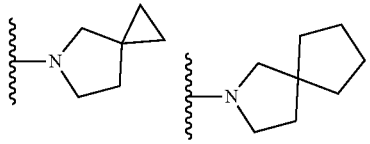
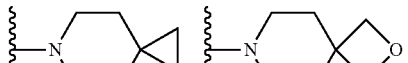
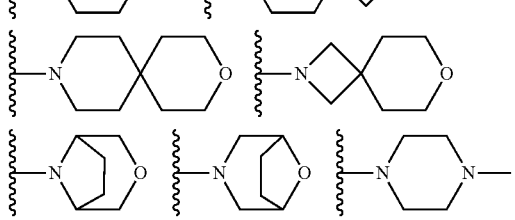
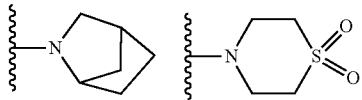
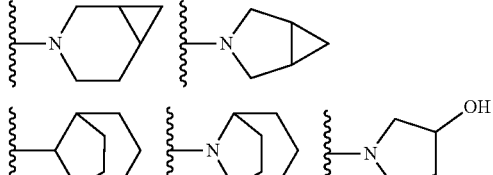
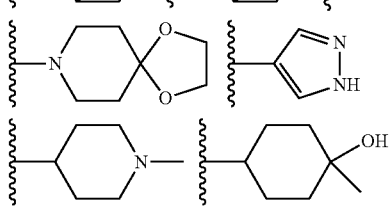
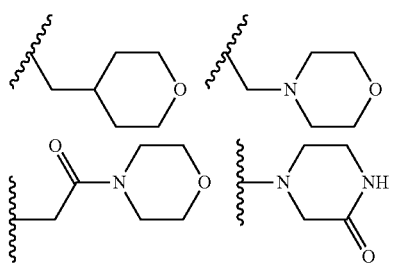
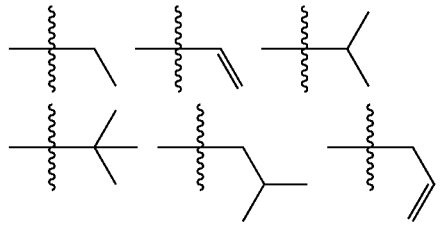

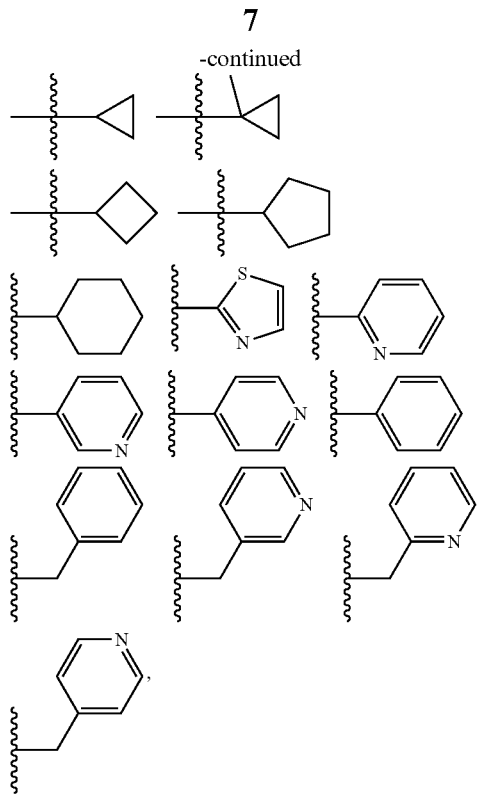

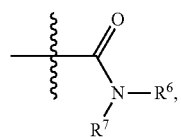

wherein each of the above shown groups is optionally substituted.

In certain embodiments, the present invention relates to compounds of Formula I, or a pharmaceutically acceptable salt or ester thereof, wherein $R^3$ is

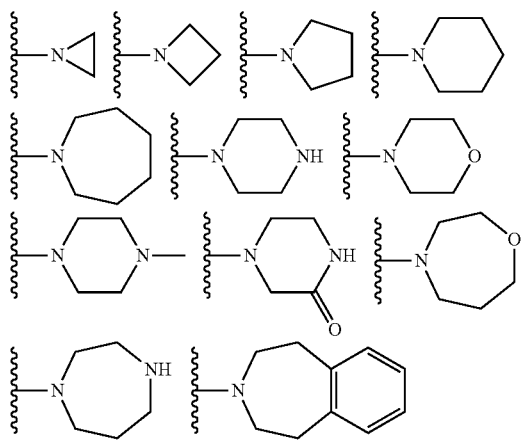

$R^6$ and $R^7$, together with the nitrogen atom to which they are they attached, form an optionally substituted heterocycloalkyl is selected from the groups below:

In another embodiment, the present invention relates to compounds of Formula I, or a pharmaceutically acceptable salt or ester thereof, wherein $R^3$ is

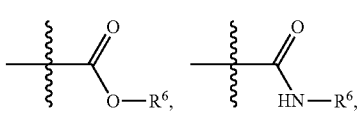

wherein $R^6$ is selected from the groups below:

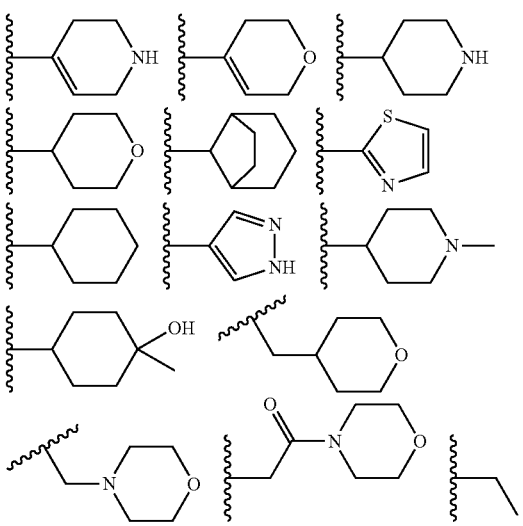

In certain embodiments, the present invention relates to compounds of Formula I, and pharmaceutically acceptable salts and esters thereof, wherein R³ is selected from the groups below:

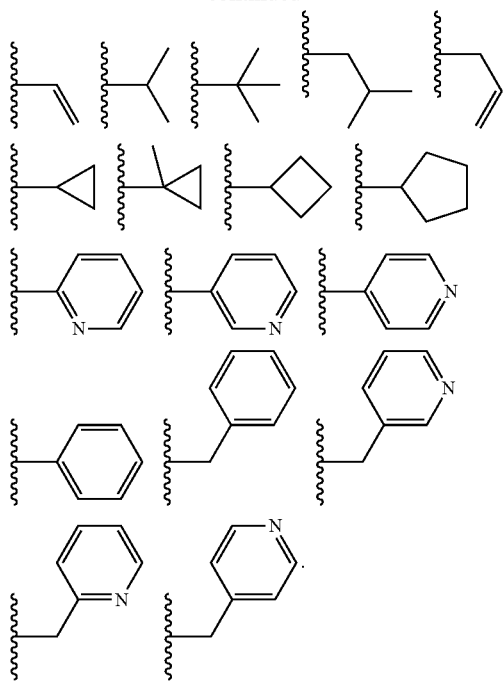
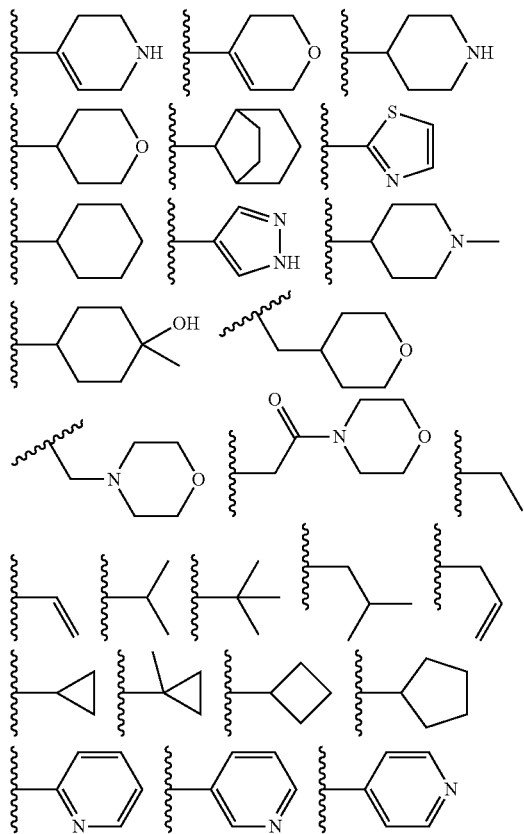
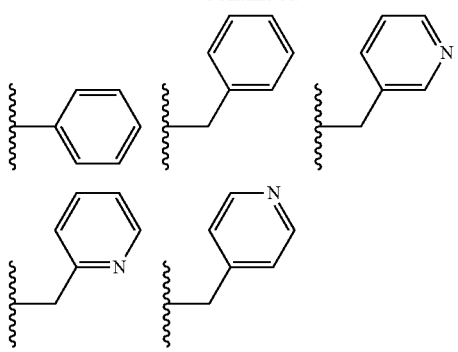

wherein each of these groups is optionally substituted.

In certain embodiments, the present invention relates to compounds of Formula I, or a pharmaceutically acceptable salt or ester thereof, wherein X³ is selected from C—H, C—F, C—OMe, and N.

In certain embodiments, the compound of Formula I is represented by Formula Ia-1, Ia-2, Ib-1, Ib-2, Ic-1, Ic-2, or Ie, or a pharmaceutically acceptable salt or ester thereof:

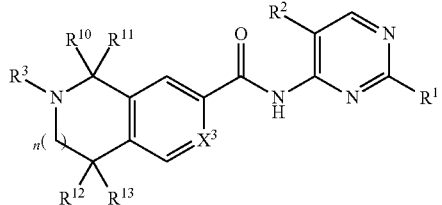

(Ia-1)

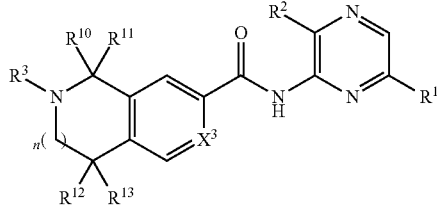

(Ia-2)

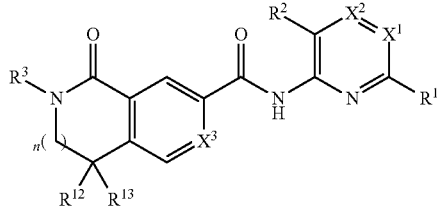

(Ib-1)

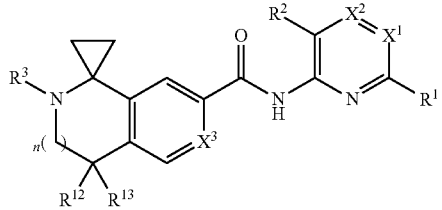

(Ib-2)

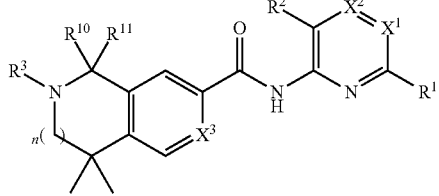
(Ic-1)

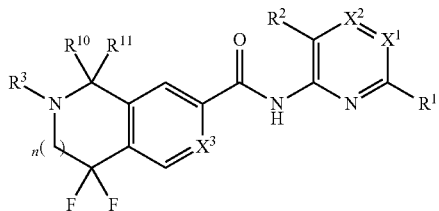
(Ic-2)

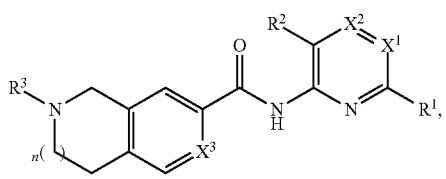
(Ie)

wherein $R^1$, $R^2$, $R^3$, $R^{10}$, $R^{11}$, $R^{12}$, $R^{13}$, $X^1$, $X^2$, $X^3$, and n are as previously defined.

In certain embodiments, the compound of Formula I is represented by Formula II or a pharmaceutically acceptable salt or ester thereof:

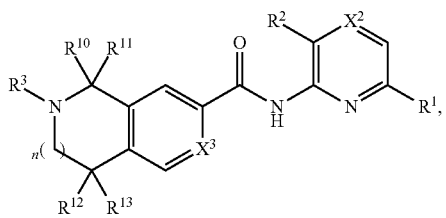
(II)

wherein $R^1$, $R^2$, $R^3$, $R^{10}$, $R^{11}$, $R^{12}$, $R^{13}$, $X^2$, $X^3$ and n are as previously defined.

In certain embodiments, the compound of Formula I is represented by Formula III or a pharmaceutically acceptable salt or ester thereof:

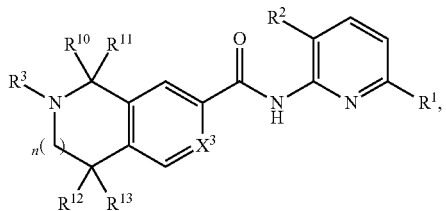
(III)

wherein $R^1$, $R^2$, $R^3$, $R^{10}$, $R^{11}$, $R^{12}$, $R^{13}$, $X^3$ and n are as previously defined.

In certain embodiments, the compound of Formula I is represented by Formula IV or a pharmaceutically acceptable salt or ester thereof:

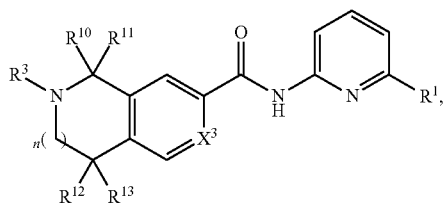
(IV)

wherein $R^1$, $R^3$, $R^{10}$, $R^{11}$, $R^{12}$, $R^{13}$, $X^3$ and n are as previously defined.

In certain embodiments, the compound of Formula I is represented by Formula V or a pharmaceutically acceptable salt or ester thereof:

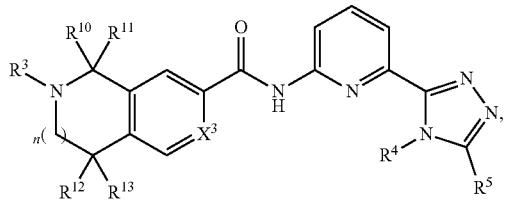
(V)

wherein $R^3$, $R^4$, $R^5$, $R^{10}$, $R^{11}$, $R^{12}$, $R^{13}$, $X^3$ and n are as previously defined.

In certain embodiments, the compound of Formula I is represented by Formula VI or a pharmaceutically acceptable salt or ester:

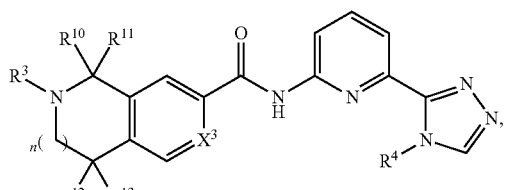
(VI)

wherein $R^3$, $R^4$, $R^{10}$, $R^{11}$, $R^{12}$, $R^{13}$, $X^3$ and n are as previously defined.

In certain embodiments, the compound of Formula I is represented by Formula VII or a pharmaceutically acceptable salt or ester thereof:

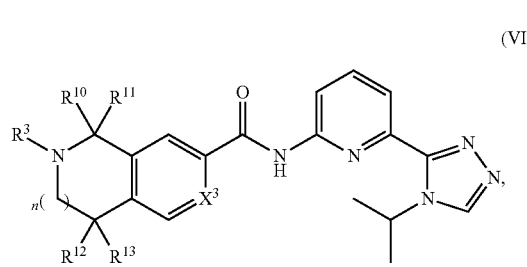

(VII)

wherein $R^3$, $R^{10}$, $R^{11}$, $R^{12}$, $R^{13}$, $X^3$ and n are as previously defined.

In certain embodiments, the compound of Formula I is represented by Formula VIII or a pharmaceutically acceptable salt or ester thereof:

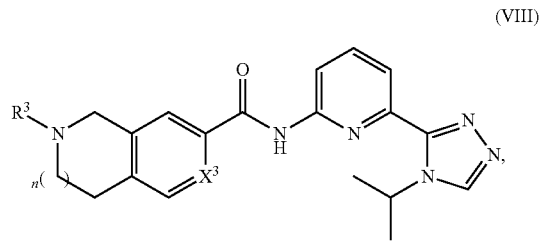

(VIII)

wherein $R^3$, $X^3$, and n are as previously defined.

In certain embodiments, the compound of Formula I is represented by Formula VIII' or a pharmaceutically acceptable salt or ester thereof:

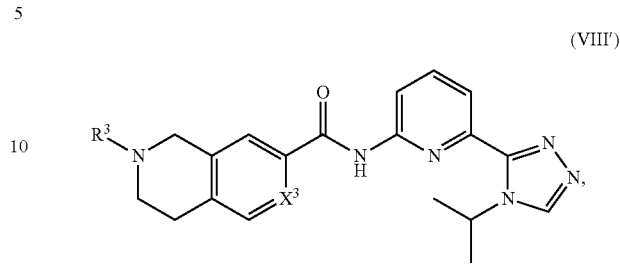

(VIII')

wherein $R^3$ and $X^3$ are as previously defined.

Representative compounds of the invention include, but are not limited to, the following compounds (compound 1 to compound 25) according to Formula VIII', and pharmaceutically acceptable salts thereof, are delineated in Table 1.

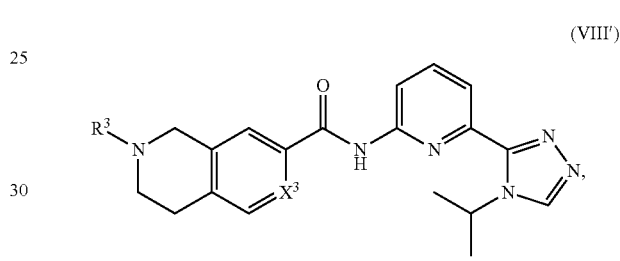

(VIII')

TABLE 1

| Compound | Structure |
|---|---|
| 1 | 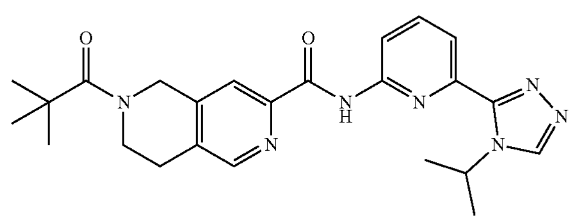 [SMILES: CC(C)n1cnnc1-c1cccc(NC(=O)c2cc3c(cn2)CCN(C(=O)C(C)(C)C)C3)n1] |
| 2 | 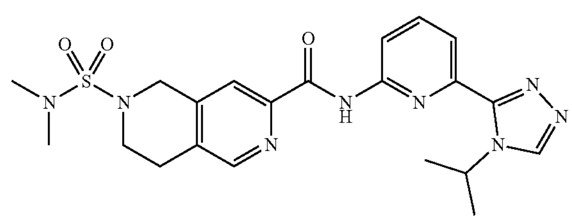 [SMILES: CC(C)n1cnnc1-c1cccc(NC(=O)c2cc3c(cn2)CCN(S(=O)(=O)N(C)C)C3)n1] |
| 3 | 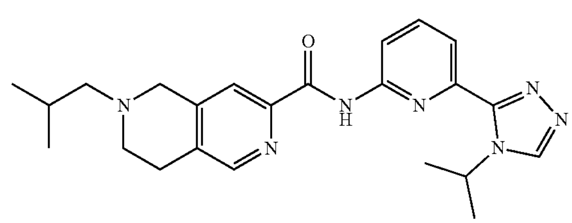 [SMILES: CC(C)CN1CCc2cnc(C(=O)Nc3cccc(-c4nncn4C(C)C)n3)cc2C1] |

TABLE 1-continued

| Compound | Structure |
|---|---|
| 4 | 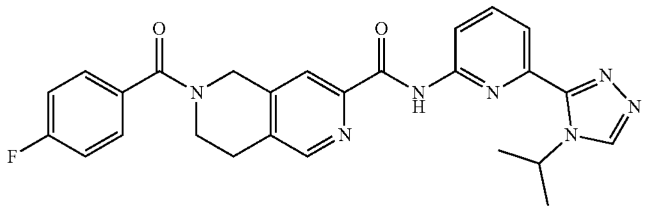 [SMILES: CC(C)n1cnnc1-c1cccc(NC(=O)c2cc3c(cn2)CCN(C(=O)c2ccc(F)cc2)C3)n1] |
| 5 | 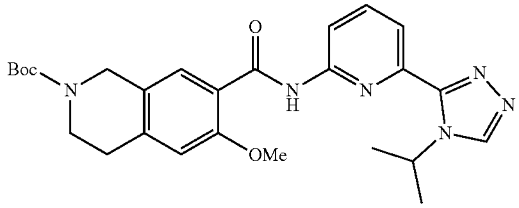 |
| 6 | 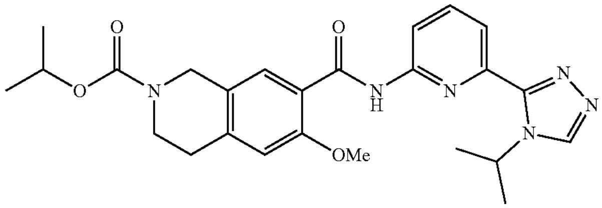 [SMILES: COc1cc2c(cc1C(=O)Nc1cccc(-c3nncn3C(C)C)n1)CN(C(=O)OC(C)C)CC2] |
| 7 | 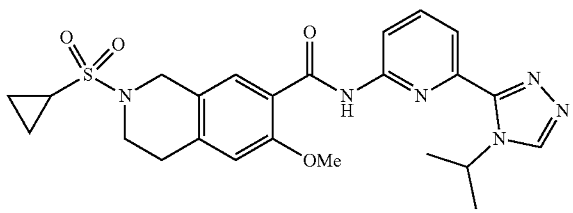 [SMILES: COc1cc2c(cc1C(=O)Nc1cccc(-c3nncn3C(C)C)n1)CN(S(=O)(=O)C1CC1)CC2] |
| 8 | 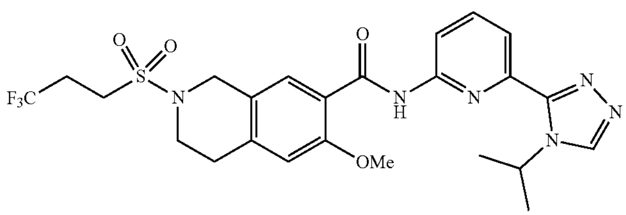 [SMILES: COc1cc2c(cc1C(=O)Nc1cccc(-c3nncn3C(C)C)n1)CN(S(=O)(=O)CCC(F)(F)F)CC2] |
| 9 | 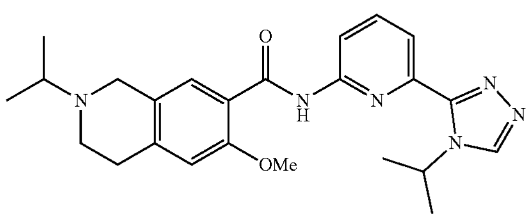 [SMILES: COc1cc2c(cc1C(=O)Nc1cccc(-c3nncn3C(C)C)n1)CN(C(C)C)CC2] |
| 10 | 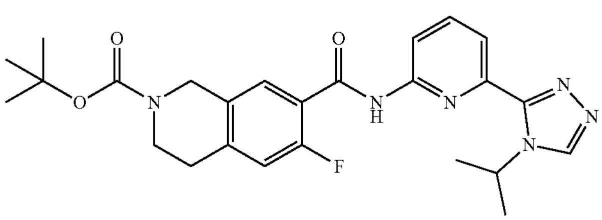 [SMILES: CC(C)n1cnnc1-c1cccc(NC(=O)c2cc3c(cc2F)CCN(C(=O)OC(C)(C)C)C3)n1] |

TABLE 1-continued
| Compound | Structure |
| --- | --- |
| 11 | 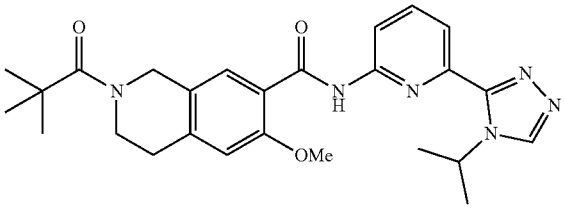 |
| 12 | 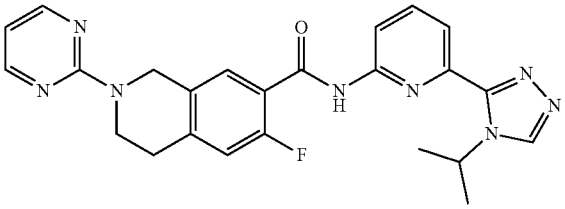 [SMILES: CC(C)n1cnnc1-c1cccc(NC(=O)c2cc3c(cc2F)CCN(c2ncccn2)C3)n1] |
| 13 | 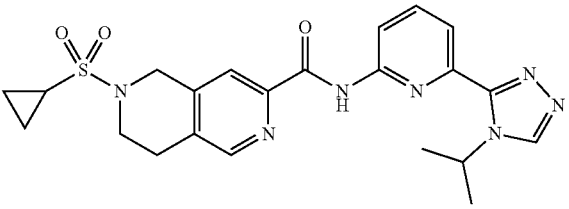 [SMILES: CC(C)n1cnnc1-c1cccc(NC(=O)c2cc3c(cn2)CCN(S(=O)(=O)C2CC2)C3)n1] |
| 14 | 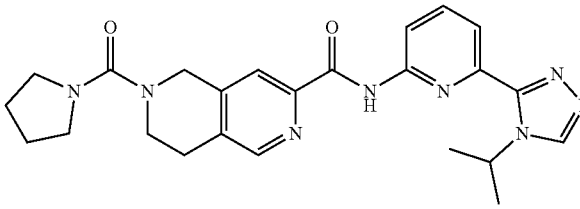 |
| 15 | 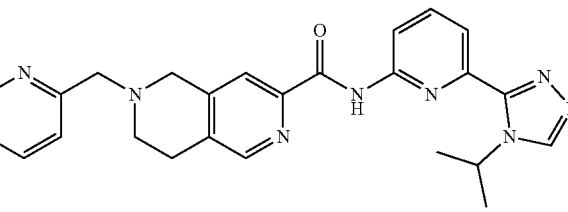 |
| 16 | 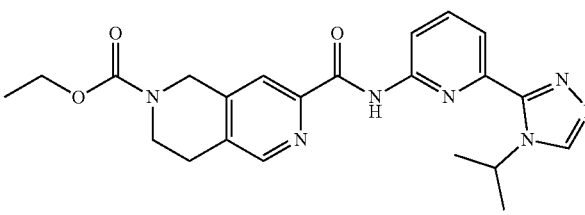 |
| 17 | 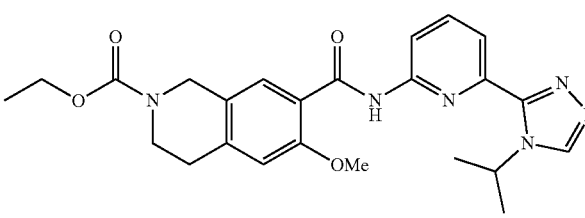 |

TABLE 1-continued

| Compound | Structure |
|---|---|
| 18 | 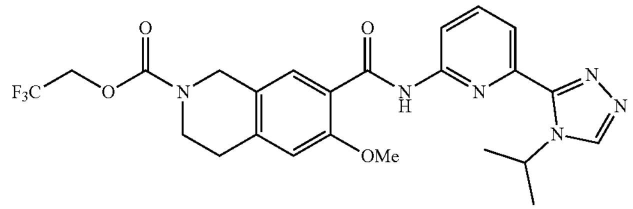 [SMILES: COc1cc2c(cc1C(=O)Nc1cccc(-c3nncn3C(C)C)n1)CN(C(=O)OCC(F)(F)F)CC2] |
| 19 | 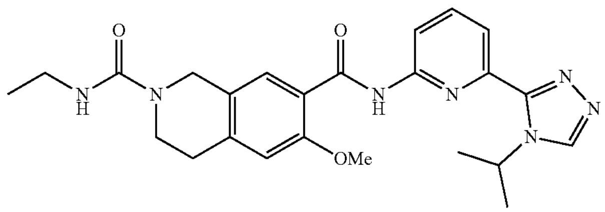 [SMILES: CCNC(=O)N1CCc2cc(OC)c(C(=O)Nc3cccc(-c4nncn4C(C)C)n3)cc2C1] |
| 20 | 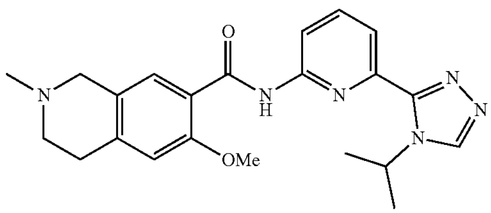 [SMILES: COc1cc2c(cc1C(=O)Nc1cccc(-c3nncn3C(C)C)n1)CN(C)CC2] |
| 21 | 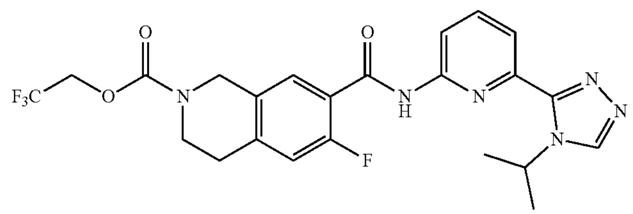 [SMILES: CC(C)n1cnnc1-c1cccc(NC(=O)c2cc3c(cc2F)CCN(C(=O)OCC(F)(F)F)C3)n1] |
| 22 | 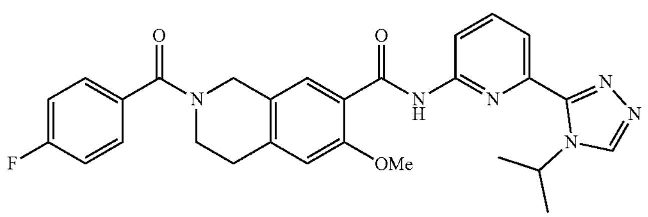 [SMILES: COc1cc2c(cc1C(=O)Nc1cccc(-c3nncn3C(C)C)n1)CN(C(=O)c1ccc(F)cc1)CC2] |
| 23 | 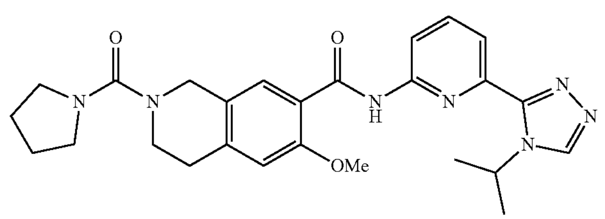 [SMILES: COc1cc2c(cc1C(=O)Nc1cccc(-c3nncn3C(C)C)n1)CN(C(=O)N1CCCC1)CC2] |
| 24 | 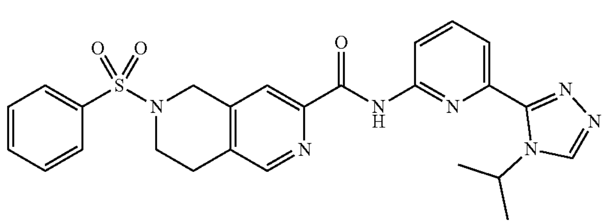 [SMILES: CC(C)n1cnnc1-c1cccc(NC(=O)c2cc3c(cn2)CCN(S(=O)(=O)c2ccccc2)C3)n1] |

TABLE 1-continued

| Compound | Structure |
|---|---|
| 25 | (structure shown) |

In certain embodiments, the compound of Formula I is represented by Formula IX or a pharmaceutically acceptable salt or ester thereof:

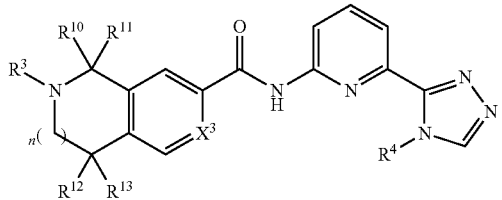

(IX)

wherein $R^3$, $R^4$, $R^{10}$, $R^{11}$, $R^{12}$, $R^{13}$, $X^3$ and n are as previously defined.

In certain embodiments, the compound of Formula I is represented by Formula X or a pharmaceutically acceptable salt or ester thereof:

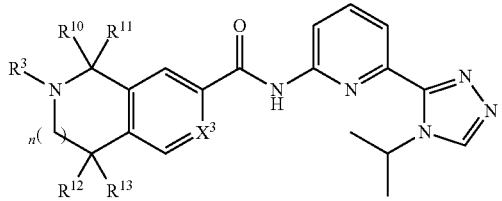

(X)

wherein $R^3$, $R^{10}$, $R^{11}$, $R^{12}$, $R^{13}$, $X^3$ and n are as previously defined.

In certain embodiments, the compound of Formula I is represented by Formula XI or a pharmaceutically acceptable salt or ester thereof:

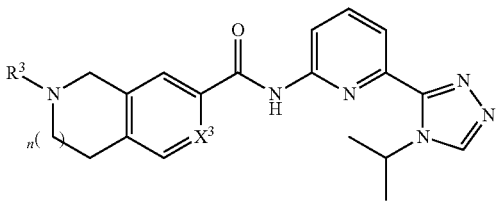

(XI)

wherein $R^3$, $X^3$, and n are as previously defined.

In certain embodiments, the compound of Formula I is represented by Formula XI' or a pharmaceutically acceptable salt or ester thereof:

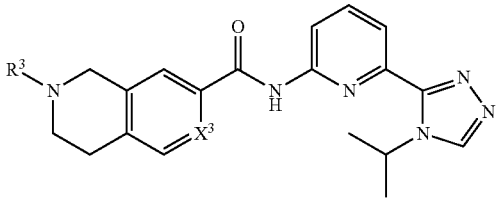

(XI')

wherein $R^3$ and $X^3$ are as previously defined.

Representative compounds of the invention include, but are not limited to, the following compounds (compound 26 to compound 37) according to Formula XI', and pharmaceutically acceptable salts thereof, are delineated in Table 2.

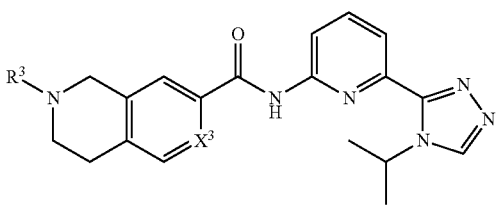

(XI')

TABLE 2
| Compound | Structure |
|---|---|
| 26 | 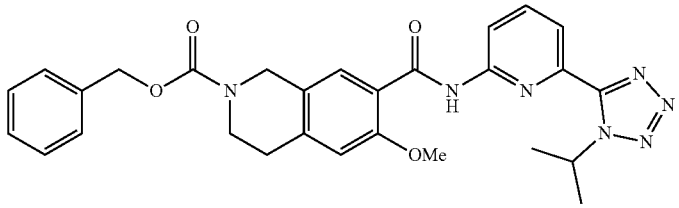 [SMILES: COc1cc2c(cc1C(=O)Nc1cccc(-c3nnnn3C(C)C)n1)CN(C(=O)OCc1ccccc1)CC2] |
| 27 | 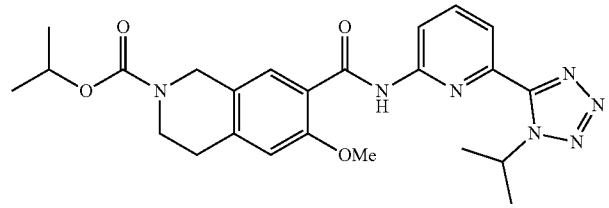 |
| 28 | 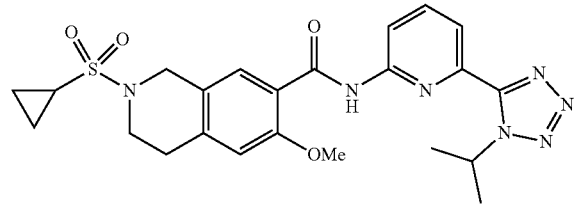 [SMILES: COc1cc2c(cc1C(=O)Nc1cccc(-c3nnnn3C(C)C)n1)CN(S(=O)(=O)C1CC1)CC2] |
| 29 | 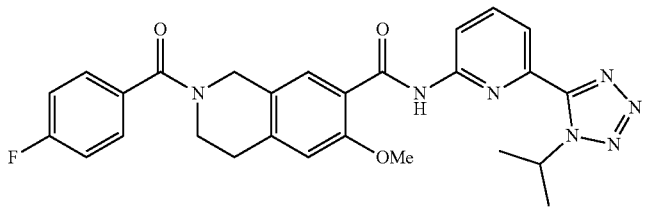 [SMILES: COc1cc2c(cc1C(=O)Nc1cccc(-c3nnnn3C(C)C)n1)CN(C(=O)c1ccc(F)cc1)CC2] |
| 30 | 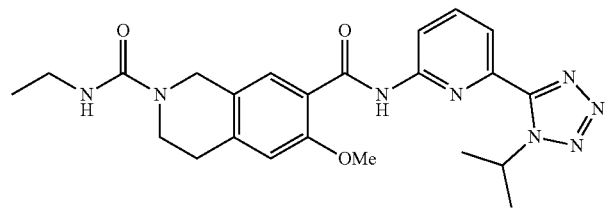 |
| 31 | 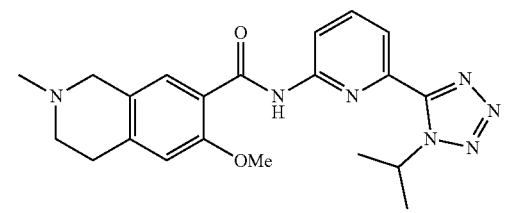 [SMILES: COc1cc2c(cc1C(=O)Nc1cccc(-c3nnnn3C(C)C)n1)CN(C)CC2] |
| 32 | 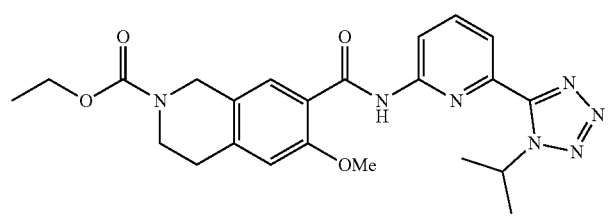 [SMILES: CCOC(=O)N1CCc2cc(OC)c(C(=O)Nc3cccc(-c4nnnn4C(C)C)n3)cc2C1] |

TABLE 2-continued

| Compound | Structure |
|---|---|
| 33 | 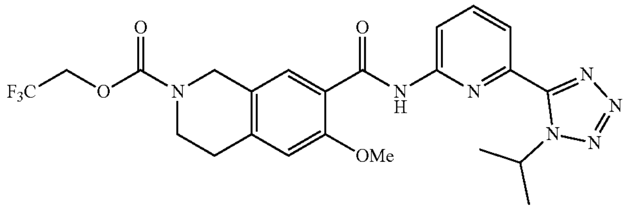 [SMILES: COc1cc2c(cc1C(=O)Nc1cccc(-c3nnnn3C(C)C)n1)CN(C(=O)OCC(F)(F)F)CC2] |
| 34 | 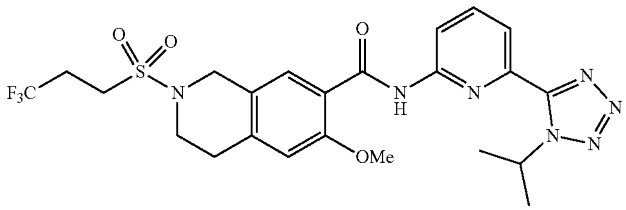 |
| 35 | 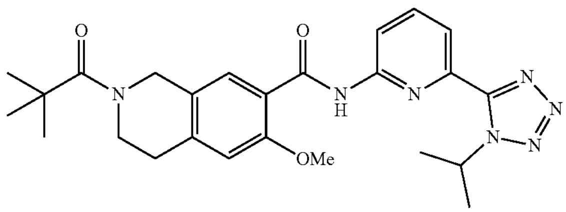 [SMILES: COc1cc2c(cc1C(=O)Nc1cccc(-c3nnnn3C(C)C)n1)CN(C(=O)C(C)(C)C)CC2] |
| 36 | 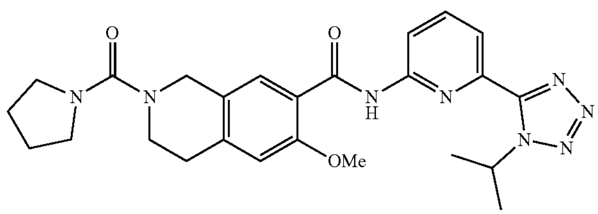 |
| 37 | 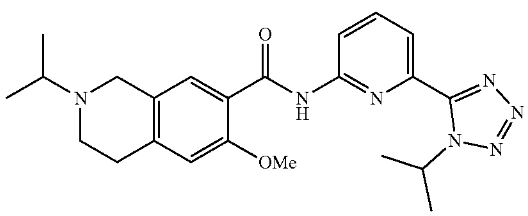 |

In certain embodiments, the compound of Formula I is represented by Formula XII or a pharmaceutically acceptable salt or ester thereof:

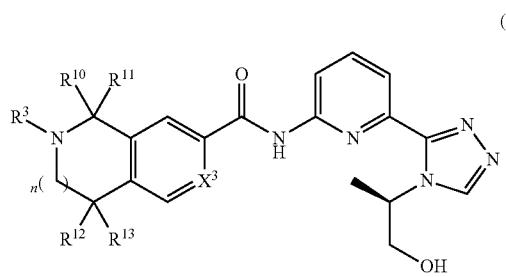

(XII)

wherein $R^3$, $R^{10}$, $R^{11}$, $R^{12}$, $R^{13}$, $X^3$ and n are as previously defined.

In certain embodiments, the compound of Formula I is represented by Formula XIII or a pharmaceutically acceptable salt or ester thereof:

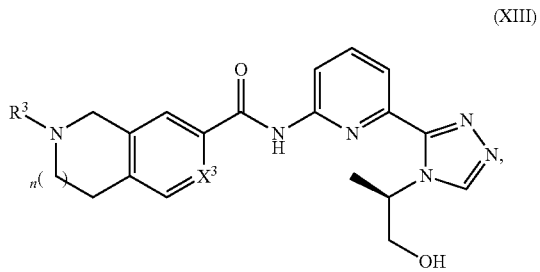

(XIII)

wherein $R^3$, $X^3$, and n are as previously defined.

In certain embodiments, the compound of Formula I is represented by Formula XIII' or a pharmaceutically acceptable salt or ester thereof:

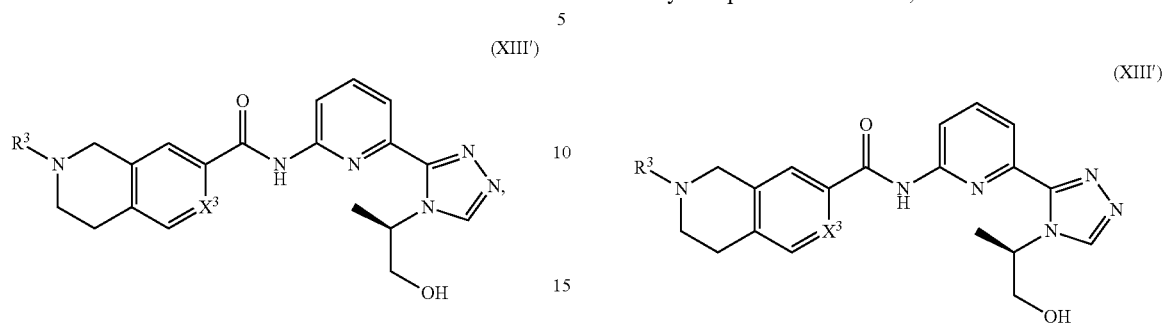

(XIII')

wherein R³ and X³ are as previously defined.

Representative compounds of the invention include, but are not limited to, the following compounds (compound 38 to compound 75) according to Formula XIII', and pharmaceutically acceptable salts thereof, are delineated in Table 3.

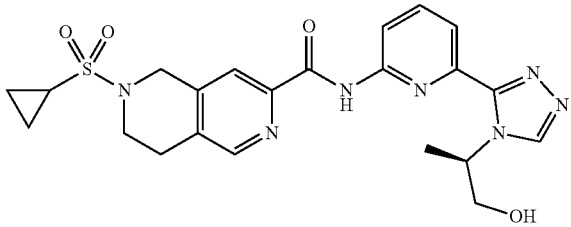

(XIII')

TABLE 3

| Compound | Structure |
|---|---|
| 38 | 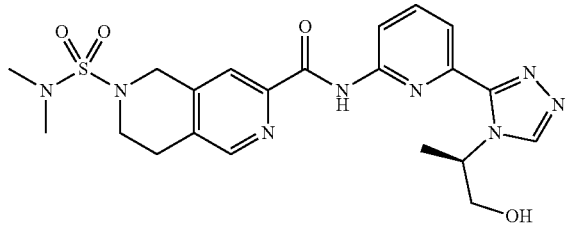 |
| 39 | 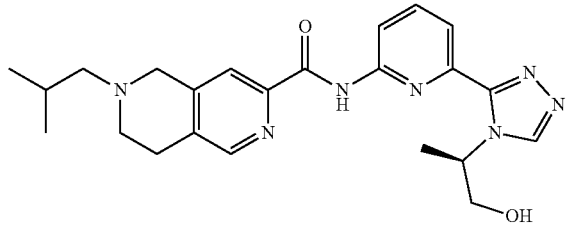 |
| 40 | 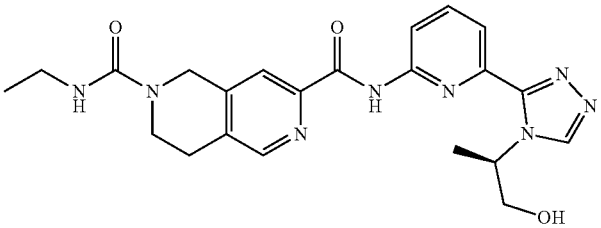 |
| 41 | 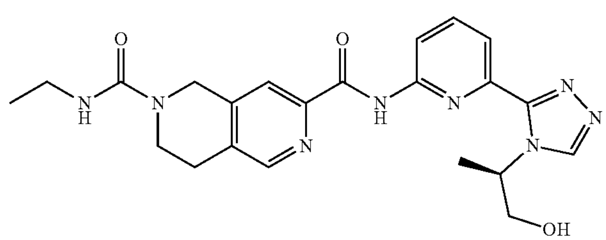 |

TABLE 3-continued

| Compound | Structure |
|---|---|
| 42 | 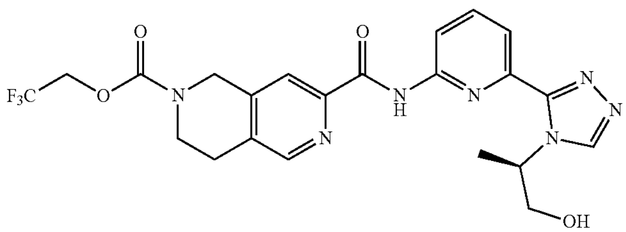 |
| 43 | 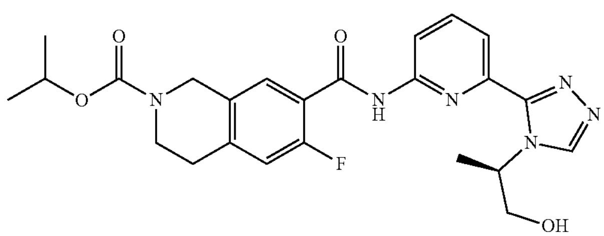 |
| 44 | 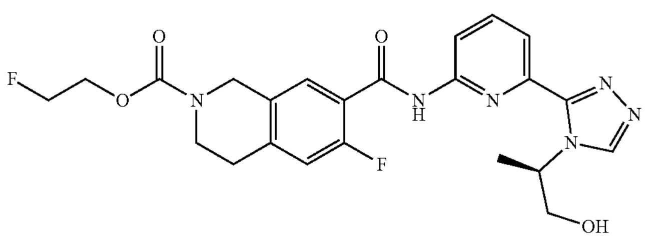 |
| 45 | 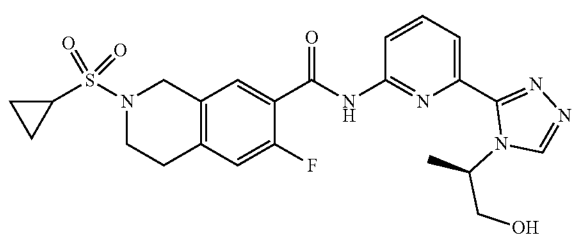 |
| 46 | 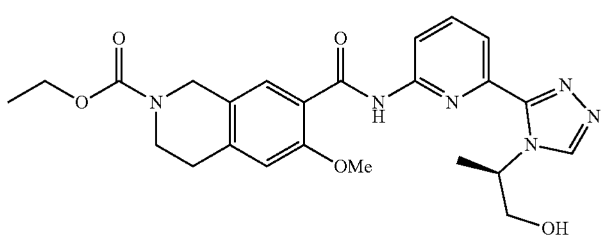 |
| 47 | 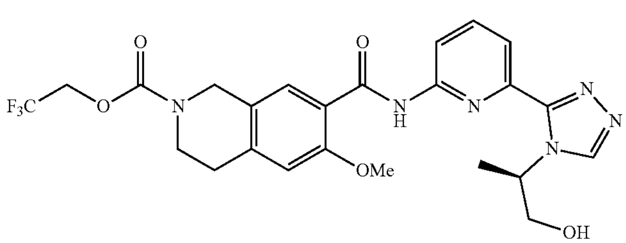 |

TABLE 3-continued

| Compound | Structure |
|---|---|
| 48 | 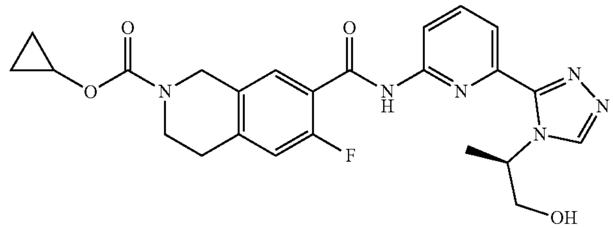 |
| 49 | 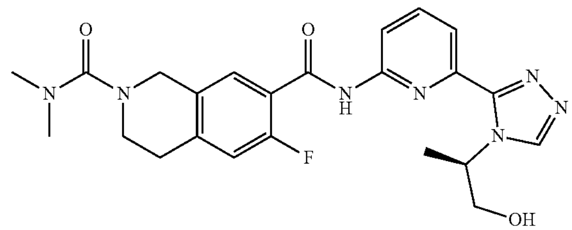 |
| 50 | 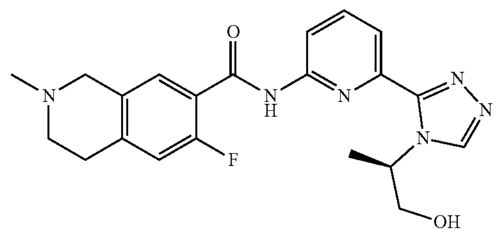 |
| 51 | 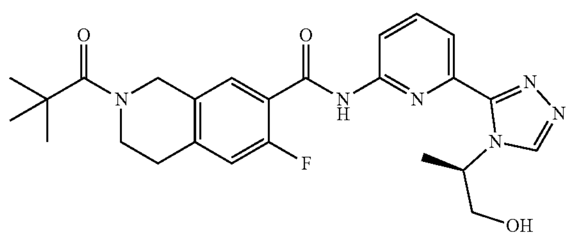 |
| 52 | 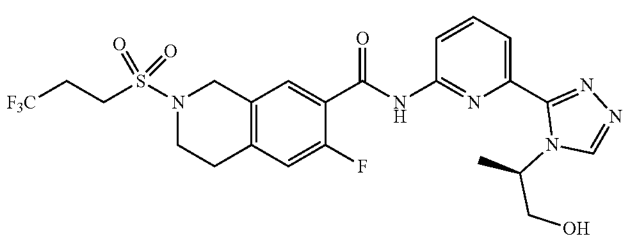 |
| 53 | 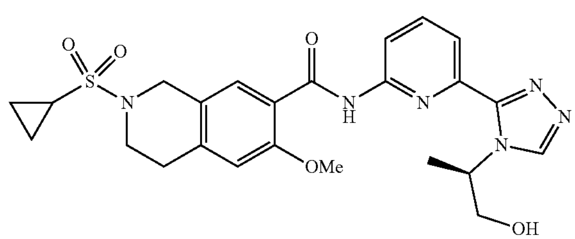 |

TABLE 3-continued

| Compound | Structure |
|---|---|
| 54 | 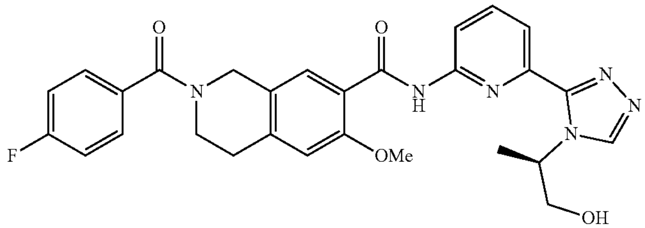 [SMILES: COc1cc2c(cc1C(=O)Nc1cccc(-c3nncn3[C@H](C)CO)n1)CN(C(=O)c1ccc(F)cc1)CC2] |
| 55 | 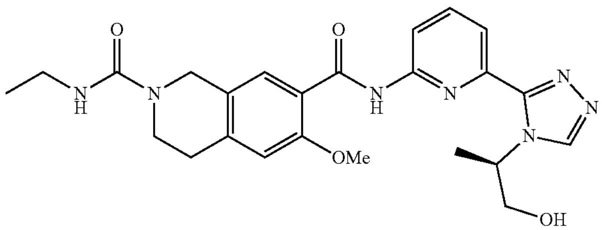 [SMILES: CCNC(=O)N1CCc2cc(OC)c(C(=O)Nc3cccc(-c4nncn4[C@H](C)CO)n3)cc2C1] |
| 56 | 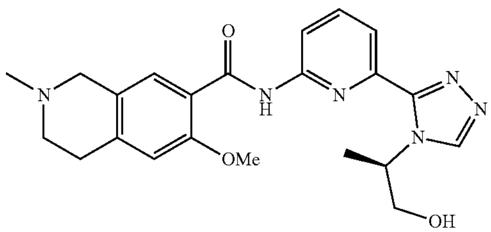 [SMILES: COc1cc2c(cc1C(=O)Nc1cccc(-c3nncn3[C@H](C)CO)n1)CN(C)CC2] |
| 57 | 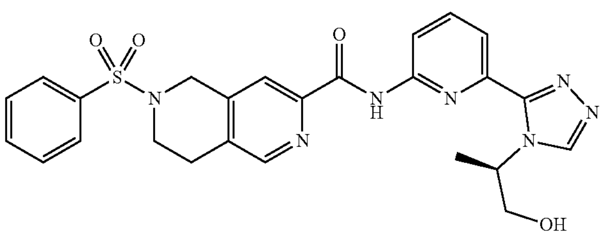 |
| 58 | 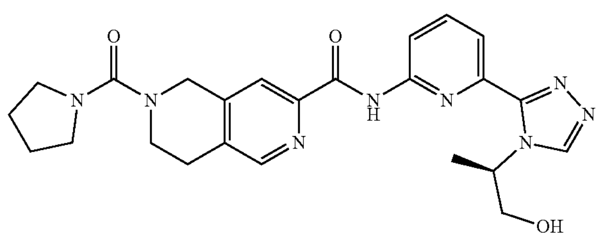 [SMILES: C[C@H](CO)n1cnnc1-c1cccc(NC(=O)c2cc3c(cn2)CCN(C(=O)N2CCCC2)C3)n1] |
| 59 | 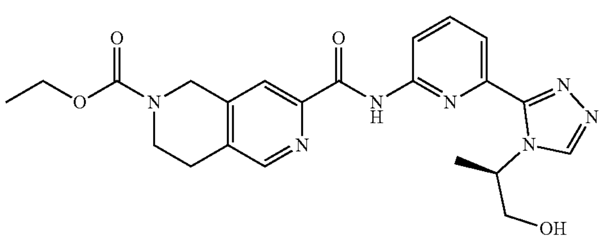 |

TABLE 3-continued

| Compound | Structure |
|---|---|
| 60 | 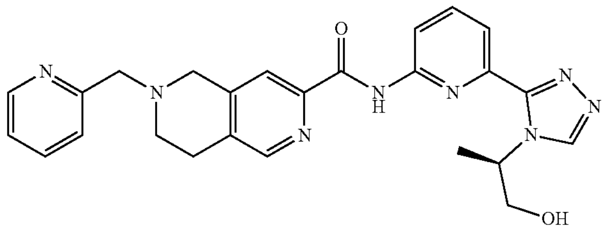 [SMILES: C[C@H](CO)n1cnnc1-c1cccc(NC(=O)c2cc3c(cn2)CCN(Cc2ccccn2)C3)n1] |
| 61 | 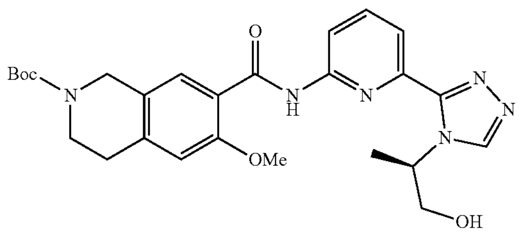 |
| 62 | 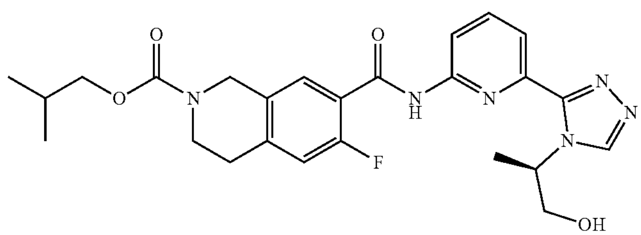 |
| 63 | 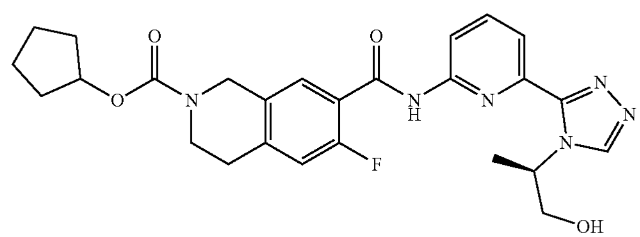 [SMILES: C[C@H](CO)n1cnnc1-c1cccc(NC(=O)c2cc3c(cc2F)CCN(C(=O)OC2CCCC2)C3)n1] |
| 64 | 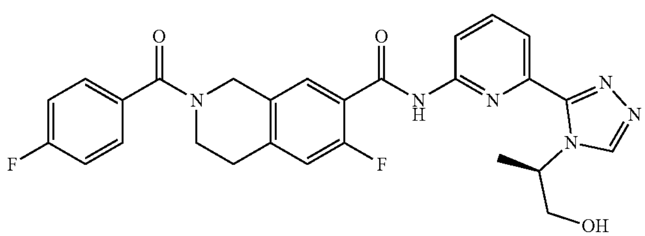 [SMILES: C[C@H](CO)n1cnnc1-c1cccc(NC(=O)c2cc3c(cc2F)CCN(C(=O)c2ccc(F)cc2)C3)n1] |
| 65 | 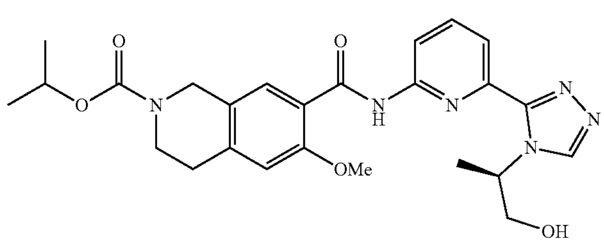 |

TABLE 3-continued

| Compound | Structure |
|---|---|
| 66 | 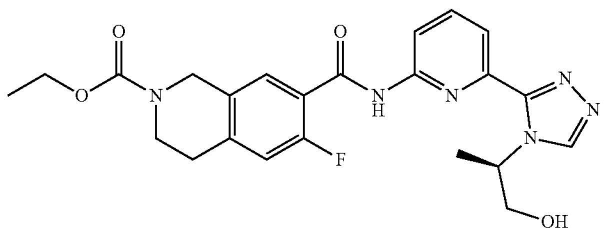 |
| 67 | 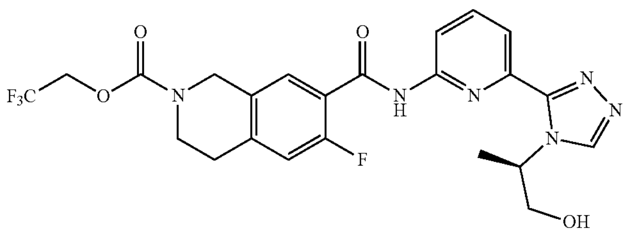 |
| 68 | 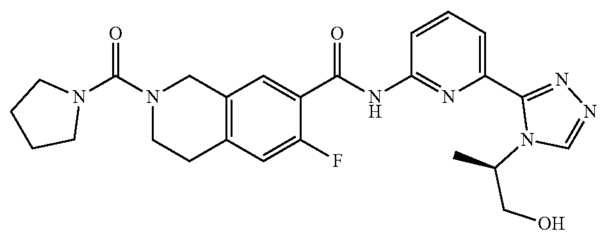 [SMILES: C[C@H](CO)n1cnnc1-c1cccc(NC(=O)c2cc3c(cc2F)CCN(C(=O)N2CCCC2)C3)n1] |
| 69 | 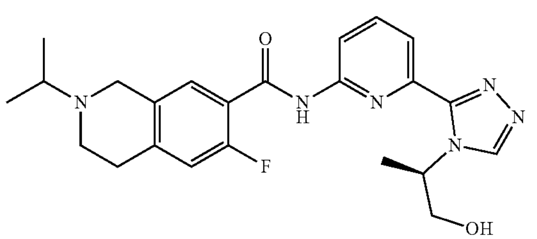 [SMILES: CC(C)N1CCc2cc(F)c(C(=O)Nc3cccc(-c4nncn4[C@H](C)CO)n3)cc2C1] |
| 70 | 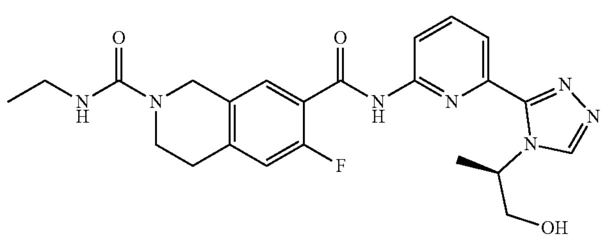 |
| 71 | 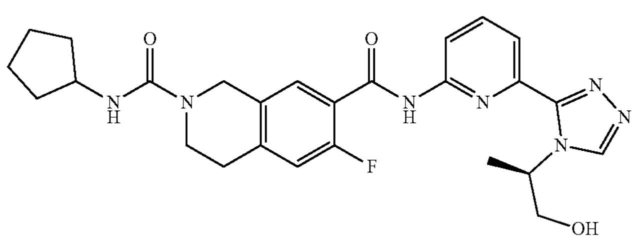 |

TABLE 3-continued

| Compound | Structure |
|---|---|
| 72 | 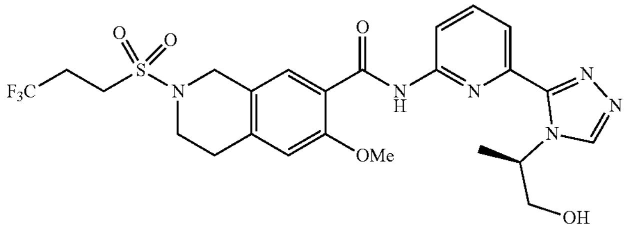 |
| 73 | 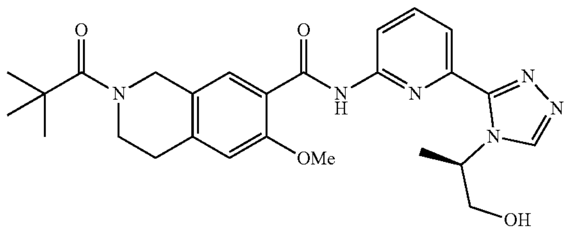 [SMILES: COc1cc2c(cc1C(=O)Nc1cccc(-c3nncn3[C@H](C)CO)n1)CN(C(=O)C(C)(C)C)CC2] |
| 74 | 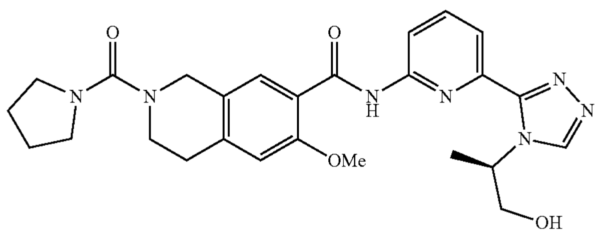 [SMILES: COc1cc2c(cc1C(=O)Nc1cccc(-c3nncn3[C@H](C)CO)n1)CN(C(=O)N1CCCC1)CC2] |
| 75 | 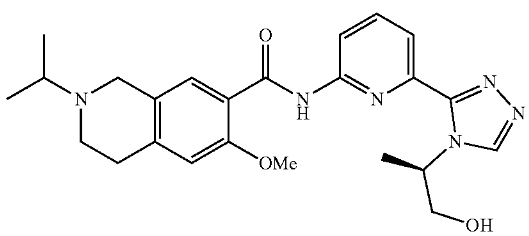 [SMILES: COc1cc2c(cc1C(=O)Nc1cccc(-c3nncn3[C@H](C)CO)n1)CN(C(C)C)CC2] |

In certain embodiments, the compound of Formula I is represented by Formula XIV or a pharmaceutically acceptable salt or ester thereof:

(XIV)

wherein $R^3$, $R^{10}$, $R^{11}$, $R^{12}$, $R^{13}$, $X^3$ and n are as previously defined.

In certain embodiments, the compound of Formula I is represented by Formula XV or a pharmaceutically acceptable salt or ester thereof:

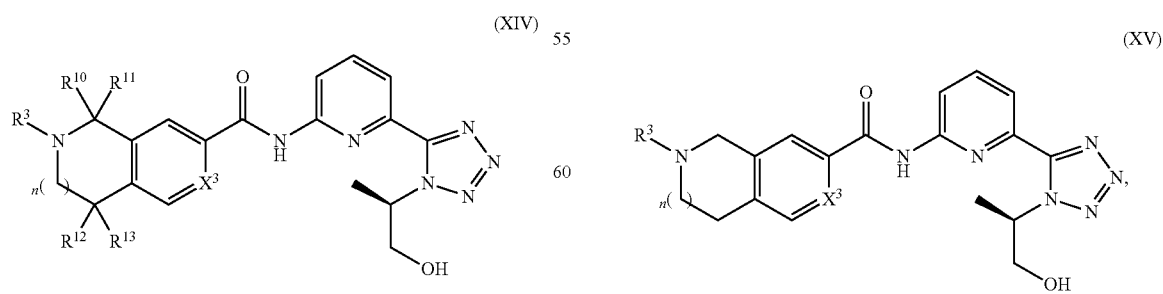

(XV)

wherein $R^3$, $X^3$, and n are as previously defined.

In certain embodiments, the compound of Formula I is represented by Formula XV' or a pharmaceutically acceptable salt or ester thereof:

Representative compounds of the invention include, but are not limited to, the following compounds (compound 76 to compound 93) according to Formula XV', and pharmaceutically acceptable salts thereof, are delineated in Table 4.

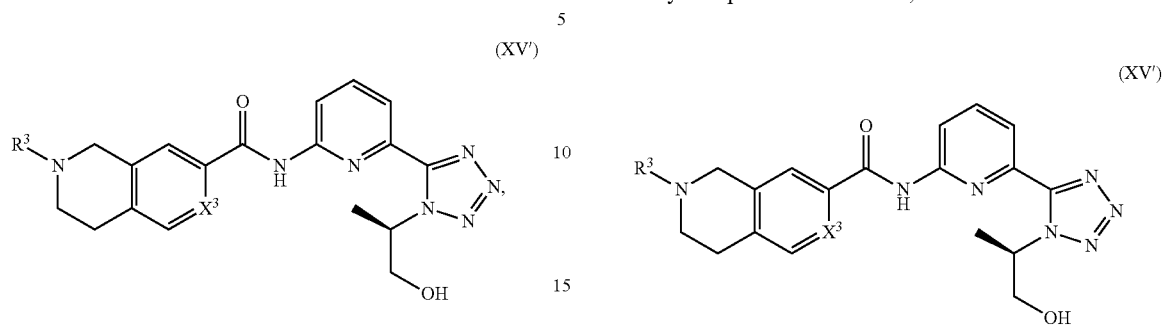

wherein $R^3$ and $X^3$ are as previously defined.

TABLE 4

| Compound | Structure |
|---|---|
| 76 | 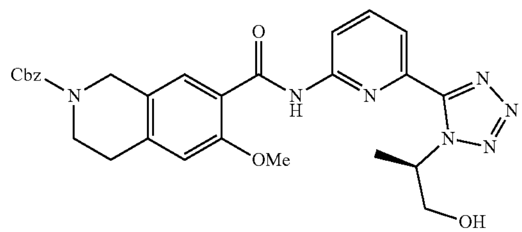 [SMILES: COc1cc2c(cc1C(=O)Nc1cccc(-c3nnnn3[C@H](C)CO)n1)CN(C(=O)OCc1ccccc1)CC2] |
| 77 | 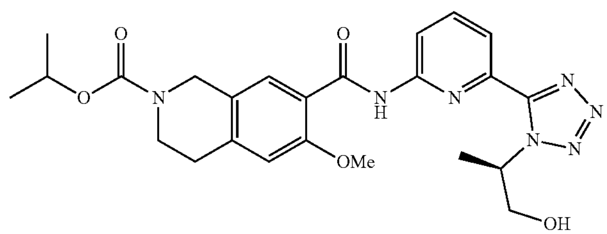 [SMILES: COc1cc2c(cc1C(=O)Nc1cccc(-c3nnnn3[C@H](C)CO)n1)CN(C(=O)OC(C)C)CC2] |
| 78 | 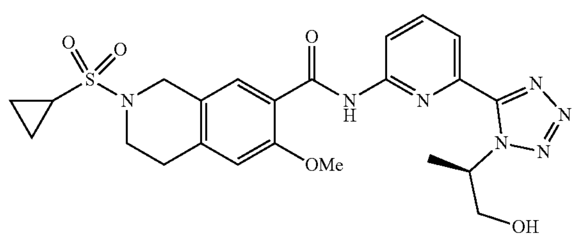 [SMILES: COc1cc2c(cc1C(=O)Nc1cccc(-c3nnnn3[C@H](C)CO)n1)CN(S(=O)(=O)C1CC1)CC2] |
| 79 | 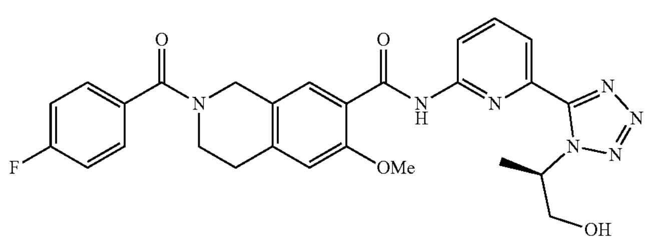 [SMILES: COc1cc2c(cc1C(=O)Nc1cccc(-c3nnnn3[C@H](C)CO)n1)CN(C(=O)c1ccc(F)cc1)CC2] |

TABLE 4-continued
| Compound | Structure |
|---|---|
| 80 | 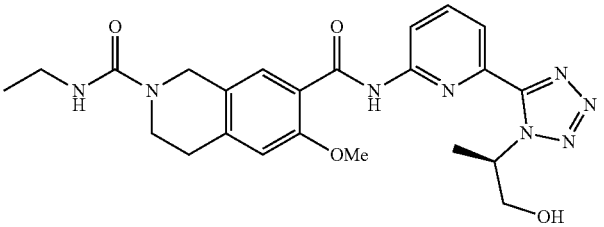 [SMILES: CCNC(=O)N1CCc2cc(OC)c(C(=O)Nc3cccc(-c4nnnn4[C@H](C)CO)n3)cc2C1] |
| 81 | 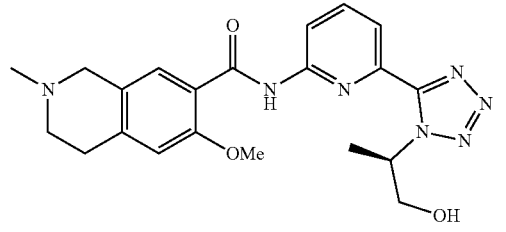 [SMILES: COc1cc2c(cc1C(=O)Nc1cccc(-c3nnnn3[C@H](C)CO)n1)CN(C)CC2] |
| 82 | 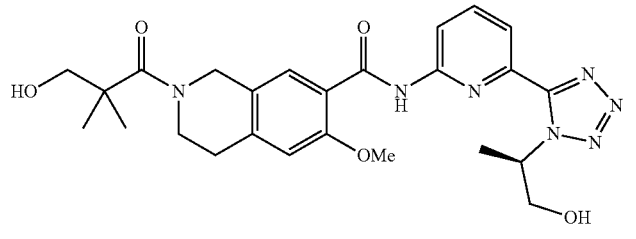 [SMILES: COc1cc2c(cc1C(=O)Nc1cccc(-c3nnnn3[C@H](C)CO)n1)CN(C(=O)C(C)(C)CO)CC2] |
| 83 | 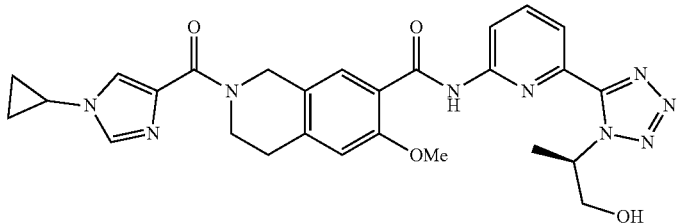 [SMILES: COc1cc2c(cc1C(=O)Nc1cccc(-c3nnnn3[C@H](C)CO)n1)CN(C(=O)c1cn(C3CC3)cn1)CC2] |
| 84 | 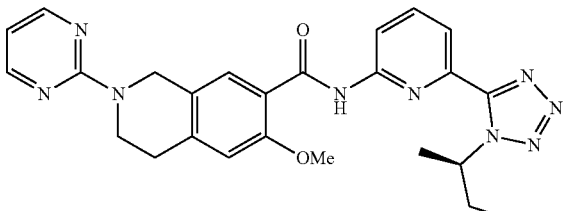 |
| 85 | 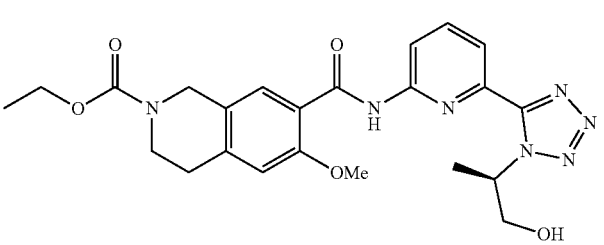 [SMILES: CCOC(=O)N1CCc2cc(OC)c(C(=O)Nc3cccc(-c4nnnn4[C@H](C)CO)n3)cc2C1] |

TABLE 4-continued

| Compound | Structure |
|---|---|
| 86 | 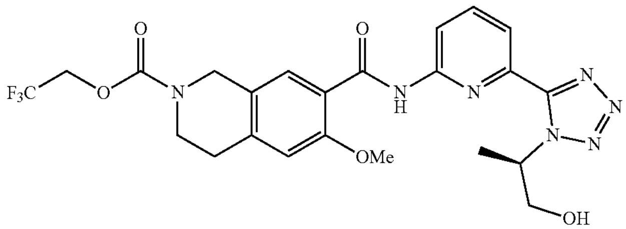 |
| 87 | 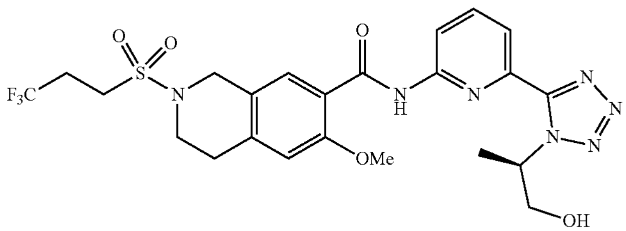 [SMILES: COc1cc2c(cc1C(=O)Nc1cccc(-c3nnnn3[C@H](C)CO)n1)CN(S(=O)(=O)CCC(F)(F)F)CC2] |
| 88 | 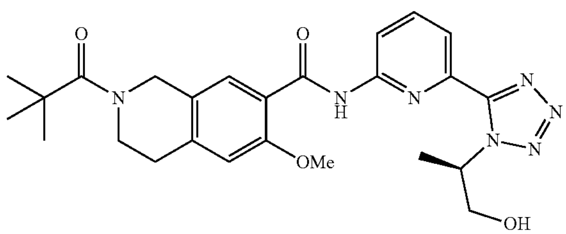 |
| 89 | 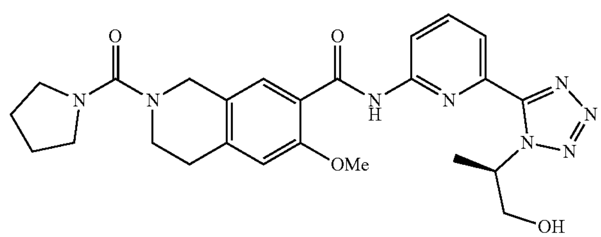 [SMILES: COc1cc2c(cc1C(=O)Nc1cccc(-c3nnnn3[C@H](C)CO)n1)CN(C(=O)N1CCCC1)CC2] |
| 90 | 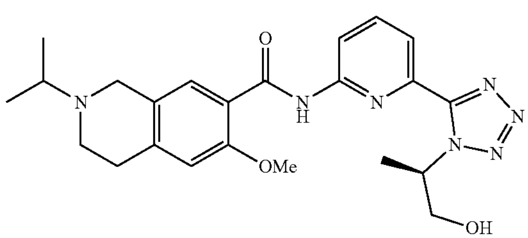 [SMILES: COc1cc2c(cc1C(=O)Nc1cccc(-c3nnnn3[C@H](C)CO)n1)CN(C(C)C)CC2] |
| 91 | 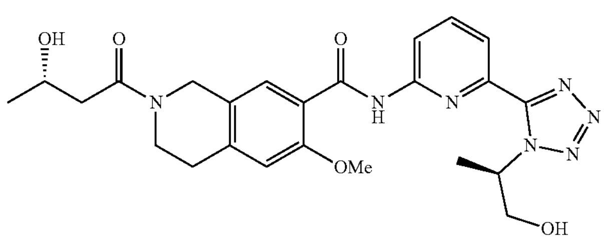 [SMILES: COc1cc2c(cc1C(=O)Nc1cccc(-c3nnnn3[C@H](C)CO)n1)CN(C(=O)C[C@H](C)O)CC2] |

TABLE 4-continued

| Compound | Structure |
|---|---|
| 92 | (structure) |
| 93 | (structure) |

Representative compounds of the invention further include, but are not limited to, the compounds 94 and 95, and pharmaceutically acceptable salts thereof, as shown in Table 5.

TABLE 5

| Compound | Structure |
|---|---|
| 94 | (structure) |
| 95 | (structure) |

In certain embodiments, the present invention provides a method for the treatment of an ASK-1 mediated disease or condition. The method comprises administering a therapeutically effective amount of a compound of Formula (I). The present invention also provides the use of a compound of Formula (I) for the preparation of a medicament for the treatment of an ASK-1 mediated disease or condition.

In certain embodiments, the ASK-1 mediated disease or condition is an autoimmune disorder, a neurodegenerative disorder, an inflammatory disease, chronic kidney disease, renal disease, cardiovascular disease, a metabolic disease, or an acute or chronic liver disease.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohns disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, reperfusion/ischemia in stroke, cardiac hypertrophy, respiratory diseases, heart attacks, myocardial ischemia.

In certain embodiments, the metabolic disease is insulin resistance, Type I and Type II diabetes, or obesity.

In certain embodiments, the chronic kidney disease is polycystic kidney disease, pyelonephritis, kidney fibrosis and glomerulonephritis.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl", "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted. The term "bicyclic aryl" or "bicyclic heteroaryl" refers to a ring system consisting of two rings wherein at least one ring is aromatic; and the two rings can be fused or covalently attached.

As used herein, the term "arylalkyl" means a functional group wherein an alkylene chain is attached to an aryl group, e.g., —CH$_2$CH$_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

The term "alkylene" as used herein, refers to a diradical of a branched or unbranched saturated hydrocarbon chain, typically having from 1 to 20 carbon atoms (e.g. 1-10 carbon atoms, or 1, 2, 3, 4, 5, or 6 carbon atoms). This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—), and the like.

The term "substituted" as used herein, refers to independent replacement of one, two, or three or more of the hydrogen atoms thereon with substituents including, but not limited to, deuterium, —F, —Cl, —Br, —I, —OH, protected hydroxy, —NO$_2$, —CN, —NH$_2$, N$_3$, protected amino, alkoxy, thioalkoxy, oxo, $C_1$-$C_{12}$-alkyl, $C_2$-$C_{12}$-alkenyl, $C_2$-$C_{12}$-alkynyl, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH— heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)— $C_2$-$C_{12}$-alkenyl, —C(O)— $C_2$-$C_{12}$-alkynyl, —C(O)—$C_3$-$C_{12}$-cycloalkyl, —C(O)-aryl, —C(O)-heteroaryl, —C(O)-heterocycloalkyl, —CONH$_2$, —CONH— $C_1$-$C_{12}$-alkyl, —CONH—$C_2$-$C_{12}$-alkenyl, —CONH— $C_2$-$C_{12}$-alkynyl, —CONH—$C_3$-$C_{12}$-cycloalkyl, —CONH-aryl, —CONH— heteroaryl, —CONH-heterocycloalkyl, —OCO$_2$— $C_1$-$C_{12}$-alkyl, —OCO$_2$— C$_2$-C$_{12}$-alkenyl, —OCO$_2$— C$_2$-C$_{12}$-alkynyl, —OCO$_2$—C$_3$-C$_{12}$-cycloalkyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH— C$_2$-C$_{12}$-alkenyl, —OCONH— C$_2$-C$_{12}$-alkynyl, —OCONH—C$_3$-C$_{12}$-cycloalkyl, —OCONH— aryl, —OCONH— heteroaryl, —OCONH— heterocycloalkyl, —NHC(O)— C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_{12}$-cycloalkyl, —NHC(O)-aryl, —NHC(O)-heteroaryl, —NHC(O)-heterocycloalkyl, —NHCO$_2$— C$_1$-C$_{12}$-alkyl, —NHCO$_2$— C$_2$-C$_{12}$-alkenyl, —NHCO$_2$— C$_2$-C$_{12}$-alkynyl, —NHCO$_2$— C$_3$-C$_{12}$-cycloalkyl, —NHCO$_2$— aryl, —NHCO$_2$— heteroaryl, —NHCO$_2$— heterocycloalkyl, —NHC(O)NH$_2$, —NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, —NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, —NHC(NH)NH— C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, —NHC(NH)— C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(NH)-heteroaryl, —NHC(NH)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_3$-C$_{12}$-cycloalkyl, —S(O)-aryl, —S(O)-heteroaryl, —S(O)-heterocycloalkyl —SO$_2$NH$_2$, —SO$_2$NH—C$_1$-C$_{12}$-alkyl, —SO$_2$NH—C$_2$-C$_{12}$-alkenyl, —SO$_2$NH— C$_2$-C$_{12}$-alkynyl, —SO$_2$NH—C$_3$-C$_{12}$-cycloalkyl, —SO$_2$NH— aryl, —SO$_2$NH— heteroaryl, —SO$_2$NH— heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$— heterocycloalkyl, —CH$_2$NH$_2$, —CH$_2$SO$_2$CH$_3$, -aryl, -arylalkyl, -heteroaryl, -heterarylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_2$-alkyl, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, methylthiomethyl, or -L'-R', wherein L' is C$_1$-C$_6$alkylene, C$_2$-C$_6$alkenylene or C$_2$-C$_6$alkynylene, and R$^1$ is aryl, heteroaryl, heterocyclic, C$_3$-C$_{12}$cycloalkyl or C$_3$-C$_{12}$cycloalkenyl. It is understood that the aryls, heteroaryls, alkyls, and the like can be further substituted. In some cases, each substituent in a substituted moiety is additionally optionally substituted with one or more groups, each group being independently selected from C$_1$-C$_6$-alkyl, —F, —Cl, —Br, —I, —OH, —NO$_2$, —CN, or —NH$_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic" as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are (C$_1$-C$_3$) alkoxy.

The term "aryloxy" refers to the group aryl-O— wherein the aryl group is as defined above, and includes optionally substituted aryl groups as also defined above. The term "arylthio" refers to the group R—S—, where R is as defined for aryl.

The terms "heterocyclic" or "heterocycloalkyl" can be used interchangeably and refer to a non-aromatic ring or a bi- or tri-cyclic group fused, bridged or spiro system, where (i) the ring system contains at least one heteroatom independently selected from oxygen, sulfur and nitrogen, (ii) the ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, cycloalkyl, heterocyclic and cycloalkenyl moiety described herein can also be an aliphatic group or an alicyclic group.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions, and are applicable to provide the Formulas herein with proper valency.

The terms "halo" and "halogen," as used herein, refer to an atom selected from fluorine, chlorine, bromine and iodine.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs. Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part-2.* (Biotechnology: Pharmaceutical Aspects), edited by V. J. Stella, et al, Springer and AAPSPress, 2007, pp 31-99.

The term "amino" as used herein, refers to the group —NH$_2$.

The term "substituted amino" as used herein, refers to the group —NRR where each R is independently selected from the group consisting of hydrogen, alkyl, cycloalkyl, aryl, heteroaryl and heterocycloalkyl provided that both R groups are not hydrogen, or a group —Y—Z, in which Y is optionally substituted alkylene and Z is alkenyl, cycloalkenyl, or alkynyl.

The term "amino protecting group" as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38 (1992); Bundgaard, J. of *Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H$_2$O, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series,* John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations,* VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragées, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
ASK1 for apoptosis signal-regulating kinase 1;
ATP for adenosine triphosphate;
Boc for tert-butyloxycarbonyl;
$Boc_2O$ for di-tert-butyl dicarbonate;
BOP—Cl for bis(2-oxo-3-oxazolidinyl)phosphinic chloride;
Cbz for benzyloxycarbonyl;
Cbz-Cl for benzyl chloroformate;
CDI for carbonyldiimidazole;
$(COCl)_2$ for oxalyl chloride;
DBU for 1,8-diazabicycloundec-7-ene;
DCC for N,N'-dicyclohexylcarbodiimide;
1,2-DCE for 1,2-dichloroethane;
DCM for dichloromethane;
DIPEA or Hunig's base or i-$Pr_2NEt$ for N,N-diisopropylethylamine;
DMA for N,N-dimethylacetamide;
DMAP for N,N-dimethylaminopyridine;
DMF for N,N-dimethyl formamide;
DMF-DMA for N,N-dimethylformamide dimethyl acetal;
dppp for 1,3-bis(diphenylphosphino)propane;
EDC for 1-(3-diethylaminopropyl)-3-ethylcarbodiimide hydrochloride;
EGTA for ethylene glycol-bis(2-aminoethylether)-N,N,N',N'-tetraacetic acid;
ESI for electrospray ionization;
$Et_3N$ or TEA for triethylamine;
EtOAc for ethyl acetate;
Ghosez's Reagent for 1-chloro-N,N,2-trimethyl-1-propenylamine;
h, hr, or hrs for hours;
HATU for 1-[bis(dimethylamino)methylene]-1H-1,2,3-triazolo[4,5-b]pyridinium 3-oxid hexafluorophosphate;
HEPES for 4-(2-Hydroxyethyl)piperazine-1-ethanesulfonic acid, N-(2-hydroxyethyl)piperazine-N'-(2-ethanesulfonic acid);
$IC_{50}$ for half maximal inhibitory concentration;
KOt-Bu for potassium tert-butoxide;
LC-MS for liquid chromatography-mass spectrometry;
MeCN or ACN for acetonitrile;
min or mins for minutes;
MTBE or TBME for methyl tert-butyl ether;
m/z for mass-to-charge ratio;
NaOt-Bu for sodium tert-butoxide;
NMP for 1-methyl-2-pyrrolidinone;
NMR for nuclear magnetic resonance spectroscopy;
Pd/C for palladium on carbon;
PhMe or tol for toluene;
—OTBS for tert-butyldimethylsiloxy
—OTf or triflate for trifluoromethanesulfonate;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
rt for room temperature;
STK3 for serine/threonine-protein kinase 3;
TBAF for tetra-N-butylammonium fluoride;
TBSCl or TBS-Cl for tert-butyldimethylsilyl chloride;
$Tf_2O$ for trifluoromethanesulfonic anhydride;
TFA for trifluoroacetic acid;
THF for tetrahydrofuran;
TR-FRET for time-resolved fluorescence energy transfer.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, compounds of Formula (Ie) are prepared from the compound of Formula (1-1) wherein $X^3$ and n are as previously defined. $X^4$ is Br, Cl, I, or OTf. Thus, the compound of Formula (1-1) is reacted with a suitable N-functionalizing reagent to afford a compound of Formula (1-2), wherein $R^{15}$ is a suitable nitrogen protecting group, such as, but not limited to Boc or Cbz. If $R^{15}$ is Cbz, a compound of Formula (1-1) is reacted with Cbz-Cl to afford a compound of Formula (1-2) using a suitable base such as, but not limited to, $Et_3N$, DIPEA, DMAP, or pyridine. The reaction solvent can be, but is not limited to, THF or DCM. The reaction temperature is from −20° C. to 40° C. If $R^{15}$ is Boc, a compound of Formula (1-1) is reacted with $Boc_2O$ to afford a compound of Formula (1-2) using a suitable base such as, but not limited to, $Et_3N$, DIPEA, DMAP, or pyridine. The reaction solvent can be, but is not limited to, THF or DCM. The reaction temperature is from −20° C. to 40° C. The compound of Formula (1-2) is converted to a compound of Formula (1-3), wherein $R^{14}$ is an alkyl group, such as, but not limited to, methyl, ethyl, propyl, tert-butyl, and isopropyl. Thus, the compound of Formula (1-2) is reacted with a suitable metallating reagent, such as, but not limited to, isopropylmagnesium chloride, followed by reacting the resultant intermediate with carbon dioxide to afford a compound of Formula (1-3). The reaction solvent can be, but is not limited to, THF. The reaction temperature is from −80° C. to 25° C. Alternatively, the compound of Formula (1-2) is reacted with a suitable palladium catalyst, a suitable ligand, a suitable base, a suitable alcohol, and carbon monoxide to afford a compound of Formula (1-3). The palladium catalyst can be, but is not limited to, palladium(II) acetate, [1,1'-bis(diphenylphosphino)ferrocene]dichloropalladium(II), or tetrakis(triphenylphosphine) palladium(0). The ligand, can be, but is not limited to, 1,3-bis(diphenylphosphino)propane, or 1,4-bis(diphenylphosphino)butane. The base can be, but is not limited to, $Et_3N$, DIPEA, $K_2CO_3$, $Na_2CO_3$, or $Cs_2CO_3$. The alcohol can be, but is not limited to, methanol, ethanol, 2-propanol, n-propanol, or tert-butanol. The reaction solvent can be, but is not limited to, DMF, NMP, or DMA. The reaction temperature is from 25° C. to 150° C. The compound of Formula (1-3) is hydrolyzed to afford a compound of Formula (1-4) using a suitable hydroxide source such as, but not limited to, NaOH or LiOH. Alternatively, if $R^{14}$ is tert-butyl, then the compound of Formula (1-3) is reacted with a suitable acid to afford a compound of Formula (1-4). The acid can be, but is not limited to, hydrochloric acid or TFA. The compound of Formula (1-4) is reacted with a suitable chlorinating reagent such as, but not limited to, oxalyl chloride in combination with a catalytic quantity of DMF, thionyl chloride, or Ghosez's reagent to afford a compound of Formula (1-5). The reaction solvent can be, but is not limited to, THF or DCM. The reaction temperature is from −20° C. to 40° C. The compound of Formula (1-5) is reacted with a compound of Formula (1-6), wherein $X^1$, $X^2$, $R^1$ and $R^2$ are as previously defined, to afford a compound of Formula (1-6) using a suitable base such as, but not limited to, $Et_3N$, DMAP, pyridine, or DIPEA. The reaction solvent can be, but is not limited to, THF, DCM, pyridine and toluene. The reaction temperature is from −20° C. to 40° C. Alternatively, the compound of Formula (1-4) is reacted with a compound of Formula (1-6) to afford a compound of Formula (1-7) using a suitable coupling reagent such as, but not limited to, BOP—Cl, CDI, DCC, EDC, HATU, PyAOP or PyBOP in the presence of a suitable base such as, but not limited to, $Et_3N$ or DIPEA. The reaction solvent can be, but is not limited to, THF, DCM and DMF. The reaction temperature is from −20° C. to 40° C. Alternatively, the compound of Formula (1-3) is reacted with a compound of Formula (1-6) in the presence of trimethylaluminum to afford a compound of Formula (1-7). The reaction solvent can be, but is not limited to, DCM or PhMe. The reaction temperature is from 0° C. to 100° C. Alternatively, the compound of Formula (1-2) can be reacted with a compound of Formula (1-6) and carbon monoxide in the presence of a suitable palladium catalyst, a suitable ligand and a suitable base to afford a compound of Formula (1-7). The palladium catalyst can be, but is not limited to, palladium(II) acetate, [1,1′-bis(diphenylphosphino)ferrocene]dichloropalladium(II), or tetrakis(triphenylphosphine) palladium(0). The ligand, can be, but is not limited to, 1,3-bis(diphenylphosphino)propane, or 1,4-bis(diphenylphosphino)butane. The base can be, but is not limited to, $Et_3N$, DIPEA, $K_2CO_3$, $Na_2CO_3$, or $Cs_2CO_3$. The reaction solvent can be, but is not limited to, DMF, NMP, or DMA. The reaction temperature is from 25° C. to 150° C. If $R^{15}$ is Cbz, the compound of Formula (1-7) is reacted with palladium on carbon in the presence of hydrogen gas to afford a compound of Formula (1-8). The reaction solvent can be, but is not limited to, MeOH, EtOH, EtOAc, and THF. If $R^{15}$ is Boc, the compound of Formula (1-7) is reacted with a suitable acid, such as, but not limited to, hydrochloric acid or TFA to afford a compound of Formula (1-8). The reaction solvent can be, but is not limited to, MeOH, EtOH, EtOAc, THF, and 1,4-dioxane. Compounds of Formula (1-8) are reacted with a suitable combination of reagents to afford compounds of Formula (Ie). The reagent combinations may be, but are not limited to:

1) An aldehyde in combination with a suitable reducing agent, such as, but not limited to, $NaBH_4$, $NaBH(OAc)_3$, or $NaBH_3CN$. The reaction solvent can be, but is not limited to, DCM, 1,2-DCE, or THF.
2) A ketone in combination with a suitable reducing agent, such as, but not limited to, $NaBH_4$, $NaBH(OAc)_3$, or $NaBH_3CN$. The reaction solvent can be, but is not limited to, DCM, 1,2-DCE, or THF.
3) An alkyl halide, alkyl mesylate, or alkyl tosylate in combination with a suitable base such as, but not limited to, NaH, NaOt-Bu, KOt-Bu, $Et_3N$, or DIPEA. The reaction solvent can be, but is not limited to, DCM or THF.
4) An aryl-, heteroaryl-, or alkenyl-halide, or an aryl- or heteroaryl-, or alkenyl-triflate in combination with a suitable base, palladium(0) catalyst, ligand, and solvent. The base can be, but is not limited to, NaOt-Bu or KOt-Bu. The palladium(0) catalyst can be, but is not limited to, $Pd(PPh_3)_4$ or $Pd_2(dba)_3$. The ligand can be, but is not limited to, P(o-tolyl)$_3$ or (2-biphenyl)di-tert-butylphosphine. The solvent can be, but is not limited to, toluene or THF.
5) An acyl chloride in the presence of a suitable base such as, but not limited to, $Et_3N$, DIPEA, or DMAP. The reaction solvent can be, but is not limited to, DCM or THF.
6) A chloroformate in the presence of a suitable base such as, but not limited to, $Et_3N$, DIPEA, or DMAP. The reaction solvent can be, but is not limited to, DCM or THF.
7) A sulfonyl chloride in the presence of a suitable base such as, but not limited to, $Et_3N$, DIPEA, or DMAP. The reaction solvent can be, but is not limited to, DCM or THF.
8) An isocyanate in the presence of a suitable base such as, but not limited to, $Et_3N$, DIPEA, or DMAP. The reaction solvent can be, but is not limited to, DCM or THF.
9) A primary or secondary amine in the presence of a suitable activating reagent such as, but not limited to, phosgene, triphosgene, or CDI. The reaction solvent can be, but is not limited to, DCM or THF.
10) A carboxylic acid in the presence of a suitable coupling reagent, and base. The coupling reagent can be, but is not limited to, BOP—Cl, CDI, DCC, EDC, HATU, PyAOP or PyBOP. The base can be, but is not limited to, $Et_3N$, DIPEA, or pyridine.
11) An aryl or heteroaryl halide in the presence of a suitable base, such as, but not limited to, $Cs_2CO_3$, $K_2CO_3$, $Et_3N$, DBU, DIPEA, or pyridine. The reaction solvent can be, but is not limited to, DCM, THF, DMF, or NMP.

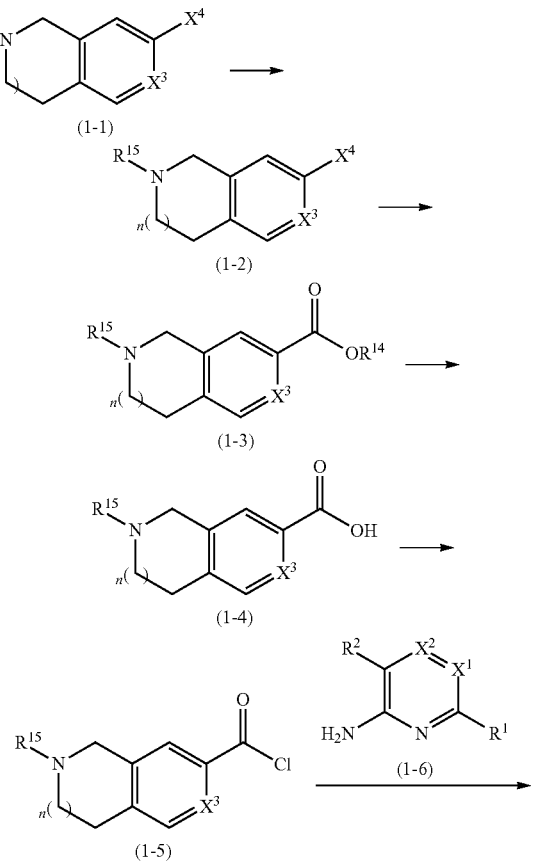

Scheme 1

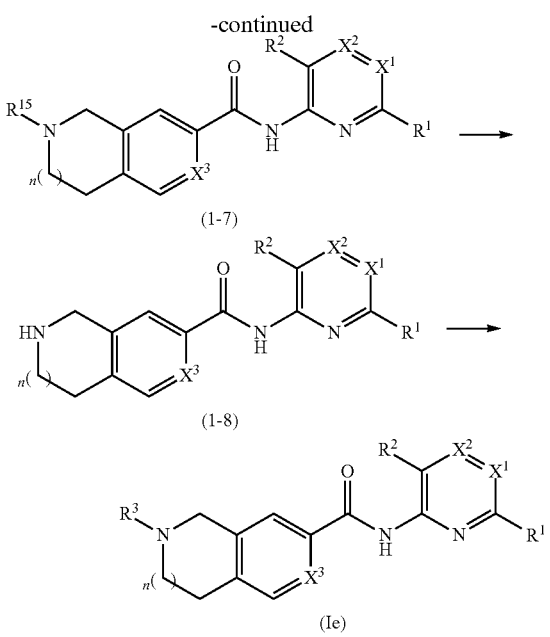

As shown in Scheme 2, compounds of Formula (Ie) are prepared from the compound of Formula (1-1) wherein $X^3$ and n are as previously defined. $X^4$ is Br, Cl, I, or OTf. Thus, the compound of Formula (1-1) is reacted with a suitable N-functionalizing reagent to afford a compound of Formula (1-2), wherein $R^{15}$ is a suitable nitrogen protecting group, such as, but not limited to Boc or Cbz. If $R^{15}$ is Cbz, a compound of Formula (1-1) is reacted with Cbz-Cl to afford a compound of Formula (1-2) using a suitable base such as, but not limited to, $Et_3N$, DIPEA, DMAP, or pyridine. The reaction solvent can be, but is not limited to, THF or DCM. The reaction temperature is from −20° C. to 40° C. If $R^{15}$ is Boc, a compound of Formula (1-1) is reacted with $Boc_2O$ to afford a compound of Formula (1-2) using a suitable base such as, but not limited to, $Et_3N$, DIPEA, DMAP, or pyridine. The reaction solvent can be, but is not limited to, THF or DCM. The reaction temperature is from −20° C. to 40° C. The compound of Formula (1-2) is converted to a compound of Formula (2-1), wherein $R^{16}$, $R^{17}$, and $R^{18}$ are hydrogen, substituted or unsubstituted —$C_1$-$C_8$ alkyl, substituted or unsubstituted aryl, substituted or unsubstituted heteroaryl, substituted or unsubstituted —$C_3$-$C_8$ cycloalkyl, substituted or unsubstituted arylalkyl, substituted or unsubstituted 3- to 8-membered heterocycloalkyl, substituted or unsubstituted heteroarylalkyl, or $R^{16}$ and $R^{17}$ are taken together to form an optionally substituted cycloalkyl or heterocycloalkyl, or $R^{17}$ and $R^{18}$ are taken together to form an optionally substituted cycloalkyl or heterocycloalkyl. Thus, the compound of Formula (1-2) is reacted with a suitable boronic ester or boronic acid in the presence of a suitable palladium catalyst, a suitable ligand, and a suitable base to afford a compound of Formula (2-1). The boronic ester or boronic acid can be, but is not limited to, vinylboronic acid pinacol ester or trans-2-(phenyl)vinylboronic acid pinacol ester. The palladium catalyst can be, but is not limited to, palladium(II) acetate, [1,1'-bis(diphenylphosphino)ferrocene]dichloropalladium(II), or tetrakis(triphenylphosphine) palladium(0). The ligand, can be, but is not limited to, 1,3-bis(diphenylphosphino)propane, $PCy_3HBF_4$, $PCy_3$, or $PPh_3$. The base can be, but is not limited to, $Et_3N$, DIPEA, $K_2CO_3$, $Na_2CO_3$, $Cs_2CO_3$, or $K_3PO_4$. The reaction solvent can be, but is not limited to, DMF, NMP, DMA, $H_2O$, or 1,4-dioxane. The reaction temperature is from 25° C. to 150° C. Alternatively, the compound of Formula (1-2) is reacted with a suitable organotin reagent in the presence of a suitable palladium catalyst and a suitable ligand to afford a compound of Formula (2-1). The organotin reagent can be, but is not limited to, tributyl(vinyl)tin. The palladium catalyst can be, but is not limited to, tetrakis(triphenylphosphine) palladium(0), palladium(II) acetate, or tris(dibenzylideneacetone)dipalladium(0). The ligand can be, but is not limited to, triphenylphosphine, tri-tert-butylphosphine, tri(ortho-tolyl)phosphine, or 2-dicyclohexylphosphino-2',4',6'-triisopropylbiphenyl. The reaction solvent can be, but is not limited to, THF, 1,4-dioxane, or toluene. The reaction temperature is from 25° C. to 150° C. The compound of Formula (2-1) is reacted with a suitable oxidant in the presence of a suitable base to afford a compound of Formula (2-2). The oxidant can be, but is not limited to osmium tetroxide, or a combination of osmium tetroxide and sodium periodate. The base can be, but is not limited to, 2,6-lutidine. The reaction solvent can be, but is not limited to, 1,4-dioxane, $H_2O$ or a combination of these. The reaction temperature is from 0° C. to 50° C. Alternatively, the compound of Formula (2-1) is reacted with ozone followed by a suitable reducing agent to afford a compound of Formula (2-2). The reducing agent can be, but is not limited to, dimethylsulfide or triphenylphosphine. The reaction solvent can be, but is not limited to, methanol or dichloromethane. The reaction temperature is from −80° C. to 25° C.

The compound of Formula (2-2) is reacted with a suitable chlorous acid source in the presence of a suitable hypochlorous acid scavenger and a suitable buffer to afford a compound of Formula (1-4). The chlorous acid source can be, but is not limited to, $NaClO_2$. The hypochlorous acid scavenger can be, but is not limited to, 2-methyl-2-butene. The buffer can be, but is not limited to, $NaH_2PO_4$. The reaction solvent can be, but is not limited to, THF, tert-butanol, $CH_3CN$, $H_2O$, or a combination of these. The reaction temperature is from 0° C. to 50° C. Alternatively, the compound of Formula (2-1) is reacted with a catalytic quantity of $RuCl_3$ in the presence of a suitable oxidant to afford a compound of Formula (1-4). The oxidant can be, but is not limited to sodium periodate. The reaction solvent can be, but is not limited to, EtOAc, $CCl_4$, $CH_2Cl_2$, $CH_3CN$, $H_2O$, or a combination of these. The reaction temperature is from 0° C. to 50° C. The compound of Formula (1-4) is reacted with a suitable chlorinating reagent such as, but not limited to, oxalyl chloride in combination with a catalytic quantity of DMF, thionyl chloride, or Ghosez's reagent to afford a compound of Formula (1-5). The reaction solvent can be, but is not limited to, THF or DCM. The reaction temperature is from −20° C. to 40° C. The compound of Formula (1-5) is reacted with a compound of Formula (1-6), wherein $X^1$, $X^2$, $R^1$ and $R^2$ are as previously defined, to afford a compound of Formula (1-6) using a suitable base such as, but not limited to, $Et_3N$, DMAP, pyridine, or DIPEA. The reaction solvent can be, but is not limited to, THF, DCM, pyridine and toluene. The reaction temperature is from −20° C. to 40° C. Alternatively, the compound of Formula (1-4) is reacted with a compound of Formula (1-6) to afford a compound of Formula (1-7) using a suitable coupling reagent such as, but not limited to, BOP—Cl, CDI, DCC, EDC, HATU, PyAOP or PyBOP in the presence of a suitable base such as, but not limited to, $Et_3N$ or DIPEA. The reaction solvent can be, but is not limited to, THF, DCM and DMF. The reaction temperature is from −20° C. to 40° C. Alternatively, the compound of Formula (1-3) is reacted with a compound of Formula (1-6) in the presence of trimethylaluminum to afford a compound of Formula (1-7). The reaction solvent can be, but is not limited to, DCM or PhMe. The reaction temperature is from 0° C. to 100° C. Alternatively, the compound of Formula (1-2) can be reacted with a compound of Formula (1-6) and carbon monoxide in the presence of a suitable palladium catalyst, a suitable ligand and a suitable base to afford a compound of Formula (1-7). The palladium catalyst can be, but is not limited to, palladium(II) acetate, [1,1'-bis(diphenylphosphino)ferrocene]dichloropalladium(II), or tetrakis(triphenylphosphine)palladium(0). The ligand, can be, but is not limited to, 1,3-bis(diphenylphosphino)propane, or 1,4-bis(diphenylphosphino)butane. The base can be, but is not limited to, $Et_3N$, DIPEA, $K_2CO_3$, $Na_2CO_3$, or $Cs_2CO_3$. The reaction solvent can be, but is not limited to, DMF, NMP, or DMA. The reaction temperature is from 25° C. to 150° C. If $R^{15}$ is Cbz, the compound of Formula (1-7) is reacted with palladium on carbon in the presence of hydrogen gas to afford a compound of Formula (1-8). The reaction solvent can be, but is not limited to, MeOH, EtOH, EtOAc, and THF. If $R^{15}$ is Boc, the compound of Formula (1-7) is reacted with a suitable acid, such as, but not limited to, hydrochloric acid or TFA to afford a compound of Formula (1-8). The reaction solvent can be, but is not limited to, MeOH, EtOH, EtOAc, THF, and 1,4-dioxane. Compounds of Formula (1-8) are reacted with a suitable combination of reagents to afford compounds of Formula (Ie). The reagent combinations may be, but are not limited to:

1) An aldehyde in combination with a suitable reducing agent, such as, but not limited to, $NaBH_4$, $NaBH(OAc)_3$, or $NaBH_3CN$. The reaction solvent can be, but is not limited to, DCM, 1,2-DCE, or THF.
2) A ketone in combination with a suitable reducing agent, such as, but not limited to, $NaBH_4$, $NaBH(OAc)_3$, or $NaBH_3CN$. The reaction solvent can be, but is not limited to, DCM, 1,2-DCE, or THF.
3) An alkyl halide, alkyl mesylate, or alkyl tosylate in combination with a suitable base such as, but not limited to, NaH, NaOt-Bu, KOt-Bu, $Et_3N$, or DIPEA. The reaction solvent can be, but is not limited to, DCM or THF.
4) An aryl-, heteroaryl-, or alkenyl-halide, or an aryl- or heteroaryl-, or alkenyl-triflate in combination with a suitable base, palladium(0) catalyst, ligand, and solvent. The base can be, but is not limited to, NaOt-Bu or KOt-Bu. The palladium(0) catalyst can be, but is not limited to, $Pd(PPh_3)_4$ or $Pd_2(dba)_3$. The ligand can be, but is not limited to, $P(o-tolyl)_3$ or (2-biphenyl)di-tert-butylphosphine. The solvent can be, but is not limited to, toluene or THF.
5) An acyl chloride in the presence of a suitable base such as, but not limited to, $Et_3N$, DIPEA, or DMAP. The reaction solvent can be, but is not limited to, DCM or THF.
6) A chloroformate in the presence of a suitable base such as, but not limited to, $Et_3N$, DIPEA, or DMAP. The reaction solvent can be, but is not limited to, DCM or THF.
7) A sulfonyl chloride in the presence of a suitable base such as, but not limited to, $Et_3N$, DIPEA, or DMAP. The reaction solvent can be, but is not limited to, DCM or THF.
8) An isocyanate in the presence of a suitable base such as, but not limited to, $Et_3N$, DIPEA, or DMAP. The reaction solvent can be, but is not limited to, DCM or THF.
9) A primary or secondary amine in the presence of a suitable activating reagent such as, but not limited to, phosgene, triphosgene, or CDI. The reaction solvent can be, but is not limited to, DCM or THF.
10) A carboxylic acid in the presence of a suitable coupling reagent, and base. The coupling reagent can be, but is not limited to, BOP—Cl, CDI, DCC, EDC, HATU, PyAOP or PyBOP. The base can be, but is not limited to, $Et_3N$, DIPEA, or pyridine.
11) An aryl or heteroaryl halide in the presence of a suitable base, such as, but not limited to, $Cs_2CO_3$, $K_2CO_3$, $Et_3N$, DBU, DIPEA, or pyridine. The reaction solvent can be, but is not limited to, DCM, THF, DMF, or NMP.

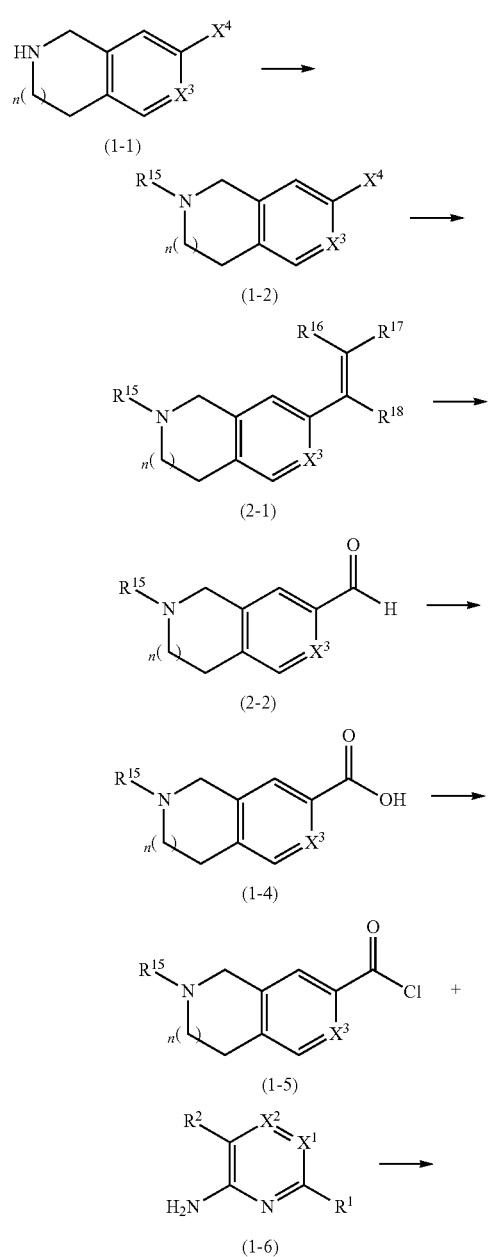

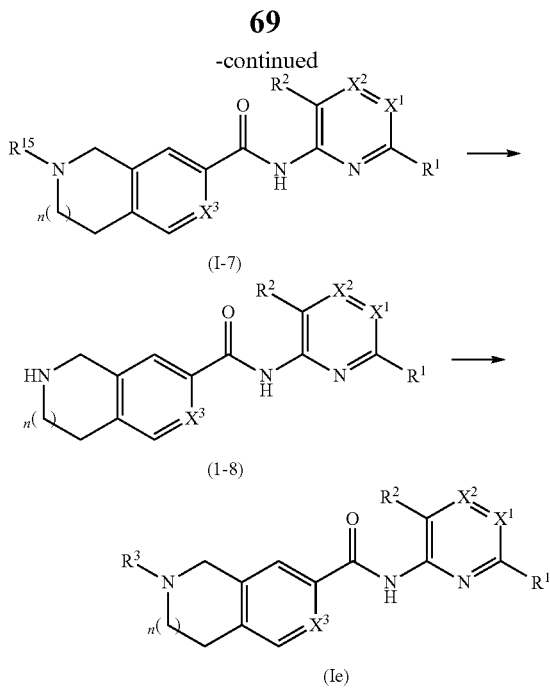

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or methods of the invention may be made without departing from the spirit of the invention and the scope of the appended claims.

Example 1: N-(6-(4-isopropyl-4H-1,2,4-triazol-3-yl)pyridin-2-yl)-6-pivaloyl-5,6,7,8-tetrahydro-2,6-naphthyridine-3-carboxamide

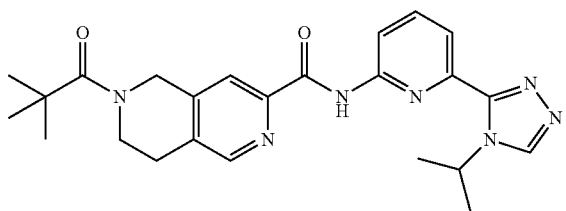 [SMILES: CC(C)n1cnnc1-c1cccc(NC(=O)c2cc3c(cn2)CCN(C(=O)C(C)(C)C)C3)n1]

Step 1. Synthesis of 2-(tert-butyl) 7-ethyl 3,4-dihydro-2,6-naphthyridine-2,7(1H)-dicarboxylate

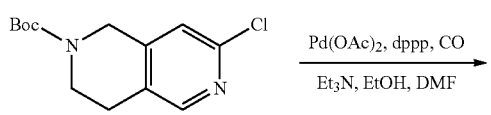

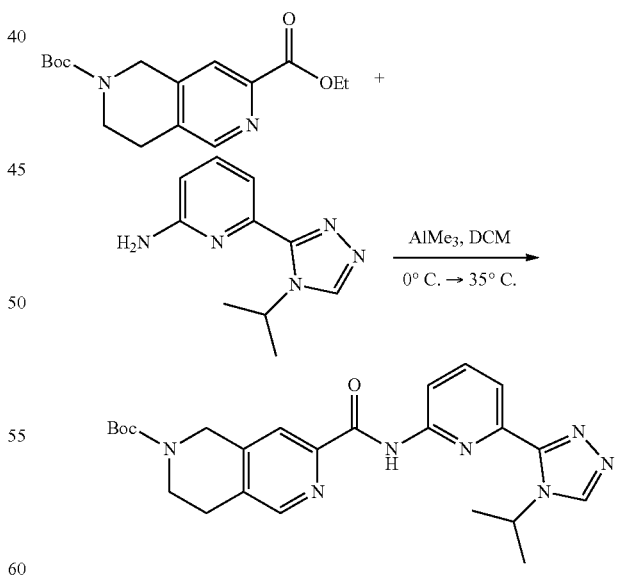

A mixture of tert-butyl 7-chloro-3,4-dihydro-2,6-naphthyridine-2(1H)-carboxylate (3.0 g, 11.16 mmol), Pd(OAc)$_2$ (0.251 g, 1.12 mmol), 1,3-bis(diphenylphosphino)propane (0.921 g, 2.23 mmol), and Et$_3$N (4.67 ml, 33.5 mmol) in DMF (29.8 ml)/EtOH (14.9 ml) were stirred under a balloon of CO at 80° C. overnight. The reaction was quenched with H$_2$O/brine and diluted with EtOAc. The layers were separated and the organic layer was washed with H$_2$O/brine (2×). The organic layer was dried (MgSO$_4$), filtered, and concentrated under reduced pressure. The resultant brown gum was purified by column chromatography eluting with hexanes/EtOAc (0%/EtOAc→75% EtOAc) to afford 2-(tert-butyl) 7-ethyl 3,4-dihydro-2,6-naphthyridine-2,7(1H)-dicarboxylate (2.17 g, 7.08 mmol, 64% yield) as a pale yellow oil: $^1$H NMR (400 MHz, Chloroform-d) δ 8.52 (s, 1H), 7.89 (s, 1H), 4.64 (s, 2H), 4.47 (q, J=7.1 Hz, 2H), 3.70 (t, J=5.8 Hz, 2H), 2.90 (t, J=5.8 Hz, 2H), 1.50 (s, 9H), 1.44 (t, J=7.1 Hz, 3H).

Step 2. Synthesis of tert-butyl 7-((6-(4-isopropyl-4H-1,2,4-triazol-3-yl)pyridin-2-yl)carbamoyl)-3,4-dihydro-2,6-naphthyridine-2(1H)-carboxylate 6-(4-isopropyl-4H-1,2,4-triazol-3-yl)pyridin-2-amine was prepared according to the method disclosed in WO 2016106384, the entire contents of which are incorporated herein by reference.
Representative procedure for amide formation with trimethylaluminum.

Trimethylaluminum (2.61 mL, 5.22 mmol of a 2.0M solution in PhMe) was added dropwise to CH$_2$Cl$_2$ (7.9 mL) at 0° C. A solution of 6-(4-isopropyl-4H-1,2,4-triazol-3-yl)pyridin-2-amine (530 mg, 2.61 mmol) in DCM (7.9 mL) was added at 0° C., and the mixture was stirred for 20 min at 0° C. then for 1 h at rt. A solution of 2-(tert-butyl) 7-ethyl 3,4-dihydro-2,6-naphthyridine-2,7(1H)-dicarboxylate (800 mg, 2.61 mmol) in DCM (6.4 mL) was added and the reaction was heated at 35° C. overnight. The reaction was quenched with sat. potassium sodium tartrate and diluted with CH$_2$Cl$_2$. The layers were separated and the aqueous layer was extracted with CH$_2$Cl$_2$ (2×). The combined organic layers were washed with brine, dried (MgSO$_4$), filtered, and concentrated under reduced pressure. The resultant yellow gum was purified by column chromatography eluting with CH$_2$Cl$_2$/MeOH (0% MeOH→8% MeOH) to afford tert-butyl 7-((6-(4-isopropyl-4H-1,2,4-triazol-3-yl)pyridin-2-yl)carbamoyl)-3,4-dihydro-2,6-naphthyridine-2(1H)-carboxylate (700 mg, 1.51 mmol, 58% yield) as a colorless solid: LC-MS, ES$^+$: m/z 464.26 [M+H]$^+$; $^1$H NMR (500 MHz, DMSO-d$_6$) δ 10.59 (s, 1H), 8.90 (s, 1H), 8.57 (s, 1H), 8.32 (d, J=8.2 Hz, 1H), 8.13-8.05 (comp, 2H), 7.88 (dd, J=7.6, 0.9 Hz, 1H), 5.49 (p, J=6.7 Hz, 1H), 4.69 (s, 2H), 3.63 (t, J=5.8 Hz, 2H), 2.91 (t, J=5.8 Hz, 2H), 1.50 (d, J=6.7 Hz, 5H), 1.44 (s, 9H).

Step 3. Synthesis of N-(6-(4-isopropyl-4H-1,2,4-triazol-3-yl)pyridin-2-yl)-5,6,7,8-tetrahydro-2,6-naphthyridine-3-carboxamide hydrochloride Representative procedure for Boc deprotection.

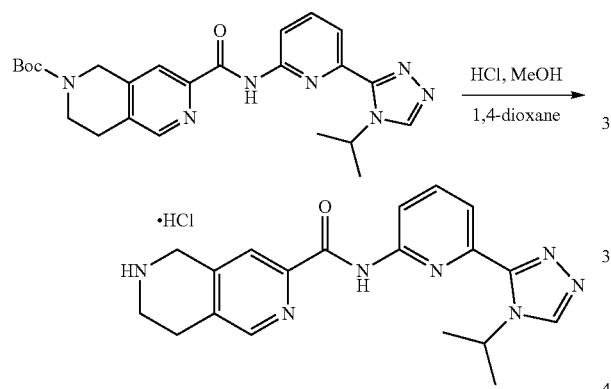

4M HCl in dioxane (0.56 mL) was added to a solution of tert-butyl 7-((6-(4-isopropyl-4H-1,2,4-triazol-3-yl)pyridin-2-yl)carbamoyl)-3,4-dihydro-2,6-naphthyridine-2(1H)-carboxylate (103 mg, 0.22 mmol) in MeOH (0.56 mL) and the reaction was stirred for 3 h at rt. The reaction was concentrated under reduced pressure to afford N-(6-(4-isopropyl-4H-1,2,4-triazol-3-yl)pyridin-2-yl)-5,6,7,8-tetrahydro-2,6-naphthyridine-3-carboxamide hydrochloride (97 mg, 0.22 mmol, 100% yield) as a tan solid: LC-MS, ES$^+$: m/z 364.21 [M+H]$^+$.

Step 4. Synthesis of N-(6-(4-isopropyl-4H-1,2,4-triazol-3-yl)pyridin-2-yl)-6-pivaloyl-5,6,7,8-tetrahydro-2,6-naphthyridine-3-carboxamide Representative procedure for amide formation.

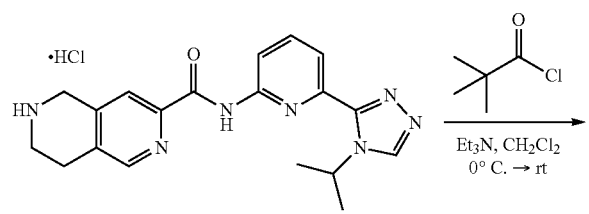

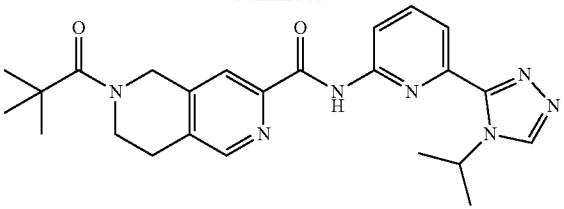

Pivaloyl chloride (18.5 μl, 18.1 mg, 0.15 mmol) was added dropwise to a solution of N-(6-(4-isopropyl-4H-1,2,4-triazol-3-yl)pyridin-2-yl)-5,6,7,8-tetrahydro-2,6-naphthyridine-3-carboxamide hydrochloride (40 mg, 0.10 mmol) and Et$_3$N (70 μL, 50 mg, 0.50 mmol) in CH$_2$Cl$_2$ (1.0 mL) at 0° C. The cold bath was removed and the reaction was stirred 1 h at rt. The reaction was quenched with sat. NaHCO$_3$ and diluted with CH$_2$Cl$_2$. The layers were separated and the aqueous layer was extracted with CH$_2$Cl$_2$ (2×). The combined organic layers were washed with brine, dried (MgSO$_4$), filtered, and concentrated under reduced pressure. The resultant yellow gum was purified by column chromatography eluting with CH$_2$Cl$_2$/MeOH (0% MeOH→8% MeOH) to afford N-(6-(4-isopropyl-4H-1,2,4-triazol-3-yl)pyridin-2-yl)-6-pivaloyl-5,6,7,8-tetrahydro-2,6-naphthyridine-3-carboxamide (14.4 mg, 0.032 mmol, 32% yield) as a pale yellow amorphous solid.

Example 4 was prepared according to the representative procedure for amide formation.

Example 2: 6-(N,N-dimethylsulfamoyl)-N-(6-(4-isopropyl-4H-1,2,4-triazol-3-yl)pyridin-2-yl)-5,6,7,8-tetrahydro-2,6-naphthyridine-3-carboxamide

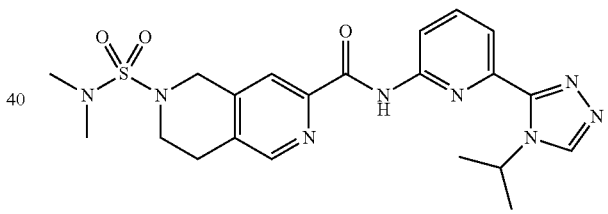

Representative procedure for sulfonyl urea formation.

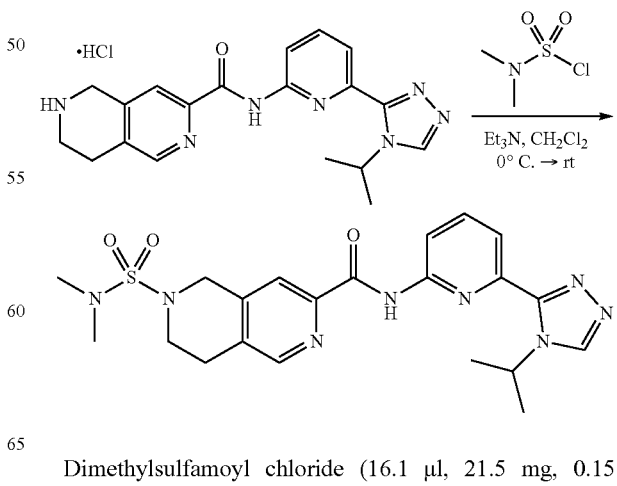

Dimethylsulfamoyl chloride (16.1 μl, 21.5 mg, 0.15 mmol) was added dropwise to a solution of N-(6-(4-isopropyl-4H-1,2,4-triazol-3-yl)pyridin-2-yl)-5,6,7,8-tetrahydro-2,6-naphthyridine-3-carboxamide hydrochloride (40 mg, 0.10 mmol) and Et₃N (70 µL, 50 mg, 0.50 mmol) in CH₂Cl₂ (1.0 mL) at 0° C. The cold bath was removed and the reaction was stirred 1 h at rt. The reaction was quenched with sat. NaHCO₃ and diluted with CH₂Cl₂. The layers were separated and the aqueous layer was extracted with CH₂Cl₂ (2×). The combined organic layers were washed with brine, dried (MgSO₄), filtered, and concentrated under reduced pressure. The resultant yellow gum was purified by column chromatography eluting with CH₂Cl₂/MeOH (0% MeOH→8% MeOH) to afford 6-(N,N-dimethylsulfamoyl)-N-(6-(4-isopropyl-4H-1,2,4-triazol-3-yl)pyridin-2-yl)-5,6,7,8-tetrahydro-2,6-naphthyridine-3-carboxamide (6.4 mg, 0.014 mmol, 9% yield) as a pale yellow amorphous solid.

Example 3: 6-isobutyl-N-(6-(4-isopropyl-4H-1,2,4-triazol-3-yl)pyridin-2-yl)-5,6,7,8-tetrahydro-2,6-naphthyridine-3-carboxamide

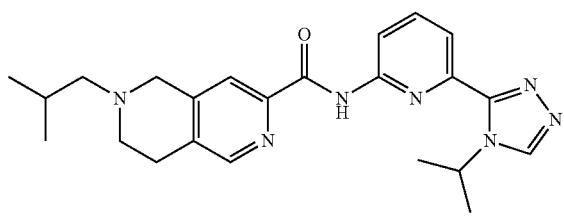 [SMILES: CC(C)CN1CCc2cnc(C(=O)Nc3cccc(-c4nncn4C(C)C)n3)cc2C1]

Representative procedure for reductive alkylation.

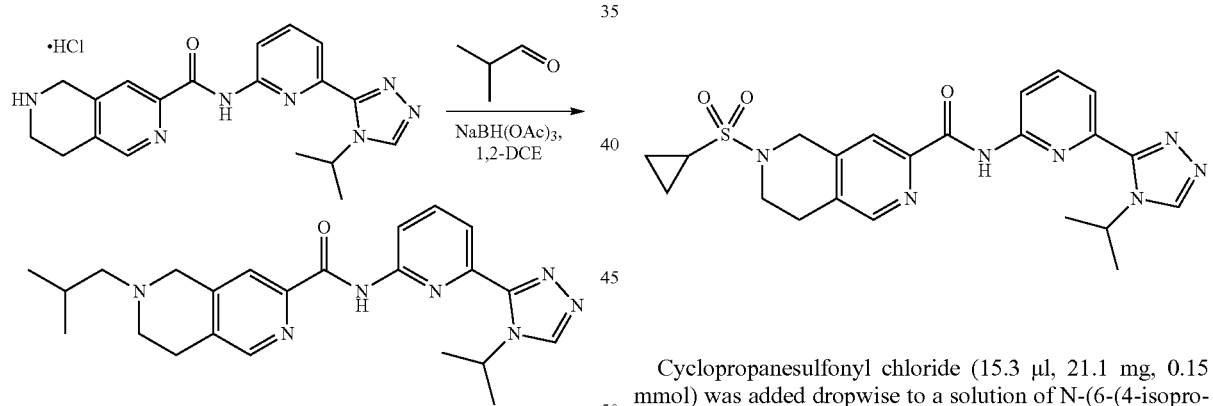

Sodium triacetoxyborohydride (106 mg, 0.50 mmol) was added to a solution of N-(6-(4-isopropyl-4H-1,2,4-triazol-3-yl)pyridin-2-yl)-5,6,7,8-tetrahydro-2,6-naphthyridine-3-carboxamide hydrochloride (40 mg, 0.10 mmol) and isobutyraldehyde (46 µL, 36 mg, 0.50 mmol) in 1,2-DCE (1.3 mL) and the reaction was stirred overnight. The reaction was quenched with sat. NaHCO₃ and diluted with CH₂Cl₂. The layers were separated and the aqueous layer was extracted with DCM (2×). The combined organic layers were dried (MgSO₄), filtered, and concentrated under reduced pressure. The resultant yellow residue was purified by column chromatography eluting with DCM/MeOH (0% MeOH→20% MeOH) to afford 6-isobutyl-N-(6-(4-isopropyl-4H-1,2,4-triazol-3-yl)pyridin-2-yl)-5,6,7,8-tetrahydro-2,6-naphthyridine-3-carboxamide (16.3 mg, 0.039 mmol, 39%) as a yellow gum.

Example 15 was prepared according to the representative procedure for reductive alkylation.

Example 13: 6-(cyclopropylsulfonyl)-N-(6-(4-isopropyl-4H-1,2,4-triazol-3-yl)pyridin-2-yl)-5,6,7,8-tetrahydro-2,6-naphthyridine-3-carboxamide

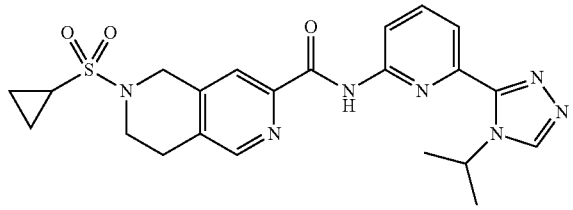 [SMILES: CC(C)n1cnnc1-c1cccc(NC(=O)c2cc3c(cn2)CCN(S(=O)(=O)C2CC2)C3)n1]

Representative procedure for sulfonamide formation.

Cyclopropanesulfonyl chloride (15.3 µl, 21.1 mg, 0.15 mmol) was added dropwise to a solution of N-(6-(4-isopropyl-4H-1,2,4-triazol-3-yl)pyridin-2-yl)-5,6,7,8-tetrahydro-2,6-naphthyridine-3-carboxamide hydrochloride (40 mg, 0.10 mmol) and Et₃N (70 µL, 50 mg, 0.50 mmol) in CH₂Cl₂ (1.0 mL) at 0° C. The cold bath was removed and the reaction was stirred 1 h at rt. The reaction was quenched with sat. NaHCO₃ and diluted with CH₂Cl₂. The layers were separated and the aqueous layer was extracted with CH₂Cl₂ (2×). The combined organic layers were washed with brine, dried (MgSO₄), filtered, and concentrated under reduced pressure. The resultant yellow gum was purified by column chromatography eluting with CH₂Cl₂/MeOH (0% MeOH→8% MeOH) to afford 6-(cyclopropylsulfonyl)-N-(6-(4-isopropyl-4H-1,2,4-triazol-3-yl)pyridin-2-yl)-5,6,7,8-tetrahydro-2,6-naphthyridine-3-carboxamide (13.1 mg, 0.028 mmol, 28% yield) as a pale yellow amorphous solid.

Example 24 was prepared according to the representative procedure for sulfonamide formation.

Example 14: N-(6-(4-isopropyl-4H-1,2,4-triazol-3-yl)pyridin-2-yl)-6-(pyrrolidine-1-carbonyl)-5,6,7,8-tetrahydro-2,6-naphthyridine-3-carboxamide

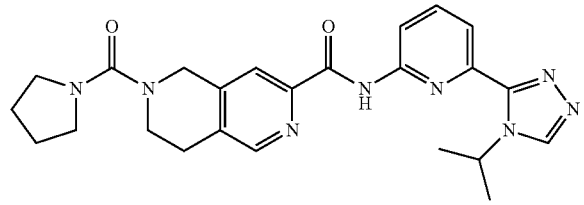 [SMILES: CC(C)n1cnnc1-c1cccc(NC(=O)c2cc3c(cn2)CCN(C(=O)N2CCCC2)C3)n1]

Representative procedure for secondary urea formation.

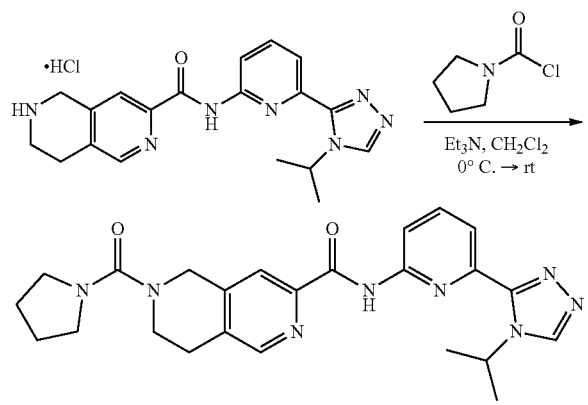

1-Pyrrolidinecarbonyl chloride (16.6 µl, 20.0 mg, 0.15 mmol) was added dropwise to a solution of N-(6-(4-isopropyl-4H-1,2,4-triazol-3-yl)pyridin-2-yl)-5,6,7,8-tetrahydro-2,6-naphthyridine-3-carboxamide hydrochloride (40 mg, 0.10 mmol) and Et₃N (70 µL, 50 mg, 0.50 mmol) in CH₂Cl₂ (1.0 mL) at 0° C. The cold bath was removed and the reaction was stirred 1 h at rt. The reaction was quenched with sat. NaHCO₃ and diluted with CH₂Cl₂. The layers were separated and the aqueous layer was extracted with CH₂Cl₂ (2×). The combined organic layers were washed with brine, dried (MgSO₄), filtered, and concentrated under reduced pressure. The resultant yellow gum was purified by column chromatography eluting with CH₂Cl₂/MeOH (0% MeOH→8% MeOH) to afford N-(6-(4-isopropyl-4H-1,2,4-triazol-3-yl)pyridin-2-yl)-6-(pyrrolidine-1-carbonyl)-5,6,7,8-tetrahydro-2,6-naphthyridine-3-carboxamide (14.2 mg, 0.031 mmol, 31% yield) as a pale yellow amorphous solid.

Example 25: 2,2,2-trifluoroethyl 7-((6-(4-isopropyl-4H-1,2,4-triazol-3-yl)pyridin-2-yl)carbamoyl)-3,4-dihydro-2,6-naphthyridine-2(1H)-carboxylate

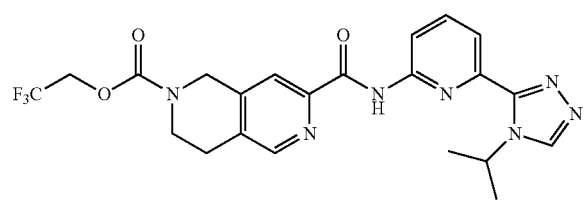 [SMILES: CC(C)n1cnnc1-c1cccc(NC(=O)c2cc3c(cn2)CCN(C(=O)OCC(F)(F)F)C3)n1]

Representative procedure for carbamate formation.

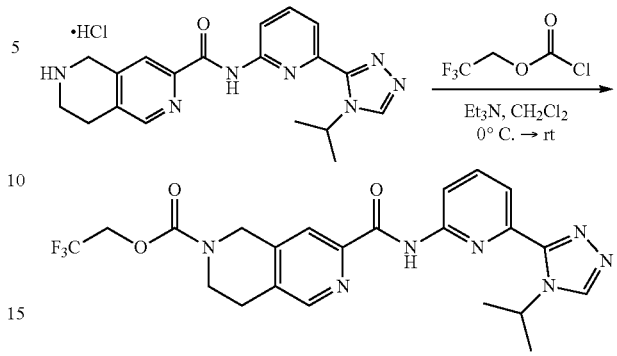

2,2,2-Trifluoroethyl carbonochloridate (98 µl, 98 mg, 0.60 mmol) was added dropwise to a solution of N-(6-(4-isopropyl-4H-1,2,4-triazol-3-yl)pyridin-2-yl)-5,6,7,8-tetrahydro-2,6-naphthyridine-3-carboxamide hydrochloride (200 mg, 0.50 mmol) and Et₃N (418 µL, 304 mg, 3.0 mmol) in CH₂Cl₂ (3.0 mL) at 0° C. The cold bath was removed and the reaction was stirred 1 h at rt. The reaction was quenched with sat. NaHCO₃ and diluted with CH₂Cl₂. The layers were separated and the aqueous layer was extracted with CH₂Cl₂ (2×). The combined organic layers were washed with brine, dried (MgSO₄), filtered, and concentrated under reduced pressure. The resultant yellow gum was purified by column chromatography eluting with hexanes/acetone (0% acetone→70% acetone) to afford 2,2,2-trifluoroethyl 7-((6-(4-isopropyl-4H-1,2,4-triazol-3-yl)pyridin-2-yl)carbamoyl)-3,4-dihydro-2,6-naphthyridine-2(1H)-carboxylate (171 mg, 0.35 mmol, 70% yield) as a white solid.

Example 16 was prepared according to the representative procedure for carbamate formation.

Example 5: tert-butyl 7-((6-(4-isopropyl-4H-1,2,4-triazol-3-yl)pyridin-2-yl)carbamoyl)-6-methoxy-3,4-dihydroisoquinoline-2(1H)-carboxylate

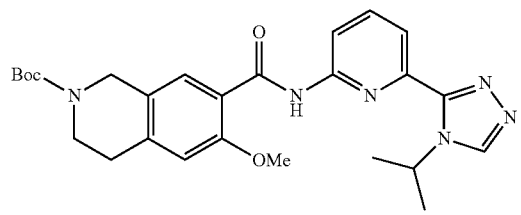 [SMILES: COc1cc2c(cc1C(=O)Nc1cccc(-c3nncn3C(C)C)n1)CN(C(=O)OC(C)(C)C)CC2]

Step 1. Synthesis of tert-butyl 7-chloro-6-methoxy-3,4-dihydroisoquinoline-2(1H)-carboxylate

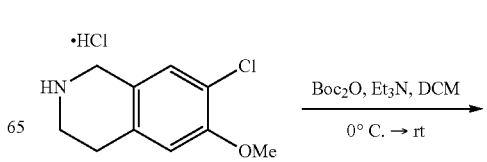

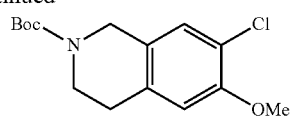

Boc-anhydride (3.57 mL, 3.36 g, 15.38 mmol) was added to a solution of 7-chloro-6-methoxy-1,2,3,4-tetrahydroisoquinoline, Hydrochloride (3.0 g, 12.81 mmol) and Et$_3$N (3.93 mL, 2.85 g, 28.2 mmol) in CH$_2$Cl$_2$ (256 mL) at 0° C. The reaction was stirred for 10 minutes at 0° C. The cold bath was removed and the reaction was stirred overnight. The reaction was quenched with H$_2$O and the layers were separated. The organic layer was washed with brine, dried (MgSO$_4$), filtered, and concentrated under reduced pressure. The resultant yellow solid was purified by column chromatography eluting with hexanes/EtOAc (0% EtOAc→20% EtOAc) to afford tert-butyl 7-chloro-6-methoxy-3,4-dihydroisoquinoline-2(1H)-carboxylate (3.5 g, 11.75 mmol, 92% yield) as a colorless solid: $^1$H NMR (400 MHz, Chloroform-d) δ 7.10 (s, 1H), 6.67 (s, 1H), 4.47 (s, 2H), 3.87 (s, 3H), 3.62 (t, J=5.9 Hz, 2H), 2.79 (t, J=5.9 Hz, 2H), 1.49 (s, 9H).

Step 2. Synthesis of tert-butyl 6-methoxy-7-vinyl-3,4-dihydroisoquinoline-2(1H)-carboxylate

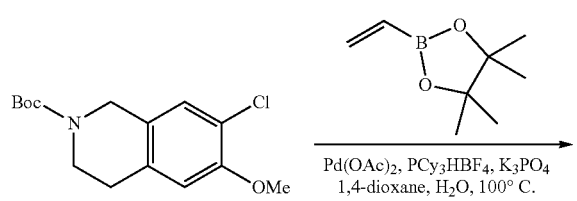

A mixture of tert-butyl 7-chloro-6-methoxy-3,4-dihydroisoquinoline-2(1H)-carboxylate (500 mg, 1.68 mmol), 4,4,5,5-tetramethyl-2-vinyl-1,3,2-dioxaborolane (0.57 mL, 0.52 g, 3.36 mmol), Pd(OAc)$_2$ (37.7 mg, 0.168 mmol), PCy$_3$HBF$_4$ (155 mg, 0.420 mmol), and K$_3$PO$_4$ (1.07 g, 5.04 mmol) in 1,4-dioxane (6.8 mL)/H$_2$O (0.17 mL) was stirred at 100° C. overnight. The reaction was quenched with H$_2$O and diluted with EtOAc. The layers were separated and the aqueous layer was extracted with EtOAc (2×). The combined organic layers were dried (MgSO$_4$), filtered, and concentrated under reduced pressure. The resultant yellow gum was purified by column chromatography eluting with hexanes/EtOAc (0% EtOAc→20% EtOAc) to afford tert-butyl 6-methoxy-7-vinyl-3,4-dihydroisoquinoline-2(1H)-carboxylate (456 mg, 1.58 mmol, 94% yield) as a pale yellow oil: $^1$H NMR (400 MHz, Chloroform-d) δ 7.19 (s, 1H), 6.99 (dd, J=17.8, 11.1 Hz, 1H), 6.62 (s, 1H), 5.70 (dd, J=17.8, 1.5 Hz, 1H), 5.23 (dd, J=11.2, 1.5 Hz, 1H), 4.51 (s, 2H), 3.82 (s, 3H), 3.63 (t, J=7.7 Hz, 2H), 2.80 (t, J=5.8 Hz, 2H), 1.49 (s, 9H).

Step 3. Synthesis of tert-butyl 7-formyl-6-methoxy-3,4-dihydroisoquinoline-2(1H)-carboxylate

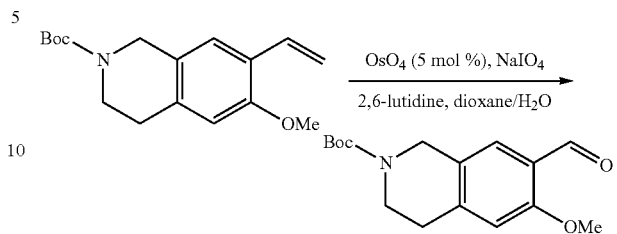

2,6-Lutidine (0.325 mL, 2.80 mmol) was added to a solution of tert-butyl 6-methoxy-7-vinyl-3,4-dihydroisoquinoline-2(1H)-carboxylate (404 mg, 1.40 mmol) in 1,4-dioxane (10.5 mL)/H$_2$O (3.5 mL). Osmium tetroxide (0.88 mL, 0.070 mmol of a 2.5 wt % solution in t-BuOH) and sodium periodate (1.19 g, 5.58 mmol) were added and the reaction was stirred for 30 min at rt. The reaction was partitioned between CH$_2$Cl$_2$ and H$_2$O and the layers were separated. The aqueous layer was extracted with CH$_2$Cl$_2$ (2×). The combined organic layers were dried (MgSO$_4$), filtered, and concentrated under reduced pressure. The resultant brown oil was purified by column chromatography eluting with hexanes/EtOAc (0% EtOAc→40% EtOAc) to afford tert-butyl 7-formyl-6-methoxy-3,4-dihydroisoquinoline-2(1H)-carboxylate (326 mg, 1.12 mmol, 80% yield) as a tan solid: $^1$H NMR (400 MHz, Chloroform-d) δ 10.41 (s, 1H), 7.58 (s, 1H), 6.74 (s, 1H), 4.53 (s, 2H), 3.91 (s, 3H), 3.64 (t, J=5.8 Hz, 2H), 2.87 (t, J=5.8 Hz, 2H), 1.49 (s, 9H).

Step 4. Synthesis of 2-(tert-butoxycarbonyl)-6-methoxy-1,2,3,4-tetrahydroisoquinoline-7-carboxylic acid

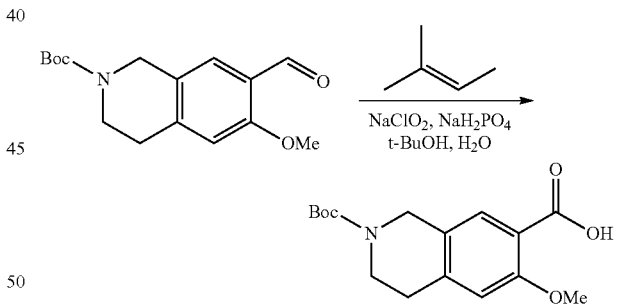

2-methylbut-2-ene (9.52 mL, 19.05 mmol of a 2.0M solution in THF) was added to a solution of tert-butyl 7-formyl-6-methoxy-3,4-dihydroisoquinoline-2(1H)-carboxylate (1.11 g, 3.81 mmol) in t-BuOH (19.1 mL). A solution of NaH$_2$PO$_4$ (2.1 g, 15.24 mmol) and sodium chlorite (2.2 g, 19.05 mmol) in H$_2$O (19.1 mL) was added and the reaction was stirred for 3 h at rt. The reaction was quenched with H$_2$O/brine and diluted with EtOAc. The layers were separated and the aqueous layer was extracted with EtOAc (2×). The combined organic layers were dried (MgSO$_4$), filtered, and concentrated under reduced pressure. The resultant clear oil was purified by column chromatography eluting with hexanes/EtOAc (0% EtOAc→90% EtOAc) to afford 2-(tert-butoxycarbonyl)-6-methoxy-1,2,3,4-tetrahydroisoquinoline-7-carboxylic acid (698 mg, 2.27 mmol, 60% yield) as a colorless amorphous solid: ¹H NMR (400 MHz, Chloroform-d) δ 7.93 (s, 1H), 6.81 (s, 1H), 4.55 (s, 2H), 4.05 (s, 3H), 3.66 (t, J=5.7 Hz, 2H), 2.88 (t, J=5.9 Hz, 2H), 1.49 (s, 9H).

Step 5. Synthesis of tert-butyl 7-((6-(4-isopropyl-4H-1,2,4-triazol-3-yl)pyridin-2-yl)carbamoyl)-6-methoxy-3,4-dihydroisoquinoline-2(1H)-carboxylate Representative procedure for amide formation with Ghosez's reagent.

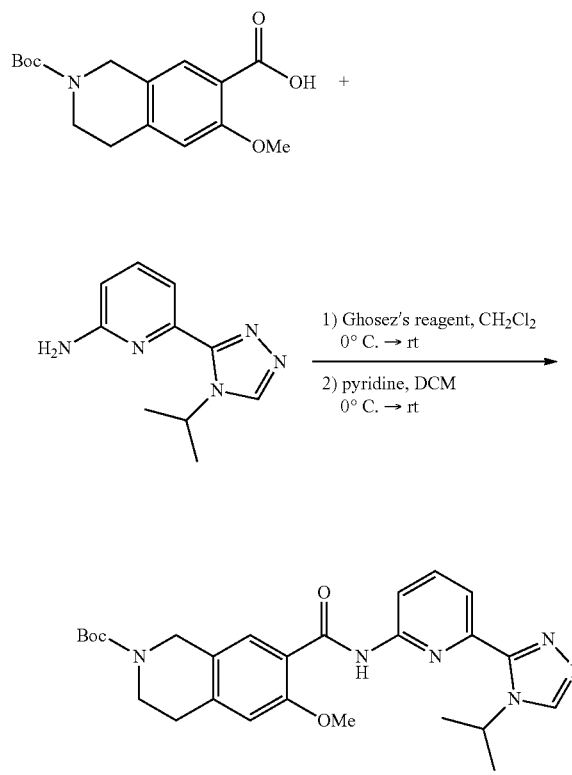

Ghosez's Reagent (0.43 mL, 3.28 mmol) was added dropwise to a solution of 2-(tert-butoxycarbonyl)-6-methoxy-1,2,3,4-tetrahydroisoquinoline-7-carboxylic acid (442 mg, 1.44 mmol) in CH₂Cl₂ (3.91 mL) at 0° C. The cold bath was removed and the reaction was stirred at rt for 1 h. The reaction was concentrated under reduced pressure and the resultant acid chloride was dissolved in CH₂Cl₂ (3.91 mL) and cooled to 0° C. 6-(4-Isopropyl-4H-1,2,4-triazol-3-yl)pyridin-2-amine (278 mg, 1.37 mmol) was added, followed by pyridine (0.44 mL, 0.43 g, 5.47 mmol). The reaction was stirred overnight, slowly warming to rt. The reaction was quenched with sat. NaHCO₃ and diluted with CH₂Cl₂. The layers were separated and the organic layer was washed with H₂O and brine. The organic layer was dried (MgSO₄), filtered, and concentrated under reduced pressure. The resultant pale yellow gum was purified by column chromatography eluting with CH₂Cl₂/MeOH (0% MeOH→5% MeOH) to afford tert-butyl 7-((6-(4-isopropyl-4H-1,2,4-triazol-3-yl)pyridin-2-yl)carbamoyl)-6-methoxy-3,4-dihydroisoquinoline-2(1H)-carboxylate (403 mg, 0.82 mmol, 60% yield) as a pale yellow amorphous solid.

Example 17: ethyl 7-((6-(4-isopropyl-4H-1,2,4-triazol-3-yl)pyridin-2-yl)carbamoyl)-6-methoxy-3,4-dihydroisoquinoline-2(1H)-carboxylate

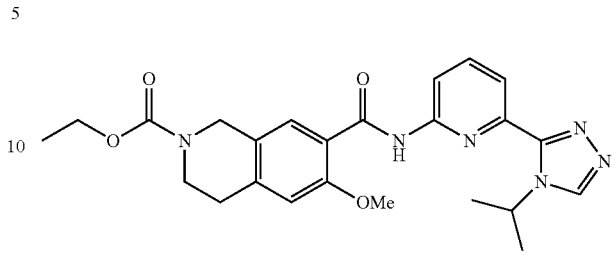

Example 17 was prepared from N-(6-(4-isopropyl-4H-1,2,4-triazol-3-yl)pyridin-2-yl)-6-methoxy-1,2,3,4-tetrahydroisoquinoline-7-carboxamide hydrochloride according to the representative procedure for carbamate formation. N-(6-(4-isopropyl-4H-1,2,4-triazol-3-yl)pyridin-2-yl)-6-methoxy-1,2,3,4-tetrahydroisoquinoline-7-carboxamide hydrochloride was synthesized from tert-butyl 7-((6-(4-isopropyl-4H-1,2,4-triazol-3-yl)pyridin-2-yl)carbamoyl)-6-methoxy-3,4-dihydroisoquinoline-2(1H)-carboxylate according to the representative procedure for Boc deprotection.

Examples 6 and 18 were prepared from N-(6-(4-isopropyl-4H-1,2,4-triazol-3-yl)pyridin-2-yl)-6-methoxy-1,2,3,4-tetrahydroisoquinoline-7-carboxamide hydrochloride according to the representative procedure for carbamate formation.

Examples 7 and 8 were prepared from N-(6-(4-isopropyl-4H-1,2,4-triazol-3-yl)pyridin-2-yl)-6-methoxy-1,2,3,4-tetrahydroisoquinoline-7-carboxamide hydrochloride according to the representative procedure for sulfonamide formation.

Examples 9 and 20 were prepared from N-(6-(4-isopropyl-4H-1,2,4-triazol-3-yl)pyridin-2-yl)-6-methoxy-1,2,3,4-tetrahydroisoquinoline-7-carboxamide hydrochloride according to the representative procedure for reductive alkylation.

Examples 11 and 22 were prepared from N-(6-(4-isopropyl-4H-1,2,4-triazol-3-yl)pyridin-2-yl)-6-methoxy-1,2,3,4-tetrahydroisoquinoline-7-carboxamide hydrochloride according to the representative procedure for amide formation.

Example 23 was prepared from N-(6-(4-isopropyl-4H-1,2,4-triazol-3-yl)pyridin-2-yl)-6-methoxy-1,2,3,4-tetrahydroisoquinoline-7-carboxamide hydrochloride according to the representative procedure for secondary urea formation.

Example 19: N2-ethyl-N7-(6-(4-isopropyl-4H-1,2,4-triazol-3-yl)pyridin-2-yl)-6-methoxy-3,4-dihydroisoquinoline-2,7(1H)-dicarboxamide

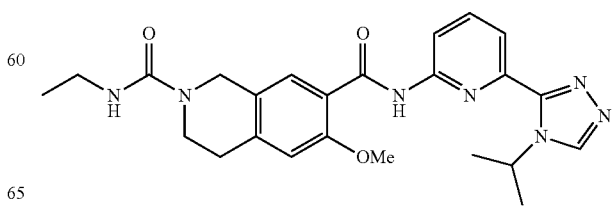

Representative procedure for primary urea formation.

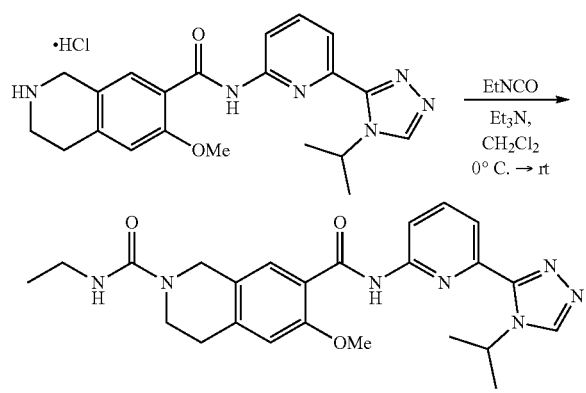

Ethyl isocyanate (14 μL, 12.8 mg, 0.18 mmol) was added dropwise to a solution of N-(6-(4-isopropyl-4H-1,2,4-triazol-3-yl)pyridin-2-yl)-6-methoxy-1,2,3,4-tetrahydroisoquinoline-7-carboxamide hydrochloride (50 mg, 0.12 mmol) and Et$_3$N (67 μL, 48.6 mg, 0.48 mmol) in CH$_2$Cl$_2$ (1.2 mL) at 0° C. The cold bath was removed and the reaction was stirred 1 h at rt. The reaction was quenched with sat. NaHCO$_3$ and diluted with CH$_2$Cl$_2$. The layers were separated and the aqueous layer was extracted with CH$_2$Cl$_2$ (2×). The combined organic layers were washed with brine, dried (MgSO$_4$), filtered, and concentrated under reduced pressure. The resultant yellow gum was purified by column chromatography eluting with CH$_2$Cl$_2$/MeOH (0% MeOH→5% MeOH) to afford N2-ethyl-N7-(6-(4-isopropyl-4H-1,2,4-triazol-3-yl)pyridin-2-yl)-6-methoxy-3,4-dihydroisoquinoline-2,7(1H)-dicarboxamide (11.5 mg, 0.025 mmol, 21% yield) as a colorless solid.

Example 10: tert-butyl 6-fluoro-7-((6-(4-isopropyl-4H-1,2,4-triazol-3-yl)pyridin-2-yl)carbamoyl)-3,4-dihydroisoquinoline-2(1H)-carboxylate

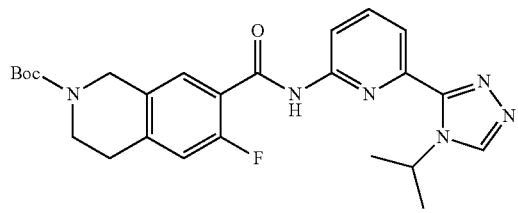 [SMILES: CC(C)n1cnnc1-c1cccc(NC(=O)c2cc3c(cc2F)CCN(C(=O)OC(C)(C)C)C3)n1]

Step 1. Synthesis of 7-bromo-6-fluoro-1,2,3,4-tetrahydroisoquinoline

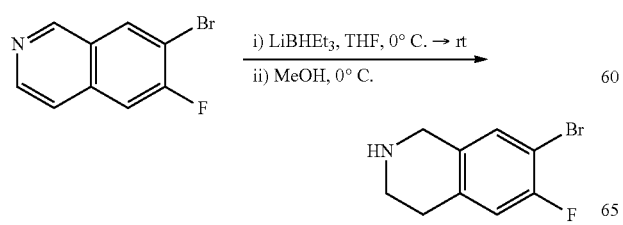

Lithium triethylborohydride (74.0 mL, 74.0 mmol of a 1.0M solution in THF) was added dropwise to a solution of 7-bromo-6-fluoroisoquinoline (7.6 g, 33.6 mmol) in THF (210 mL) at 0° C. The cold bath was removed, and the reaction was stirred at rt overnight. The reaction was cooled to 0° C. and quenched dropwise with MeOH until gas evolution ceased. The mixture was diluted with 1M HCl and MTBE. The layers were separated and the organic layer was extracted with 1M HCl (2×). The combined aqueous layers were washed with MTBE (3×). The aqueous layer was made basic (pH 14) with 50% NaOH, then extracted (5×100 mL) with DCM. The combined organic layers were dried (Na$_2$SO$_4$), filtered, and concentrated under reduced pressure to afford crude 7-bromo-6-fluoro-1,2,3,4-tetrahydroisoquinoline (6.4 g) as a yellow oil: $^1$H NMR (400 MHz, Chloroform-d) δ 7.18 (d, J=6.9 Hz, 1H), 6.85 (d, J=9.3 Hz, 1H), 3.94 (s, 2H), 3.10 (t, J=6.1 Hz, 2H), 2.73 (t, J=6.0 Hz, 2H).

Step 2. Synthesis of tert-butyl 7-bromo-6-fluoro-3,4-dihydroisoquinoline-2(1H-carboxylate

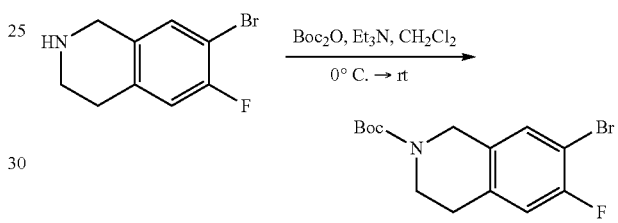

Boc-anhydride (7.75 ml, 33.4 mmol) was added to a solution of crude 7-bromo-6-fluoro-1,2,3,4-tetrahydroisoquinoline (6.4 g, 27.8 mmol) and Et$_3$N (4.65 ml, 33.4 mmol) in CH$_2$Cl$_2$ (556 ml) at 0° C. The reaction was stirred for 10 minutes at 0° C. The cold bath removed and the reaction stirred for 1 h at rt. The reaction was quenched with H$_2$O and the layers were separated. The organic layer was washed with brine, dried (MgSO$_4$), filtered, and concentrated under reduced pressure. The resultant yellow oil was purified by column chromatography eluting with hexanes/EtOAc (0% EtOAc→15% EtOAc) to afford tert-butyl 7-bromo-6-fluoro-3,4-dihydroisoquinoline-2(1H)-carboxylate (6.4 g, 19.38 mmol, 58% yield over 2 steps) as a colorless solid: $^1$H NMR (400 MHz, Chloroform-d) δ 7.28 (d, J=6.8 Hz, 1H), 6.90 (d, J=9.0 Hz, 1H), 4.51 (s, 2H), 3.62 (t, J=5.8 Hz, 2H), 2.77 (t, J=6.0 Hz, 2H), 1.48 (s, 9H).

Step 3. Synthesis of 2-(tert-butyl) 7-ethyl 6-fluoro-3,4-dihydroisoquinoline-2,7(1H)-dicarboxylate

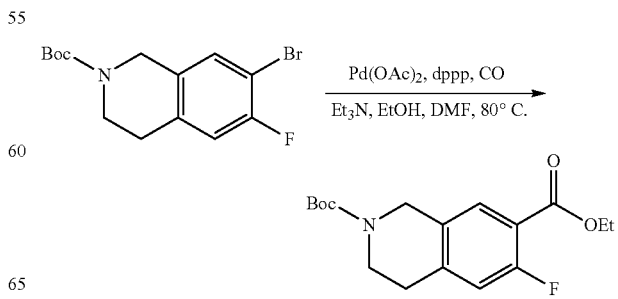

A mixture of tert-butyl 7-bromo-6-fluoro-3,4-dihydroisoquinoline-2(1H)-carboxylate (6.4 g, 19.4 mmol), Pd(OAc)$_2$ (0.435 g, 1.94 mmol), 1,3-bis(diphenylphosphino)propane (1.6 g, 3.88 mmol), and Et$_3$N (8.10 mL, 5.88 g, 58.1 mmol) in DMF (52.7 mL)/EtOH (26.4 mL) were stirred under a balloon of CO at 80° C. for 24 h. The reaction was cooled to rt, quenched with H$_2$O/brine, and diluted with EtOAc. The layers were separated and the organic layer was washed with H$_2$O/brine (2×). The organic layer was dried (MgSO$_4$), filtered, and concentrated under reduced pressure. The resultant brown gum was purified by column chromatography eluting with hexanes/EtOAc (0% EtOAc→20% EtOAc) to afford 2-(tert-butyl) 7-ethyl 6-fluoro-3,4-dihydroisoquinoline-2,7(1H)-dicarboxylate (4.5 g, 13.92 mmol, 72% yield) as a colorless solid: $^1$H NMR (400 MHz, Chloroform-d) δ 7.68 (d, J=7.1 Hz, 1H), 6.91 (d, J=11.1 Hz, 1H), 4.56 (s, 2H), 4.38 (q, J=7.1 Hz, 2H), 3.64 (t, J=5.9 Hz, 2H), 2.85 (t, J=5.9 Hz, 2H), 1.49 (s, 9H), 1.39 (t, J=7.1 Hz, 3H).

Step 4. Example 10 was prepared from 2-(tert-butyl) 7-ethyl 6-fluoro-3,4-dihydroisoquinoline-2,7(1H)-dicarboxylate and 6-(4-isopropyl-4H-1,2,4-triazol-3-yl)pyridin-2-amine according to the representative procedure for amide formation with trimethylaluminum with the following modifications: The reaction was performed at 80° C. using PhMe as the solvent.

Example 21: 2,2,2-trifluoroethyl 6-fluoro-7-((6-(4-isopropyl-4H-1,2,4-triazol-3-yl)pyridin-2-yl)carbamoyl)-3,4-dihydroisoquinoline-2(1H)-carboxylate

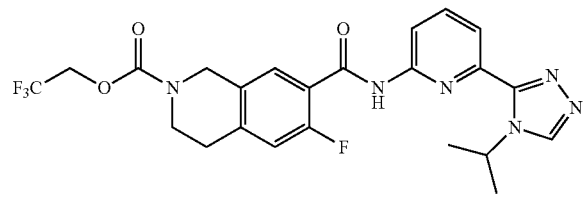 [SMILES: CC(C)n1cnnc1-c1cccc(NC(=O)c2cc3c(cc2F)CCN(C(=O)OCC(F)(F)F)C3)n1]

Example 21 was prepared from 6-fluoro-N-(6-(4-isopropyl-4H-1,2,4-triazol-3-yl)pyridin-2-yl)-1,2,3,4-tetrahydroisoquinoline-7-carboxamide hydrochloride according to the representative procedure for carbamate formation, and 6-fluoro-N-(6-(4-isopropyl-4H-1,2,4-triazol-3-yl)pyridin-2-yl)-1,2,3,4-tetrahydroisoquinoline-7-carboxamide hydrochloride was synthesized from tert-butyl 6-fluoro-7-((6-(4-isopropyl-4H-1,2,4-triazol-3-yl)pyridin-2-yl)carbamoyl)-3,4-dihydroisoquinoline-2(1H)-carboxylate according to the representative procedure for Boc deprotection.

Example 12: 6-fluoro-N-(6-(4-isopropyl-4H-1,2,4-triazol-3-yl)pyridin-2-yl)-2-(pyrimidin-2-yl)-1,2,3,4-tetrahydroisoquinoline-7-carboxamide

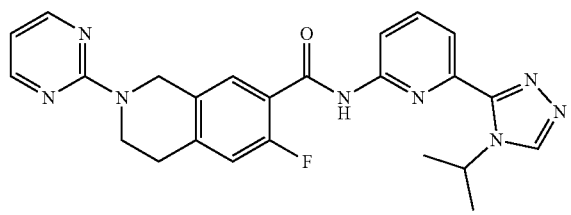

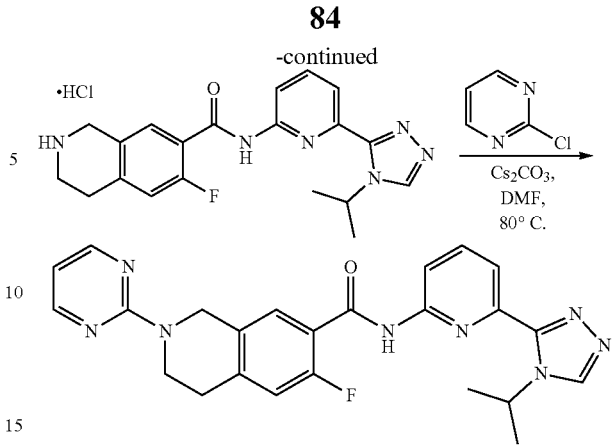

A mixture of 6-fluoro-N-(6-(4-isopropyl-4H-1,2,4-triazol-3-yl)pyridin-2-yl)-1,2,3,4-tetrahydroisoquinoline-7-carboxamide hydrochloride (10.7 mg, 0.026 mmol), 2-chloropyrimidine (3.53 mg, 0.031 mmol), and Cs$_2$CO$_3$ (18.40 mg, 0.056 mmol) in DMF (0.32 mL) was heated at 80° C. for 20 h. The reaction was quenched with sat. NaHCO$_3$ and diluted with CH$_2$Cl$_2$. The layers were separated and the aqueous layer was extracted with CH$_2$Cl$_2$ (2×). The combined organic layers were washed with water and brine, dried (MgSO$_4$), filtered, and concentrated under reduced pressure. The resultant yellow solid was purified by column chromatography eluting with CH$_2$Cl$_2$/MeOH (0% MeOH→5% MeOH) to afford 6-fluoro-N-(6-(4-isopropyl-4H-1,2,4-triazol-3-yl)pyridin-2-yl)-2-(pyrimidin-2-yl)-1,2,3,4-tetrahydroisoquinoline-7-carboxamide (5.5 mg, 0.012 mmol, 47% yield) as a pale yellow residue.

Example 26: benzyl 7-((6-(1-isopropyl-1H-tetrazol-5-yl)pyridin-2-yl)carbamoyl)-6-methoxy-3,4-dihydroisoquinoline-2(1H)-carboxylate

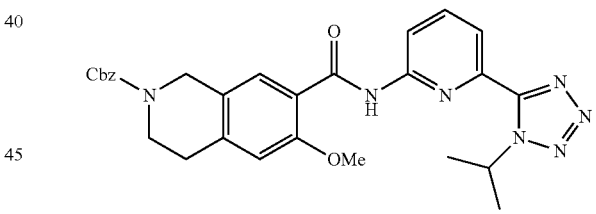

Step 1. Synthesis of N-isopropyl-6-nitropicolinamide

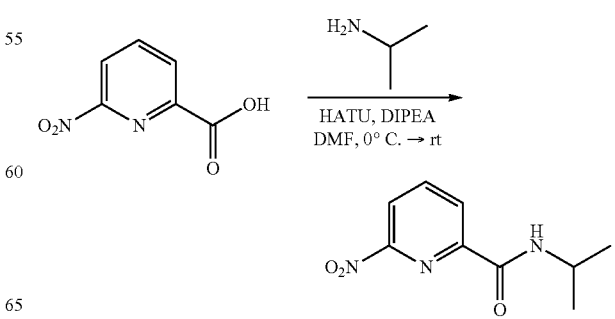

To a solution of 6-nitropicolinic acid (10 g, 59.5 mmol) and Hunig's base (31.1 mL, 178 mmol, 3 eq) in dry DMF (200 mL) at 0° C. was added isopropylamine (6.64 mL, 77 mmol, 1.3 eq) followed by HATU (29.4 g, 77 mmol, 1.3 eq). The resulting mixture was allowed to warm to rt and stirred until the starting material was consumed. The reaction was quenched by the addition of water (500 mL). The mixture was extracted with EtOAc (3×200 mL) and the combined organic layers were washed with $H_2O$ (2×200 mL), brine (200 mL), dried ($Na_2SO_4$) and concentrated under reduced pressure. The resultant residue was purified by $SiO_2$ column chromatography (100% hexanes to 40% EtOAc/Hexanes) to afford N-isopropyl-6-nitropicolinamide (10.81 g, 87% yield) as a light yellow solid: $^1$H NMR (400 MHz, Chloroform-d) δ 8.58 (dd, J=7.7, 1.0 Hz, 1H), 8.36 (dd, J=8.0, 1.0 Hz, 1H), 8.21 (t, J=7.8 Hz, 1H), 7.70 (s, 1H), 4.31 (hept, J=6.6 Hz, 1H), 1.32 (d, J=6.6 Hz, 6H).

Step 2. Synthesis of
2-(1-isopropyl-1H-tetrazol-5-yl)-6-nitropyridine

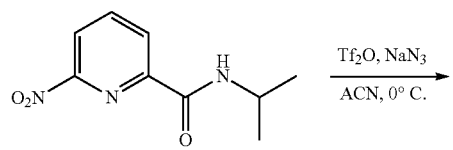

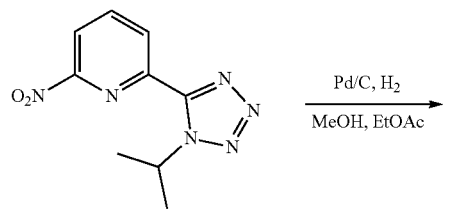

To a mixture of N-isopropyl-6-nitropicolinamide (350 mg, 1.67 mmol) and sodium azide (120 mg, 1.84 mmol) in anhydrous acetonitrile (5.58 mL) under $N_2$ at 0° C. behind a blast shield was added dropwise trifluoromethanesulfonic anhydride (1M solution in DCM, 1.84 mL, 1.84 mmol). The resulting mixture was stirred at 0° C. for 1 h and then rt for 2 hrs. The reaction was then cooled to 0° C. and quenched with sat. $NaHCO_3$ (50 mL). The mixture was extracted with EtOAc (2×). The combined organic layers were washed with sat. $NaHCO_3$ and brine, and concentrated under reduced pressure. The resultant dark red solid was purified by $SiO_2$ chromatography (100% hexanes to 35% EtOAc/Hexanes) to give 2-(1-isopropyl-1H-tetrazol-5-yl)-6-nitropyridine (170 mg, 43% yield) as a colorless solid: $^1$H NMR (400 MHz, Chloroform-d) δ 8.74 (dd, J=7.7, 0.9 Hz, 1H), 8.41 (dd, J=8.1, 0.9 Hz, 1H), 8.32 (t, J=7.9 Hz, 1H), 5.95 (hept, J=6.7 Hz, 1H), 1.72 (d, J=6.7 Hz, 6H).

Step 3. Synthesis of
6-(1-isopropyl-1H-tetrazol-5-yl)pyridin-2-amine

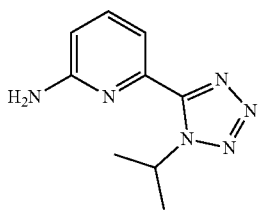

A mixture of 2-(1-isopropyl-1H-tetrazol-5-yl)-6-nitropyridine (100 mg, 0.427 mmol) and Pd/C (10% Pd on dry base, contained 50% water, 23 mg, 0.025 eq) in MeOH (1 mL)/EtOAc (1 mL) was stirred at rt under $H_2$ balloon of $H_2$ overnight. The reaction was filtered and the filtrate was concentrated under reduced pressure to provide 6-(1-isopropyl-1H-tetrazol-5-yl)pyridin-2-amine (85 mg, 97% yield), which was used without further purification. LC-MS, ES$^+$: m/z 163.05 [M+H]$^+$, $^1$H NMR (400 MHz, Chloroform-d) δ 7.72-7.54 (m, 2H), 6.63 (dd, J=7.4, 1.7 Hz, 1H), 5.85 (hept, J=6.7 Hz, 1H), 4.57 (s, 2H), 1.65 (d, J=6.7 Hz, 6H).

Step 4. Synthesis of benzyl 7-chloro-6-methoxy-3,4-dihydroisoquinoline-2(1H)-carboxylate

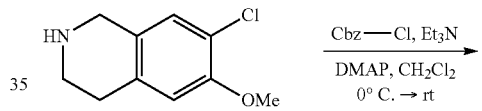

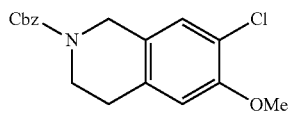

Benzyl chloroformate (1.8 mL, 12.81 mmol) was added dropwise to a solution of a mixture of 7-chloro-6-methoxy-1,2,3,4-tetrahydroisoquinoline, Hydrochloride (2.0 g, 8.54 mmol), $Et_3N$ (3.9 mL, 28.2 mmol), and DMAP (0.104 g, 0.854 mmol) in $CH_2Cl_2$ (17.1 mL) at 0° C. The reaction was stirred overnight, warming slowly to room temperature. The reaction was quenched with sat. $NaHCO_3$ and diluted with $CH_2Cl_2$. The layers were separated and the aqueous layer was extracted with $CH_2Cl_2$ (2×). The combined organic layers were washed with brine, dried ($MgSO_4$), filtered, and concentrated under reduced pressure. The resultant yellow oil was purified by column chromatography eluting with hexanes/EtOAc (0% EtOAc→25% EtOAc) to give benzyl 7-chloro-6-methoxy-3,4-dihydroisoquinoline-2(1H)-carboxylate (2.47 g, 7.44 mmol, 87% yield) as a colorless oil: $^1$H NMR (400 MHz, Chloroform-d) δ 7.41-7.30 (comp, 5H), 7.10 (d, J=11.9 Hz, 1H), 6.68 (s, 1H), 5.18 (s, 2H), 4.55 (s, 2H), 3.87 (s, 3H), 3.71 (br s, 2H), 2.81 (br s, 2H).

Step 5. Synthesis of benzyl 6-methoxy-7-vinyl-3,4-dihydroisoquinoline-2(1H)-carboxylate

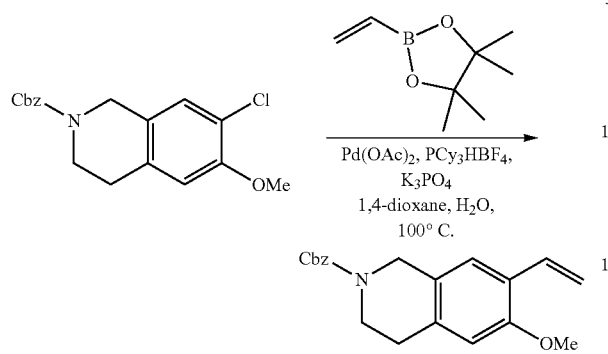

A mixture of benzyl 7-chloro-6-methoxy-3,4-dihydroisoquinoline-2(1H)-carboxylate (2.0 g, 6.03 mmol), 4,4,5,5-tetramethyl-2-vinyl-1,3,2-dioxaborolane (2.0 mL, 1.86 g, 12.06 mmol), Pd(OAc)$_2$ (135 mg, 0.603 mmol), PCy$_3$HBF$_4$ (555 mg, 1.51 mmol), and K$_3$PO$_4$ (3.84 g, 18.08 mmol) in 1,4-dioxane (24.5 mL)/H$_2$O (0.61 mL) was stirred at 100° C. overnight. The reaction was quenched with H$_2$O and diluted with EtOAc. The layers were separated and the aqueous layer was extracted with EtOAc (2×). The combined organic layers were dried (MgSO$_4$), filtered, and concentrated under reduced pressure. The resultant yellow gum was purified by column chromatography eluting with hexanes/EtOAc (0% EtOAc→20% EtOAc) to afford benzyl 6-methoxy-7-vinyl-3,4-dihydroisoquinoline-2(1H)-carboxylate (1.8 g) as a yellow oil. The material was still impure, and thus was moved to the next reaction without further purification and a yield was recorded over two steps.

Step 6. Synthesis of benzyl 7-formyl-6-methoxy-3,4-dihydroisoquinoline-2(1H)-carboxylate

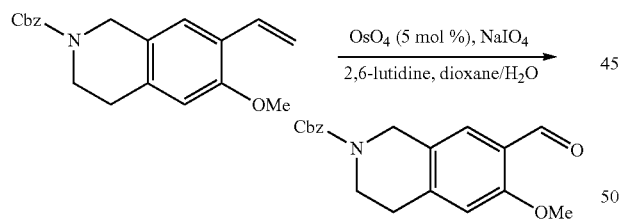

2,6-Lutidine (1.3 mL, 1.2 g, 11.13 mmol) was added to a solution of benzyl 6-methoxy-7-vinyl-3,4-dihydroisoquinoline-2(1H)-carboxylate (1.8 g, 5.57 mmol) in 1,4-dioxane (41.7 mL)/H$_2$O (13.9 mL). Osmium tetroxide (3.5 mL, 0.28 mmol of a 2.5 wt % solution in t-BuOH) and sodium periodate (4.8 g, 22.3 mmol) were added and the reaction was stirred for 4 h at rt. The reaction was partitioned between CH$_2$Cl$_2$ and H$_2$O and the layers were separated. The aqueous layer was extracted with CH$_2$Cl$_2$ (2×). The combined organic layers were dried (MgSO$_4$), filtered, and concentrated under reduced pressure. The resultant brown oil was purified by column chromatography eluting with hexanes/EtOAc (0% EtOAc→40% EtOAc) to afford benzyl 7-formyl-6-methoxy-3,4-dihydroisoquinoline-2(1H)-carboxylate (1.04 g, 3.20 mmol, 53% yield over 2 steps) as a yellow solid: $^1$H NMR (400 MHz, Chloroform-d) δ 10.40 (s, 1H), 7.57 (br s, 1H), 7.41-7.29 (comp, 5H), 6.74 (s, 1H), 5.18 (s, 2H), 4.62 (s, 2H), 3.91 (s, 3H), 3.72 (t, J=5.7 Hz, 2H), 2.89 (br s, 2H).

Step 7. Synthesis of 2-((benzyloxy)carbonyl)-6-methoxy-1,2,3,4-tetrahydroisoquinoline-7-carboxylic acid

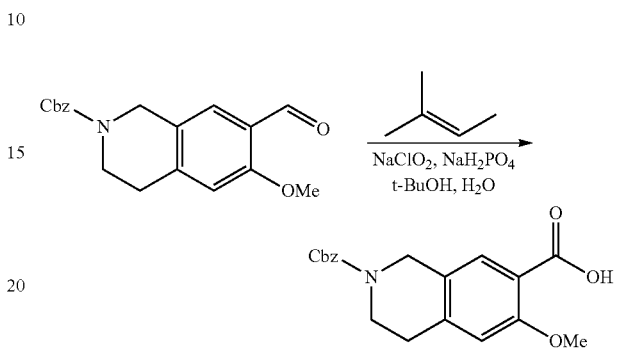

2-methylbut-2-ene (8.0 mL, 16.0 mmol of a 2.0M solution in THF) was added to a solution of benzyl 7-formyl-6-methoxy-3,4-dihydroisoquinoline-2(1H)-carboxylate (1.04 g, 3.20 mmol) in t-BuOH (16.0 mL). A solution of NaH$_2$PO$_4$ (1.8 g, 12.8 mmol) and sodium chlorite (1.8 g, 16.0 mmol) in H$_2$O (16.0 mL) was added and the reaction was stirred for 4 h at rt. The reaction was quenched with H$_2$O/brine and diluted with EtOAc. The layers were separated and the aqueous layer was extracted with EtOAc (2×). The combined organic layers were dried (MgSO$_4$), filtered, and concentrated under reduced pressure. The resultant clear oil was purified by column chromatography eluting with hexanes/EtOAc (0% EtOAc→85% EtOAc) to afford 2-((benzyloxy)carbonyl)-6-methoxy-1,2,3,4-tetrahydroisoquinoline-7-carboxylic acid (730 mg, 2.14 mmol, 67% yield) as a colorless amorphous solid: $^1$H NMR (500 MHz, Chloroform-d) δ 10.62 (br s, 1H), 7.93 (s, 1H), 7.40-7.30 (comp, 5H), 6.81 (s, 1H), 5.18 (s, 2H), 4.64 (s, 2H), 4.05 (s, 3H), 3.73 (t, J=6.1 Hz, 2H), 2.90 (br s, 2H).

Step 8. Example 26 was prepared from 2-((benzyloxy)carbonyl)-6-methoxy-1,2,3,4-tetrahydroisoquinoline-7-carboxylic acid and 6-(1-isopropyl-1H-tetrazol-5-yl)pyridin-2-amine according to the representative procedure for amide formation with Ghosez's reagent.

Example 27: Synthesis of isopropyl 7-((6-(1-isopropyl-1H-tetrazol-5-yl)pyridin-2-yl)carbamoyl)-6-methoxy-3,4-dihydroisoquinoline-2(1H)-carboxylate

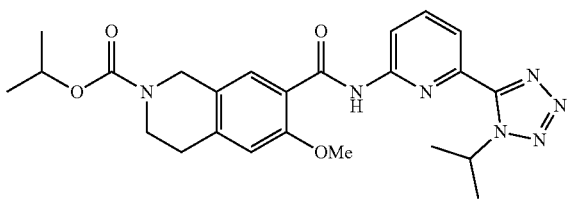

Step 1. Synthesis of N-(6-(1-isopropyl-1H-tetrazol-5-yl)pyridin-2-yl)-6-methoxy-1,2,3,4-tetrahydroisoquinoline-7-carboxamide

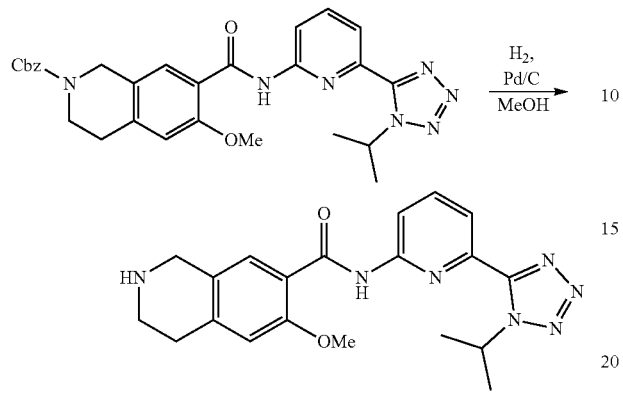

Pd—C (50 mg, 10% loading) was added to a solution of benzyl 7-(((6-(1-isopropyl-1H-tetrazol-5-yl)pyridin-2-yl)carbamoyl)-6-methoxy-3,4-dihydroisoquinoline-2(1H)-carboxylate (271 mg, 0.514 mmol) in MeOH (10.3 mL). The reaction was evacuated and backfilled with $H_2$ (3×) and the reaction was stirred overnight under a balloon of $H_2$. The reaction was filtered through Celite, rinsing with MeOH, EtOAc, and DCM and concentrated under reduced pressure. The resultant clear residue was dissolved in DCM/EtOAc and filtered through Celite, rinsing with DCM and EtOAc. The filtrate was concentrated under reduced pressure to afford N-(6-(1-isopropyl-1H-tetrazol-5-yl)pyridin-2-yl)-6-methoxy-1,2,3,4-tetrahydroisoquinoline-7-carboxamide (171 mg, 0.44 mmol, 85% yield) as a yellow solid: LC-MS, ES+: m/z 394.24 [M+H]+; 1H NMR (400 MHz, Chloroform-d) δ 10.54 (s, 1H), 8.58 (dd, J=8.3, 1.1 Hz, 1H), 8.15-7.87 (comp, 3H), 6.78 (s, 1H), 5.78 (p, J=6.7 Hz, 1H), 4.06-4.01 (comp, 5H), 3.16 (t, J=5.9 Hz, 2H), 2.87 (t, J=6.0 Hz, 2H), 1.75 (d, J=6.7 Hz, 6H).

Step 2. Example 27 was prepared from N-(6-(1-isopropyl-1H-tetrazol-5-yl)pyridin-2-yl)-6-methoxy-1,2,3,4-tetrahydroisoquinoline-7-carboxamide according to the representative procedure for carbamate formation Examples 32 and 33 were prepared from N-(6-(1-isopropyl-1H-tetrazol-5-yl)pyridin-2-yl)-6-methoxy-1,2,3,4-tetrahydroisoquinoline-7-carboxamide according to the representative procedure for carbamate formation.
Examples 28 and 34 were prepared from N-(6-(1-isopropyl-1H-tetrazol-5-yl)pyridin-2-yl)-6-methoxy-1,2,3,4-tetrahydroisoquinoline-7-carboxamide according to the representative procedure for sulfonamide formation.
Examples 29 and 35 were prepared from N-(6-(1-isopropyl-1H-tetrazol-5-yl)pyridin-2-yl)-6-methoxy-1,2,3,4-tetrahydroisoquinoline-7-carboxamide according to the representative procedure for amide formation.
Example 30 was prepared from N-(6-(1-isopropyl-1H-tetrazol-5-yl)pyridin-2-yl)-6-methoxy-1,2,3,4-tetrahydroisoquinoline-7-carboxamide according to the representative procedure for primary urea formation.
Example 36 was prepared from N-(6-(1-isopropyl-1H-tetrazol-5-yl)pyridin-2-yl)-6-methoxy-1,2,3,4-tetrahydroisoquinoline-7-carboxamide according to the representative procedure for secondary urea formation.
Examples 31 and 37 were prepared from N-(6-(1-isopropyl-1H-tetrazol-5-yl)pyridin-2-yl)-6-methoxy-1,2,3,4-tetrahydroisoquinoline-7-carboxamide according to the representative procedure for reductive alkylation.

Example 76: Synthesis of benzyl (R)-7-((6-(1-(1-hydroxypropan-2-yl)-1H-tetrazol-5-yl)pyridin-2-yl)carbamoyl)-6-methoxy-3,4-dihydroisoquinoline-2(1H)-carboxylate

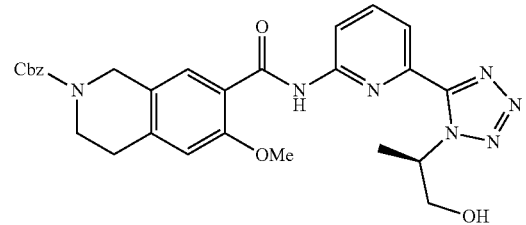

Step 1. Synthesis of (R)-1-acetoxypropan-2-ammonium 2,2,2-trifluoroacetate

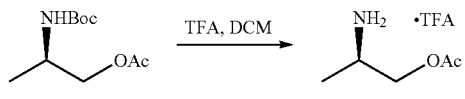

TFA (3.2 mL) was added to a solution of (R)-2-((tert-butoxycarbonyl)amino)propyl acetate (992 mg, 4.57 mmol) in DCM (6.5 mL) and the reaction was stirred for 3.5 hrs. The reaction was concentrated under reduced pressure at 45° C. until TFA was removed. Dried oil under vacuum 40° C. give crude (R)-1-acetoxypropan-2-ammonium 2,2,2-trifluoroacetate as a clear oil that was used without purification: 1H NMR (400 MHz, DMSO-d6) δ 4.12 (dd, J=11.8, 4.1 Hz, 1H), 4.02 (dd, J=11.8, 7.1 Hz, 1H), 3.55-3.41 (m, 1H), 2.06 (s, 3H), 1.18 (d, J=6.7 Hz, 3H).

Step 2. Synthesis of (R)-2-(6-nitropicolinamido)propyl acetate

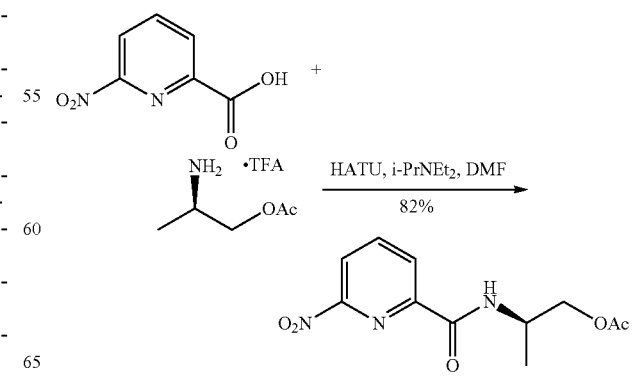

Hunig's base (3.1 mL, 17.6 mmol), a solution of (R)-1-acetoxypropan-2-ammonium 2,2,2-trifluoroacetate (1.1 g, 4.57 mmol) in DMF (5 mL), and HATU (2.0 g, 5.28 mmol) was added to a solution of 6-nitropicolinic acid (592 mg, 3.52 mmol) in DMF (6.73 mL) and the reaction was stirred overnight. The reaction was quenched with H₂O and diluted with EtOAc. The layers were separated and the aqueous layer was extracted with EtOAc (2×). The combined organic layers were washed with water (1×), brine (2×), dried (MgSO₄), filtered, and concentrated under reduced pressure. The resultant yellow gum was purified by column chromatography eluting with hexanes/EtOAc (0% EtOAc→40% EtOAc) to give (R)-2-(6-nitropicolinamido)propyl acetate (770 mg, 2.88 mmol, 82% yield) as a yellow gum: $^1$H NMR (400 MHz, Chloroform-d) δ 8.57 (dd, J=7.7, 1.0 Hz, 1H), 8.39 (dd, J=8.1, 1.0 Hz, 1H), 8.23 (t, J=7.9 Hz, 1H), 7.92 (d, J=8.6 Hz, 1H), 4.58-4.43 (m, 1H), 4.24 (dd, J=11.3, 4.4 Hz, 1H), 4.18 (dd, J=11.3, 5.5 Hz, 1H), 2.11 (s, 3H), 1.36 (d, J=6.8 Hz, 3H).

Step 3. Synthesis of (R)-2-(5-(6-nitropyridin-2-yl)-1H-tetrazol-1-yl)propyl acetate

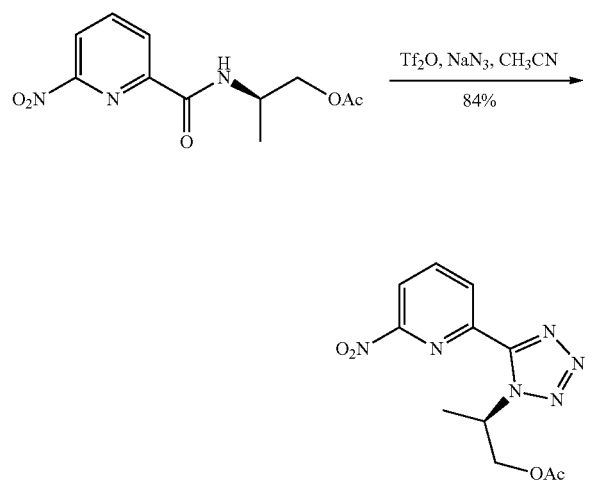

To a mixture of (R)-2-(6-nitropicolinamido)propyl acetate (765 mg, 2.86 mmol) and sodium azide (298 mg, 4.58 mmol) in acetonitrile (19.1 mL) behind a blast shield at 0° C. was added Tf₂O (4.29 mL, 4.29 mmol, 1.0M solution in DCM) dropwise, and the resulting mixture was stirred for 30 min at 0° C. The cold bath was removed, and the mixture was stirred at rt for 1 h. The reaction was quenched with sat. NaHCO₃ and diluted with EtOAc. The organic layer was separated and washed with brine, dried, filtered and concentrated under reduced pressure. The resultant residue was purified by column chromatography eluting with hexanes/EtOAc (0% EtOAc→60% EtOAc) to afford (R)-2-(5-(6-nitropyridin-2-yl)-1H-tetrazol-1-yl)propyl acetate (699 mg, 2.392 mmol, 84% yield) as a pale yellow solid: $^1$H NMR (500 MHz, Chloroform-d) δ 8.79 (dd, J=7.8, 0.9 Hz, 1H), 8.43 (dd, J=8.1, 1.0 Hz, 1H), 8.32 (dd, J=8.4, 7.4 Hz, 1H), 6.17 (pd, J=7.0, 4.5 Hz, 1H), 4.64 (dd, J=11.8, 4.6 Hz, 1H), 4.59 (dd, J=11.7, 7.5 Hz, 1H), 1.88 (d, J=1.0 Hz, 3H), 1.82 (dd, J=6.9, 1.1 Hz, 3H).

Step 4. Synthesis of (R)-2-(5-(6-aminopyridin-2-yl)-1H-tetrazol-1-yl)propyl acetate

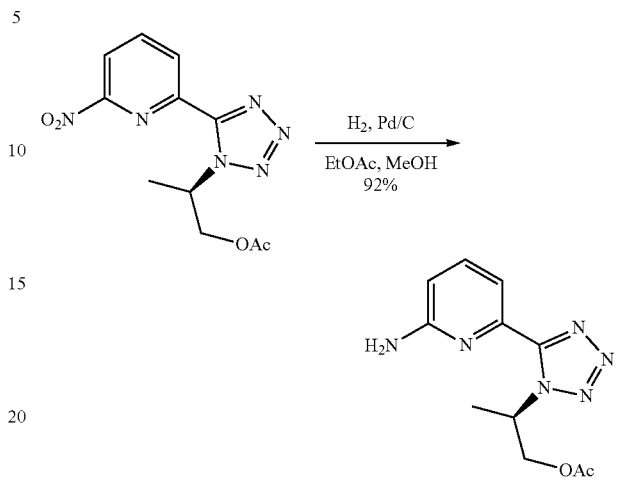

Pd—C (140 mg, 10% loading) was added to a solution of (R)-2-(5-(6-nitropyridin-2-yl)-1H-tetrazol-1-yl)propyl acetate (699 mg, 2.392 mmol) in MeOH (18.4 mL) and EtOAc (18.4 mL). The reaction was evacuated and back-filled with H₂ (3×) and the reaction was stirred under a balloon of H₂ overnight. The reaction was filtered through Celite, rinsing with DCM. The filtrate was concentrated under reduced pressure, dissolved in DCM, and filtered through Celite, rinsing with DCM. The filtrate was concentrated under reduced pressure to give (R)-2-(5-(6-amino-pyridin-2-yl)-1H-tetrazol-1-yl)propyl acetate (575 mg, 2.192 mmol, 92% yield) as a colorless gum that solidified upon standing: $^1$H NMR (500 MHz, Chloroform-d) δ 7.67-7.60 (comp, 2H), 6.66 (d, J=7.0 Hz, 1H), 6.21 (d, J=10.4 Hz, 1H), 4.67 (dd, J=11.4, 4.3 Hz, 1H), 4.30 (dd, J=11.4, 9.4 Hz, 1H), 1.84 (s, 3H), 1.70 (d, J=6.8 Hz, 3H).

Step 5. Synthesis of (R)-2-(5-(6-aminopyridin-2-yl)-1H-tetrazol-1-yl)propan-1-ol

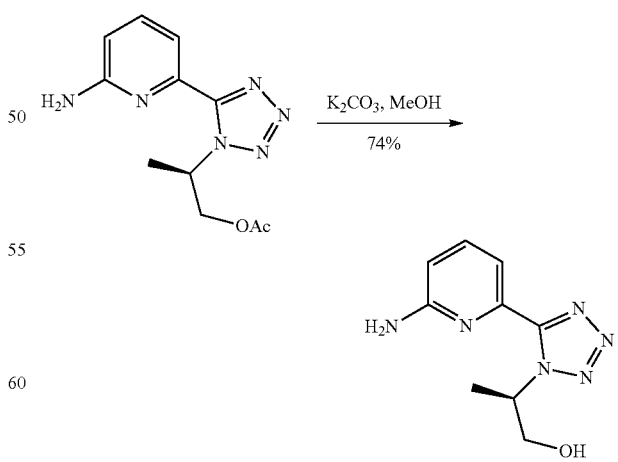

K₂CO₃ (1.1 g, 8.20 mmol) was added to a solution of (R)-2-(5-(6-aminopyridin-2-yl)-1H-tetrazol-1-yl)propyl acetate (430 mg, 1.64 mmol) in MeOH (6.6 mL) and the reaction was stirred for 30 min. The reaction was concentrated to remove MeOH and the residue was partitioned between DCM and H₂O. The layers were separated and the aqueous layer was extracted with DCM (3×). The combined organic layers were washed with brine, dried (MgSO₄), filtered, and concentrated under reduced pressure to give (R)-2-(5-(6-aminopyridin-2-yl)-1H-tetrazol-1-yl)propan-1-ol (327 mg, 1.485 mmol, 91% yield) as a yellow gum: ¹H NMR (400 MHz, DMSO-d₆) δ 7.59 (dd, J=8.4, 7.3 Hz, 1H), 7.27 (dd, J=7.3, 0.8 Hz, 1H), 6.62 (dd, J=8.4, 0.8 Hz, 1H), 6.36 (s, 2H), 5.83-5.76 (m, 1H), 4.96 (t, J=5.6 Hz, 1H), 3.80 (ddd, J=11.2, 8.1, 5.9 Hz, 1H), 3.71 (dt, J=11.0, 5.3 Hz, 1H), 1.52 (d, J=6.8 Hz, 3H).

Step 6. Synthesis of (R)-6-(1-(1-(((tert-butyldimethylsilyl)oxy)propan-2-yl)-1H-tetrazol-5-yl)pyridin-2-amine

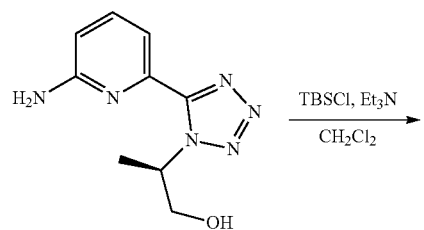

TBS-Cl (8.6 g, 56.8 mmol) was added to a solution of (R)-2-(5-(6-aminopyridin-2-yl)-1H-tetrazol-1-yl)propan-1-ol (5.0 g, 22.7 mmol) and Et₃N (9.5 mL, 6.9 g, 68.1 mmol) in CH₂Cl₂ (76 mL) at 0° C. The reaction was stirred overnight, warming slowly to rt. The reaction was quenched with sat. NaHCO₃ and diluted with CH₂Cl₂. The layers were separated and the organic layer was washed with H₂O and brine. The organic layer was dried (MgSO₄), filtered, and concentrated under reduced pressure. The resultant residue was purified by column chromatography eluting with hexanes/EtOAc (0% EtOAc→40% EtOAc) to afford (R)-6-(1-(1-(((tert-butyldimethylsilyl)oxy)propan-2-yl)-1H-tetrazol-5-yl)pyridin-2-amine (7.12 g, 21.3 mmol, 94% yield) as a pale brown solid: ¹H NMR (400 MHz, Chloroform-d) δ 7.67-7.56 (comp, 2H), 6.68 (d, J=8.1 Hz, 1H), 5.89-5.76 (m, 1H), 3.99 (dd, J=10.2, 8.3 Hz, 1H), 3.89 (dd, J=10.2, 5.3 Hz, 1H), 1.68 (d, J=6.8 Hz, 3H), 0.71 (s, 9H), −0.09 (s, 3H), −0.13 (s, 3H).

Step 7. Synthesis of benzyl (R)-7-((6-(1-(1-((tert-butyldimethylsilyl)oxy)propan-2-yl)-1H-tetrazol-5-yl)pyridin-2-yl)carbamoyl)-6-methoxy-3,4-dihydroisoquinoline-2(1H)-carboxylate

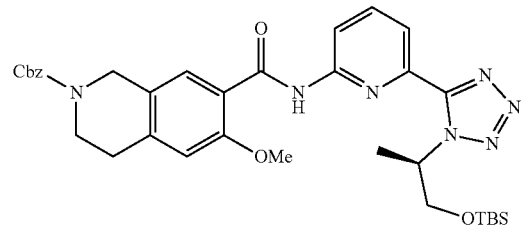 [SMILES: COc1cc2c(cc1C(=O)Nc1cccc(-c3nnnn3[C@H](C)CO[Si](C)(C)C(C)(C)C)n1)CN(C(=O)OCc1ccccc1)CC2]

Benzyl (R)-7-((6-(1-(1-((tert-butyldimethylsilyl)oxy)propan-2-yl)-1H-tetrazol-5-yl)pyridin-2-yl)carbamoyl)-6-methoxy-3,4-dihydroisoquinoline-2(1H)-carboxylate was synthesized from (R)-6-(1-(1-(((tert-butyldimethylsilyl)oxy)propan-2-yl)-1H-tetrazol-5-yl)pyridin-2-amine and 2-((benzyloxy)carbonyl)-6-methoxy-1,2,3,4-tetrahydroisoquinoline-7-carboxylic acid according to the representative procedure for amide formation with Ghosez's reagent: LC-MS, ES⁺: m/z 658.32 [M+H]⁺; ¹H NMR (400 MHz, DMSO-d) δ 10.74 (s, 1H), 8.40 (d, J=8.3 Hz, 1H), 8.11 (t, J=8.0 Hz, 1H), 7.94 (d, J=7.9 Hz, 1H), 7.71 (s, 1H), 7.44-7.28 (comp, 5H), 7.11 (s, 1H), 6.06-5.98 (m, 1H), 5.14 (s, 2H), 4.60 (d, J=19.8 Hz, 2H), 4.03-3.83 (comp, 5H), 3.65 (br s, 2H), 2.90 (t, J=5.9 Hz, 2H), 1.63 (d, J=6.8 Hz, 3H), 0.59 (s, 9H), −0.21 (d, J=5.4 Hz, 6H).

Step 8. Synthesis of benzyl (R)-7-((6-(1-(1-hydroxypropan-2-yl)-1H-tetrazol-5-yl)pyridin-2-yl)carbamoyl)-6-methoxy-3,4-dihydroisoquinoline-2(1H)-carboxylate

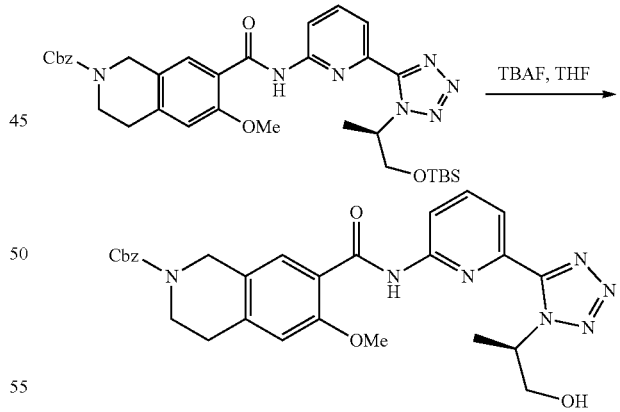

TBAF (91 µl, 0.091 mmol of a 1.0M solution in THF) was added to a solution of benzyl (R)-7-((6-(1-(1-((tert-butyldimethylsilyl)oxy)propan-2-yl)-1H-tetrazol-5-yl)pyridin-2-yl)carbamoyl)-6-methoxy-3,4-dihydroisoquinoline-2(1H)-carboxylate (30 mg, 0.046 mmol) in THF (456 µl) and the reaction was stirred for 2 h. The reaction was quenched with H₂O and diluted with CH₂Cl₂. The layers were separated and the aqueous layer was extracted with CH₂Cl₂ (2×). The combined organic layers were dried (MgSO₄), filtered, and concentrated under reduced pressure. The resultant yellow gum was purified by column chromatography eluting with hexanes/EtOAc (0% EtOAc→80% EtOAc) to give benzyl (R)-7-((6-(1-(1-hydroxypropan-2-yl)-1H-tetrazol-5-yl)pyridin-2-yl)carbamoyl)-6-methoxy-3,4-dihydroisoquinoline-2(1H)-carboxylate (17.4 mg, 0.032 mmol, 70% yield) as a colorless amorphous solid.

Example 77: Synthesis of isopropyl (R)-7-((6-(1-(1-hydroxypropan-2-yl)-1H-tetrazol-5-yl)pyridin-2-yl)carbamoyl)-6-methoxy-3,4-dihydroisoquinoline-2(1H)-carboxylate

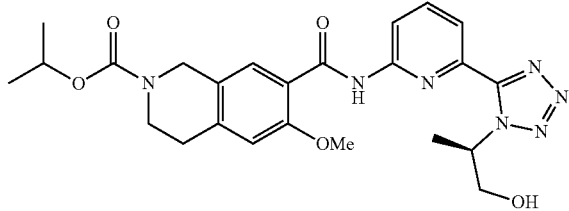 [SMILES: COc1cc2c(cc1C(=O)Nc1cccc(-c3nnnn3[C@H](C)CO)n1)CN(C(=O)OC(C)C)CC2]

Step 1. Synthesis of (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide

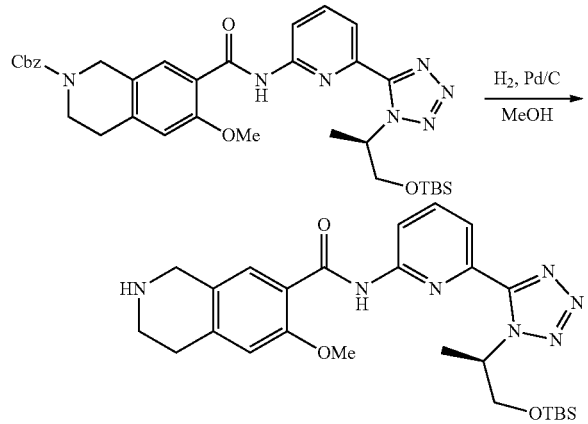

Pd—C (50 mg, 10% loading) was added to a solution of benzyl (R)-7-((6-(1-(1-((tert-butyldimethylsilyl)oxy)propan-2-yl)-1H-tetrazol-5-yl)pyridin-2-yl)carbamoyl)-6-methoxy-3,4-dihydroisoquinoline-2(1H)-carboxylate (336 mg, 0.511 mmol) in MeOH (10.2 mL). The reaction was evacuated and backfilled with H$_2$ (3×) and the reaction was stirred overnight under a balloon of H$_2$. The reaction was filtered through Celite, rinsing with MeOH, EtOAc, and DCM and concentrated under reduced pressure. The resultant clear residue was dissolved in DCM/EtOAc and filtered through Celite, rinsing with DCM and EtOAc. The filtrate was concentrated under reduced pressure to afford (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide (243 mg, 0.46 mmol, 91% yield) as a tan solid: LC-MS, ES$^+$: m/z 524.31 [M+H]$^+$; $^1$H NMR (400 MHz, Chloroform-d) δ 10.58 (s, 1H), 8.56 (dd, J=8.3, 1.1 Hz, 1H), 8.03-7.96 (comp, 2H), 7.93 (t, J=7.9 Hz, 1H), 6.77 (s, 1H), 5.95-5.82 (m, 1H), 4.13-4.02 (comp, 6H), 3.97 (dd, J=10.2, 5.7 Hz, 1H), 3.16 (t, J=5.9 Hz, 2H), 2.87 (t, J=5.9 Hz, 2H), 1.73 (d, J=6.8 Hz, 3H), 0.71 (s, 9H), −0.08 (s, 3H), −0.12 (s, 3H).

Step 2. Synthesis of isopropyl (R)-7-((6-(1-(1-hydroxypropan-2-yl)-1H-tetrazol-5-yl)pyridin-2-yl)carbamoyl)-6-methoxy-3,4-dihydroisoquinoline-2(1H)-carboxylate

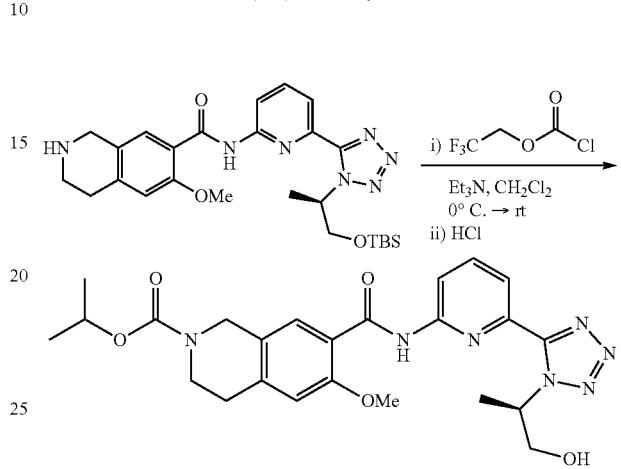

Representative procedure for N-functionalization and TBS deprotection.

Isopropyl chloroformate (0.175 mL, 0.175 mmol of a 1.0M solution in PhMe) was added dropwise to a solution of (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide (61 mg, 0.116 mmol) and Et$_3$N (65 µL, 47.1 mg, 0.466 mmol) in CH$_2$Cl$_2$ (1.17 mL) at 0° C. The cold bath was removed and the reaction was stirred for 2 h at rt. HCl (0.243 mL, 2.91 mmol of a 37% aqueous solution) was added and the reaction was stirred for 1 h at rt. The reaction was quenched carefully with sat. NaHCO$_3$ and diluted with CH$_2$Cl$_2$. The layers were separated and the aqueous layer was extracted with CH$_2$Cl$_2$ (2×). The combined organic layers were dried (MgSO$_4$), filtered, and concentrated under reduced pressure. The resultant pale yellow gum was purified by column chromatography eluting with hexanes/EtOAc (0% EtOAc→80% EtOAc, 4 g column) to give isopropyl (R)-7-((6-(1-(1-hydroxypropan-2-yl)-1H-tetrazol-5-yl)pyridin-2-yl)carbamoyl)-6-methoxy-3,4-dihydroisoquinoline-2(1H)-carboxylate (33.2 mg, 0.067 mmol, 58% yield) as a colorless amorphous solid.

Examples 85, 86, and 93 were prepared from (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide and the corresponding chloroformate according to the representative procedure for N-functionalization and TBS deprotection.

Examples 78 and 87 were prepared from (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide and the corresponding sulfonyl chloride according to the representative procedure for N-functionalization and TBS deprotection.

Examples 79, 88, and 92 were prepared from (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide and the corresponding acid chloride according to the representative procedure for N-functionalization and TBS deprotection.

Example 80 was prepared from (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide and ethyl isocyanate according to the representative procedure for N-functionalization and TBS deprotection.

Example 89 was prepared from (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide and 1-pyrrolidinecarbonyl chloride according to the representative procedure for N-functionalization and TBS deprotection.

Examples 81 and 90 were prepared from (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide and the corresponding aldehyde according to the representative procedure for reductive alkylation, with the following modification: HCl (10 equivalents of a 37% aqueous solution) was added to the reaction after the completion of the reductive alkylation step to remove the TBS protecting group.

Example 91: Synthesis of 2-((S)-3-hydroxybutanoyl)-N-(6-(1-((R)-1-hydroxypropan-2-yl)-1H-tetrazol-5-yl)pyridin-2-yl)-6-methoxy-1,2,3,4-tetrahydroisoquinoline-7-carboxamide

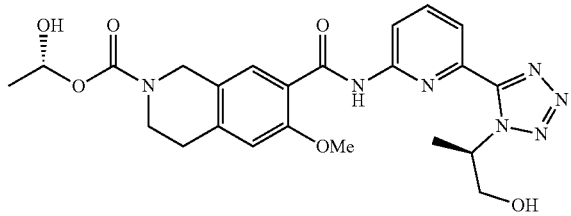

Representative procedure for HATU coupling and TBS deprotection.

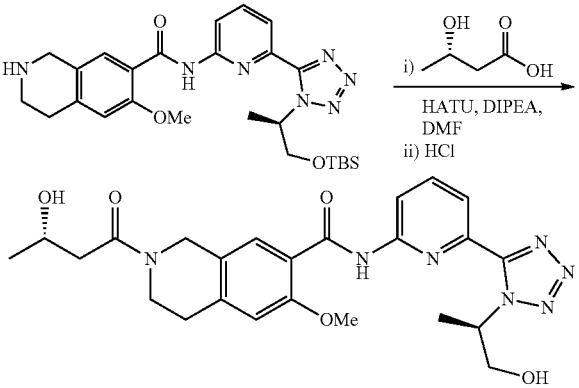

HATU (32.7 mg, 0.086 mmol) was added to a solution of (S)-3-hydroxybutanoic acid (6.0 mg, 0.057 mmol) in DMF (0.24 mL) and the reaction was stirred for 5 min at rt. (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide (30 mg, 0.057 mmol) was added, followed by DIPEA (30 µL, 22.2 mg, 0.172 mmol), and the reaction was stirred for 2 h at rt. HCl (0.048 mL, 0.573 mmol of a 37% aqueous solution) was added and the reaction was stirred for 1 h at rt. The reaction was carefully quenched with sat. NaHCO$_3$ and diluted with CH$_2$Cl$_2$. The layers were separated and the aqueous layer was extracted with CH$_2$Cl$_2$ (2×). The combined organic layers were washed with brine, dried (MgSO$_4$), filtered, and concentrated under reduced pressure. The resultant yellow gum was purified by column chromatography eluting with CH$_2$Cl$_2$/MeOH (0% MeOH→7% MeOH) to afford 2-((S)-3-hydroxybutanoyl)-N-(6-(1-((R)-1-hydroxypropan-2-yl)-1H-tetrazol-5-yl)pyridin-2-yl)-6-methoxy-1,2,3,4-tetrahydroisoquinoline-7-carboxamide (18.7 mg, 0.038 mmol, 66% yield) as a colorless amorphous solid.

Examples 82 and 83 were prepared from (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide and the corresponding carboxylic acid according to the representative procedure for HATU coupling and TBS deprotection.

Example 84: Synthesis of (R)—N-(6-(1-(1-hydroxypropan-2-yl)-1H-tetrazol-5-yl)pyridin-2-yl)-6-methoxy-2-(pyrimidin-2-yl)-1,2,3,4-tetrahydroisoquinoline-7-carboxamide

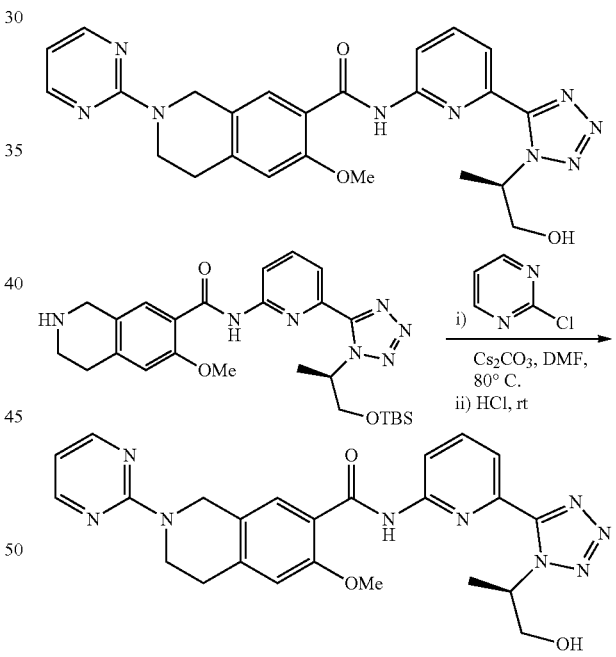

A mixture of (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide (30 mg, 0.057 mmol), 2-chloropyrimidine (7.87 mg, 0.069 mmol), and Cs$_2$CO$_3$ (41.1 mg, 0.126 mmol) in DMF (573 µl) was heated at 80° C. for 24 h. The reaction was cooled to rt and HCl (47.7 µl, 0.573 mmol of a 37% aqueous solution) was added. The reaction was stirred for 5 h at rt. The reaction was quenched with sat. NaHCO$_3$ and diluted with CH$_2$Cl$_2$. The layers were separated and aqueous layer was extracted with CH$_2$Cl$_2$ (2×). The combined organic layers were washed with brine, dried (MgSO$_4$), filtered, and concentrated under reduced pressure. The resultant yellow gum was purified by column chromatography eluting with CH₂Cl₂/MeOH (0% MeOH→7% MeOH) to afford (R)—N-(6-(1-(1-hydroxypropan-2-yl)-1H-tetrazol-5-yl)pyridin-2-yl)-6-methoxy-2-(pyrimidin-2-yl)-1,2,3,4-tetrahydroisoquinoline-7-carboxamide (5.3 mg, 10.87 μmol, 19% yield) as a white solid.

Example 61: Synthesis of tert-butyl (R)-7-((6-(4-(1-hydroxypropan-2-yl)-4H-1,2,4-triazol-3-yl)pyridin-2-yl)carbamoyl)-6-methoxy-3,4-dihydroisoquinoline-2(1H)-carboxylate

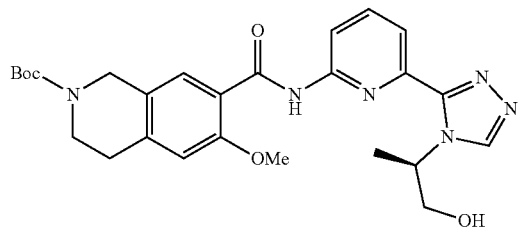

Step 1. Synthesis of 6-aminopicolinohydrazide

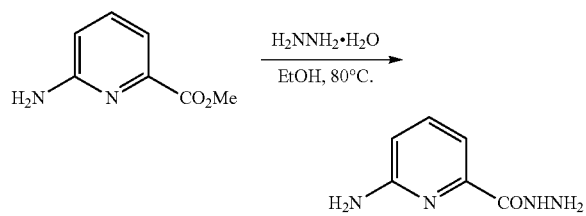

Hydrazine hydrate (32.9 g, 658.00 mmol) was added to a mixture of methyl 6-aminopicolinate (20 g, 131.45 mmol) in EtOH (200 mL), and the resulting solution was stirred for 2 h at 80° C. The reaction was cooled to rt and the solids were collected by filtration and dried in vacuo to give 6-aminopicolinohydrazide (18.2 g, 90.5%) as an off-white solid.

Step 2. Synthesis of (E)-N'-(6-aminopicolinoyl)-N,N-dimethylformohydrazonamide

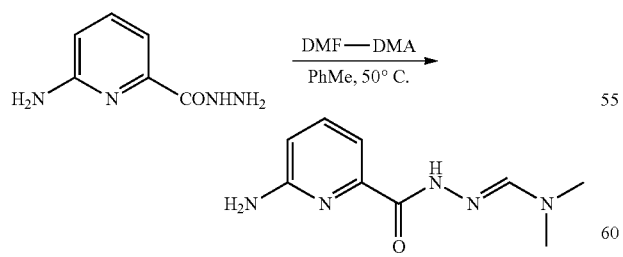

DMF-DMA (21.5 g, 180.4 mmol) was added to a solution of 6-aminopicolinohydrazide (18.3 g, 120.27 mmol) in PhMe (200 mL), and the resulting solution was stirred overnight at 50° C. The reaction was cooled to rt and the solids were collected by filtration and dried in vacuo to give (E)-N'-(6-aminopicolinoyl)-N,N-dimethylformohydrazonamide (23.0 g, 92.3%) as a light yellow solid.

Step 3. Synthesis of (R)-2-(3-(6-aminopyridin-2-yl)-4H-1,2,4-triazol-4-yl)propan-1-ol

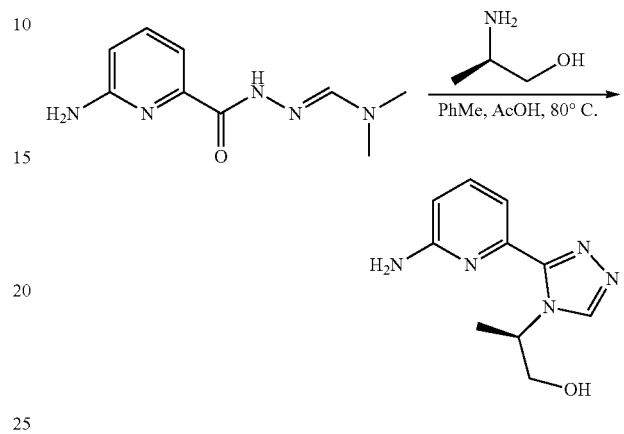

(R)-2-aminopropan-1-ol (25 g, 332.97 mmol) was added to a mixture of ((E)-N'-(6-aminopicolinoyl)-N,N-dimethylformohydrazonamide (23 g, 110.99 mmol) in acetic acid (24 mL) and toluene (120 mL). The resulting solution was stirred overnight at 80° C. The reaction was concentrated under reduced pressure. The crude residue was purified by column chromatography eluting with DCM/MeOH (0% MeOH→10% MeOH), then further purified by reverse phase prep HPLC eluting with H₂O/CH₃CN (0% CH₃CN→20% CH₃CN) to give (R)-2-(3-(6-aminopyridin-2-yl)-4H-1,2,4-triazol-4-yl)propan-1-ol (7.8 g, 32%) as an off-white solid.

Step 4. Synthesis of (R)-6-(4-(1-((tert-butyldimethylsilyl)oxy)propan-2-yl)-4H-1,2,4-triazol-3-yl)pyridin-2-amine

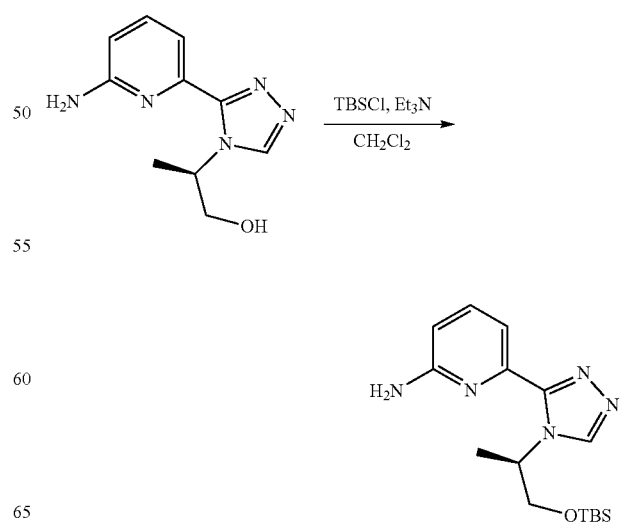

TBS-Cl (859 mg, 5.70 mmol) was added to a solution of (R)-2-(3-(6-aminopyridin-2-yl)-4H-1,2,4-triazol-4-yl)propan-1-ol (500 mg, 2.28 mmol) and Et$_3$N (0.954 mL, 692 mg, 6.84 mmol) in CH$_2$Cl$_2$ (7.6 mL) at 0° C. The reaction was stirred overnight, warming slowly to rt. The reaction was quenched with sat. NaHCO$_3$ and diluted with CH$_2$Cl$_2$. The layers were separated and the aqueous layer was extracted with CH$_2$Cl$_2$ (2×). The combined organic layers were dried (MgSO$_4$), filtered, and concentrated under reduced pressure. The resultant clear oil was purified by column chromatography eluting with CH$_2$Cl$_2$/MeOH (0% MeOH→8% MeOH) to afford (R)-6-(4-(1-((tert-butyldimethylsilyl)oxy)propan-2-yl)-4H-1,2,4-triazol-3-yl)pyridin-2-amine (563 mg, 1.69 mmol, 74.0% yield) as a colorless amorphous solid: $^1$H NMR (400 MHz, Chloroform-d) δ 8.42 (s, 1H), 7.61 (dd, J=7.6, 1.1 Hz, 1H), 7.56 (t, J=7.7 Hz, 1H), 6.55 (dd, J=7.9, 1.1 Hz, 1H), 5.65 (tt, J=7.1, 3.4 Hz, 1H), 4.46 (s, 2H), 3.87 (dd, J=10.6, 3.6 Hz, 1H), 3.80 (dd, J=10.5, 3.9 Hz, 1H), 1.54 (d, J=7.0 Hz, 3H), 0.86 (s, 9H), −0.01 (s, 3H), −0.04 (s, 3H).

Step 5. Synthesis of tert-butyl (R)-7-((6-(4-(1-((tert-butyldimethylsilyl)oxy)propan-2-yl)-4H-1,2,4-triazol-3-yl)pyridin-2-yl)carbamoyl)-6-methoxy-3,4-dihydroisoquinoline-2(1H)-carboxylate

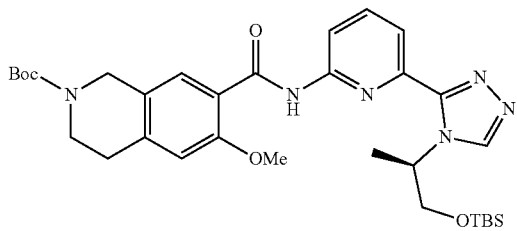 [SMILES: COc1cc2c(cc1C(=O)Nc1cccc(-c3nncn3[C@H](C)CO[Si](C)(C)C(C)(C)C)n1)CN(C(=O)OC(C)(C)C)CC2]

tert-butyl (R)-7-((6-(4-(1-((tert-butyldimethylsilyl)oxy)propan-2-yl)-4H-1,2,4-triazol-3-yl)pyridin-2-yl)carbamoyl)-6-methoxy-3,4-dihydroisoquinoline-2(1H)-carboxylate was synthesized from (R)-6-(4-(1-((tert-butyldimethylsilyl)oxy)propan-2-yl)-4H-1,2,4-triazol-3-yl)pyridin-2-amine and 2-((benzyloxy)carbonyl)-6-methoxy-1,2,3,4-tetrahydroisoquinoline-7-carboxylic acid according to the representative procedure for amide formation with Ghosez's reagent: LC-MS, ES$^+$: m/z 623.33 [M+H]$^+$; $^1$H NMR (400 MHz, DMSO-d$_6$) δ 10.58 (s, 1H), 8.80 (s, 1H), 8.30 (dd, J=8.3, 0.9 Hz, 1H), 8.02 (t, J=8.0 Hz, 1H), 7.84 (dd, J=7.7, 0.9 Hz, 1H), 7.72 (s, 1H), 7.09 (s, 1H), 5.71-5.56 (m, 1H), 4.51 (s, 2H), 3.97 (s, 3H), 3.90-3.76 (m, 2H), 3.56 (t, J=5.9 Hz, 2H), 2.86 (t, J=5.9 Hz, 2H), 1.54 (d, J=6.9 Hz, 3H), 1.43 (s, 9H), 0.70 (s, 9H), −0.15 (d, J=12.3 Hz, 6H).

Step 6. Synthesis of tert-butyl (R)-7-((6-(4-(1-hydroxypropan-2-yl)-4H-1,2,4-triazol-3-yl)pyridin-2-yl)carbamoyl)-6-methoxy-3,4-dihydroisoquinoline-2(1H)-carboxylate

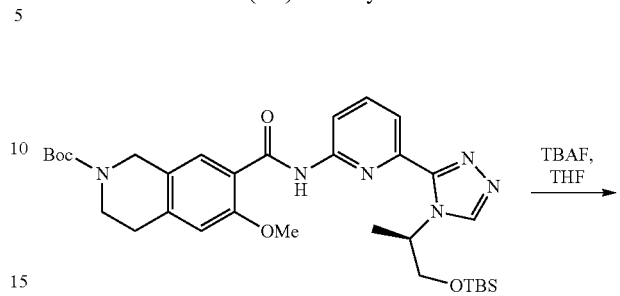

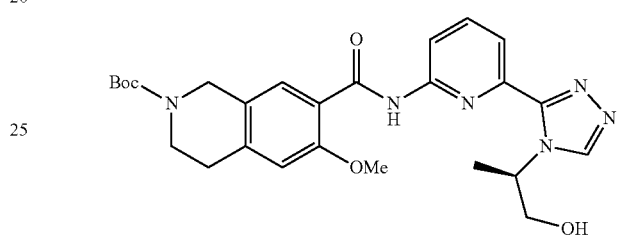

TBAF (0.128 mL, 0.128 mmol of a 1.0M solution in THF) was added dropwise to a solution of tert-butyl (R)-7-((6-(4-(1-((tert-butyldimethylsilyl)oxy)propan-2-yl)-4H-1,2,4-triazol-3-yl)pyridin-2-yl)carbamoyl)-6-methoxy-3,4-dihydroisoquinoline-2(1H)-carboxylate (40 mg, 0.064 mmol) in THF (0.64 mL) and the reaction was stirred overnight. The reaction was quenched with H$_2$O and diluted with CH$_2$Cl$_2$. The layers were separated and the aqueous layer was extracted with CH$_2$Cl$_2$ (2×). The combined organic layers were washed with brine, dried (MgSO$_4$), filtered, and concentrated under reduced pressure. The resultant colorless solid was purified by column chromatography eluting with CH$_2$Cl$_2$/MeOH (0% MeOH→10% MeOH) to afford tert-butyl (R)-7-((6-(4-(1-hydroxypropan-2-yl)-4H-1,2,4-triazol-3-yl)pyridin-2-yl)carbamoyl)-6-methoxy-3,4-dihydroisoquinoline-2(1H)-carboxylate (13.5 mg, 0.027 mmol, 41.3% yield) as a colorless amorphous solid.

Example 46: Synthesis of ethyl (R)-7-((6-(4-(1-hydroxypropan-2-yl)-4H-1,2,4-triazol-3-yl)pyridin-2-yl)carbamoyl)-6-methoxy-3,4-dihydroisoquinoline-2(1H)-carboxylate

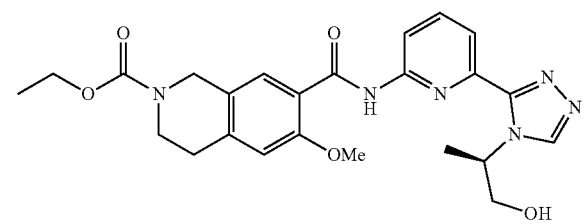

Step 1. (R)—N-(6-(4-(1-hydroxypropan-2-yl)-4H-1,2,4-triazol-3-yl)pyridin-2-yl)-6-methoxy-1,2,3,4-tetrahydroisoquinoline-7-carboxamide hydrochloride was synthesized from tert-butyl (R)-7-((6-(4-(1-((tert-butyldimethylsilyl)oxy)propan-2-yl)-4H-1,2,4-triazol-3-yl)pyridin-2-yl)carbamoyl)-6-methoxy-3,4-dihydroisoquinoline-2(1H)-carboxylate according to the representative procedure for Boc deprotection, and under these conditions the TBS ether was also deprotected.

Step 2. Synthesis of (R)—N-(6-(4-(1-(((tert-butyldimethylsilyl)oxy)propan-2-yl)-4H-1,2,4-triazol-3-yl)pyridin-2-yl)-6-methoxy-1,2,3,4-tetrahydroisoquinoline-7-carboxamide Representative procedure for TBS protection.

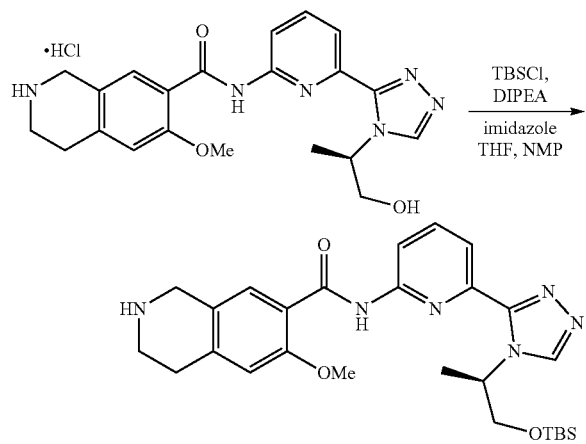

TBS-Cl (339 mg, 2.25 mmol) was added to a mixture of (R)—N-(6-(4-(1-hydroxypropan-2-yl)-4H-1,2,4-triazol-3-yl)pyridin-2-yl)-6-methoxy-1,2,3,4-tetrahydroisoquinoline-7-carboxamide hydrochloride (200 mg, 0.45 mmol), imidazole (153 mg, 2.25 mmol), and DIPEA (0.39 mL, 291 mg, 2.25 mmol) in THF (4.4 mL) and NMP (2.2 mL). The reaction was stirred for 4 h at rt. The reaction was quenched with sat. NaHCO$_3$ and diluted with EtOAc. The layers were separated and the organic layer was washed with H$_2$O and brine. The organic layer was dried (MgSO$_4$), filtered, and concentrated under reduced pressure. The resultant yellow gum was purified by column chromatography eluting with CH$_2$Cl$_2$/MeOH (0% MeOH→5% MeOH) to give (R)—N-(6-(4-(1-(((tert-butyldimethylsilyl)oxy)propan-2-yl)-4H-1,2,4-triazol-3-yl)pyridin-2-yl)-6-methoxy-1,2,3,4-tetrahydroisoquinoline-7-carboxamide (100 mg, 0.19 mmol, 42% yield) as a colorless amorphous solid.

Examples 46, 47, and 65 were prepared from (R)—N-(6-(4-(1-(((tert-butyldimethylsilyl)oxy)propan-2-yl)-4H-1,2,4-triazol-3-yl)pyridin-2-yl)-6-methoxy-1,2,3,4-tetrahydroisoquinoline-7-carboxamide and the corresponding chloroformate according to the representative procedure for N-functionalization and TBS deprotection.

Examples 53 and 72 were prepared from (R)—N-(6-(4-(1-(((tert-butyldimethylsilyl)oxy)propan-2-yl)-4H-1,2,4-triazol-3-yl)pyridin-2-yl)-6-methoxy-1,2,3,4-tetrahydroisoquinoline-7-carboxamide and the corresponding sulfonyl chloride according to the representative procedure for N-functionalization and TBS deprotection.

Examples 54 and 73 were prepared from (R)—N-(6-(4-(1-(((tert-butyldimethylsilyl)oxy)propan-2-yl)-4H-1,2,4-triazol-3-yl)pyridin-2-yl)-6-methoxy-1,2,3,4-tetrahydroisoquinoline-7-carboxamide and the corresponding acid chloride according to the representative procedure for N-functionalization and TBS deprotection.

Example 55 was prepared from (R)—N-(6-(4-(1-(((tert-butyldimethylsilyl)oxy)propan-2-yl)-4H-1,2,4-triazol-3-yl)pyridin-2-yl)-6-methoxy-1,2,3,4-tetrahydroisoquinoline-7-carboxamide and ethyl isocyanate according to the representative procedure for N-functionalization and TBS deprotection.

Example 74 was prepared from (R)—N-(6-(4-(1-(((tert-butyldimethylsilyl)oxy)propan-2-yl)-4H-1,2,4-triazol-3-yl)pyridin-2-yl)-6-methoxy-1,2,3,4-tetrahydroisoquinoline-7-carboxamide and 1-pyrrolidinecarbonyl chloride according to the representative procedure for N-functionalization and TBS deprotection.

Examples 56 and 75 were prepared from (R)—N-(6-(4-(1-(((tert-butyldimethylsilyl)oxy)propan-2-yl)-4H-1,2,4-triazol-3-yl)pyridin-2-yl)-6-methoxy-1,2,3,4-tetrahydroisoquinoline-7-carboxamide and the corresponding aldehyde according to the representative procedure for reductive alkylation, with the following modification: HCl (10 equivalents of a 37% aqueous solution) was added to the reaction after the completion of the reductive alkylation step to remove the TBS protecting group.

Example 38: Synthesis of (R)-6-(cyclopropylsulfonyl)-N-(6-(4-(1-hydroxypropan-2-yl)-4H-1,2,4-triazol-3-yl)pyridin-2-yl)-5,6,7,8-tetrahydro-2,6-naphthyridine-3-carboxamide

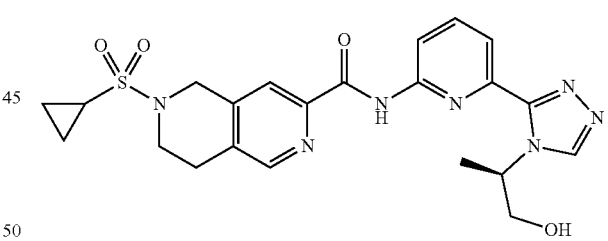

Step 1. tert-butyl (R)-7-((6-(4-(1-(((tert-butyldimethylsilyl)oxy)propan-2-yl)-4H-1,2,4-triazol-3-yl)pyridin-2-yl)carbamoyl)-3,4-dihydro-2,6-naphthyridine-2(1H)-carboxylate was synthesized from 2-(tert-butyl) 7-ethyl 3,4-dihydro-2,6-naphthyridine-2,7(1H)-dicarboxylate and (R)-6-(4-(1-(((tert-butyldimethylsilyl)oxy)propan-2-yl)-4H-1,2,4-triazol-3-yl)pyridin-2-amine according to the representative procedure for amide formation with trimethylaluminum.

Step 2. (R)—N-(6-(4-(1-hydroxypropan-2-yl)-4H-1,2,4-triazol-3-yl)pyridin-2-yl)-5,6,7,8-tetrahydro-2,6-naphthyridine-3-carboxamide hydrochloride was synthesized from tert-butyl (R)-7-((6-(4-(1-(((tert-butyldimethylsilyl)oxy)propan-2-yl)-4H-1,2,4-triazol-3-yl)pyridin-2-yl)carbamoyl)-3,4-dihydro-2,6-naphthyridine-2(1H)-carboxylate according to the representative procedure for Boc deprotection, and under these conditions the TBS ether was also deprotected.

Step 3. (R)—N-(6-(4-(1-((tert-butyldimethylsilyl)oxy) propan-2-yl)-4H-1,2,4-triazol-3-yl)pyridin-2-yl)-5,6,7,8-tetrahydro-2,6-naphthyridine-3-carboxamide was synthesized from (R)—N-(6-(4-(1-hydroxypropan-2-yl)-4H-1,2,4-triazol-3-yl)pyridin-2-yl)-5,6,7,8-tetrahydro-2,6-naphthyridine-3-carboxamide hydrochloride according to the representative procedure for TBS protection.

Step 4. (R)-6-(cyclopropylsulfonyl)-N-(6-(4-(1-hydroxypropan-2-yl)-4H-1,2,4-triazol-3-yl)pyridin-2-yl)-5,6,7,8-tetrahydro-2,6-naphthyridine-3-carboxamide was synthesized from (R)—N-(6-(4-(1-((tert-butyldimethylsilyl)oxy)propan-2-yl)-4H-1,2,4-triazol-3-yl)pyridin-2-yl)-5,6,7,8-tetrahydro-2,6-naphthyridine-3-carboxamide and cyclopropanesulfonyl chloride according to the representative procedure for N-functionalization and TBS deprotection.

Example 57 was prepared from (R)—N-(6-(4-(1-((tert-butyldimethylsilyl)oxy)propan-2-yl)-4H-1,2,4-triazol-3-yl)pyridin-2-yl)-5,6,7,8-tetrahydro-2,6-naphthyridine-3-carboxamide and benzenesulfonyl chloride according to the representative procedure for N-functionalization and TBS deprotection.

Example 39 was prepared from (R)—N-(6-(4-(1-((tert-butyldimethylsilyl)oxy)propan-2-yl)-4H-1,2,4-triazol-3-yl)pyridin-2-yl)-5,6,7,8-tetrahydro-2,6-naphthyridine-3-carboxamide and N,N-dimethylsulfamoyl chloride according to the representative procedure for N-functionalization and TBS deprotection.

Example 58 was prepared from (R)—N-(6-(4-(1-((tert-butyldimethylsilyl)oxy)propan-2-yl)-4H-1,2,4-triazol-3-yl)pyridin-2-yl)-5,6,7,8-tetrahydro-2,6-naphthyridine-3-carboxamide and 1-pyrrolidinecarbamoyl chloride according to the representative procedure for N-functionalization and TBS deprotection.

Examples 40 and 60 were prepared from (R)—N-(6-(4-(1-((tert-butyldimethylsilyl)oxy)propan-2-yl)-4H-1,2,4-triazol-3-yl)pyridin-2-yl)-5,6,7,8-tetrahydro-2,6-naphthyridine-3-carboxamide and the corresponding aldehyde according to the representative procedure for reductive alkylation, with the following modification: HCl (10 equivalents of a 37% aqueous solution) was added to the reaction after the completion of the reductive alkylation step to remove the TBS protecting group.

Examples 42 and 59 were prepared from (R)—N-(6-(4-(1-((tert-butyldimethylsilyl)oxy)propan-2-yl)-4H-1,2,4-triazol-3-yl)pyridin-2-yl)-5,6,7,8-tetrahydro-2,6-naphthyridine-3-carboxamide and the corresponding chloroformate according to the representative procedure for N-functionalization and TBS deprotection.

Example 41 was prepared from (R)—N-(6-(4-(1-((tert-butyldimethylsilyl)oxy)propan-2-yl)-4H-1,2,4-triazol-3-yl)pyridin-2-yl)-5,6,7,8-tetrahydro-2,6-naphthyridine-3-carboxamide and ethyl isocyanate according to the representative procedure for N-functionalization and TBS deprotection.

Example 43: Synthesis isopropyl (R)-6-fluoro-7-((6-(4-(1-hydroxypropan-2-yl)-4H-1,2,4-triazol-3-yl) pyridin-2-yl)carbamoyl)-3,4-dihydroisoquinoline-2 (1H)-carboxylate

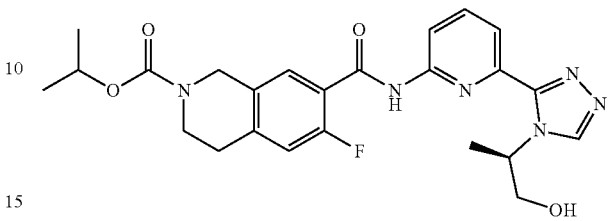

Step 1. tert-butyl (R)-7-((6-(4-(1-((tert-butyldimethylsilyl)oxy)propan-2-yl)-4H-1,2,4-triazol-3-yl)pyridin-2-yl) carbamoyl)-6-fluoro-3,4-dihydroisoquinoline-2(1H)-carboxylate was synthesized from 2-(tert-butyl) 7-ethyl 6-fluoro-3,4-dihydroisoquinoline-2,7(1H)-dicarboxylate and (R)-6-(4-(1-((tert-butyldimethylsilyl)oxy)propan-2-yl)-4H-1,2,4-triazol-3-yl)pyridin-2-amine according to the representative procedure for amide formation with trimethylaluminum with the following modifications: The reaction was performed at 80° C. using PhMe as the solvent.

Step 2. (R)-6-fluoro-N-(6-(4-(1-hydroxypropan-2-yl)-4H-1,2,4-triazol-3-yl)pyridin-2-yl)-1,2,3,4-tetrahydroisoquinoline-7-carboxamide hydrochloride was synthesized from tert-butyl (R)-7-((6-(4-(1-((tert-butyldimethylsilyl) oxy)propan-2-yl)-4H-1,2,4-triazol-3-yl)pyridin-2-yl)carbamoyl)-6-fluoro-3,4-dihydroisoquinoline-2(1H)-carboxylate according to the representative procedure for Boc deprotection, and under these conditions the TBS ether was also deprotected.

Step 3. (R)—N-(6-(4-(1-((tert-butyldimethylsilyl)oxy) propan-2-yl)-4H-1,2,4-triazol-3-yl)pyridin-2-yl)-6-fluoro-1, 2,3,4-tetrahydroisoquinoline-7-carboxamide was synthesized from (R)-6-fluoro-N-(6-(4-(1-hydroxypropan-2-yl)-4H-1,2,4-triazol-3-yl)pyridin-2-yl)-1,2,3,4-tetrahydroisoquinoline-7-carboxamide hydrochloride according to the representative procedure for TBS protection.

Step 4. (R)-6-fluoro-7-((6-(4-(1-hydroxypropan-2-yl)-4H-1,2,4-triazol-3-yl)pyridin-2-yl)carbamoyl)-3,4-dihydroisoquinoline-2(1H)-carboxylate was synthesized from (R)—N-(6-(4-(1-((tert-butyldimethylsilyl)oxy)propan-2-yl)-4H-1,2,4-triazol-3-yl)pyridin-2-yl)-6-fluoro-1,2,3,4-tetrahydroisoquinoline-7-carboxamide and isopropyl chloroformate according to the representative procedure for N-functionalization and TBS deprotection.

Examples 44, 48, 52, 63, 66, and 67 were prepared from (R)—N-(6-(4-(1-((tert-butyldimethylsilyl)oxy)propan-2-yl)-4H-1,2,4-triazol-3-yl)pyridin-2-yl)-6-fluoro-1,2,3,4-tetrahydroisoquinoline-7-carboxamide and the corresponding chloroformate according to the representative procedure for N-functionalization and TBS deprotection.

Examples 45 and 52 were prepared from (R)—N-(6-(4-(1-((tert-butyldimethylsilyl)oxy)propan-2-yl)-4H-1,2,4-triazol-3-yl)pyridin-2-yl)-6-fluoro-1,2,3,4-tetrahydroisoquinoline-7-carboxamide and the corresponding sulfonyl chloride according to the representative procedure for N-functionalization and TBS deprotection.

Examples 51 and 64 were prepared from (R)—N-(6-(4-(1-(((tert-butyldimethylsilyl)oxy)propan-2-yl)-4H-1,2,4-triazol-3-yl)pyridin-2-yl)-6-fluoro-1,2,3,4-tetrahydroisoquinoline-7-carboxamide and the corresponding acid chloride according to the representative procedure for N-functionalization and TBS deprotection.

Examples 70 and 71 were prepared from (R)—N-(6-(4-(1-(((tert-butyldimethylsilyl)oxy)propan-2-yl)-4H-1,2,4-triazol-3-yl)pyridin-2-yl)-6-fluoro-1,2,3,4-tetrahydroisoquinoline-7-carboxamide and the corresponding isocyanate according to the representative procedure for N-functionalization and TBS deprotection.

Examples 49 and 68 were prepared from (R)—N-(6-(4-(1-(((tert-butyldimethylsilyl)oxy)propan-2-yl)-4H-1,2,4-triazol-3-yl)pyridin-2-yl)-6-fluoro-1,2,3,4-tetrahydroisoquinoline-7-carboxamide and the corresponding carbamoyl chloride according to the representative procedure for N-functionalization and TBS deprotection.

Examples 50 and 69 were prepared from (R)—N-(6-(4-(1-(((tert-butyldimethylsilyl)oxy)propan-2-yl)-4H-1,2,4-triazol-3-yl)pyridin-2-yl)-6-fluoro-1,2,3,4-tetrahydroisoquinoline-7-carboxamide and the corresponding aldehyde according to the representative procedure for reductive alkylation, with the following modification: HCl (10 equivalents of a 37% aqueous solution) was added to the reaction after the completion of the reductive alkylation step to remove the TBS protecting group.

Examples 96 and 143 were prepared from (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide and the corresponding chloroformate according to the representative procedure for N-functionalization and TBS deprotection.

Examples 97, 101, 102, 105, 112, 113, 114, 115 and 149 were prepared from (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide and the corresponding carboxylic acid according to the representative procedure for HATU coupling and TBS deprotection.

Example 98: Synthesis of (R)-2-(2-amino-3,4-dioxocyclobut-1-en-1-yl)-N-(6(1-(1-hydroxypropan-2-yl)-1H-tetrazol-5-yl)pyridin-2-yl)-6-methoxy-1,2,3,4-tetrahydroisoquinoline-7-carboxamide

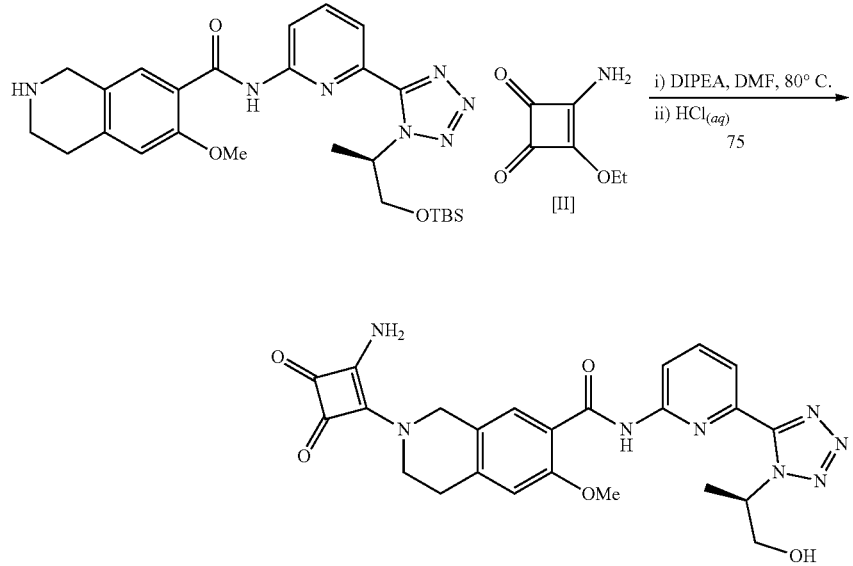

A mixture of (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide (73 mg, 0.139 mmol), 3-amino-4-ethoxycyclobut-3-ene-1,2-dione (23.61 mg, 0.167 mmol), and DIPEA (0.073 mL, 0.418 mmol) in DMF (0.820 mL) were heated at 80° C. over the weekend. The reaction was cooled to rt. Concentrated HCl (0.116 mL, 1.394 mmol) was added and the reaction stirred for 1 h. The reaction was quenched with sat. NaHCO$_3$ and diluted with EtOAc. There was an insoluble solid at the interface between H$_2$O and EtOAc during the extraction. The solid was collected, rinsing with H$_2$O and EtOAc, and drying under hi-vac to give (R)-2-(2-amino-3,4-dioxocyclobut-1-en-1-yl)-N-(6-(1-(1-hydroxypropan-2-yl)-1H-tetrazol-5-yl)pyridin-2-yl)-6-methoxy-1,2,3,4-tetrahydroisoquinoline-7-carboxamide (52.7 mg, 0.104 mmol, 74.9% yield) as a tan solid.

Examples 99, 100, 106, and 140 were prepared from (R)—N-(6-(1-(1-(((tert-butyldimethylsilyl)oxy)propan-2-yl)-1H-tetrazol-5-yl)pyridin-2-yl)-5,6,7,8-tetrahydro-2,6-naphthyridine-3-carboxamide and the corresponding carboxylic acid according to the representative procedure for N-functionalization and TBS deprotection.

Example 104 was prepared from (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide and pyridine-2-sulfonyl chloride according to the representative procedure for N-functionalization and TBS deprotection.

Example 108: Synthesis of (R)—N-(6-(1-(1-hydroxypropan-2-yl)-1H-tetrazol-5-yl)pyridin-2-yl)-6-(pyrimidin-2-yl)-5,6,7,8-tetrahydro-2,6-naphthyridine-3-carboxamide

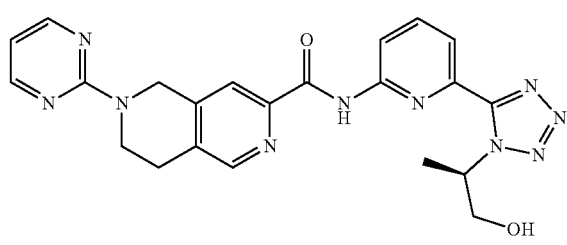 [SMILES: C[C@H](CO)n1nnnc1-c1cccc(NC(=O)c2cc3c(cn2)CCN(c2ncccn2)C3)n1]

Step 1: Synthesis of (R)—N-(6-(1-(1-(((tert-butyldimethylsilyl)oxy)propan-2-yl)-1H-tetrazol-5-yl)pyridin-2-yl)-6-(pyrimidin-2-yl)-5,6,7,8-tetrahydro-2,6-naphthyridine-3-carboxamide

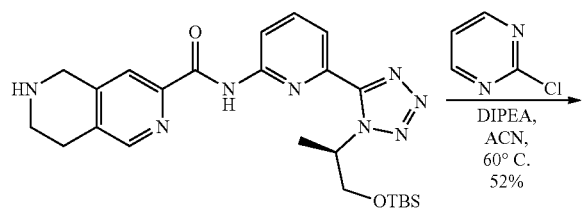

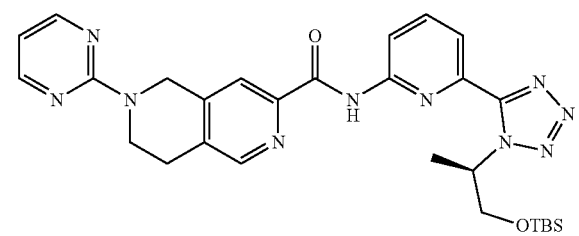

A mixture of (R)—N-(6-(1-(1-(((tert-butyldimethylsilyl)oxy)propan-2-yl)-1H-tetrazol-5-yl)pyridin-2-yl)-5,6,7,8-tetrahydro-2,6-naphthyridine-3-carboxamide (50 mg, 0.10 mmol) and DIPEA (47.1 μl, 0.303 mmol) were heated in Acetonitrile (1.01 mL) at 60° C. for 48 h. The reaction was purified by column chromatography eluting with hexanes/EtOAc (0% EtOAc→60% EtOAc) to give (R)—N-(6-(1-(1-(((tert-butyldimethylsilyl)oxy)propan-2-yl)-1H-tetrazol-5-yl)pyridin-2-yl)-6-(pyrimidin-2-yl)-5,6,7,8-tetrahydro-2,6-naphthyridine-3-carboxamide (30 mg, 0.052 mmol, 52% yield) as a pale yellow solid.

Step 2: Synthesis of (R)—N-(6-(1-(1-hydroxypropan-2-yl)-1H-tetrazol-5-yl)pyridin-2-yl)-6-(pyrimidin-2-yl)-5,6,7,8-tetrahydro-2,6-naphthyridine-3-carboxamide

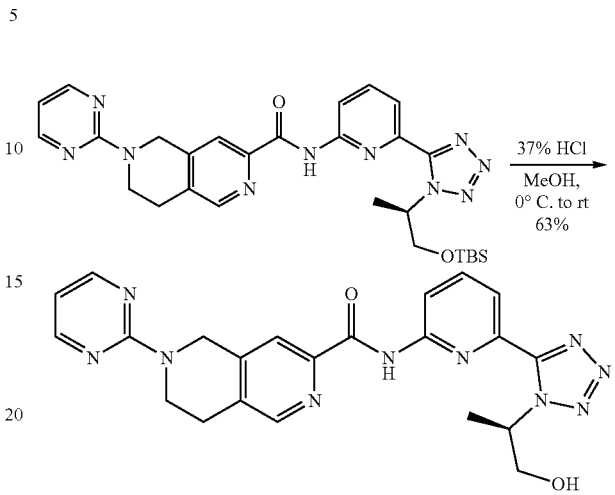

Concentrated HCl (43.6 μL, 0.52 mmol) was added to a solution of (R)—N-(6-(1-(1-(((tert-butyldimethylsilyl)oxy)propan-2-yl)-1H-tetrazol-5-yl)pyridin-2-yl)-6-(pyrimidin-2-yl)-5,6,7,8-tetrahydro-2,6-naphthyridine-3-carboxamide (30 mg, 0.052 mmol) in MeOH (0.8 mL) and the reaction was stirred for 30 minutes. The reaction was concentrated to remove MeOH. The residue was partitioned between EtOAc and sat. NaHCO₃. The layers were separated and the organic layer was washed with brine, dried (MgSO₄), filtered, and concentrated under reduced pressure. The resultant residue was purified by column chromatography eluting with DCM/MeOH (0% MeOH→10% MeOH) to give (R)—N-(6-(1-(1-hydroxypropan-2-yl)-1H-tetrazol-5-yl)pyridin-2-yl)-6-(pyrimidin-2-yl)-5,6,7,8-tetrahydro-2,6-naphthyridine-3-carboxamide (15 mg, 0.033 mmol, 63% yield).

Examples 109 and 110 were prepared from (R)—N-(6-(1-(1-(((tert-butyldimethylsilyl)oxy)propan-2-yl)-1H-tetrazol-5-yl)pyridin-2-yl)-6-fluoro-1,2,3,4-tetrahydroisoquinoline-7-carboxamide and the corresponding chloroformate according to the representative procedure N-functionalization and TBS deprotection.

Examples 111 and 134 were prepared from (R)—N-(6-(1-(1-(((tert-butyldimethylsilyl)oxy)propan-2-yl)-1H-tetrazol-5-yl)pyridin-2-yl)-6-fluoro-1,2,3,4-tetrahydroisoquinoline-7-carboxamide and the corresponding isocyanate according to the representative procedure for N-functionalization and TBS deprotection.

Examples 116 and 135 were prepared from (R)—N-(6-(1-(1-(((tert-butyldimethylsilyl)oxy)propan-2-yl)-1H-tetrazol-5-yl)pyridin-2-yl)-6-fluoro-1,2,3,4-tetrahydroisoquinoline-7-carboxamide and piperidine-1-carbonyl chloride or azetidine-1-carbonyl chloride, respectively, according to the representative procedure for N-functionalization and TBS deprotection.

Examples 117, 118, and 136 were prepared from (R)—N-(6-(1-(1-(((tert-butyldimethylsilyl)oxy)propan-2-yl)-1H-tetrazol-5-yl)pyridin-2-yl)-6-fluoro-1,2,3,4-tetrahydroisoquinoline-7-carboxamide and cyclopropylsulfamoyl chloride or ethylsulfamoyl chloride, respectively, according to the representative procedure for N-functionalization and TBS deprotection.

Examples 119 and 137 were prepared from (R)—N-(6-(1-(1-(((tert-butyldimethylsilyl)oxy)propan-2-yl)-1H-tetrazol-5-yl)pyridin-2-yl)-6-fluoro-1,2,3,4-tetrahydroisoquinoline-7-carboxamide and the corresponding sulfonyl chloride according to the representative procedure for N-functionalization and TBS deprotection.

Examples 124 and 142 were prepared from (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide and the corresponding acid chloride according to the representative procedure for N-functionalization and TBS deprotection.

Example 125 was prepared from N-(6-(4-isopropyl-4H-1,2,4-triazol-3-yl)pyridin-2-yl)-6-methoxy-1,2,3,4-tetrahydroisoquinoline-7-carboxamide dihydrochloride and 3-methoxypropanoyl chloride according to the representative procedure for amide formation.

Example 126: Synthesis of 2-(3-hydroxy-2,2-dimethylpropanoyl)-N-(6-(4-isopropyl-4H-1,2,4-triazol-3-yl)pyridin-2-yl)-6-methoxy-1,2,3,4-tetrahydroisoquinoline-7-carboxamide

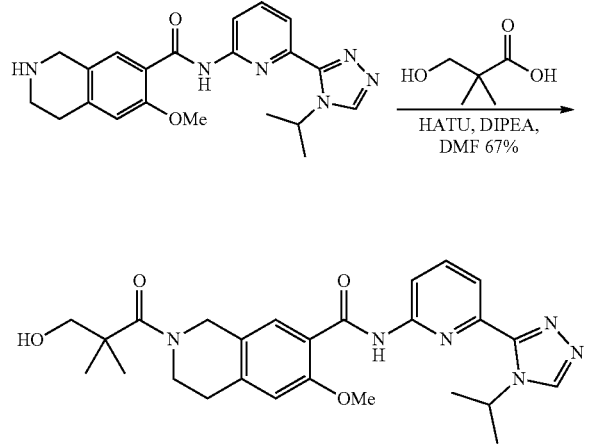

Representative procedure for HATU coupling:

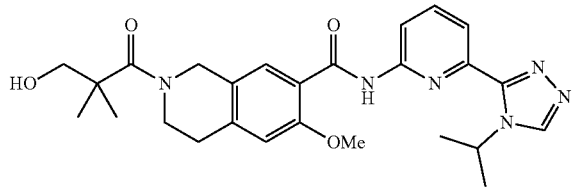 [SMILES: COc1cc2c(cc1C(=O)Nc1cccc(-c3nncn3C(C)C)n1)CN(C(=O)C(C)(C)CO)CC2]

HATU (61.3 mg, 0.161 mmol) was added to a solution of 3-hydroxy-2,2-dimethylpropanoic acid (12.69 mg, 0.107 mmol) in DMF (0.448 mL) and the reaction was stirred for 5 min at rt. N-(6-(4-isopropyl-4H-1,2,4-triazol-3-yl)pyridin-2-yl)-6-methoxy-1,2,3,4-tetrahydroisoquinoline-7-carboxamide dihydrochloride (50 mg, 0.107 mmol) was added, followed by DIPEA (0.094 mL, 0.537 mmol) and the reaction was stirred for 2 h at rt. The reaction was quenched with sat. NaHCO$_3$ and diluted with CH$_2$Cl$_2$. The layers were separated and the aqueous layer was extracted with CH$_2$Cl$_2$ (2×). The combined organic layers were washed with brine, dried (MgSO$_4$), filtered, and concentrated under reduced pressure. The resultant yellow oil was purified by column chromatography eluting with CH2Cl/MeOH (0% MeOH→7% MeOH) to give 2-(3-hydroxy-2,2-dimethylpropanoyl)-N-(6-(4-isopropyl-4H-1,2,4-triazol-3-yl)pyridin-2-yl)-6-methoxy-1,2,3,4-tetrahydroisoquinoline-7-carboxamide (35.2 mg, 0.071 mmol, 66.5% yield) as a colorless amorphous solid.

Examples 127, 128, 129, and 148 were prepared from N-(6-(4-isopropyl-4H-1,2,4-triazol-3-yl)pyridin-2-yl)-6-methoxy-1,2,3,4-tetrahydroisoquinoline-7-carboxamide dihydrochloride and the corresponding carboxylic acid according to the representative procedure for HATU coupling.

Example 130: Synthesis of 2-hydroxy-2-methylpropyl (R)-7-((6-(1-(1-hydroxypropan-2-yl)-1H-tetrazol-5-yl)pyridin-2-yl)carbamoyl)-6-methoxy-3,4-dihydroisoquinoline-2(1H)-carboxylate

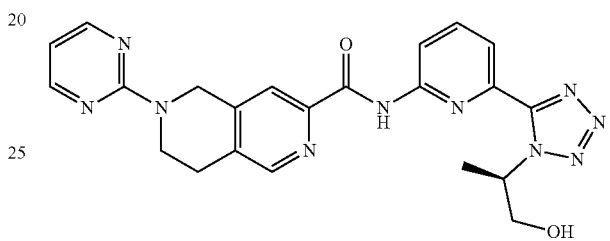

Representative procedure for the stepwise formation of carbamates and ureas.

Step 1: Synthesis of (R)—N-(6-(1-(1-(((tert-butyldimethylsilyl)oxy)propan-2-yl)-1H-tetrazol-5-yl)pyridin-2-yl)-2-(1H-imidazole-1-carbonyl)-6-methoxy-1,2,3,4-tetrahydroisoquinoline-7-carboxamide

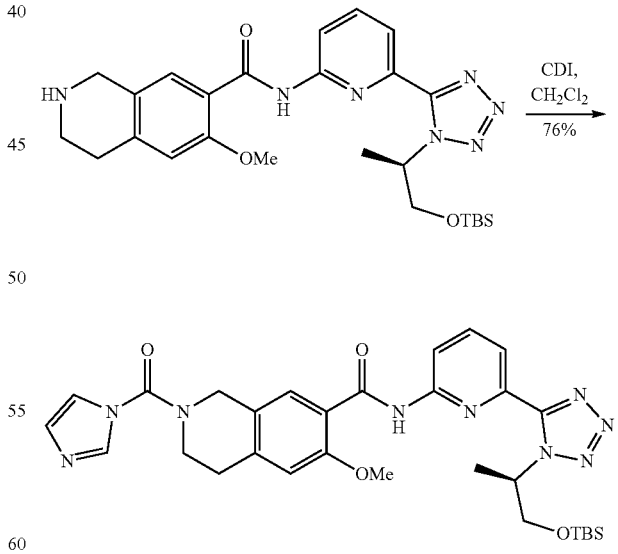

(R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide (50 mg, 0.095 mmol) was added to a solution of CDI (16.26 mg, 0.100 mmol) in DCM (199 µl) and the reaction stirred for 18 h. Added another 0.5 eq CDI (7.74 mg, 0.048 mmol) and stirred for 4 h at rt. The reaction was quenched with sat. NaHCO₃ and diluted with DCM. The layers were separated and the organic layer was washed with 10% citric acid/brine. The organic layer was dried (MgSO₄), filtered, and concentrated to give (R)—N-(6-(1-(1-(((tert-butyldimethylsilyl)oxy)propan-2-yl)-1H-tetrazol-5-yl)pyridin-2-yl)-2-(1H-imidazole-1-carbonyl)-6-methoxy-1,2,3,4-tetrahydroisoquinoline-7-carboxamide (44.7 mg, 0.072 mmol, 76% yield) as a pale yellow amorphous solid.

Step 2: Synthesis of 2-hydroxy-2-methylpropyl (R)-7-((6-(1-(1-(((tert-butyldimethylsilyl)oxy)propan-2-yl)-1H-tetrazol-5-yl)pyridin-2-yl)carbamoyl)-6-methoxy-3,4-dihydroisoquinoline-2(1H)-carboxylate

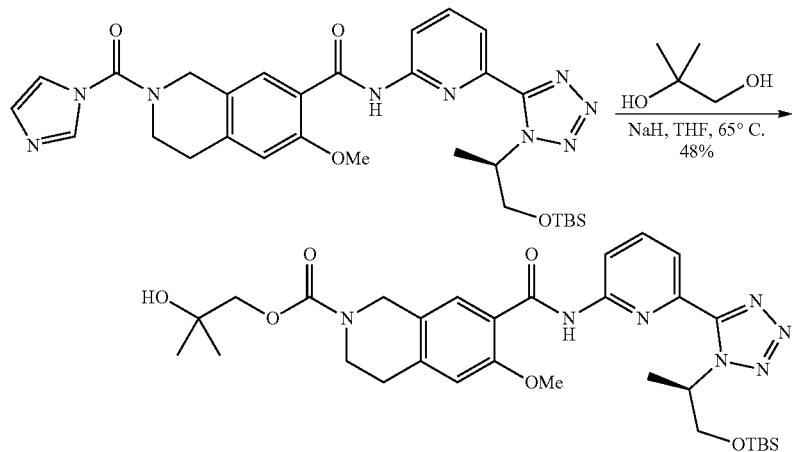

2-Methylpropane-1,2-diol (22.34 mg, 0.258 mmol) was added to a solution of (R)—N-(6-(1-(1-(((tert-butyldimethylsilyl)oxy)propan-2-yl)-1H-tetrazol-5-yl)pyridin-2-yl)-2-(1H-imidazole-1-carbonyl)-6-methoxy-1,2,3,4-tetrahydroisoquinoline-7-carboxamide (40 mg, 0.065 mmol). NaH (12.95 mg, 0.324 mmol) was added and reaction stirred at rt for 5 h. The reaction was quenched with sat. NH₄Cl and diluted with DCM. The layers were separated, and the aqueous layer was extracted with DCM (2×). The combined organic layers were dried (MgSO₄), filtered, and concentrated under reduced pressure. The resultant clear residue was purified by column chromatography eluting with DCM/MeOH (0% MeOH→5% MeOH) to give 2-hydroxy-2-methylpropyl (R)-7-((6-(1-(1-(((tert-butyldimethylsilyl)oxy)propan-2-yl)-1H-tetrazol-5-yl)pyridin-2-yl)carbamoyl)-6-methoxy-3,4-dihydroisoquinoline-2(1H)-carboxylate (19.7 mg, 0.031 mmol, 47.6% yield) as a colorless solid.

Step 3: Synthesis of 2-hydroxy-2-methylpropyl (R)-7-((6-(1-(1-hydroxypropan-2-yl)-1H-tetrazol-5-yl)pyridin-2-yl)carbamoyl)-6-methoxy-3,4-dihydroisoquinoline-2(1H)-carboxylate

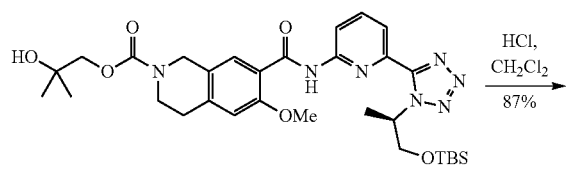

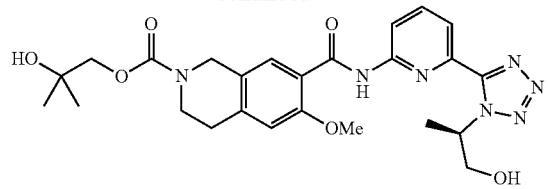

Concentrated HCl (25.7 μl, 0.308 mmol) was added to a solution of (R)-7-((6-(1-(1-(((tert-butyldimethylsilyl)oxy)propan-2-yl)-1H-tetrazol-5-yl)pyridin-2-yl)carbamoyl)-6-methoxy-3,4-dihydroisoquinoline-2(1H)-carboxylate (19.7 mg, 0.031 mmol) in CH₂Cl₂ (308 μl) and the reaction was stirred for 2.5 h at rt. The reaction was quenched with sat. NaHCO₃ and diluted with CH₂Cl₂. The layers were separated and aqueous layer was extracted with CH₂Cl₂ (2×). The combined organic layers were washed with 10% citric acid then brine, dried (MgSO₄), filtered, and concentrated to give 2-hydroxy-2-methylpropyl (R)-7-((6-(1-(1-hydroxypropan-2-yl)-1H-tetrazol-5-yl)pyridin-2-yl)carbamoyl)-6-methoxy-3,4-dihydroisoquinoline-2(1H)-carboxylate (14.1 mg, 0.027 mmol, 87% yield) as a colorless solid.

Example 131 was prepared from (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide and morpholine-4-carbonyl chloride according to the representative procedure for N-functionalization and TBS deprotection.

Example 132 was prepared from (R)—N-(6-(1-(1-(((tert-butyldimethylsilyl)oxy)propan-2-yl)-1H-tetrazol-5-yl)pyridin-2-yl)-6-methoxy-1,2,3,4-tetrahydroisoquinoline-7-carboxamide and 2-chloro-1-(pyrrolidin-1-yl)ethan-1-one according to the representative procedure for HATU coupling and TBS deprotection.

Example 133 was prepared from (R)—N-(6-(1-(1-(((tert-butyldimethylsilyl)oxy)propan-2-yl)-1H-tetrazol-5-yl)pyridin-2-yl)-6-fluoro-1,2,3,4-tetrahydroisoquinoline-7-carboxamide and picolinic acid according to the representative procedure for N-functionalization and TBS deprotection.

Example 139 was prepared from (R)—N-(6-(1-(1-(((tert-butyldimethylsilyl)oxy)propan-2-yl)-1H-tetrazol-5-yl)pyridin-2-yl)-5,6,7,8-tetrahydro-2,6-naphthyridine-3-carboxamide and morpholine-4-carbonyl chloride according to the representative procedure for N-functionalization and TBS deprotection.

Example 141 was prepared from (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide according to the representative procedure for the stepwise formation of carbamates and ureas.

Example 144: Synthesis of N-(6-(1-((R)-1-hydroxypropan-2-yl)-1H-tetrazol-5-yl)pyridin-2-yl)-2-((R)-3-hydroxypyrrolidine-1 carbonyl)-6-methoxy-1,2,3, 4-tetrahydroisoquinoline-7-carboxamide

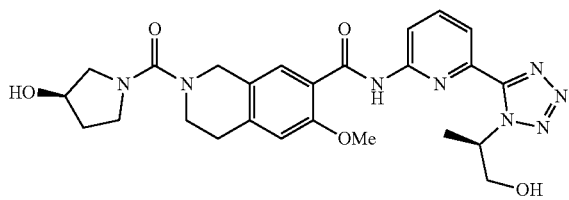 [SMILES: COc1cc2c(cc1C(=O)Nc1cccc(-c3nnnn3[C@H](C)CO)n1)CN(C(=O)N1CC[C@@H](O)C1)CC2]

Step 1: Synthesis of 4-nitrophenyl (1R)-3-((tert-butyldimethylsilyl) 1 oxy)pyrrolidine-1-carboxylate

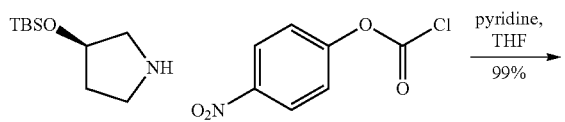

4-Nitrophenyl carbonochloridate (62.1 mg, 0.308 mmol) was added to a solution of (R)-3-((tert-butyldimethylsilyl)oxy)pyrrolidine (62 mg, 0.308 mmol) and pyridine (0.025 mL, 0.308 mmol) in THF (2.052 mL) and the reaction stirred for 1 h. The reaction was quenched with sat. NaHCO₃ and diluted with CH₂Cl₂. Layers separated and aqueous layer extracted with CH₂Cl₂ (2×). The combined organic layers were dried (MgSO₄), filtered, and concentrated to give 4-nitrophenyl (R)-3-((tert-butyldimethylsilyl)oxy)pyrrolidine-1-carboxylate (112 mg, 0.306 mmol, 99% yield).

Step 2: Synthesis of N-(6-(1-((R)-1-((tert-butyldimethylsilyl)oxy)propan-2-yl)-1H-tetrazol-5-yl)pyridin-2-yl)-2-((R)-3-((tert-butyldimethylsilyl)oxy)pyrrolidine-1-carbonyl)-6-methoxy-1,2,3,4-tetrahydroisoquinoline-7-carboxamide

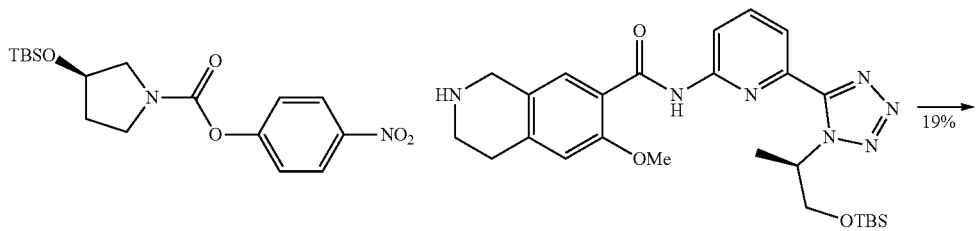

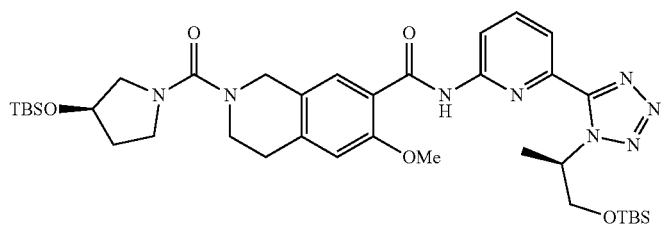

Hunig's base (0.040 mL, 0.229 mmol) was added to a solution of 4-nitrophenyl (R)-3-((tert-butyldimethylsilyl)oxy)pyrrolidine-1-carboxylate (42.0 mg, 0.115 mmol) and (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide (40 mg, 0.076 mmol) in DMF (0.196 mL) and the reaction heated at 100° C. for 24 h. The reaction was quenched with sat. NaHCO₃/brine and diluted with CH₂Cl₂. The layers were separated and the aqueous layer was extracted with CH₂Cl₂ (2×). The combined organic layers were dried (MgSO₄), filtered, and concentrated under reduced pressure. The resultant orange oil was purified by column chromatography eluting with hexanes/EtOAc (0% EtOAc→100% EtOAc) to give N-(6-(1-((R)-1-((tert-butyldimethylsilyl)oxy)propan-2-yl)-1H-tetrazol-5-yl)pyridin-2-yl)-2-((R)-3-((tert-butyldimethylsilyl)oxy)pyrrolidine-1-carbonyl)-6-methoxy-1,2,3,4-tetrahydroisoquinoline-7-carboxamide (11.1 mg, 0.015 mmol, 19.35% yield) as a colorless residue.

Step 2: Synthesis of N-(6-(1-((R)-1-hydroxypropan-2-yl)-1H-tetrazol-5-yl)pyridin-2-yl)-2-((R)-3-hydroxypyrrolidine-1-carbonyl)-6-methoxy-1,2,3,4-tetrahydroisoquinoline-7-carboxamide

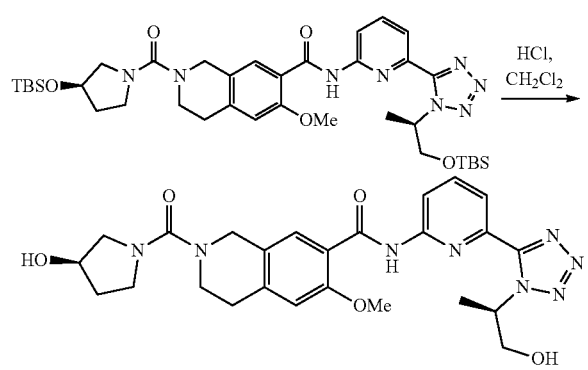

Concentrated HCl (30.8 µl, 0.369 mmol) was added to a solution of N-(6-(1-((R)-1-((tert-butyldimethylsilyl)oxy)propan-2-yl)-1H-tetrazol-5-yl)pyridin-2-yl)-2-((R)-3-((tert-butyldimethylsilyl)oxy)pyrrolidine-1-carbonyl)-6-methoxy-1,2,3,4-tetrahydroisoquinoline-7-carboxamide (11.1 mg, 0.015 mmol) in CH₂Cl₂ (0.148 mL) and the reaction stirred for 4 h. The reaction was carefully quenched with sat. NaHCO₃ and diluted with CH₂Cl₂. The layers were separated and the aqueous layer was extracted with CH₂Cl₂ (2×). The combined organic layers were dried (MgSO₄), filtered, and concentrated under reduced pressure. The resultant colorless residue was purified by column chromatography eluting with CH₂Cl₂/MeOH (0% MeOH→10% MeOH) to give N-(6-(1-((R)-1-hydroxypropan-2-yl)-1H-tetrazol-5-yl)pyridin-2-yl)-2-((R)-3-hydroxypyrrolidine-1-carbonyl)-6-methoxy-1,2,3,4-tetrahydroisoquinoline-7-carboxamide (5.6 mg, 10.72 µmol, 72.5% yield) as a colorless residue.

Example 147 was prepared from (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide according to the representative procedure for the stepwise formation of carbamates and ureas.

Example 150: Synthesis of (R)—N-(6-(1-(1-hydroxypropan-2-yl)-1H-tetrazol-5-yl)pyridin-2-yl)-6-methoxy-2-(pyridin-3-yl)-1,2,3,4-tetrahydroisoquinoline-7-carboxamide

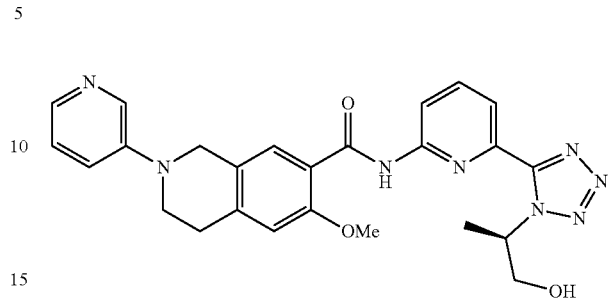

Step 1: Synthesis of methyl 6-methoxy-1,2,3,4-tetrahydroisoquinoline-7-carboxylate

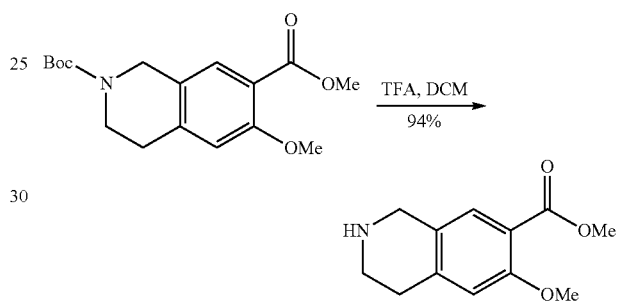

TFA (4.32 mL) was added to a solution of 2-(tert-butyl) 7-methyl 6-methoxy-3,4-dihydroisoquinoline-2,7(1H)-dicarboxylate (1.0 g, 3.11 mmol) in DCM (8.64 mL) at 0° C. The reaction was stirred at 0° C. for 30 min. The cold bath was removed and the reaction stirred for 4 h. The reaction was concentrated to remove solvents methyl 6-methoxy-1,2,3,4-tetrahydroisoquinoline-7-carboxylate (646 mg, 2.92 mmol, 94% yield) was isolated as a pale yellow solid.

Step 2: Synthesis of methyl 6-methoxy-2-(pyridin-3-yl)-1,2,3,4-tetrahydroisoquinoline-7-carboxylate

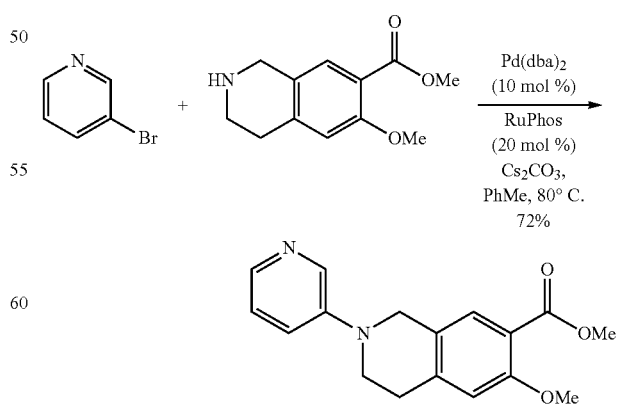

Methyl 6-methoxy-1,2,3,4-tetrahydroisoquinoline-7-carboxylate (40 mg, 0.181 mmol), Pd(dba)₂ (10.40 mg, 0.018 mmol), RuPhos (16.87 mg, 0.036 mmol), and Cs2CO (118 mg, 0.362 mmol) were combined in a vial. The vial was evacuated and backfilled with N₂. Toluene (0.822 ml) and 3-bromopyridine (31.4 mg, 0.199 mmol) were added and the reaction was heated at 80° C. for 24 h. The reaction was filtered through celite, rinsing with DCM. Concentrated to give an orange gum. Purified by column chromatography eluting with CH₂Cl₂/MeOH (0% MeOH→5% MeOH, 4 g column) to give methyl 6-methoxy-2-(pyridin-3-yl)-1,2,3,4-tetrahydroisoquinoline-7-carboxylate (38.9 mg, 0.130 mmol, 72.1% yield) as a yellow gum.

Example 150 was completed according to the representative procedure for amide formation with trimethylaluminum and deprotection by HCl.

Example 151: Synthesis of N-(6-(4-isopropyl-4H-1,2,4-triazol-3-yl)pyridin-2-yl)-6-methoxy-2-(pyrimidin-5-yl)-1,2,3,4-tetrahydroisoquinoline-7-carboxamide

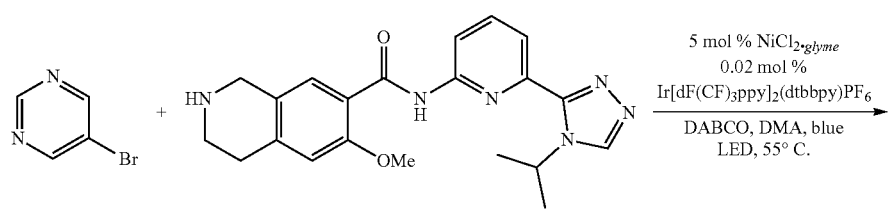

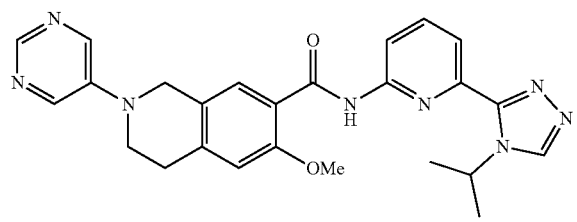

A solution of Ir[dF (CF₃)ppy]₂(dtbbpy)PF₆ (3.77 μl, 0.019 μmol) and a solution of NiCl₂-glyme (189 μl, 4.72 μmol) were added to a suspension of N-(6-(4-isopropyl-4H-1,2,4-triazol-3-yl)pyridin-2-yl)-6-methoxy-1,2,3,4-tetrahydroisoquinoline-7-carboxamide (48.1 mg, 0.123 mmol), 5-bromopyrimidine (15 mg, 0.094 mmol), and DABCO (19.05 mg, 0.170 mmol) in DMA (0.189 ml). The reaction was de-gassed by a freeze-pump-thaw cycle (3×). The vial was sealed with parafilm and irradiated with a blue LED overnight (about 6 cm away). The reaction was quenched with sat. NaHCO₃ and diluted with brine and CH₂Cl₂. Layers separated and aqueous layer extracted with CH₂Cl₂ (2×). Combined organic layers washed with brine, dried (MgSO₄), filtered, and concentrated to give a yellow solid. Purified by column chromatography eluting with CH₂Cl₂/MeOH (0% MeOH→5% MeOH, 12 g gold column) to give N-(6-(4-isopropyl-4H-1,2,4-triazol-3-yl)pyridin-2-yl)-6-methoxy-2-(pyrimidin-5-yl)-1,2,3,4-tetrahydroisoquinoline-7-carboxamide (7.0 mg, 0.094 mmol, 16% yield).

Example 152: Synthesis of (R)-2-(5-fluoropyrimidin-2-yl)-N-(6-(1-(1-hydroxypropan-2-yl)-1H-tetrazol-5-yl)pyridin-2-yl)-6-methoxy-1,2,3,4-tetrahydroisoquinoline-7-carboxamide

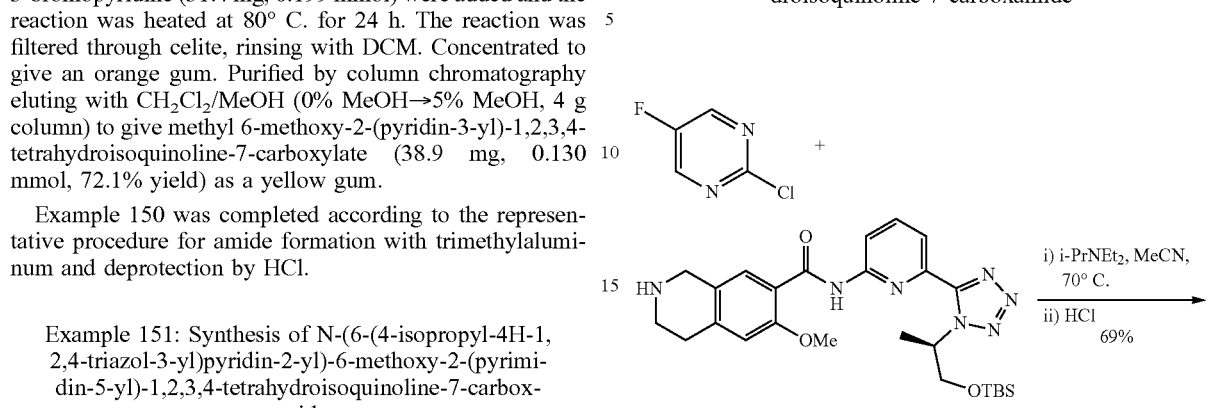

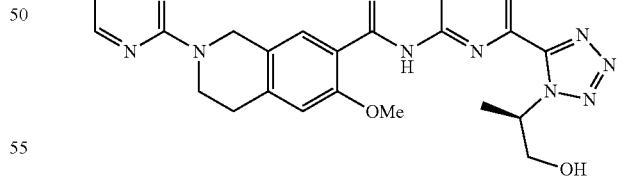

Hunig's base (78 μl, 0.447 mmol) was added to a solution of (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide (52 mg, 0.099 mmol) and 2-chloro-5-fluoropyrimidine (52.6 μl, 0.397 mmol) in MeCN (0.993 ml) and the reaction heated at 70° C. overnight. The reaction was cooled to rt and concentrated HCl (207 μl, 2.482 mmol) was added and the reaction stirred for 1 h. The reaction was quenched carefully with sat. NaHCO₃ and diluted with CH₂Cl₂. Layers separated and aqueous layer extracted with CH₂Cl₂ (2×). Combined organic layers dried (MgSO₄), filtered, and concentrated to give a pale yellow solid. Purified by column chromatography eluting with CH₂Cl₂/MeOH (0% MeOH→3% MeOH, 4 g column) to give (R)-2-(5-fluoropyrimidin-2-yl)-N-(6-(1-(1-hydroxypropan-2-yl)-1H-tetrazol-5-yl)pyridin-2-yl)-6-methoxy-1,2,3,4-tetrahydroisoquinoline-7-carboxamide (34.5 mg, 0.068 mmol, 68.7% yield) as a colorless solid.

Example 153 was prepared from (R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide and 5-bromo-1,2,4-thiadiazole following the procedure for the preparation of example 152.

Example 154: Synthesis of (R)-2-(5-fluoropyrazine-2-yl)-N-(6-(1-(1-hydroxypropan-2-yl)-1H-tetrazol-5-yl)pyridin-2-yl)-6-methoxy-1,2,3,4-tetrahydroisoquinoline-7-carboxamide

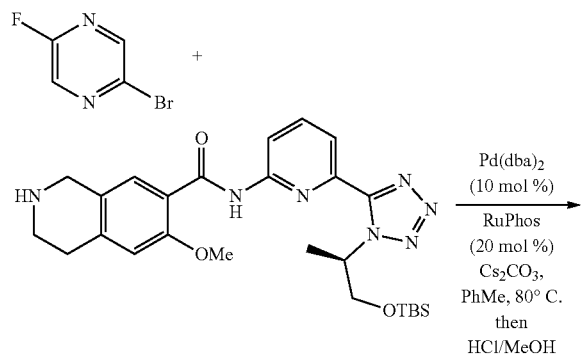

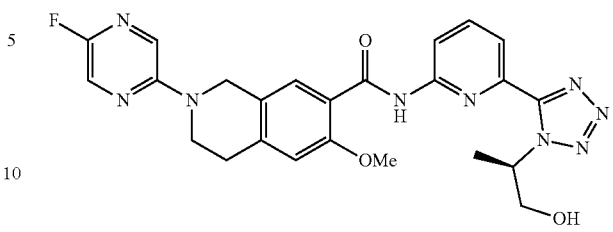

(R)—N-(6-(1-(1-((tert-butyldimethylsilyl)oxy)propan-2-yl)-1H-tetrazol-5-yl)pyridin-2-yl)-6-methoxy-1,2,3,4-tetrahydroisoquinoline-7-carboxamide (97 mg, 0.185 mmol), 2-bromo-5-fluoropyrazine (49.2 mg, 0.278 mmol), RuPhos (17.29 mg, 0.037 mmol), Pd(dba)₂ (10.65 mg, 0.019 mmol) and Cs₂CO₃ (121 mg, 0.370 mmol) were combined in a vial. Toluene (0.842 ml) was added and the mixture was evacuated and back-filled with N2 three times. Heated under N₂ at 80° C. overnight. The reaction was filtered through celite, rinsing with EtOAc. The filtrate was concentrated to give an orange gum. The crude sample was treated with conc. HCl/MeOH (1:10, 3 mL) at rt until the TBS group was cleaved. After concentration, the crude sample was purified by preparative HPLC (10% ACN/water to 90% ACN/water in ~40 min with 0.1% FA buffer) to give (R)-2-(5-fluoropyrazine-2-yl)-N-(6-(1-(1-hydroxypropan-2-yl)-1H-tetrazol-5-yl)pyridin-2-yl)-6-methoxy-1,2,3,4-tetrahydroisoquinoline-7-carboxamide (6 mg, 0.012 mmol, 6% yield).

Characterization data for examples are shown in Table 6.

TABLE 6

| Example | Structure | LC-MS [M + H]⁺ unless otherwise noted | ¹H-NMR |
|---|---|---|---|
| 1 | 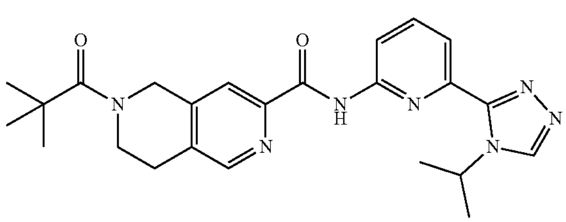 [SMILES: CC(C)n1cnnc1-c1cccc(NC(=O)c2cc3c(cn2)CCN(C(=O)C(C)(C)C)C3)n1] | 448 | ¹H NMR (400 MHz, Chloroform-d) δ 10.42 (s, 1H), 8.54-8.46 (m, 2H), 8.44 (s, 1H), 8.12 (s, 1H), 8.07 (d, J = 7.6 Hz, 1H), 7.95 (t, J = 7.9 Hz, 1H), 5.64 (m, 1H), 4.91 (s, 2H), 3.96 (t, J = 5.7 Hz, 2H), 3.01 (t, J = 5.8 Hz, 2H), 1.63 (d, J = 6.6 Hz, 6H), 1.36 (s, 9H), 0.09 (s, 2H) |
| 2 | 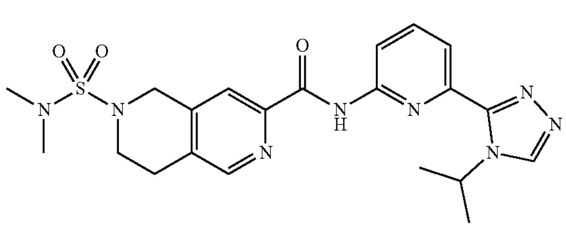 [SMILES: CC(C)n1cnnc1-c1cccc(NC(=O)c2cc3c(cn2)CCN(S(=O)(=O)N(C)C)C3)n1] | 471 | ¹H NMR (400 MHz, Chloroform-d) δ 10.41 (s, 1H), 8.55-8.47 (m, 3H), 8.07 (d, J = 8.7 Hz, 2H), 7.96 (t, J = 8.0 Hz, 1H), 5.65 (m, 1H), 4.55 (s, 2H), 3.65 (t, J = 5.8 Hz, 2H), 3.08 (t, J = 5.7 Hz, 2H), 2.90 (s, 6H), 1.64 (d, J = 6.7 Hz, 6H) |

TABLE 6-continued

| Example | Structure | LC-MS [M + H]+ unless otherwise noted | ¹H-NMR |
|---|---|---|---|
| 3 | 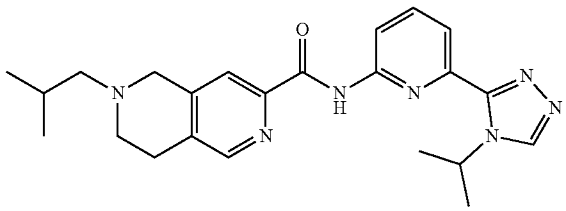 [SMILES: CC(C)CN1CCc2cnc(C(=O)Nc3cccc(-c4nncn4C(C)C)n3)cc2C1] | 420 | ¹H NMR (400 MHz, Chloroform-d) δ 10.44 (s, 1H), 8.50 (d, J = 8.3 Hz, 1H), 8.41 (d, J = 14.8 Hz, 2H), 8.08-8.00 (m, 2H), 7.94 (t, J = 8.0 Hz, 1H), 5.64 (m, 1H), 3.77 (s, 2H), 3.04 (s, 2H), 2.86 (s, 2H), 2.40 (s, 2H), 1.98 (m, 1H), 1.62 (d, J = 6.7 Hz, 6H), 1.00 (d, J = 6.5 Hz, 6H) |
| 4 | 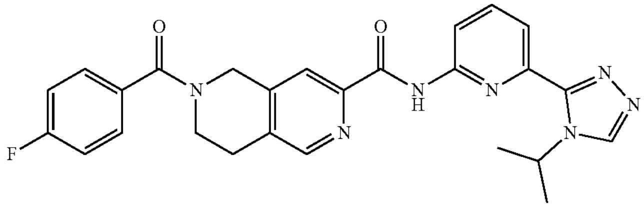 [SMILES: CC(C)n1cnnc1-c1cccc(NC(=O)c2cc3c(cn2)CCN(C(=O)c2ccc(F)cc2)C3)n1] | 486 | ¹H NMR (400 MHz, Chloroform-d) δ 10.41 (s, 1H), 8.61-8.51 (m, 3H), 8.08 (d, J = 7.6 Hz, 2H), 7.96 (t, J = 8.0 Hz, 1H), 7.56-7.48 (m, 2H), 7.18 (t, J = 8.6 Hz, 2H), 5.65 (m, 1H), 4.96 (brs, 2H), 3.83 (brs, 2H), 3.06 (s, 2H), 1.64 (d, J = 6.7 Hz, 6H) |
| 5 | 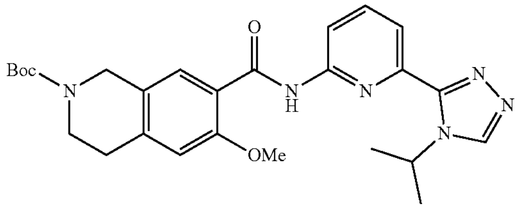 [SMILES: COc1cc2c(cc1C(=O)Nc1cccc(-c3nncn3C(C)C)n1)CN(C(=O)OC(C)(C)C)CC2] | 493 | ¹H NMR (400 MHz, DMSO-d₆) δ 10.60 (s, 1H), 8.90 (s, 1H), 8.32 (dd, J = 8.3, 0.9 Hz, 1H), 8.03 (t, J = 8.0 Hz, 1H), 7.87 (dd, J = 7.7, 0.9 Hz, 1H), 7.74 (s, 1H), 7.09 (s, 1H), 5.50 (p, J = 6.7 Hz, 1H), 4.51 (s, 2H), 3.97 (s, 3H), 3.57 (t, J = 5.9 Hz, 2H), 2.86 (t, J = 5.8 Hz, 2H), 1.52 (d, J = 6.7 Hz, 6H), 1.43 (s, 9H) |
| 6 | 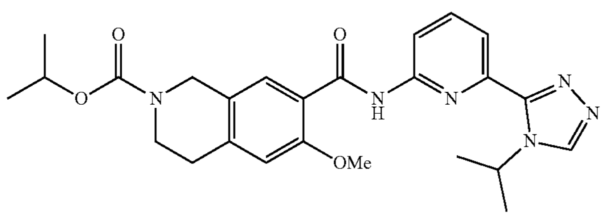 [SMILES: COc1cc2c(cc1C(=O)Nc1cccc(-c3nncn3C(C)C)n1)CN(C(=O)OC(C)C)CC2] | 479 | ¹H NMR (500 MHz, DMSO-d₆) δ 10.60 (s, 1H), 8.89 (s, 1H), 8.32 (d, J = 8.3 Hz, 1H), 8.03 (t, J = 8.0 Hz, 1H), 7.87 (dd, J = 7.6, 0.9 Hz, 1H), 7.75 (s, 1H), 7.10 (s, 1H), 5.51 (h, J = 6.8 Hz, 1H), 4.82 (hept, J = 6.3 Hz, 1H), 4.54 (s, 2H), 3.97 (s, 3H), 3.60 (t, J = 5.9 Hz, 2H), 2.87 (t, J = 5.9 Hz, 2H), 1.52 (d, J = 6.7 Hz, 6H), 1.22 (d, J = 6.2 Hz, 6H) |
| 7 | 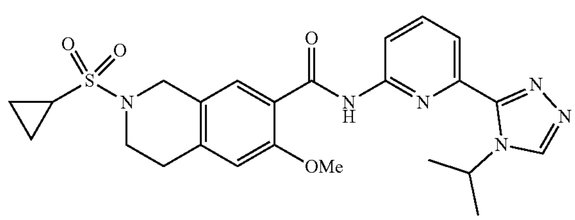 [SMILES: COc1cc2c(cc1C(=O)Nc1cccc(-c3nncn3C(C)C)n1)CN(S(=O)(=O)C1CC1)CC2] | 497 | ¹H NMR (400 MHz, DMSO-d₆) δ 10.61 (s, 1H), 8.91 (s, 1H), 8.33 (d, J = 8.3 Hz, 1H), 8.04 (t, J = 8.0 Hz, 1H), 7.88 (d, J = 7.6 Hz, 1H), 7.79 (s, 1H), 7.12 (s, 1H), 5.51 (m, 1H), 4.46 (s, 2H), 3.98 (s, 3H), 3.53 (t, J = 6.0 Hz, 2H), 3.00 (t, J = 6.0 Hz, 2H), 2.65 (m, 1H), 1.53 (d, J = 6.7 Hz, 6H), 1.03-0.92 (m, 4H) |
| 8 | 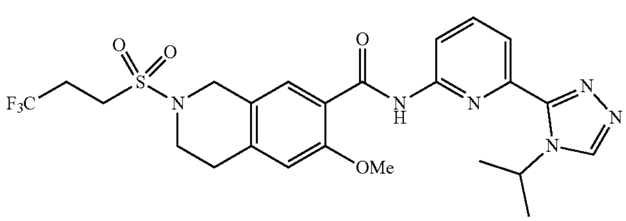 [SMILES: COc1cc2c(cc1C(=O)Nc1cccc(-c3nncn3C(C)C)n1)CN(S(=O)(=O)CCC(F)(F)F)CC2] | 553 | ¹H NMR (400 MHz, DMSO-d₆) δ 10.61 (s, 1H), 8.91 (d, J = 1.4 Hz, 1H), 8.33 (d, J = 8.3 Hz, 1H), 8.04 (t, J = 8.0 Hz, 1H), 7.88 (d, J = 7.6 Hz, 1H), 7.76 (s, 1H), 7.12 (s, 1H), 5.51 (m, 1H), 4.50 (s, 2H), 3.98 (s, 3H), 3.57 (t, J = 6.0 Hz, 2H), 3.44 (d, J = 16.2 Hz, 2H), 2.99 (t, J = 5.9 Hz, 2H), 2.74 (m, 2H), 1.53 (d, J = 6.7 Hz, 6H) |

TABLE 6-continued

| Example | Structure | LC-MS [M + H]+ unless otherwise noted | 1H-NMR |
|---|---|---|---|
| 9 | 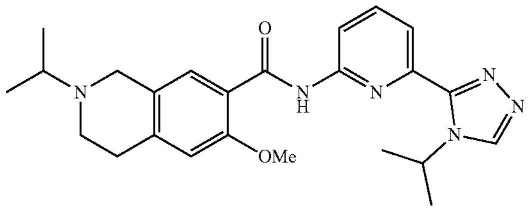 [SMILES: COc1cc2c(cc1C(=O)Nc1cccc(-c3nncn3C(C)C)n1)CN(C(C)C)CC2] | 435 | 1H NMR (400 MHz, DMSO-d6) δ 10.60 (s, 1H), 8.91 (s, 1H), 8.33 (d, J = 8.3 Hz, 1H), 8.03 (t, J = 8.0 Hz, 1H), 7.87 (dd, J = 7.7, 0.9 Hz, 1H), 7.70 (s, 1H), 7.01 (s, 1H), 5.49 (m, 1H), 3.97 (s, 3H), 3.66 (s, 2H), 2.83-2.92 (m, 3H), 2.72 (s, 2H), 1.54 (d, J = 6.7 Hz, 6H), 1.08 (d, J = 6.4 Hz, 6H) |
| 10 | 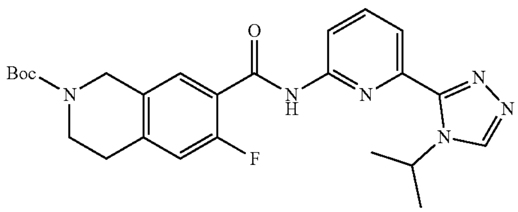 [SMILES: CC(C)n1cnnc1-c1cccc(NC(=O)c2cc3c(cc2F)CCN(C(=O)OC(C)(C)C)C3)n1] | 481 | 1H NMR (500 MHz, DMSO-d6) δ 10.78 (s, 1H), 8.86 (s, 1H), 8.20 (dd, J = 8.4, 0.9 Hz, 1H), 8.02 (t, J = 8.0 Hz, 1H), 7.89 (dd, J = 7.6, 0.9 Hz, 1H), 7.57 (d, J = 7.1 Hz, 1H), 7.21 (d, J = 10.8 Hz, 1H), 5.66 (p, J = 6.7 Hz, 1H), 4.54 (s, 2H), 3.56 (t, J = 5.9 Hz, 2H), 2.85 (t, J = 5.9 Hz, 2H), 1.43-1.42 (comp, 15H) |
| 11 | 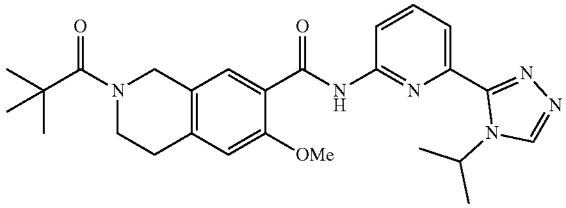 [SMILES: COc1cc2c(cc1C(=O)Nc1cccc(-c3nncn3C(C)C)n1)CN(C(=O)C(C)(C)C)CC2] | 477 | 1H NMR (400 MHz, Chloroform-d) δ 10.44 (s, 1H), 8.50 (d, J = 8.0 Hz, 1H), 8.40 (s, 1H), 8.10 (s, 1H), 8.03 (d, J = 7.7 Hz, 1H), 7.92 (t, J = 8.0 Hz, 1H), 6.84 (s, 1H), 5.56 (m, 1H), 4.82 (s, 2H), 4.06 (s, 3H), 3.90 (t, J = 5.9 Hz, 2H), 2.96 (t, J = 5.9 Hz, 2H), 1.65 (d, J = 6.7 Hz, 6H), 1.34 (s, 9H) |
| 12 | 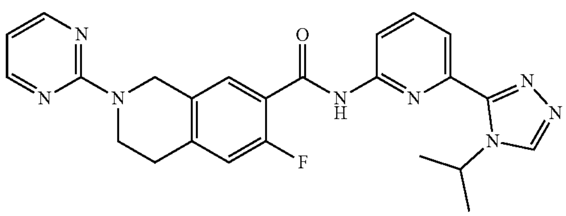 [SMILES: CC(C)n1cnnc1-c1cccc(NC(=O)c2cc3c(cc2F)CCN(c2ncccn2)C3)n1] | 459 | 1H NMR (400 MHz, Chloroform-d) δ 9.09 (d, J = 16.4 Hz, 1H), 8.44 (d, J = 8.3 Hz, 1H), 8.41-8.34 (comp, 3H), 8.06 (d, J = 7.6 Hz, 2H), 7.92 (t, J = 8.0 Hz, 1H), 7.03 (d, J = 12.7 Hz, 1H), 6.55 (t, J = 4.8 Hz, 1H), 5.51 (p, J = 6.7 Hz, 1H), 4.99 (s, 2H), 4.10 (t, J = 5.9 Hz, 2H), 3.00 (t, J = 5.9 Hz, 2H), 1.59 (d, J = 6.8 Hz, 6H) |
| 13 | 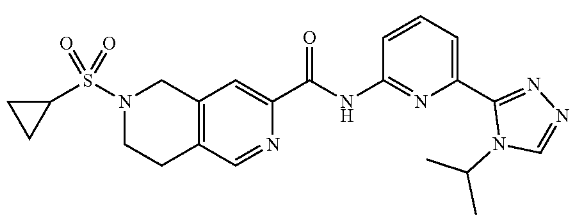 [SMILES: CC(C)n1cnnc1-c1cccc(NC(=O)c2cc3c(cn2)CCN(S(=O)(=O)C2CC2)C3)n1] | 468 | 1H NMR (400 MHz, Chloroform-d) δ 10.41 (s, 1H), 8.67 (s, 1H), 8.56-8.49 (m, 2H), 8.08 (d, J = 11.8 Hz, 2H), 7.97 (t, J = 7.7 Hz, 1H), 5.68 (s, 1H), 4.65 (s, 2H), 3.72 (t, J = 5.8 Hz, 2H), 3.12 (t, J = 5.9 Hz, 2H), 2.38 (m, 1H), 1.65 (d, J = 6.0 Hz, 6H), 1.29 (d, J = 5.4 Hz, 2H), 1.07 (t, J = 6.8 Hz, 2H) |
| 14 | 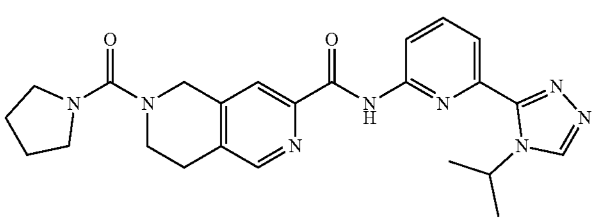 [SMILES: CC(C)n1cnnc1-c1cccc(NC(=O)c2cc3c(cn2)CCN(C(=O)N2CCCC2)C3)n1] | 461 | 1H NMR (400 MHz, Chloroform-d) δ 10.43 (s, 1H), 8.52-8.46 (m, 3H), 8.07 (m, 2H), 7.95 (t, J = 8.0 Hz, 1H), 5.65 (m, 1H), 4.59 (s, 2H), 3.62 (t, J = 5.7 Hz, 2H), 3.48-3.45 (m, 4H), 3.03 (t, J = 5.6 Hz, 2H), 1.94-1.87 (m, 4H), 1.63 (d, J = 6.8 Hz, 6H) |

TABLE 6-continued

| Example | Structure | LC-MS [M + H]+ unless otherwise noted | ¹H-NMR |
|---|---|---|---|
| 15 | 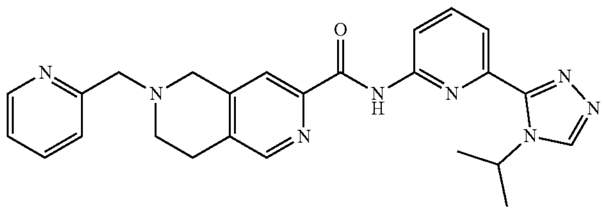 [SMILES: CC(C)n1cnnc1-c1cccc(NC(=O)c2cc3c(cn2)CCN(Cc2ccccn2)C3)n1] | 455 | ¹H NMR (400 MHz, Chloroform-d) δ 10.43 (s, 1H), 8.64 (d, J = 5.0 Hz, 1H), 8.49 (d, J = 8.2 Hz, 2H), 8.45 (s, 1H), 8.40 (s, 1H), 8.05 (d, J = 7.6 Hz, 2H), 7.99 (s, 1H), 7.93 (t, J = 8.0 Hz, 1H), 7.75 (t, J = 7.6 Hz, 1H), 5.64 (m, 1H), 3.99 (s, 2H), 3.91 (s, 2H), 3.09 (s, 2H), 2.99 (s, 2H), 1.62 (d, J = 6.7 Hz, 6H) |
| 16 | 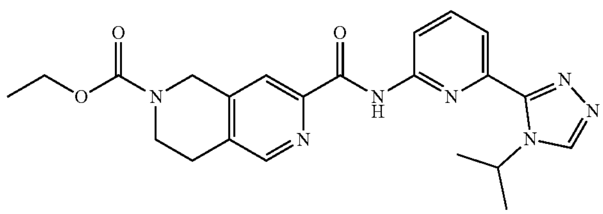 [SMILES: CCOC(=O)N1CCc2cnc(C(=O)Nc3cccc(-c4nncn4C(C)C)n3)cc2C1] | 436 | ¹H NMR (400 MHz, Chloroform-d) δ 10.43 (s, 1H), 8.55-8.46 (m, 3H), 8.11(s, 1H), 8.06 (d, J = 7.6 Hz, 1H), 7.96 (t, J = 8.0 Hz, 1H), 5.65 (m, 1H), 4.78 (s, 2H), 4.24 (q, J = 7.1 Hz, 2H), 3.82 (d, J = 5.6 Hz, 2H), 2.98 (t, J = 5.6 Hz, 2H), 1.63 (d, J = 6.7 Hz, 6H), 1.34 (t, J = 7.1 Hz, 3H) |
| 17 | 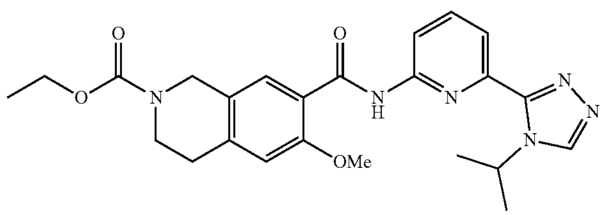 [SMILES: CCOC(=O)N1CCc2cc(OC)c(C(=O)Nc3cccc(-c4nncn4C(C)C)n3)cc2C1] | 465 | ¹H NMR (500 MHz, DMSO-d₆) δ 10.60 (s, 1H), 8.89 (s, 1H), 8.32 (d, J = 8.3 Hz, 1H), 8.03 (t, J = 8.0 Hz, 1H), 7.87 (d, J = 7.6 Hz, 1H), 7.75 (s, 1H), 7.10 (s, 1H), 5.50 (p, J = 6.7 Hz, 1H), 4.56 (s, 2H), 4.09 (q, J = 7.1 Hz, 2H), 3.97 (s, 3H), 3.61 (t, J = 6.0 Hz, 2H), 2.88 (t, J = 6.0 Hz, 2H), 1.52 (d, J = 6.7 Hz, 6H), 1.21 (t, J = 7.1 Hz, 3H) |
| 18 | 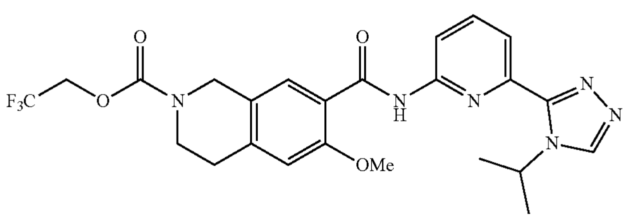 [SMILES: COc1cc2c(cc1C(=O)Nc1cccc(-c3nncn3C(C)C)n1)CN(C(=O)OCC(F)(F)F)CC2] | 519 | ¹H NMR (500 MHz, DMSO-d₆) δ 10.60 (s, 1H), 8.89 (s, 1H), 8.32 (d, J = 8.7 Hz, 1H), 8.03 (t, J = 8.0 Hz, 1H), 7.87 (dd, J = 7.6, 0.9 Hz, 1H), 7.78 (s, 1H), 7.12 (s, 1H), 5.50 (hept, J = 6.8 Hz, 1H), 4.76 (q, J = 9.1 Hz, 2H), 4.66-4.56 (m, 2H), 3.97 (s, 3H), 3.71-3.59 (m, 2H), 2.92 (t, J = 6.0 Hz, 2H), 1.52 (d, J = 6.7 Hz, 6H) |
| 19 | 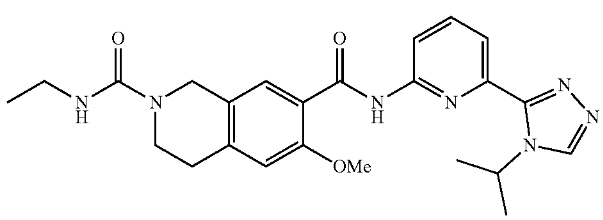 [SMILES: CCNC(=O)N1CCc2cc(OC)c(C(=O)Nc3cccc(-c4nncn4C(C)C)n3)cc2C1] | 464 | ¹H NMR (400 MHz, DMSO-d₆) δ 10.62 (s, 1H), 8.91 (s, 1H), 8.34 (d, J = 8.3 Hz, 1H), 8.04 (t, J = 8.0 Hz, 1H), 7.88 (d, J = 7.6 Hz, 1H), 7.72 (s, 1H), 7.10 (s, 1H), 6.57 (t, J = 5.4 Hz, 1H), 5.50 (m, 1H), 4.49 (s, 2H), 3.98 (s, 3H), 3.57 (t, J = 6.0 Hz, 2H), 3.14-3.03 (m, 2H), 2.85 (t, J = 5.8 Hz, 2H), 1.53 (d, J = 6.7 Hz, 6H), 1.03 (t, J = 7.1 Hz, 3H) |

TABLE 6-continued

| Example | Structure | LC-MS [M + H]+ unless otherwise noted | ¹H-NMR |
|---|---|---|---|
| 20 | 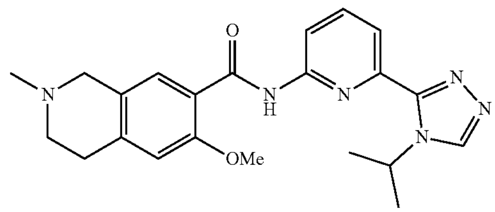 | 407 | ¹H NMR (400 MHz, DMSO-$d_6$) δ 10.60 (s, 1H), 8.91 (s, 1H), 8.33 (d, J = 8.3 Hz, 1H), 8.04 (t, J = 8.0 Hz, 1H), 7.87 (d, J = 7.6 Hz, 1H), 7.68 (s, 1H), 7.05 (s, 1H), 5.50 (m, 1H), 3.98 (s, 3H), 3.58 (s, 2H), 2.93 (t, J = 5.9 Hz, 2H), 2.69 (t, J = 5.9 Hz, 2H), 2.41 (s, 3H), 1.53 (d, J = 6.7 Hz, 6H) |
| 21 | 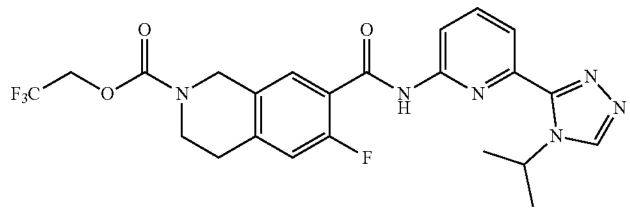 [SMILES: CC(C)n1cnnc1-c1cccc(NC(=O)c2cc3c(cc2F)CCN(C(=O)OCC(F)(F)F)C3)n1] | 507 | ¹H NMR (400 MHz, DMSO-$d_6$) δ 10.81 (s, 1H), 8.86 (s, 1H), 8.20 (dd, J = 8.3, 1.0 Hz, 1H), 8.03 (dd, J = 8.3, 7.6 Hz, 1H), 7.89 (dd, J = 7.6, 0.9 Hz, 1H), 7.63 (d, J = 7.0 Hz, 1H), 7.25 (d, J = 10.8 Hz, 1H), 5.66 (p, J = 6.7 Hz, 1H), 4.77 (q, J = 9.1 Hz, 2H), 4.64 (d, J = 13.2 Hz, 2H), 3.73-3.61 (m, 7H), 2.91 (t, J = 5.9 Hz, 2H), 1.42 (d, J = 6.7 Hz, 6H) |
| 22 | 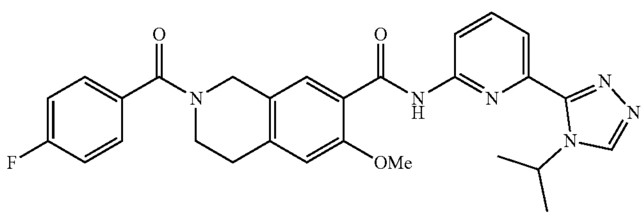 [SMILES: COc1cc2c(cc1C(=O)Nc1cccc(-c3nncn3C(C)C)n1)CN(C(=O)c1ccc(F)cc1)CC2] | 515 | ¹H NMR (400 MHz, Chloroform-d) δ 10.41 (s, 1H), 8.48 (s, 1H), 8.40 (s, 1H), 8.14 (s, 1H), 8.02 (d, J = 7.6 Hz, 1H), 7.92 (t, J = 8.2 Hz, 1H), 7.50 (t, J = 6.9 Hz, 2H), 7.16 (t, J = 8.5 Hz, 2H), 6.87 (s, 1H), 5.55 (m, 1H), 4.89 (m, 2H), 4.07 (s, 3H), 3.74 (s, 2H), 3.03 (s, 2H), 1.65 (d, J = 6.8 Hz, 6H) |
| 23 | 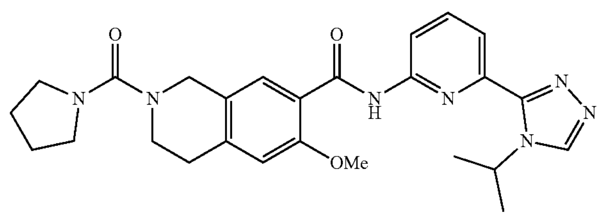 [SMILES: COc1cc2c(cc1C(=O)Nc1cccc(-c3nncn3C(C)C)n1)CN(C(=O)N1CCCC1)CC2] | 490 | ¹H NMR (400 MHz, Chloroform-d) δ 10.45 (s, 1H), 8.51 (d, J = 8.2 Hz, 1H), 8.45 (s, 1H), 8.08-8.00 (m, 2H), 7.92 (t, J = 8.0 Hz, 1H), 6.83 (s, 1H), 5.58 (m, 1H), 4.51 (s, 2H), 4.05 (s, 3H), 3.59 (t, J = 5.8 Hz, 2H), 3.45 (t, J = 6.4 Hz, 4H), 2.99 (t, J = 5.7 Hz, 2H), 1.89 (t, J = 6.4 Hz, 4H), 1.66 (d, J = 6.7 Hz, 6H) |
| 24 | 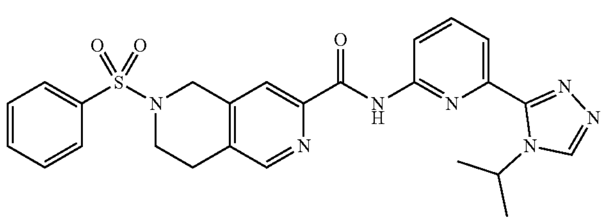 [SMILES: CC(C)n1cnnc1-c1cccc(NC(=O)c2cc3c(cn2)CCN(S(=O)(=O)c2ccccc2)C3)n1] | 504 | |
| 25 | 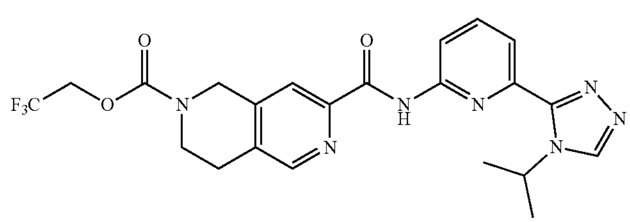 [SMILES: CC(C)n1cnnc1-c1cccc(NC(=O)c2cc3c(cn2)CCN(C(=O)OCC(F)(F)F)C3)n1] | 490 | ¹H NMR (400 MHz, DMSO-$d_6$) δ 10.59 (s, 1H), 8.90 (s, 1H), 8.60 (s, 1H), 8.32 (dd, J = 8.3, 0.9 Hz, 1H), 8.14 (s, 1H), 8.08 (t, J = 8.0 Hz, 1H), 7.88 (dd, J = 7.7, 0.9 Hz, 1H), 5.49 (p, J = 6.7 Hz, 1H), 4.92-4.72 (comp, 4H), 3.73 (s, 2H), 2.97 (t, J = 5.9 Hz, 2H), 1.50 (d, J = 6.8 Hz, 6H) |

TABLE 6-continued

| Example | Structure | LC-MS [M + H]+ unless otherwise noted | 1H-NMR |
|---------|-----------|---------------------------------------|--------|
| 26 | 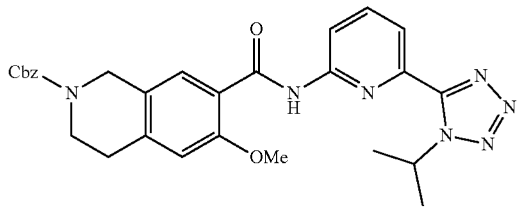 [SMILES: COc1cc2c(cc1C(=O)Nc1cccc(-c3nnnn3C(C)C)n1)CN(C(=O)OCc1ccccc1)CC2] | 528 | 1H NMR (400 MHz, DMSO-d6) δ 10.72 (s, 1H), 8.42 (d, J = 8.3 Hz, 1H), 8.13 (t, J = 8.0 Hz, 1H), 7.96 (dd, J = 7.6, 0.9 Hz, 1H), 7.73 (s, 1H), 7.44-7.28 (comp, 5H), 7.10 (s, 1H), 5.85 (p, J = 6.7 Hz, 1H), 5.14 (s, 2H), 4.60 (d, J = 20.1 Hz, 2H), 3.96 (s, 3H), 3.65 (s, 2H), 2.90 (t, J = 6.0 Hz, 2H), 1.61 (d, J = 6.6 Hz, 6H) |
| 27 | 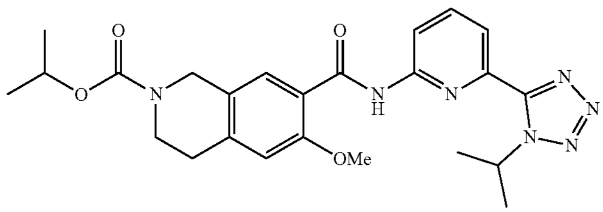 [SMILES: COc1cc2c(cc1C(=O)Nc1cccc(-c3nnnn3C(C)C)n1)CN(C(=O)OC(C)C)CC2] | 480 | 1H NMR (500 MHz, DMSO-d6) δ 10.72 (s, 1H), 8.42 (d, J = 8.7 Hz, 1H), 8.13 (t, J = 8.0 Hz, 1H), 7.96 (dd, J = 7.5, 0.9 Hz, 1H), 7.71 (s, 1H), 7.10 (s, 1H), 5.85 (hept, J = 6.6 Hz, 1H), 4.82 (p, J = 6.2 Hz, 1H), 4.54 (s, 2H), 3.96 (s, 3H), 3.60 (t, J = 5.9 Hz, 2H), 2.87 (t, J = 6.0 Hz, 2H), 1.61 (d, J = 6.6 Hz, 6H), 1.22 (d, J = 6.2 Hz, 6H) |
| 28 | 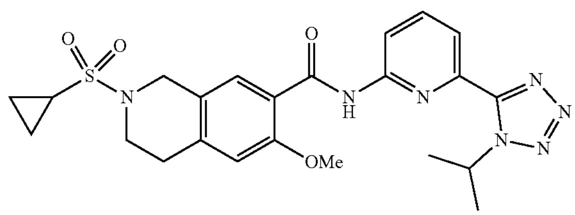 | 498 | 1H NMR (400 MHz, Chloroform-d) δ 10.51 (s, 1H), 8.60 (d, J = 8.4 Hz, 1H), 8.10-7.98 (m, 3H), 6.86 (s, 1H), 5.79 (m, 1H), 4.57 (s, 2H), 4.08 (s, 3H), 3.67 (t, J = 5.9 Hz, 2H), 3.08 (t, J = 5.9 Hz, 2H), 2.35 (m, 1H), 1.77 (d, J = 6.7 Hz, 6H), 1.27 (m, 2H), 1.03 (m, 2H) |
| 29 | 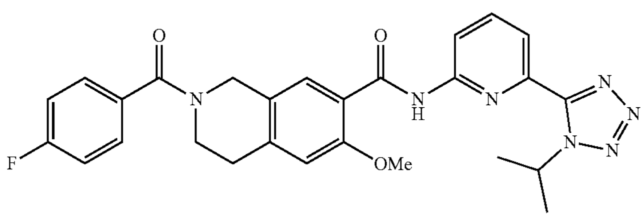 [SMILES: COc1cc2c(cc1C(=O)Nc1cccc(-c3nnnn3C(C)C)n1)CN(C(=O)c1ccc(F)cc1)CC2] | 516 | 1H NMR (400 MHz, DMSO-d6) δ 10.73 (s, 1H), 8.42 (s, 1H), 8.13 (t, J = 7.9 Hz, 1H), 7.97 (d, J = 7.6 Hz, 1H), 7.80-7.54 (m, 3H) 7.32 (t, J = 8.8 Hz, 2H), 7.13 (s, 1H), 5.86 (m, 1H), 4.76-4.62 (m, 2H), 3.97 (s, 3H), 3.91-3.45 (m, 2H), 2.96 (s, 2H), 1.62 (d, J = 6.6 Hz, 6H) |
| 30 | 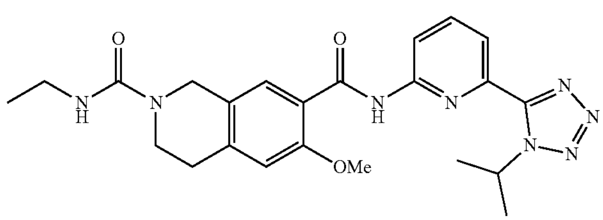 [SMILES: CCNC(=O)N1CCc2cc(OC)c(C(=O)Nc3cccc(-c4nnnn4C(C)C)n3)cc2C1] | 465 | 1H NMR (400 MHz, Chloroform-d) δ 10.53 (s, 1H), 8.60 (dd, J = 8.3, 1.0 Hz, 1H), 8.10 (s, 1H), 8.05 (dd, J = 7.6, 1.0 Hz, 1H), 7.98 (t, J = 8.0 Hz, 1H), 6.87 (s, 1H), 5.80 (m, 1H), 4.56 (s, 2H), 4.08 (s, 3H), 3.72 (t, J = 5.8 Hz, 2H), 3.37 (m, 2H), 2.96 (t, J = 5.8 Hz, 2H), 1.77 (d, J = 6.7 Hz, 6H), 1.22 (t, J = 7.2 Hz, 3H) |
| 31 | 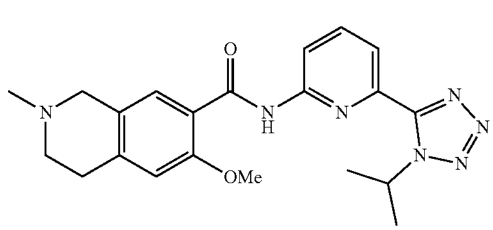 [SMILES: COc1cc2c(cc1C(=O)Nc1cccc(-c3nnnn3C(C)C)n1)CN(C)CC2] | 408 | 1H NMR (400 MHz, Chloroform-d) δ 10.55 (s, 1H), 8.60 (dd, J = 8.3, 1.0 Hz, 1H), 8.04 (dd, J = 7.6, 0.8 Hz, 1H), 8.02 (s, 1H), 7.97 (t, J = 8.0 Hz, 1H), 6.83 (s, 1H), 5.80 (m, 1H), 4.06 (s, 3H), 3.69 (s, 2H), 3.06 (t, J = 6.0 Hz, 2H), 2.80 (t, J = 6.0 Hz, 2H), 2.55 (s, 3H), 1.77 (d, J = 6.7 Hz, 6H) |

TABLE 6-continued

| Example | Structure | LC-MS [M + H]+ unless otherwise noted | 1H-NMR |
|---|---|---|---|
| 32 | 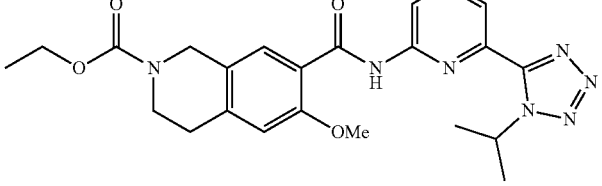 | 466 | 1H NMR (500 MHz, DMSO-d6) δ 10.72 (s, 1H), 8.42 (dd, J = 8.4, 0.9 Hz, 1H), 8.13 (t, J = 8.0 Hz, 1H), 7.96 (dd, J = 7.6, 0.9 Hz, 1H), 7.72 (s, 1H), 7.10 (s, 1H), 5.85 (hept, J = 6.5 Hz, 1H), 4.56 (s, 2H), 4.09 (q, J = 7.0 Hz, 2H), 3.96 (s, 3H), 3.61 (t, J = 5.9 Hz, 2H), 2.88 (t, J = 5.9 Hz, 2H), 1.61 (d, J = 6.7 Hz, 6H), 1.21 (t, J = 7.1 Hz, 3H) |
| 33 | 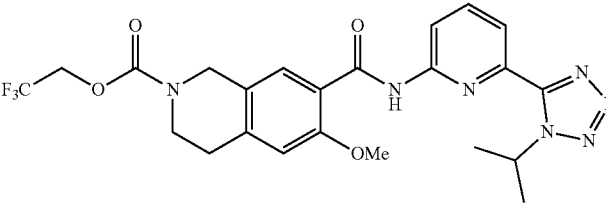 | 520 | 1H NMR (500 MHz, DMSO-d6) δ 10.72 (s, 1H), 8.42 (dd, J = 8.4, 0.9 Hz, 1H), 8.13 (t, J = 8.0 Hz, 1H), 7.97 (dd, J = 7.6, 0.9 Hz, 1H), 7.74 (s, 1H), 7.12 (s, 1H), 5.86 (p, J = 6.6 Hz, 1H), 4.76 (q, J = 9.0 Hz, 2H), 4.61 (d, J = 19.5 Hz, 2H), 3.96 (s, 3H), 3.67-3.65 (m, 2H), 2.92 (t, J = 6.0 Hz, 2H), 1.61 (d, J = 6.6 Hz, 6H) |
| 34 | 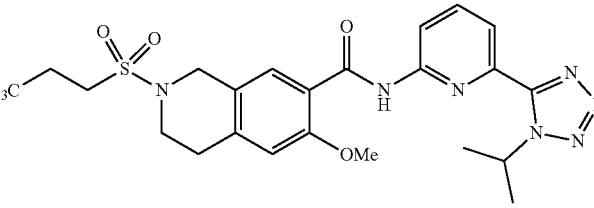 | 554 | 1H NMR (400 MHz, Chloroform-d) δ 10.50 (s, 1H), 8.59 (d, J = 8.2 Hz, 1H), 8.11-7.98 (m, 3H), 6.88 (s, 1H), 5.78 (m, 1H), 4.57 (s, 2H), 4.09 (s, 3H), 3.69 (t, J = 5.8 Hz, 2H), 3.26-3.17 (m, 2H), 3.08 (t, J = 5.9 Hz, 2H), 2.74-2.63 (m, 2H), 1.77 (d, J = 6.7 Hz, 6H) |
| 35 | 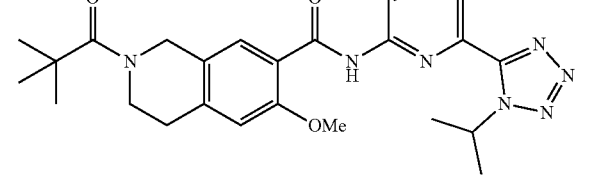 | 478 | 1H NMR (400 MHz, Chloroform-d) δ 10.53 (s, 1H), 8.60 (d, J = 8.3 Hz, 1H), 8.10 (s, 1H), 8.04 (d, J = 7.5 Hz, 1H), 7.98 (t, J = 7.9 Hz, 1H), 6.85 (s, 1H), 5.79 (m, 1H), 4.83 (s, 2H), 4.08 (s, 3H), 3.90 (t, J = 5.7 Hz, 2H), 2.97 (t, J = 5.9 Hz, 2H), 1.77 (d, J = 6.7 Hz, 6H), 1.34 (s, 9H) |
| 36 | 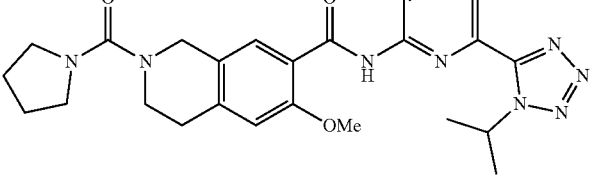 | 491 | 1H NMR (400 MHz, Chloroform-d) δ 10.55 (s, 1H), 8.60 (dd, J = 8.3, 0.9 Hz, 1H), 8.08-8.01 (m, 2H), 7.97 (t, J = 7.9 Hz, 1H), 6.84 (s, 1H), 5.80 (m, 1H), 4.52 (s, 2H), 4.07 (s, 3H), 3.60 (t, J = 5.8 Hz, 2H), 3.46 (s, 4H), 3.01 (t, J = 5.8 Hz, 2H), 1.90 (s, 4H), 1.77 (d, J = 6.7 Hz, 6H) |
| 37 | 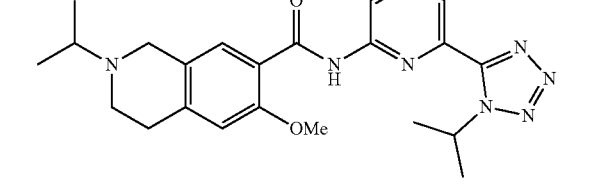 | 436 | 1H NMR (400 MHz, Chloroform-d) δ 10.40 (s, 1H), 8.57 (d, J = 8.2 Hz, 1H), 8.10 (s, 1H), 8.05 (d, J = 7.5 Hz, 1H), 7.98 (t, J = 7.9 Hz, 1H), 6.89 (s, 1H), 5.77 (m, 1H), 4.54 (d, J = 14.8 Hz, 1H), 4.15-4.09 (m, 4H), 3.78 (s, 3H), 3.15-3.06 (m, 2H), 1.76 (d, J = 6.7 Hz, 6H), 1.56 (d, J = 6.5 Hz, 6H) |

TABLE 6-continued

| Example | Structure | LC-MS [M + H]+ unless otherwise noted | 1H-NMR |
|---|---|---|---|
| 38 | 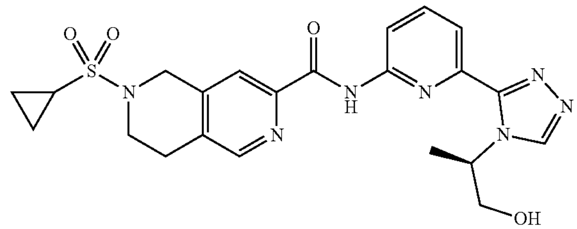 [SMILES: C[C@H](CO)n1cnnc1-c1cccc(NC(=O)c2cc3c(cn2)CCN(S(=O)(=O)C2CC2)C3)n1] | 484 | 1H NMR (400 MHz, DMSO-d6) δ 10.60 (s, 1H), 8.82 (s, 1H), 8.62 (s, 1H), 8.33 (d, J = 8.3 Hz, 1H), 8.16-8.05 (m, 2H), 7.89 (d, J = 7.6 Hz, 1H), 5.45 (m, 1H), 5.04 (t, J = 5.5 Hz, 1H), 4.65 (s, 2H), 3.69 (t, J = 5.4 Hz, 2H), 3.62 (t, J = 5.9 Hz, 2H), 3.06 (t, J = 6.1 Hz, 2H), 2.68 (m, 1H), 1.49 (d, J = 6.9 Hz, 3H), 1.07-0.93 (m, 4H) |
| 39 | 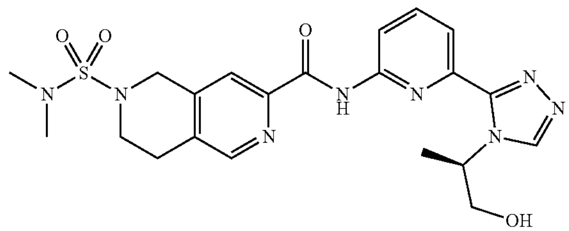 [SMILES: C[C@H](CO)n1cnnc1-c1cccc(NC(=O)c2cc3c(cn2)CCN(S(=O)(=O)N(C)C)C3)n1] | 487 | 1H NMR (400 MHz, DMSO-d6) δ 10.62 (s, 1H), 8.96 (s, 1H), 8.61 (s, 1H), 8.33 (d, J = 8.3 Hz, 1H), 8.15-8.05 (m, 2H), 7.89 (d, J = 7.6 Hz, 1H), 5.47 (m, 1H), 4.57 (s, 2H), 3.69 (d, J = 5.5 Hz, 2H), 3.57 (t, J = 5.9 Hz, 3H), 3.01 (t, J = 5.9 Hz, 2H), 2.81 (s, 6H), 1.50 (dd, J = 6.9, 1.8 Hz, 3H) |
| 40 | 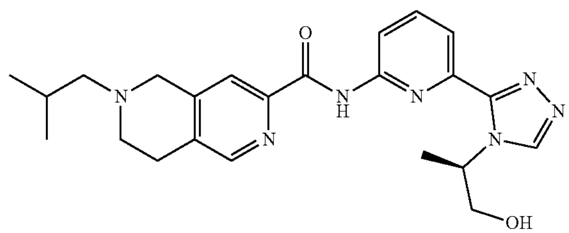 | 436 | 1H NMR (400 MHz, DMSO-d6) δ 10.58 (s, 1H), 8.82 (s, 1H), 8.53 (s, 1H), 8.32 (d, J = 8.2 Hz, 1H), 8.08 (t, J = 8.0 Hz, 1H), 7.97 (s, 1H), 7.88 (d, J = 7.6 Hz, 1H), 5.43 (m, 1H), 5.03 (t, J = 5.4 Hz, 1H), 3.72-3.65 (m, 4H), 2.93 (d, J = 6.0 Hz, 2H), 2.71 (t, J = 5.7 Hz, 2H), 2.26 (d, J = 7.4 Hz, 2H), 1.92 (m, 1H), 1.49 (d, J = 6.9 Hz, 3H), 0.91 (d, J = 6.5 Hz, 6H) |
| 41 | 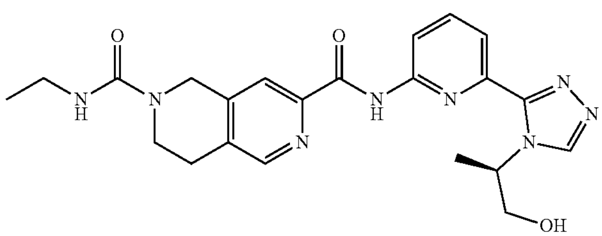 [SMILES: CCNC(=O)N1CCc2cnc(C(=O)Nc3cccc(-c4nncn4[C@H](C)CO)n3)cc2C1] | 451 | 1H NMR (400 MHz, DMSO-d6) δ 10.59 (s, 1H), 8.82 (s, 1H), 8.57 (s, 1H), 8.33 (d, J = 8.3 Hz, 1H), 8.08 (t, J = 8.0 Hz, 1H), 8.01 (s, 1H), 7.88 (d, J = 7.6 Hz, 1H), 6.69 (d, J = 5.6 Hz, 1H), 5.44 (m, 1H), 5.03 (t, J = 5.4 Hz, 1H), 4.66 (s, 2H), 3.68-3.63 (m, 4H), 3.09 (m, 2H), 2.90 (d, J = 5.8 Hz, 2H), 1.49 (d, J = 6.9 Hz, 3H), 1.04 (t, J = 7.1 Hz, 3H) |
| 42 | 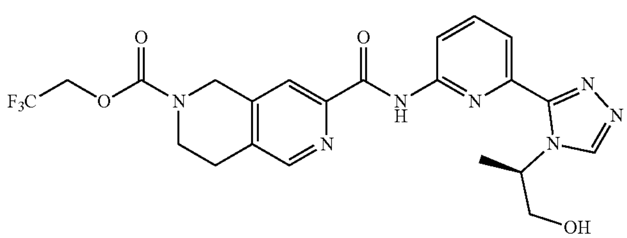 [SMILES: C[C@H](CO)n1cnnc1-c1cccc(NC(=O)c2cc3c(cn2)CCN(C(=O)OCC(F)(F)F)C3)n1] | 506 | 1H NMR (400 MHz, DMSO-d6) δ 10.60 (s, 1H), 8.82 (s, 1H), 8.61 (s, 1H), 8.33 (d, J = 8.3 Hz, 1H), 8.15 (s, 1H), 8.09 (t, J = 8.0 Hz, 1H), 7.89 (d, J = 7.7 Hz, 1H), 5.45 (m, 1H), 5.03 (t, J = 5.4 Hz, 1H), 4.79 (m, 4H), 3.74 (s, 2H), 3.69 (t, J = 5.5 Hz, 2H), 2.98 (t, J = 5.8 Hz, 2H), 1.49 (d, J = 6.9 Hz, 3H) |

TABLE 6-continued

| Example | Structure | LC-MS [M + H]+ unless otherwise noted | 1H-NMR |
|---|---|---|---|
| 43 | 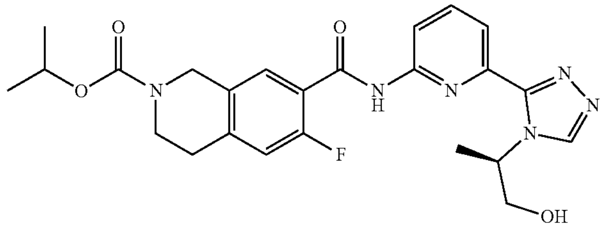 [SMILES: CC(C)OC(=O)N1CCc2cc(F)c(C(=O)Nc3cccc(-c4nncn4[C@H](C)CO)n3)cc2C1] | 483 | 1H NMR (400 MHz, Chloroform-d) δ 9.11 (d, J = 16.3 Hz, 1H), 8.52 (s, 1H), 8.38 (d, J = 7.4 Hz, 1H), 7.97 (d, J = 7.7 Hz, 1H), 7.88 (d, J = 7.9 Hz, 2H), 7.03 (d, J = 12.5 Hz, 1H), 5.46 (m, 1H), 5.00 (m, 1H), 4.69 (s, 2H), 4.15 (d, J = 11.5 Hz, 1H), 3.93 (dd, J = 11.7, 5.9 Hz, 1H), 3.74 (s, 2H), 2.93 (s, 2H), 1.63 (d, J = 7.0 Hz, 3H), 1.31 (d, J = 6.2 Hz, 6H) |
| 44 | 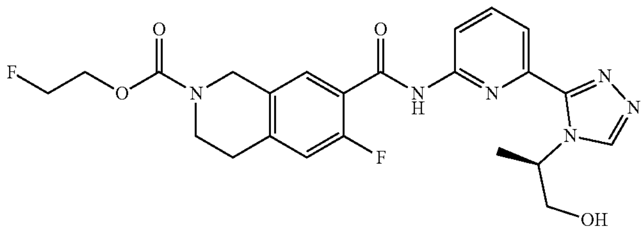 [SMILES: C[C@H](CO)n1cnnc1-c1cccc(NC(=O)c2cc3c(cc2F)CCN(C(=O)OCCF)C3)n1] | 487 | 1H NMR (400 MHz, Chloroform-d) δ 9.10 (d, J = 16.3 Hz, 1H), 8.46 (s, 1H), 8.37 (d, J = 7.7 Hz, 1H), 7.99 (d, J = 7.7 Hz, 1H), 7.93-7.88 (m, 2H), 7.05 (d, J = 12.6 Hz, 1H), 5.46 (m, 1H), 4.73 (d, J = 7.0 Hz, 3H), 4.61 (m, 1H), 4.47 (m, 1H), 4.39 (m, 1H), 4.15 (d, J = 10.9 Hz, 1H), 3.93 (s, 1H), 3.78 (t, J = 5.9 Hz, 2H), 2.96 (t, J = 5.8 Hz, 2H), 1.63 (d, J = 6.8 Hz, 3H) |
| 45 | 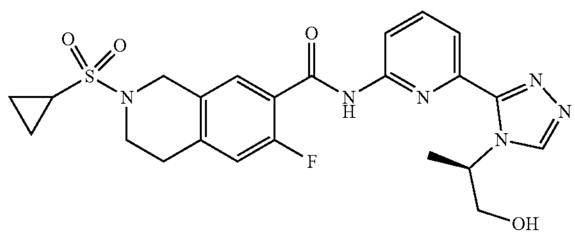 [SMILES: C[C@H](CO)n1cnnc1-c1cccc(NC(=O)c2cc3c(cc2F)CCN(S(=O)(=O)C2CC2)C3)n1] | 501 | 1H NMR (400 MHz, DMSO-d6) δ 10.78 (s, 1H), 8.78 (s, 1H), 8.21 (d, J = 8.4 Hz, 1H), 8.03 (t, J = 8.0 Hz, 1H), 7.89 (d, J = 7.6 Hz, 1H), 7.62 (d, J = 7.1 Hz, 1H), 7.25 (d, J = 10.9 Hz, 1H), 5.56 (m, 1H), 4.94 (t, J = 5.5 Hz, 1H), 4.49 (s, 2H), 3.63 (q, J = 5.1 Hz, 2H), 3.54 (t, J = 6.0 Hz, 2H), 3.04-2.96 (m, 2H), 2.65 (dd, J = 9.2, 4.0 Hz, 1H), 1.44 (d, J = 6.9 Hz, 3H), 1.00 (d, J = 6.6 Hz, 4H) |
| 46 | 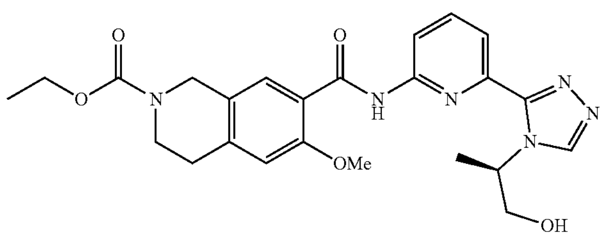 [SMILES: CCOC(=O)N1CCc2cc(OC)c(C(=O)Nc3cccc(-c4nncn4[C@H](C)CO)n3)cc2C1] | 481 | 1H NMR (500 MHz, DMSO-d6) δ 10.59 (s, 1H), 8.80 (s, 1H), 8.31 (dd, J = 8.4, 0.9 Hz, 1H), 8.03 (t, J = 8.0 Hz, 1H), 7.87 (dd, J = 7.6, 0.9 Hz, 1H), 7.76 (s, 1H), 7.10 (s, 1H), 5.52-5.38 (m, 1H), 5.04 (t, J = 5.4 Hz, 1H), 4.56 (s, 2H), 4.09 (q, J = 7.1 Hz, 2H), 3.98 (s, 3H), 3.77-3.67 (m, 2H), 3.61 (t, J = 5.9 Hz, 2H), 2.88 (t, J = 6.0 Hz, 2H), 1.50 (d, J = 7.0 Hz, 3H), 1.21 (t, J = 7.1 Hz, 3H) |
| 47 | 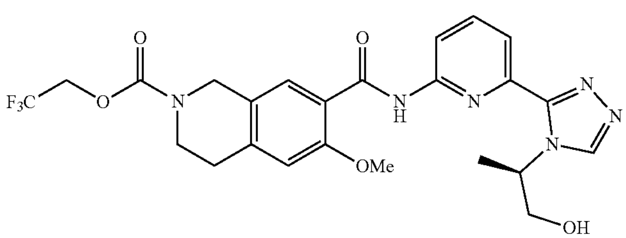 [SMILES: COc1cc2c(cc1C(=O)Nc1cccc(-c3nncn3[C@H](C)CO)n1)CN(C(=O)OCC(F)(F)F)CC2] | 535 | 1H NMR (400 MHz, DMSO-d6) δ 10.59 (s, 1H), 8.80 (s, 1H), 8.31 (dd, J = 8.4, 0.9 Hz, 1H), 8.03 (t, J = 8.0 Hz, 1H), 7.87 (dd, J = 7.7, 0.9 Hz, 1H), 7.78 (s, 1H), 7.12 (s, 1H), 5.45 (q, J = 6.2 Hz, 1H), 5.04 (t, J = 5.4 Hz, 1H), 4.76 (q, J = 9.1 Hz, 2H), 4.61 (d, J = 14.9 Hz, 2H), 3.98 (s, 3H), 3.77-3.62 (comp, 4H), 2.92 (t, J = 6.0 Hz, 2H), 1.50 (d, J = 6.9 Hz, 3H) |

TABLE 6-continued

| Example | Structure | LC-MS [M + H]+ unless otherwise noted | 1H-NMR |
|---|---|---|---|
| 48 | 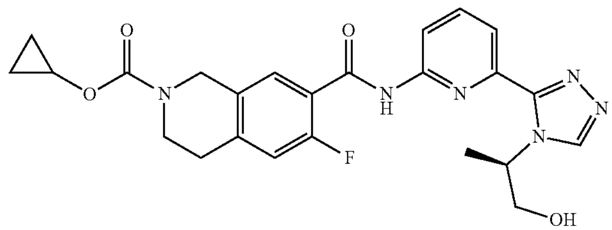 | 481 | 1H NMR (400 MHz, DMSO-d6) δ 10.78 (s, 1H), 8.78 (s, 1H), 8.20 (d, J = 8.3 Hz, 1H), 8.03 (t, J = 8.0 Hz, 1H), 7.88 (dd, J = 7.6, 0.9 Hz, 1H), 7.58 (s, 1H), 7.23 (d, J = 10.8 Hz, 1H), 5.56 (m, 1H), 4.94 (t, J = 5.5 Hz, 1H), 4.56 (s, 2H), 4.04 (m, 1H), 3.69-3.55 (m, 4H), 2.87 (s, 2H), 1.43 (d, J = 6.9 Hz, 3H), 0.70-0.61 (m, 4H) |
| 49 | 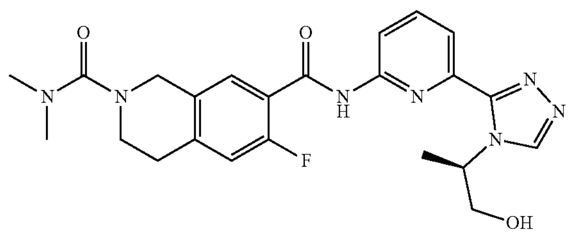 | 468 | 1H NMR (400 MHz, DMSO-d6) δ 10.76 (s, 1H), 8.78 (s, 1H), 8.20 (d, J = 8.2 Hz, 1H), 8.03 (t, J = 8.0 Hz, 1H), 7.88 (dd, J = 7.6, 0.9 Hz, 1H), 7.55 (d, J = 7.1 Hz, 1H), 7.30 (s, 1H), 7.20 (d, J = 10.9 Hz, 1H), 5.56 (m, 1H), 4.95 (t, J = 5.5 Hz, 1H), 4.36 (s, 2H), 3.62 (t, J = 5.4 Hz, 2H), 3.40 (t, J = 5.8 Hz, 2H), 2.91 (t, J = 5.8 Hz, 2H), 2.79 (s, 6H), 1.43 (d, J = 6.9 Hz, 3H) |
| 50 | 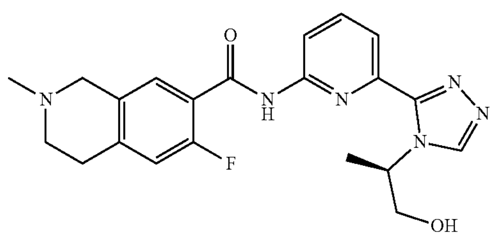 [SMILES: C[C@H](CO)n1cnnc1-c1cccc(NC(=O)c2cc3c(cc2F)CCN(C)C3)n1] | 411 | 1H NMR (400 MHz, DMSO-d6) δ 10.75-10.70 (m, 1H), 8.78 (s, 1H), 8.20 (d, J = 8.3 Hz, 1H), 8.02 (t, J = 8.0 Hz, 1H), 7.88 (dd, J = 7.7, 0.9 Hz, 1H), 7.46 (d, J = 7.2 Hz, 1H), 7.17 (d, J = 11.1 Hz, 1H), 5.55 (m, 1H), 4.95 (t, J = 5.5 Hz, 1H), 3.68-3.57 (m, 4H), 2.91 (d, J = 6.2 Hz, 2H), 2.69 (s, 2H), 2.42 (s, 3H), 1.43 (d, J = 6.9 Hz, 3H) |
| 51 | 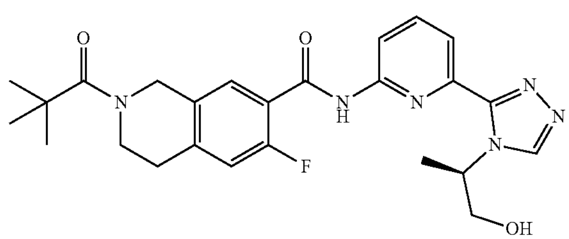 | 481 | 1H NMR (400 MHz, DMSO-d6) δ 10.76 (s, 1H), 8.77 (s, 1H), 8.20 (d, J = 8.3 Hz, 1H), 8.03 (t, J = 8.0 Hz, 1H), 7.89 (d, J = 7.6 Hz, 1H), 7.66 (d, J = 7.1 Hz, 1H), 7.22 (d, J = 10.9 Hz, 1H), 5.55 (m, 1H), 4.93 (t, J = 5.4 Hz, 1H), 4.75 (s, 2H), 3.79 (t, J = 6.1 Hz, 2H), 3.63 (dt, J = 9.7, 5.4 Hz, 2H), 2.88 (t, J = 6.0 Hz, 2H), 1.43 (d, J = 6.9 Hz, 3H), 1.24 (s, 9H) |
| 52 | 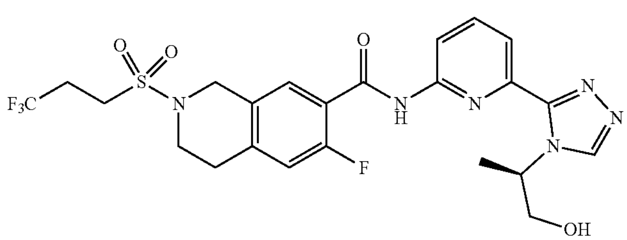 [SMILES: C[C@H](CO)n1cnnc1-c1cccc(NC(=O)c2cc3c(cc2F)CCN(S(=O)(=O)CCC(F)(F)F)C3)n1] | 557 | 1H NMR (400 MHz, DMSO-d6) δ 10.80 (s, 1H), 8.78 (s, 1H), 8.21 (d, J = 8.3 Hz, 1H), 8.03 (t, J = 8.0 Hz, 1H), 7.89 (d, J = 7.6 Hz, 1H), 7.58 (d, J = 7.1 Hz, 1H), 7.26 (d, J = 10.9 Hz, 1H), 5.56 (m, 1H), 4.95 (t, J = 5.4 Hz, 1H), 4.53 (s, 2H), 3.64-3.56 (m, 4H), 3.50-3.41 (m, 2H), 2.98 (t, J = 5.9 Hz, 2H), 2.75 (m, 1H), 1.43 (d, J = 6.9 Hz, 3H) |

TABLE 6-continued

| Example | Structure | LC-MS [M + H]+ unless otherwise noted | ¹H-NMR |
|---|---|---|---|
| 53 | 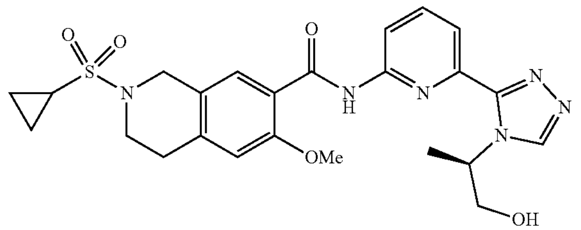 | 513 | ¹H NMR (400 MHz, Chloroform-d) δ 10.56 (s, 1H), 8.57-8.50 (m, 2H), 8.07 (s, 1H), 7.92 (s, 2H), 6.85 (s, 1H), 5.33 (m, 1H), 4.56 (s, 2H), 4.16-4.11 (m, 4H), 3.91 (s, 1H), 3.66 (dd, J = 12.8, 5.8 Hz, 2H), 3.07 (s, 2H), 2.35 (m, 1H), 1.63 (s, 3H), 1.27 (d, J = 5.1 Hz, 2H), 1.02 (d, J = 7.5 Hz, 2H). |
| 54 | 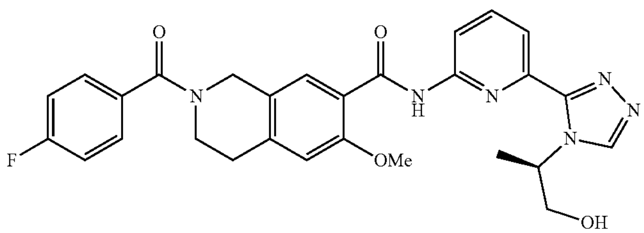 [SMILES: COc1cc2c(cc1C(=O)Nc1cccc(-c3nncn3[C@H](C)CO)n1)CN(C(=O)c1ccc(F)cc1)CC2] | 531 | ¹H NMR (400 MHz, DMSO-d₆) δ 10.60 (s, 1H), 8.81 (s, 1H), 8.32 (s, 1H), 8.03 (t, J = 8.0 Hz, 1H), 7.87 (d, J = 7.7 Hz, 2H), 7.54 (s, 2H), 7.32 (t, J = 8.8 Hz, 2H), 7.13 (s, 1H), 5.46 (m, 1H), 5.05 (t, J = 5.4 Hz, 1H), 4.76-4.63 (m, 2H), 3.99 (s, 3H), 3.99-3.59 (m, 4H), 2.95 (s, 2H), 1.51 (d, J = 6.9 Hz, 3H) |
| 55 | 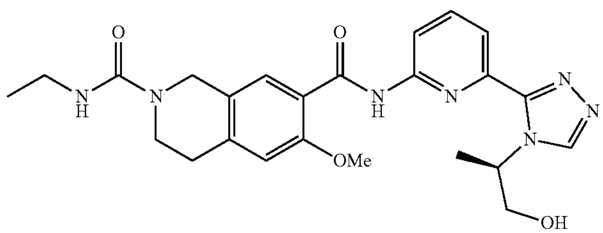 [SMILES: CCNC(=O)N1CCc2cc(OC)c(C(=O)Nc3cccc(-c4nncn4[C@H](C)CO)n3)cc2C1] | 480 | ¹H NMR (400 MHz, DMSO-d₆) δ 10.60 (s, 1H), 8.81 (s, 1H), 8.33 (d, J = 8.3 Hz, 1H), 8.04 (t, J = 8.0 Hz, 1H), 7.88 (d, J = 7.6 Hz, 1H), 7.72 (s, 1H), 7.09 (s, 1H), 6.56 (t, J = 5.5 Hz, 1H), 5.45 (m, 1H), 5.06 (t, J = 5.4 Hz, 1H), 4.49 (s, 2H), 4.00 (s, 3H), 3.73 (dt, J = 6.8, 3.6 Hz, 2H), 3.57 (t, J = 5.9 Hz, 2H), 3.08 (td, J = 7.2, 5.4 Hz, 2H), 2.85 (t, J = 5.9 Hz, 2H), 1.51 (d, J = 6.9 Hz, 3H), 1.04 (t, J = 7.1 Hz, 3H) |
| 56 | 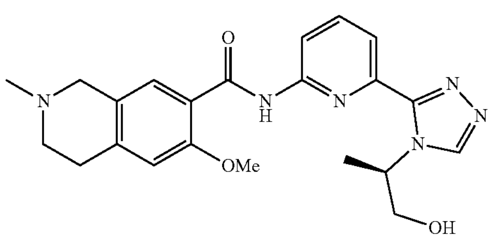 [SMILES: COc1cc2c(cc1C(=O)Nc1cccc(-c3nncn3[C@H](C)CO)n1)CN(C)CC2] | 423 | ¹H NMR (400 MHz, DMSO-d₆) δ 10.59 (s, 1H), 8.81 (s, 1H), 8.33 (d, J = 8.0 Hz, 1H), 8.03 (t, J = 8.0 Hz, 1H), 7.87 (d, J = 8.0 Hz, 1H), 7.67 (s, 1H), 7.03 (s, 1H), 5.46 (m, 1H), 5.07 (t, J = 5.4 Hz, 1H), 3.99 (s, 3H), 3.77-3.68 (m, 2H), 3.49 (s, 2H), 2.90 (t, J = 5.9 Hz, 2H), 2.60 (t, J = 5.9 Hz, 2H), 2.35 (s, 3H), 1.51 (d, J = 6.9 Hz, 3H) |
| 57 | 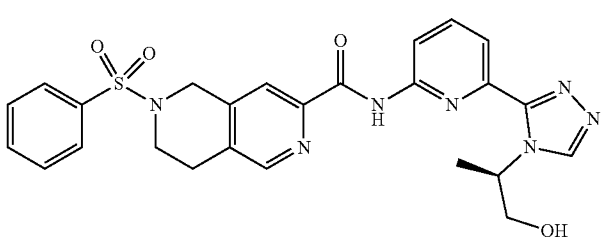 [SMILES: C[C@H](CO)n1cnnc1-c1cccc(NC(=O)c2cc3c(cn2)CCN(S(=O)(=O)c2ccccc2)C3)n1] | 520 | ¹H NMR (400 MHz, DMSO-d₆) δ 10.56 (s, 1H), 8.81 (s, 1H), 8.53 (s, 1H), 8.30 (d, J = 8.3 Hz, 1H), 8.12-8.03 (m, 2H), 7.91-7.83 (m, 3H), 7.72 (t, J = 7.3 Hz, 1H), 7.65 (dd, J = 8.3, 6.7 Hz, 2H), 5.43 (m, 1H), 5.02 (t, J = 5.5 Hz, 1H), 4.45 (s, 2H), 3.67 (t, J = 5.5 Hz, 2H), 3.42 (t, J = 6.0 Hz, 1H), 2.96 (t, J = 5.8 Hz, 2H), 1.47 (d, J = 6.9 Hz, 3H) |

TABLE 6-continued

| Example | Structure | LC-MS [M + H]+ unless otherwise noted | ¹H-NMR |
|---------|-----------|----------------------------------------|--------|
| 58 | 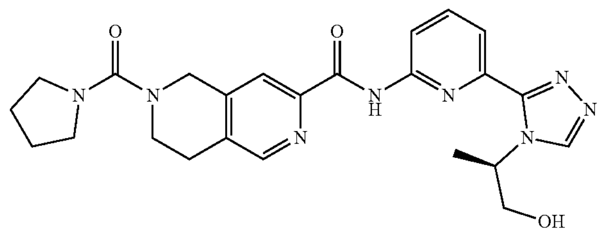 [SMILES: C[C@H](CO)n1cnnc1-c1cccc(NC(=O)c2cc3c(cn2)CCN(C(=O)N2CCCC2)C3)n1] | 477 | ¹H NMR (400 MHz, DMSO-d₆) δ 10.59 (s, 1H), 8.82 (s, 1H), 8.57 (s, 1H), 8.32 (d, J = 8.3 Hz, 1H), 8.12-8.04 (m, 2H), 7.88 (d, J = 7.6 Hz, 1H), 5.44 (m, 1H), 5.03 (t, J = 5.5 Hz, 1H), 4.54 (s, 2H), 3.69 (t, J = 5.5 Hz, 2H), 3.51 (t, J = 5.7 Hz, 2H), 3.36 (t, J = 6.0 Hz, 4H), 2.99-2.92 (m, 2H), 1.79 (t, J = 6.0 Hz, 4H), 1.49 (d, J = 6.9 Hz, 3H) |
| 59 | 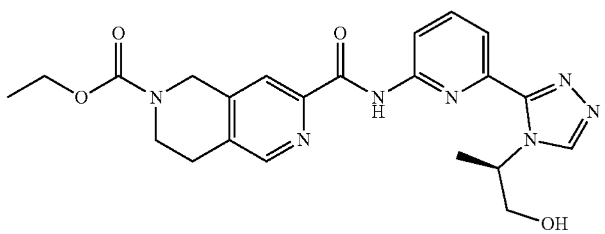 [SMILES: CCOC(=O)N1CCc2cnc(C(=O)Nc3cccc(-c4nncn4[C@H](C)CO)n3)cc2C1] | 452 | ¹H NMR (400 MHz, DMSO-d₆) δ 10.59 (s, 1H), 8.82 (s, 1H), 8.59 (s, 1H), 8.32 (d, J = 8.2 Hz, 1H), 8.13-8.04 (m, 2H), 7.88 (d, J = 7.6 Hz, 1H), 5.45 (m, 1H), 5.03 (t, J = 5.4 Hz, 1H), 4.74 (s, 2H), 4.11 (q, J = 7.2 Hz, 2H), 3.68 (t, J = 5.5 Hz, 4H), 2.94 (t, J = 5.9 Hz, 2H), 1.49 (d, J = 6.9 Hz, 3H), 1.23 (t, J = 7.1 Hz, 3H) |
| 60 | 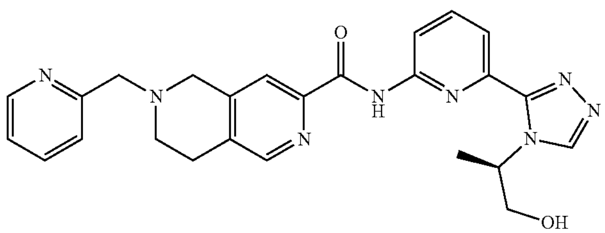 [SMILES: C[C@H](CO)n1cnnc1-c1cccc(NC(=O)c2cc3c(cn2)CCN(Cc2ccccn2)C3)n1] | 471 | ¹H NMR (400 MHz, DMSO-d₆) δ 10.58 (s, 1H), 8.82 (s, 1H), 8.54 (d, J = 5.7 Hz, 2H), 8.32 (d, J = 8.2 Hz, 1H), 8.07 (t, J = 8.0 Hz, 1H), 7.95 (s, 1H), 7.88 (d, J = 7.6 Hz, 1H), 7.79 (m, 1H), 7.50 (d, J = 7.8 Hz, 1H), 7.30 (m, 1H), 5.43 (m, 1H), 5.03 (t, J = 5.5 Hz, 1H), 3.83 (d, J = 11.5 Hz, 4H), 3.68 (t, J = 5.5 Hz, 2H), 2.97 (s, 2H), 2.82 (t, J = 5.8 Hz, 2H), 1.49 (d, J = 6.9 Hz, 3H) |
| 61 | 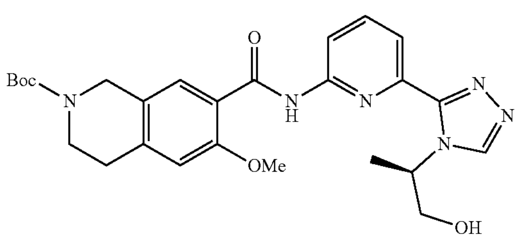 [SMILES: COc1cc2c(cc1C(=O)Nc1cccc(-c3nncn3[C@H](C)CO)n1)CN(C(=O)OC(C)(C)C)CC2] | 509 | ¹H NMR (500 MHz, Chloroform-d) δ 10.56 (s, 1H), 8.48 (dd, J = 5.5, 3.8 Hz, 1H), 8.40 (s, 1H), 8.05 (s, 1H), 7.92-7.87 (m, comp H), 6.81 (s, 1H), 5.34-5.25 (m, 1jH), 4.87 (s, 1H), 4.59 (s, 2H), 4.16-4.08 (comp, 4H), 3.91-3.80 (m, 1H), 3.68 (t, J = 6.0 Hz, 2H), 2.90-2.88 (m, 2H), 1.59 (d, J = 7.0 Hz, 3H), 1.50 (s, 9H) |
| 62 | 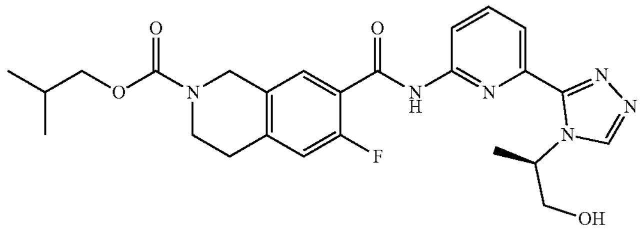 | 497 | ¹H NMR (400 MHz, Chloroform-d) δ 9.11 (d, J = 16.5 Hz, 1H), 8.50 (s, 1H), 8.37 (d, J = 6.6 Hz, 1H), 7.98 (d, J = 7.8 Hz, 1H), 7.90-7.82 (m, 2H), 7.03 (d, J = 12.6 Hz, 1H), 5.46 (m, 1H), 4.71 (s, 2H), 4.15 (d, J = 11.2 Hz, 1H), 3.95 (d, J = 6.6 Hz, 3H), 3.76 (t, J = 6.0 Hz, 2H), 2.95 (s, 2H), 2.00 (m, 1H), 1.63 (d, J = 7.0 Hz, 3H), 0.99 (d, J = 6.7 Hz, 7H) |

TABLE 6-continued

| Example | Structure | LC-MS [M + H]+ unless otherwise noted | ¹H-NMR |
|---|---|---|---|
| 63 | 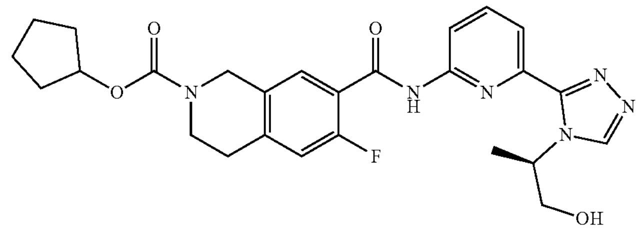 [SMILES: C[C@H](CO)n1cnnc1-c1cccc(NC(=O)c2cc3c(cc2F)CCN(C(=O)OC2CCCC2)C3)n1] | 509 | ¹H NMR (400 MHz, Chloroform-d) δ 9.11 (d, J = 16.3 Hz, 1H), 8.46 (s, 1H), 8.36 (dt, J = 7.6, 3.8 Hz, 1H), 7.97 (d, J = 7.8 Hz, 1H), 7.90-7.81 (m, 2H), 7.03 (d, J = 12.6 Hz, 1H), 5.46 (m, 1H), 5.19 (m, 1H), 4.67 (s, 2H), 4.16 (dd, J = 11.7, 3.5 Hz, 1H), 3.93 (dd, J = 11.7, 5.8 Hz, 1H), 3.73 (s, 2H), 2.93 (s, 2H), 1.90 (s, 2H), 1.81-1.74 (m, 4H), 1.70-1.66 (m, 2H), 1.64 (d, J = 6.4 Hz, 3H) |
| 64 | 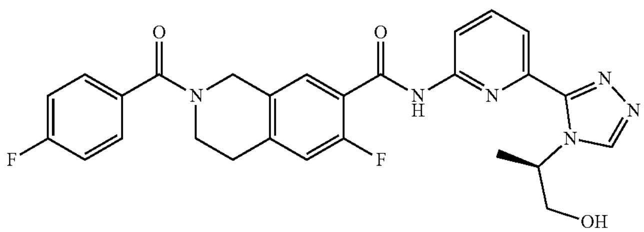 [SMILES: C[C@H](CO)n1cnnc1-c1cccc(NC(=O)c2cc3c(cc2F)CCN(C(=O)c2ccc(F)cc2)C3)n1] | 519 | ¹H NMR (400 MHz, DMSO-d₆) δ 10.77 (s, 1H), 8.78 (s, 1H), 8.19 (s, 1H), 8.03 (t, J = 7.9 Hz, 1H), 7.88 (d, J = 7.7 Hz, 1H), 7.67 (s, 1H), 7.55 (s, 2H), 7.32 (t, J = 8.7 Hz, 2H), 7.25 (d, J = 10.8 Hz, 1H), 5.55 (m, 1H), 4.93 (s, 1H), 4.79-4.66 (m, 1H), 3.84 (s, 1H), 3.61 (s, 3H), 2.95 (s, 2H), 1.43 (d, J = 6.8 Hz, 3H) |
| 65 | 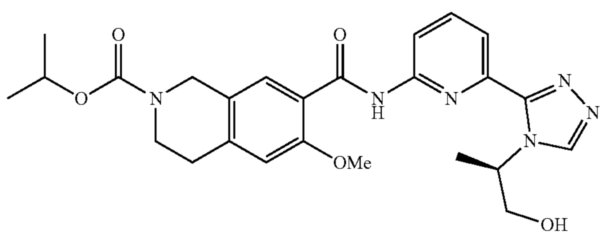 [SMILES: COc1cc2c(cc1C(=O)Nc1cccc(-c3nncn3[C@H](C)CO)n1)CN(C(=O)OC(C)C)CC2] | 495 | ¹H NMR (500 MHz, DMSO-d₆) δ 10.59 (s, 1H), 8.80 (s, 1H), 8.32 (dd, J = 8.2, 0.9 Hz, 1H), 8.03 (t, J = 8.0 Hz, 1H), 7.87 (dd, J = 7.6, 0.9 Hz, 1H), 7.75 (s, 1H), 7.10 (s, 1H), 5.51-5.40 (m, 1H), 5.04 (t, J = 5.4 Hz, 1H), 4.82 (hept, J = 6.2 Hz, 1H), 4.54 (s, 2H), 3.98 (s, 3H), 3.71 (dq, J = 8.8, 5.8 Hz, 2H), 3.60 (t, J = 5.9 Hz, 2H), 2.87 (t, J = 5.9 Hz, 2H), 1.50 (d, J = 6.9 Hz, 3H), 1.22 (d, J = 6.2 Hz, 6H) |
| 66 | 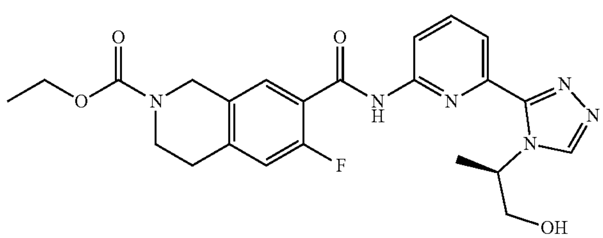 [SMILES: CCOC(=O)N1CCc2cc(F)c(C(=O)Nc3cccc(-c4nncn4[C@H](C)CO)n3)cc2C1] | 469 | ¹H NMR (400 MHz, DMSO-d₆) δ 10.79 (s, 1H), 8.78 (s, 1H), 8.20 (d, J = 8.0 Hz, 1H), 8.03 (t, J = 8.0 Hz, 1H), 7.88 (dd, J = 7.6, 0.9 Hz, 1H), 7.59 (d, J = 7.0 Hz, 1H), 7.23 (d, J = 10.9 Hz, 1H), 5.56 (m, 1H), 4.94 (t, J = 5.5 Hz, 1H), 4.60 (s, 2H), 4.10 (q, J = 7.0 Hz, 2H), 3.63 (m, 4H), 2.88 (t, J = 6.0 Hz, 2H), 1.43 (d, J = 6.9 Hz, 3H), 1.22 (t, J = 7.1 Hz, 3H) |
| 67 | 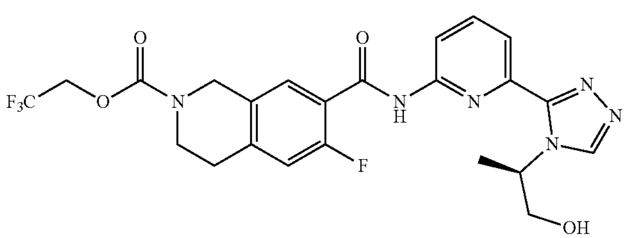 [SMILES: C[C@H](CO)n1cnnc1-c1cccc(NC(=O)c2cc3c(cc2F)CCN(C(=O)OCC(F)(F)F)C3)n1] | 523 | ¹H NMR (400 MHz, DMSO-d₆) δ 10.80 (s, 1H), 8.78 (s, 1H), 8.20 (d, J = 8.3 Hz, 1H), 8.03 (t, J = 8.0 Hz, 1H), 7.89 (d, J = 7.6 Hz, 1H), 7.64 (d, J = 7.0 Hz, 1H), 7.26 (d, J = 10.8 Hz, 1H), 5.56 (m, 1H), 4.94 (t, J = 5.4 Hz, 1H), 4.78 (q, J = 9.0 Hz, 2H), 4.65 (d, J = 14.3 Hz, 2H), 3.68-3.56 (m, 4H), 2.92 (t, J = 6.0 Hz, 2H), 1.43 (d, J = 6.9 Hz, 3H) |

TABLE 6-continued

| Example | Structure | LC-MS [M + H]+ unless otherwise noted | ¹H-NMR |
|---|---|---|---|
| 68 | 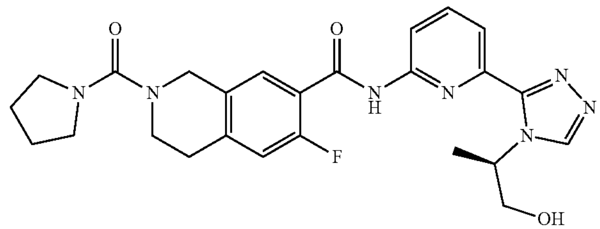 [SMILES: C[C@H](CO)n1cnnc1-c1cccc(NC(=O)c2cc3c(cc2F)CCN(C(=O)N2CCCC2)C3)n1] | 494 | ¹H NMR (400 MHz, DMSO-d₆) δ 10.75 (s, 1H), 8.78 (s, 1H), 8.20 (dd, J = 8.3, 0.9 Hz, 1H), 8.03 (t, J = 8.0 Hz, 1H), 7.88 (dd, J = 7.6, 0.9 Hz, 1H), 7.56 (d, J = 7.1 Hz, 1H), 7.20 (d, J = 11.0 Hz, 1H), 5.56 (m, 1H), 4.94 (t, J = 5.4 Hz, 1H), 4.40 (s, 2H), 3.63 (t, J = 6.0 Hz, 2H), 3.45 (t, J = 5.8 Hz, 2H), 3.32 (t, J = 6.4 Hz, 4H), 2.90 (t, J = 5.6 Hz, 2H), 1.79 (t, J = 6.4 Hz, 4H), 1.43 (d, J = 6.9 Hz, 3H) |
| 69 | 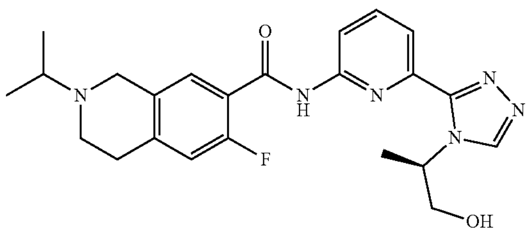 [SMILES: CC(C)N1CCc2cc(F)c(C(=O)Nc3cccc(-c4nncn4[C@H](C)CO)n3)cc2C1] | 439 | ¹H NMR (400 MHz, DMSO-d₆) δ 10.68 (s, 1H), 8.77 (s, 1H), 8.20 (d, J = 8.2 Hz, 1H), 8.02 (t, J = 8.0 Hz, 1H), 7.88 (dd, J = 7.6, 0.9 Hz, 1H), 7.46 (d, J = 7.2 Hz, 1H), 7.13 (d, J = 11.1 Hz, 1H), 5.56 (m, 1H), 4.94 (t, J = 5.5 Hz, 1H), 3.67-3.61 (m, 4H), 2.86 (s, 3H), 2.71 (s, 2H), 1.43 (d, J = 6.9 Hz, 3H), 1.07 (d, J = 6.5 Hz, 6H) |
| 70 | 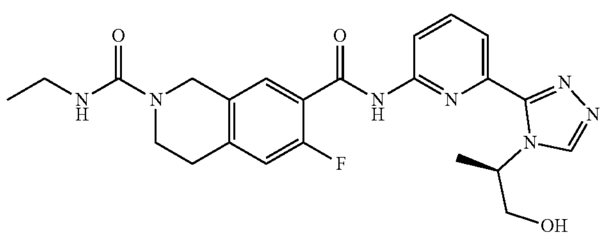 [SMILES: CCNC(=O)N1CCc2cc(F)c(C(=O)Nc3cccc(-c4nncn4[C@H](C)CO)n3)cc2C1] | 468 | ¹H NMR (400 MHz, DMSO-d₆) δ 10.76 (s, 1H), 8.78 (s, 1H), 8.21 (d, J = 8.2 Hz, 1H), 8.03 (t, J = 8.0 Hz, 1H), 7.89 (d, J = 7.7 Hz, 1H), 7.50 (d, J = 7.1 Hz, 1H), 7.22 (m, 1H), 6.59 (d, J = 5.7 Hz, 1H), 5.57 (m, 1H), 4.94 (s, 1H), 4.52 (s, 2H), 3.62 (t, J = 4.8 Hz, 2H), 3.55 (t, J = 5.8 Hz, 2H), 3.14-3.03 (m, 2H), 2.84 (t, J = 5.8 Hz, 2H), 1.43 (d, J = 6.8 Hz, 3H), 1.03 (t, J = 7.1 Hz, 3H) |
| 71 | 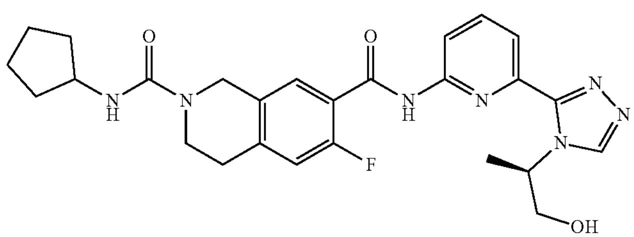 [SMILES: C[C@H](CO)n1cnnc1-c1cccc(NC(=O)c2cc3c(cc2F)CCN(C(=O)NC2CCCC2)C3)n1] | 508 | ¹H NMR (400 MHz, DMSO-d₆) δ 10.75 (s, 1H), 8.78 (s, 1H), 8.21 (d, J = 8.2 Hz, 1H), 8.03 (t, J = 8.0 Hz, 1H), 7.88 (dd, J = 7.7, 0.8 Hz, 1H), 7.50 (d, J = 7.1 Hz, 1H), 7.21 (d, J = 11.0 Hz, 1H), 6.35 (d, J = 7.0 Hz, 1H), 5.57 (m, 1H), 4.94 (t, J = 5.5 Hz, 1H), 4.53 (s, 2H), 3.94 (q, J = 6.8 Hz, 1H), 3.66-3.53 (m, 4H), 2.83 (t, J = 6.1 Hz, 2H), 1.83-1.75 (m, 2H), 1.70-1.62 (m, 2H), 1.52-1.33 (m, 7H), 1.24 (s, 1H) |
| 72 | 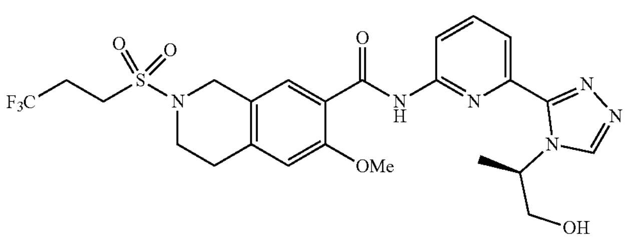 [SMILES: COc1cc2c(cc1C(=O)Nc1cccc(-c3nncn3[C@H](C)CO)n1)CN(S(=O)(=O)CCC(F)(F)F)CC2] | 569 | ¹H NMR (400 MHz, DMSO-d₆) δ 10.61 (s, 1H), 8.82 (s, 1H), 8.33 (d, J = 8.3 Hz, 1H), 8.04 (t, J = 8.0 Hz, 1H), 7.88 (d, J = 7.6 Hz, 1H), 7.77 (s, 1H), 7.13 (s, 1H), 5.46 (m, 1H), 5.06 (t, J = 5.5 Hz, 1H), 4.50 (s, 2H), 4.00 (s, 3H), 3.72 (t, J = 6.0 Hz, 2H), 3.57 (t, J = 6.0 Hz, 2H), 3.49-3.40 (m, 2H), 2.99 (t, J = 5.6 Hz, 2H), 2.80-2.69 (m, 2H), 1.51 (d, J = 6.9 Hz, 3H) |

TABLE 6-continued

| Example | Structure | LC-MS [M + H]+ unless otherwise noted | ¹H-NMR |
|---|---|---|---|
| 73 | 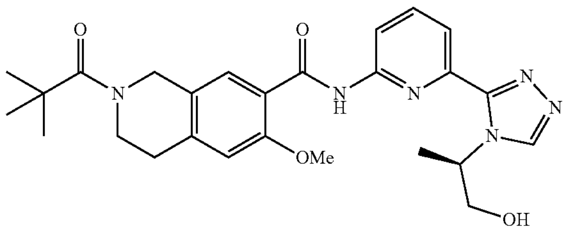 [SMILES: COc1cc2c(cc1C(=O)Nc1cccc(-c3nncn3[C@H](C)CO)n1)CN(C(=O)C(C)(C)C)CC2] | 493 | ¹H NMR (400 MHz, DMSO-d₆) δ 10.59 (s, 1H), 8.81 (s, 1H), 8.33 (d, J = 8.3 Hz, 1H), 8.04 (t, J = 8.0 Hz, 1H), 7.88 (d, J = 7.6 Hz, 1H), 7.83 (s, 1H), 7.10 (s, 1H), 5.46 (m, 1H), 5.05 (t, J = 5.4 Hz, 1H), 4.72 (s, 2H), 3.99 (s, 3H), 3.79 (t, J = 6.0 Hz, 2H), 3.72 (td, J = 5.6, 2.3 Hz, 2H), 2.89 (t, J = 5.9 Hz, 2H), 1.51 (d, J = 6.9 Hz, 3H), 1.24 (s, 9H) |
| 74 | 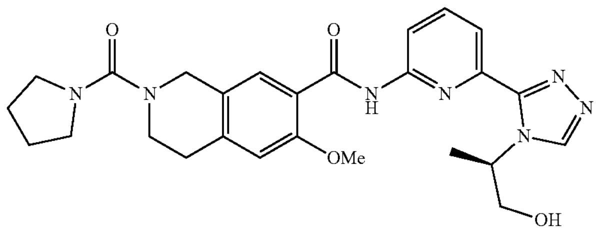 [SMILES: COc1cc2c(cc1C(=O)Nc1cccc(-c3nncn3[C@H](C)CO)n1)CN(C(=O)N1CCCC1)CC2] | 506 | ¹H NMR (400 MHz, DMSO-d₆) δ 10.60 (s, 1H), 8.81 (s, 1H), 8.33 (d, J = 8.3 Hz, 1H), 8.04 (t, J = 8.0 Hz, 1H), 7.87 (d, J = 7.6 Hz, 1H), 7.76 (s, 1H), 7.08 (s, 1H), 5.46 (m, 1H), 5.06 (t, J = 5.4 Hz, 1H), 4.38 (s, 2H), 3.99 (s, 3H), 3.77-3.69 (m, 2H), 3.45 (t, J = 5.8 Hz, 2H), 3.33 (s, 4H), 2.91 (t, J = 5.8 Hz, 2H), 1.78 (s, 4H), 1.51 (d, J = 6.9 Hz, 3H). |
| 75 | 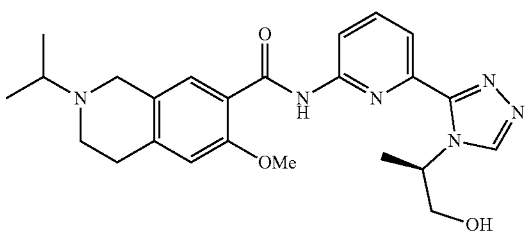 [SMILES: COc1cc2c(cc1C(=O)Nc1cccc(-c3nncn3[C@H](C)CO)n1)CN(C(C)C)CC2] | 451 | ¹H NMR (400 MHz, DMSO-d₆) δ 10.60 (s, 1H), 8.82 (s, 1H), 8.36-8.33 (d, J = 8.0 Hz, 1H), 8.03 (t, J = 8.0 Hz, 1H), 7.87 (d, J = 8.0 Hz, 1H), 7.70 (s, 1H), 7.02 (s, 1H), 5.44 (m, 1H), 5.07 (t, J = 5.4 Hz, 1H), 3.99 (s, 3H), 3.78-3.68 (m, 2H), 3.65 (s, 2H), 2.87 (t, J = 6.0 Hz, 3H), 2.70 (t, J = 6.0 Hz, 2H), 1.51 (d, J = 6.9 Hz, 3H), 1.07 (d, J = 6.5 Hz, 6H) |
| 76 | 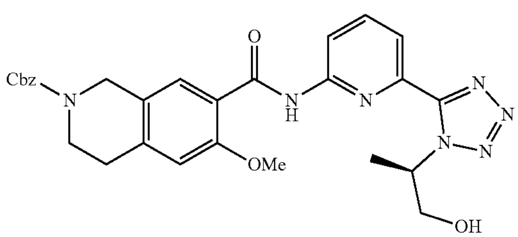 [SMILES: COc1cc2c(cc1C(=O)Nc1cccc(-c3nnnn3[C@H](C)CO)n1)CN(C(=O)OCc1ccccc1)CC2] | 544 | ¹H NMR (400 MHz, DMSO-d₆) δ 10.73 (s, 1H), 8.41 (dd, J = 8.4, 0.9 Hz, 1H), 8.19-8.06 (m, 1H), 7.95 (dd, J = 7.6, 0.9 Hz, 1H), 7.73 (s, 1H), 7.47-7.26 (comp, 5H), 7.10 (s, 1H), 5.89-5.76 (m, 1H), 5.14 (s, 2H), 5.01 (t, J = 5.5 Hz, 1H), 4.60 (d, J = 19.9 Hz, 2H), 3.97 (s, 3H), 3.89-3.73 (m, 2H), 3.65 (s, 2H), 2.89 (t, J = 5.9 Hz, 2H), 1.59 (d, J = 6.8 Hz, 3H) |
| 77 | 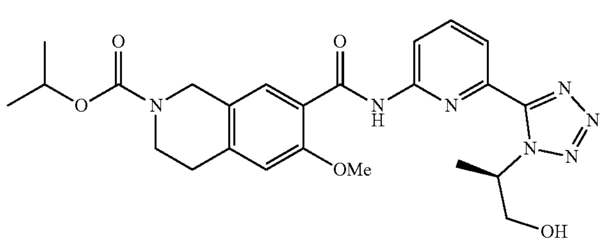 [SMILES: COc1cc2c(cc1C(=O)Nc1cccc(-c3nnnn3[C@H](C)CO)n1)CN(C(=O)OC(C)C)CC2] | 496 | ¹H NMR (500 MHz, DMSO-d₆) δ 10.73 (s, 1H), 8.42 (d, J = 8.4 Hz, 1H), 8.13 (t, J = 8.0 Hz, 1H), 7.95 (d, J = 7.5 Hz, 1H), 7.72 (s, 1H), 7.10 (s, 1H), 5.86-5.77 (m, 1H), 5.00 (t, J = 5.6 Hz, 1H), 4.82 (hept, J = 6.1 Hz, 1H), 4.54 (s, 2H), 3.98 (s, 3H), 3.89-3.73 (comp, 2H), 3.60 (t, J = 5.9 Hz, 2H), 2.87 (t, J = 5.9 Hz, 2H), 1.59 (d, J = 6.8 Hz, 3H), 1.22 (d, J = 6.2 Hz, 6H) |

TABLE 6-continued

| Example | Structure | LC-MS [M + H]+ unless otherwise noted | 1H-NMR |
|---|---|---|---|
| 78 | 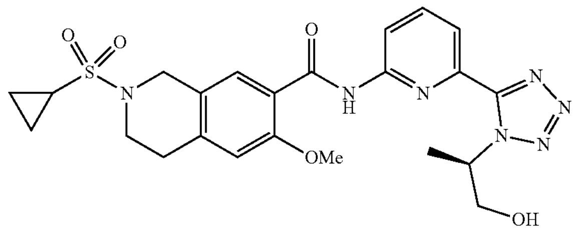 [SMILES: COc1cc2c(cc1C(=O)Nc1cccc(-c3nnnn3[C@H](C)CO)n1)CN(S(=O)(=O)C1CC1)CC2] | 514 | 1H NMR (400 MHz, DMSO-d6) δ 10.74 (s, 1H), 8.43 (dd, J = 8.3, 0.9 Hz, 1H), 8.14 (t, J = 8.0 Hz, 1H), 7.96 (dd, J = 7.6, 0.9 Hz, 1H), 7.76 (s, 1H), 7.12 (s, 1H), 5.82 (m, 1H), 5.02 (t, J = 5.6 Hz, 1H), 4.46 (s, 2H), 3.99 (s, 3H), 3.90-3.74 (m, 2H), 3.54 (t, J = 5.9 Hz, 2H), 3.01 (t, J = 5.9 Hz, 2H), 2.65 (m, 1H), 1.60 (d, J = 6.8 Hz, 3H), 1.03-0.93 (m, 4H). |
| 79 | 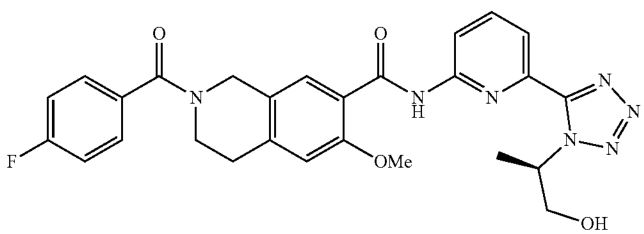 | 532 | 1H NMR (400 MHz, Chloroform-d) δ 10.63 (s, 1H), 8.57 (s, 1H), 8.15-7.92 (m, 3H), 7.50 (dd, J = 8.6, 5.3 Hz, 2H), 7.16 (t, J = 8.6 Hz, 2H), 6.88 (s, 1H), 5.64 (m, 1H), 4.90-4.68 (m, 2H), 4.19-4.11 (m, 5H), 4.02-3.73 (m, 2H), 3.03 (s, 2H), 1.75 (d, J = 6.8 Hz, 3H). |
| 80 | 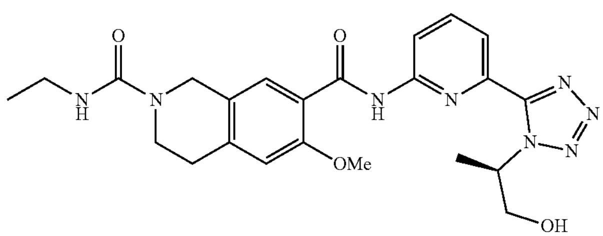 | 481 | 1H NMR (400 MHz, Chloroform-d) δ 10.65 (s, 1H), 8.57 (dd, J = 7.4, 1.9 Hz, 1H), 8.08 (s, 1H), 8.01 (d, J = 7.6 Hz, 2H), 6.86 (s, 1H), 5.66 (m, 1H), 4.55 (s, 2H), 4.16 (d, J = 6.4 Hz, 2H), 4.12 (s, 3H), 3.71 (t, J = 5.8 Hz, 2H), 3.36 (q, J = 7.2 Hz, 2H), 2.95 (t, J = 5.8 Hz, 2H), 1.75 (d, J = 6.8 Hz, 3H), 1.21 (t, J = 7.2 Hz, 3H). |
| 81 | 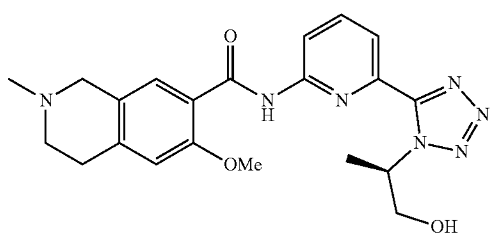 | 424 | 1H NMR (400 MHz, Chloroform-d) δ 10.65 (s, 1H), 8.58 (dd, J = 7.7, 1.7 Hz, 1H), 8.06-7.96 (m, 3H), 6.84 (s, 1H), 5.66 (m, 1H), 4.16 (d, J = 6.3 Hz, 2H), 4.11 (s, 3H), 3.75 (s, 2H), 3.10 (s, 2H), 2.87 (s, 2H), 2.61 (s, 3H), 1.75 (d, J = 6.9 Hz, 3H) |
| 82 | 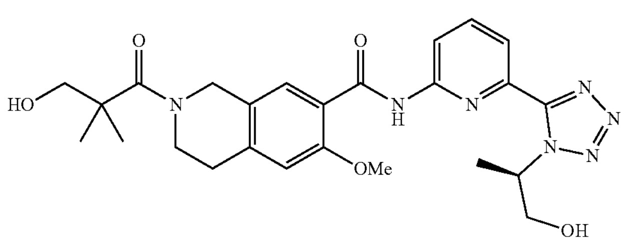 [SMILES: COc1cc2c(cc1C(=O)Nc1cccc(-c3nnnn3[C@H](C)CO)n1)CN(C(=O)C(C)(C)CO)CC2] | 510 | 1H NMR (400 MHz, Chloroform-d) δ 10.60 (s, 1H), 8.53 (dt, J = 7.6, 3.8 Hz, 1H), 8.06 (s, 1H), 8.01-7.93 (comp, 2H), 6.84 (s, 1H), 5.74-5.55 (m, 1H), 4.77 (s, 2H), 4.19-4.06 (comp, 5H), 3.86 (dq, J = 6.3, 3.1 Hz, 3H), 3.64 (t, J = 7.1 Hz, 1H), 3.51 (d, J = 6.9 Hz, 2H), 2.95 (t, J = 6.0 Hz, 2H), 1.71 (d, J = 6.8 Hz, 3H), 1.31 (s, 6H) |

US 11,345,699 B2

TABLE 6-continued

| Example | Structure | LC-MS [M + H]+ unless otherwise noted | 1H-NMR |
|---|---|---|---|
| 83 | 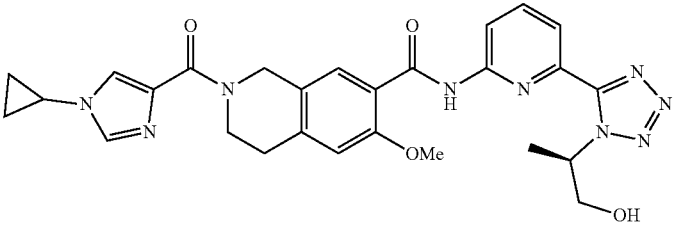 | 544 | 1H NMR (400 MHz, DMSO-$d_6$) δ 10.73 (s, 1H), 8.42 (d, J = 8.3 Hz, 1H), 8.12 (t, J = 8.0 Hz, 1H), 7.95 (dd, J = 7.6, 0.9 Hz, 1H), 7.82 (d, J = 1.4 Hz, 1H), 7.80-7.53 (comp, 2H), 7.10 (s, 1H), 5.80 (h, J = 6.8, 5.9 Hz, 1H), 5.36 (s, 1H), 5.01 (t, J = 5.6 Hz, 1H), 4.72 (s, 1H), 4.34 (s, 1H), 3.98 (s, 3H), 3.92-3.69 (comp, 3H), 3.56 (tt, J = 7.4, 3.6 Hz, 1H), 2.95 (s, 2H), 1.59 (d, J = 6.8 Hz, 3H), 1.05-0.92 (m, 4H) |
| 84 | 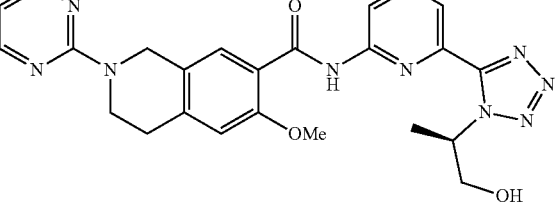 | 488 | 1H NMR (400 MHz, DMSO-$d_6$) δ 10.74 (s, 1H), 8.45-8.40 (comp, 3H), 8.17-8.09 (m, 1H), 7.95 (dd, J = 7.6, 0.9 Hz, 1H), 7.78 (s, 1H), 7.12 (s, 1H), 6.66 (t, J = 4.7 Hz, 1H), 5.88-5.73 (m, 1H), 5.01 (t, J = 5.6 Hz, 1H), 4.87 (s, 2H), 4.03-3.97 (comp, 5H), 3.89-3.72 (m, 2H), 2.96 (t, J = 5.9 Hz, 2H), 1.59 (d, J = 6.8 Hz, 3H) |
| 85 | 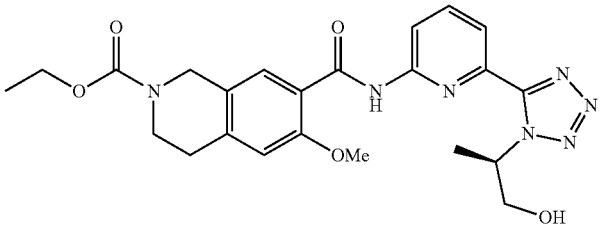 [SMILES: CCOC(=O)N1CCc2cc(OC)c(C(=O)Nc3cccc(-c4nnnn4[C@H](C)CO)n3)cc2C1] | 482 | 1H NMR (500 MHz, DMSO-$d_6$) δ 10.73 (s, 1H), 8.42 (d, J = 8.4 Hz, 1H), 8.13 (t, J = 8.0 Hz, 1H), 7.95 (dd, J = 7.6, 0.9 Hz, 1H), 7.72 (s, 1H), 7.10 (s, 1H), 5.87-5.77 (m, 1H), 5.00 (t, J = 5.6 Hz, 1H), 4.56 (s, 2H), 4.09 (q, J = 7.1 Hz, 2H), 3.98 (s, 3H), 3.89-3.75 (comp, 2H), 3.61 (t, J = 5.9 Hz, 2H), 2.88 (t, J = 5.9 Hz, 2H), 1.59 (d, J = 6.8 Hz, 3H), 1.21 (t, J = 7.1 Hz, 3H) |
| 86 | 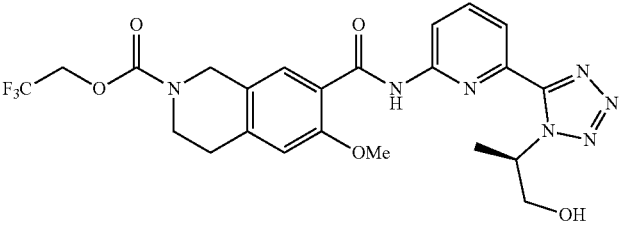 | 536 | 1H NMR (500 MHz, DMSO-$d_6$) δ 10.73 (s, 1H), 8.42 (dd, J = 8.4, 0.9 Hz, 1H), 8.13 (t, J = 8.0 Hz, 1H), 7.95 (dd, J = 7.6, 0.9 Hz, 1H), 7.75 (s, 1H), 7.12 (s, 1H), 5.81 (ddd, J = 7.9, 6.8, 5.2 Hz, 1H), 5.00 (t, J = 5.6 Hz, 1H), 4.76 (q, J = 9.1 Hz, 2H), 4.61 (d, J = 19.5 Hz, 2H), 3.98 (s, 3H), 3.89-3.73 (comp, 2H), 3.66 (s, 2H), 2.92 (t, J = 5.9 Hz, 2H), 1.59 (d, J = 6.8 Hz, 3H) |
| 87 | 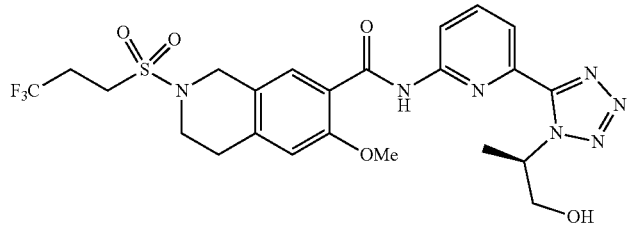 [SMILES: COc1cc2c(cc1C(=O)Nc1cccc(-c3nnnn3[C@H](C)CO)n1)CN(S(=O)(=O)CCC(F)(F)F)CC2] | 570 | 1H NMR (400 MHz, Chloroform-d) δ 10.62 (s, 1H), 8.59 (dd, J = 7.2, 2.2 Hz, 1H), 8.09 (s, 1H), 8.07-7.97 (m, 2H), 6.88 (s, 1H), 5.64 (m, 1H), 4.57 (s, 2H), 4.19-4.11 (m, 4H), 3.69 (m, J = 6.8 Hz, 2H), 3.26-3.17 (m, 2H), 3.07 (t, J = 6.0 Hz, 2H), 2.69 (m, 2H), 1.75 (d, J = 6.8 Hz, 2H), 1.57(s, 3H). |

TABLE 6-continued

| Example | Structure | LC-MS [M + H]+ unless otherwise noted | 1H-NMR |
|---|---|---|---|
| 88 | 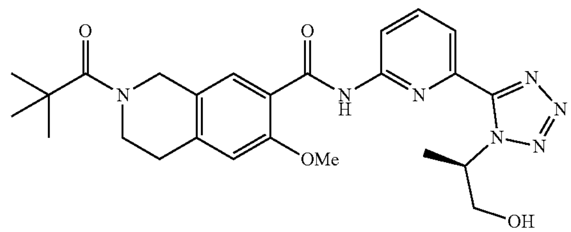 [SMILES: COc1cc2c(cc1C(=O)Nc1cccc(-c3nnnn3[C@H](C)CO)n1)CN(C(=O)C(C)(C)C)CC2] | 494 | 1H NMR (400 MHz, Chloroform-d) δ 10.65 (s, 1H), 8.59 (dd, J = 6.8, 2.4 Hz, 1H), 8.09 (s, 1H), 8.04-7.99 (m, 2H), 6.85 (s, 1H), 5.65 (m, 1H), 4.82 (s, 2H), 4.14 (d, J = 6.4 Hz, 2H), 4.01 (s, 1H), 3.90 (t, J = 5.4 Hz, 2H), 2.96 (t, J = 5.4 Hz, 2H), 1.75 (d, J = 6.8 Hz, 3H), 1.34 (s, 9H). |
| 89 | 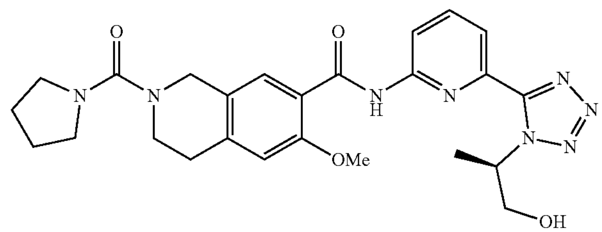 | 507 | 1H NMR (400 MHz, Chloroform-d) δ 10.66 (s, 1H), 8.58 (dd, J = 7.4, 2.0 Hz, 1H), 8.07-7.96 (m, 3H), 6.84 (s, 1H), 5.66 (m, 1H), 4.51 (s, 2H), 4.16 (d, J = 6.3 Hz, 2H), 4.11 (s, 3H), 3.59 (t, J = 5.7 Hz, 2H), 3.45 (t, J = 6.4 Hz, 4H), 2.99 (t, J = 5.7 Hz, 2H), 1.88 (t, t, J = 6.4 Hz, 4H), 1.75 (d, J = 6.8 Hz, 3H). |
| 90 | 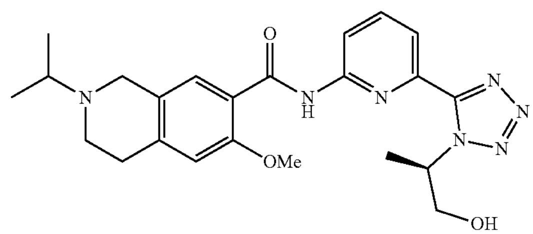 [SMILES: COc1cc2c(cc1C(=O)Nc1cccc(-c3nnnn3[C@H](C)CO)n1)CN(C(C)C)CC2] | 452 | 1H NMR (400 MHz, Chloroform-d) δ 10.66 (s, 1H), 8.57 (dd, J = 7.8, 1.6 Hz, 1H), 8.05-7.95 (m, 3H), 6.82 (s, 1H), 5.68 (m, 1H), 4.15 (d, J = 6.3 Hz, 2H), 4.09 (s, 3H), 3.86 (s, 2H), 3.16-3.00 (m, 3H), 2.93 (s, 2H), 1.74 (d, J = 6.9 Hz, 3H), 1.25 (d, J = 5.9 Hz, 6H) |
| 91 | 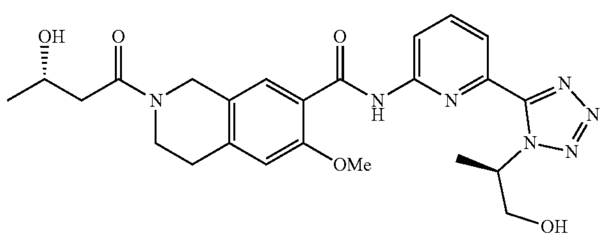 [SMILES: COc1cc2c(cc1C(=O)Nc1cccc(-c3nnnn3[C@H](C)CO)n1)CN(C(=O)C[C@H](C)O)CC2] | 496 | 1H NMR (400 MHz, DMSO-d6) δ 10.73 (s, 1H), 8.42 (d, J = 8.4 Hz, 1H), 8.17-8.08 (m, 1H), 7.95 (d, J = 7.8 Hz, 1H), 7.75 (d, J = 23.3 Hz, 1H), 7.11 (s, 1H), 5.88-5.72 (m, 1H), 5.05-4.97 (m, 1H), 4.71 (s, 1H), 4.65-4.58 (m, 2H), 4.10-3.95 (m, 4H), 3.90-3.63 (m, 4H), 2.94 (t, J = 5.9 Hz, 1H), 2.85 (t, J = 6.0 Hz, 1H), 2.58 (dd, J = 14.9, 7.3 Hz, 1H), 2.46-2.36 (m, 1H), 1.59 (dd, J = 6.8, 1.4 Hz, 3H), 1.11 (dd, J = 8.0, 6.1 Hz, 3H) |
| 92 | 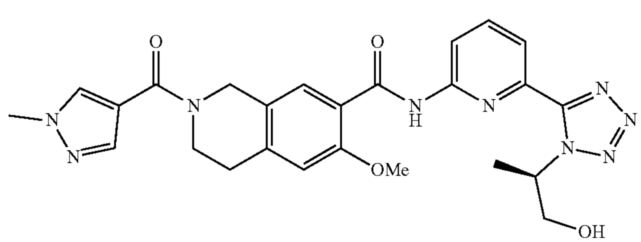 [SMILES: COc1cc2c(cc1C(=O)Nc1cccc(-c3nnnn3[C@H](C)CO)n1)CN(C(=O)c1cnn(C)c1)CC2] | 518 | 1H NMR (400 MHz, DMSO-d6) δ 10.73 (s, 1H), 8.42 (d, J = 8.9 Hz, 1H), 8.16 (s, 1H), 8.13 (t, J = 8.0 Hz, 1H), 7.95 (dd, J = 7.6, 0.9 Hz, 1H), 7.77 (s, 1H), 7.77 (s, 1H), 7.13 (s, 1H), 5.90-5.71 (m, 1H), 5.01 (t, J = 5.6 Hz, 1H), 4.79 (s, 2H), 3.99 (s, 3H), 3.88 (s, 3H), 3.85-3.76 (comp, 4H), 2.96 (s, 2H), 1.59 (d, J = 6.8 Hz, 3H) |

TABLE 6-continued

| Example | Structure | LC-MS [M + H]+ unless otherwise noted | ¹H-NMR |
|---|---|---|---|
| 93 | 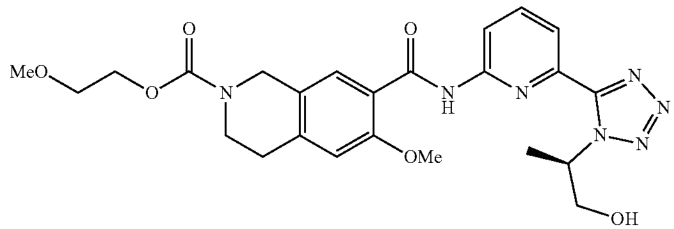 [SMILES: COCCOC(=O)N1CCc2cc(OC)c(C(=O)Nc3cccc(-c4nnnn4[C@H](C)CO)n3)cc2C1] | 512 | ¹H NMR (400 MHz, DMSO-d₆) δ 10.73 (s, 1H), 8.42 (dd, J = 8.4, 0.9 Hz, 1H), 8.13 (t, J = 8.0 Hz, 1H), 7.95 (dd, J = 7.6, 0.9 Hz, 1H), 7.72 (s, 1H), 7.10 (s, 1H), 5.89-5.76 (m, 1H), 5.01 (t, J = 5.5 Hz, 1H), 4.56 (s, 2H), 4.21-4.14 (m, 2H), 3.98 (s, 3H), 3.90-3.73 (m, 2H), 3.62 (t, J = 5.8 Hz, 2H), 3.58-3.52 (m, 2H), 3.28 (s, 3H), 2.89 (t, J = 5.9 Hz, 2H), 1.59 (d, J = 6.8 Hz, 3H) |
| 94 | 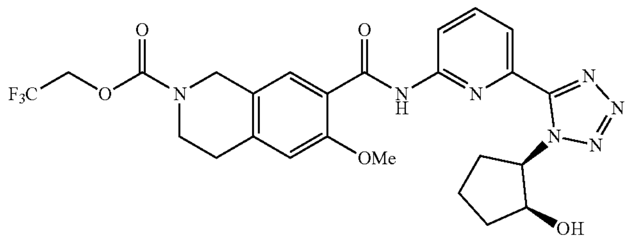 [SMILES: COc1cc2c(cc1C(=O)Nc1cccc(-c3nnnn3[C@@H]3CCC[C@@H]3O)n1)CN(C(=O)OCC(F)(F)F)CC2] | 562 | ¹H NMR (400 MHz, Chloroform-d) δ 10.61 (s, 1H), 8.59 (dd, J = 8.3, 1.0 Hz, 1H), 8.06 (s, 1H), 7.99 (t, J = 8.0 Hz, 1H), 7.91 (d, J = 7.5 Hz, 1H), 6.85 (s, 1H), 5.31 (dt, J = 7.3, 4.7 Hz, 1H), 4.77 (br s, 1H), 4.68 (s, 2H), 4.61-4.51 (comp, 3H), 4.11 (s, 3H), 3.79-3.73 (m, 2H), 2.97-2.92 (m, 2H), 2.71-2.54 (m, 1H), 2.38-2.22 (m, 2H), 2.14 (dddd, J = 12.3, 8.9, 6.2, 3.2 Hz, 1H), 1.93 (dq, J = 13.0, 8.8 Hz, 1H), 1.86-1.71 (m, 1H) |
| 96 | 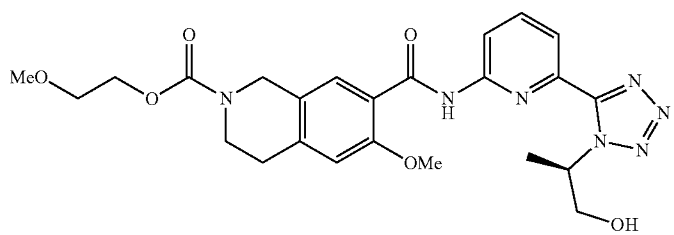 [SMILES: COCCOC(=O)N1CCc2cc(OC)c(C(=O)Nc3cccc(-c4nnnn4[C@H](C)CO)n3)cc2C1] | 512 | ¹H NMR (400 MHz, DMSO-d₆) δ 10.73 (s, 1H), 8.42 (dd, J = 8.4, 0.9 Hz, 1H), 8.13 (t, J = 8.0 Hz, 1H), 7.95 (dd, J = 7.6, 0.9 Hz, 1H), 7.72 (s, 1H), 7.10 (s, 1H), 5.89-5.75 (m, 1H), 5.01 (t, J = 5.5 Hz, 1H), 4.56 (br s, 2H), 4.20-4.15 (m, 2H), 3.98 (s, 3H), 3.86-3.74 (m, 2H), 3.62 (t, J = 5.8 Hz, 2H), 3.58-3.50 (m, 2H), 3.28 (s, 3H), 2.89 (t, J = 5.9 Hz, 2H), 1.59 (d, J = 6.8 Hz, 3H). |
| 97 | 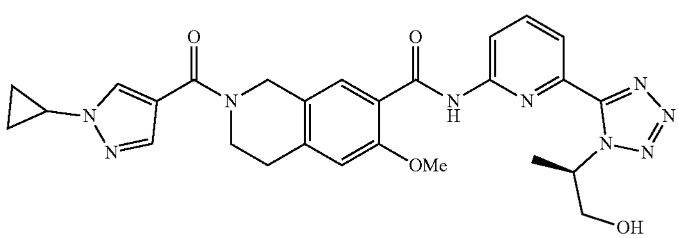 [SMILES: COc1cc2c(cc1C(=O)Nc1cccc(-c3nnnn3[C@H](C)CO)n1)CN(C(=O)c1cnn(C3CC3)c1)CC2] | 544 | ¹H NMR (400 MHz, DMSO-d₆) δ 10.73 (s, 1H), 8.42 (d, J = 8.3 Hz, 1H), 8.22 (s, 1H), 8.16-8.10 (m, 1H), 7.95 (dd, J = 7.6, 0.9 Hz, 1H), 7.78 (s, 1H), 7.75 (s, 1H), 7.13 (s, 1H), 5.88-5.76 (m, 1H), 5.01 (t, J = 5.6 Hz, 1H), 4.78 br (s, 2H), 3.99 (s, 3H), 3.87-3.76 (comp, 5H), 2.97 (br s, 2H), 1.59 (d, J = 6.8 Hz, 3H), 1.10 (ddt, J = 4.8, 4.0, 2.6 Hz, 2H), 1.06-0.93 (m, 2H). |
| 98 | 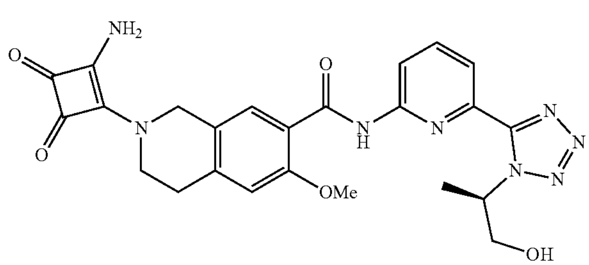 [SMILES: COc1cc2c(cc1C(=O)Nc1cccc(-c3nnnn3[C@H](C)CO)n1)CN(c1c(N)c(=O)c1=O)CC2] | 505 | ¹H NMR (400 MHz, DMSO-d₆) δ 10.75 (s, 1H), 8.42 (d, J = 8.3 Hz, 1H), 8.13 (t, J = 8.0 Hz, 1H), 7.95 (dd, J = 7.6, 0.9 Hz, 1H), 7.87 (s, 2H), 7.74 (s, 1H), 7.13 (s, 1H), 5.88-5.73 (m, 1H), 5.07 (s, 1H), 4.90 (s, 2H), 3.99 (s, 3H), 3.86-3.77 (m, 2H), 3.37-3.29 (m, 2H), 3.00 (t, J = 5.8 Hz, 2H), 1.59 (d, J = 6.8 Hz, 3H). |

TABLE 6-continued

| Example | Structure | LC-MS [M + H]+ unless otherwise noted | ¹H-NMR |
|---|---|---|---|
| 99 | 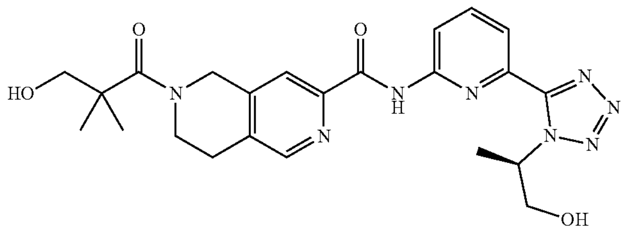 [SMILES: C[C@H](CO)n1nnnc1-c1cccc(NC(=O)c2cc3c(cn2)CCN(C(=O)C(C)(C)CO)C3)n1] | 481 | ¹H NMR (400 MHz, Chloroform-d) δ 10.51 (s, 1H), 8.49 (s, 1H), 8.43-8.37 (m, 1H), 8.12 (d, J = 6.4 Hz, 2H), 8.00 (t, J = 8.0 Hz, 1H), 5.95-5.77 (m, 1H), 4.89 (s, 2H), 4.19-4.13 (m, 2H), 3.95 (t, J = 5.8 Hz, 2H), 3.55 (s, 2H), 3.03 (t, J = 5.6 Hz, 2H), 1.71 (d, J = 6.8 Hz, 3H), 1.35 (s, 6H). |
| 100 | 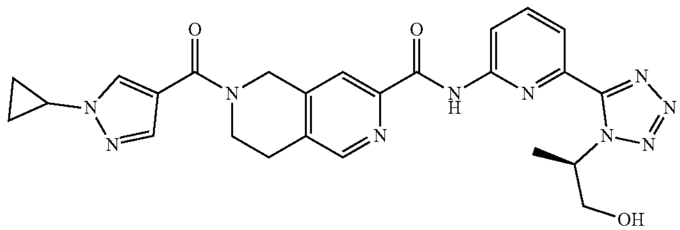 [SMILES: C[C@H](CO)n1nnnc1-c1cccc(NC(=O)c2cc3c(cn2)CCN(C(=O)c2cnn(C4CC4)c2)C3)n1] | 515 | ¹H NMR (400 MHz, Chloroform-d) δ 10.48 (s, 1H), 8.49 (s, 1H), 8.39 (d, J = 8.3 Hz, 1H), 8.15-8.05 (comp, 2H), 7.99 (t, J = 8.0 Hz, 1H), 7.87 (s, 1H), 7.69 (s, 1H), 5.86 (td, J = 6.9, 5.3 Hz, 1H), 4.98 (s, 2H), 4.21-4.12 (m, 2H), 4.01 (t, J = 5.8 Hz, 2H), 3.65 (tt, J = 7.4, 3.8 Hz, 1H), 3.06 (t, J = 5.8 Hz, 2H), 1.71 (d, J = 6.8 Hz, 3H), 1.21-1.14 (m, 2H), 1.14-1.05 (m, 2H). |
| 101 | 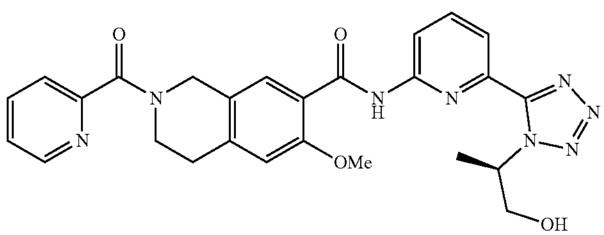 [SMILES: COc1cc2c(cc1C(=O)Nc1cccc(-c3nnnn3[C@H](C)CO)n1)CN(C(=O)c1ccccn1)CC2] | 515 | ¹H NMR (400 MHz, DMSO-d₆) (rotamers) δ 10.75 (s, 0.6 H), 10.70 (s, 0.4 H), 8.64-8.62 (m, 1H), 8.44 (d, J = 8.3 Hz, 0.6 H), 8.37 (d, J = 8.4 Hz, 0.4 H), 8.16-8.08 (m, 1H), 8.02-7.91 (m, 2H), 7.81 (s, 0.6 H), 7.64 (dt, J = 7.9, 1.1 Hz, 0.6 H), 7.60 (d, J = 7.7 Hz, 0.4 H), 7.55-7.48 (m, 1.4 H), 7.14 (s, 0.4 H), 7.11 (s, 0.6 H), 5.90-5.77 (m, 1H), 5.00 (q, J = 5.9 Hz, 1H), 4.82 (s, 1.4 H), 4.67 (s, 0.6 H), 3.98 (s, 3H), 3.90 (t, J = 6.0 Hz, 0.6 H), 3.87-3.73 (m, 1.4 H), 3.65 (t, J = 5.8 Hz, 1H), 3.01-2.94 (m, 2H), 1.51-.157 (m, 3H). |
| 102 | 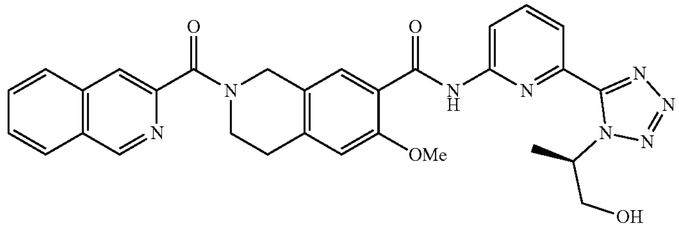 [SMILES: COc1cc2c(cc1C(=O)Nc1cccc(-c3nnnn3[C@H](C)CO)n1)CN(C(=O)c1cc3ccccc3cn1)CC2] | 565 | ¹H NMR (400 MHz, DMSO-d₆) (rotamers) δ 10.77-10.69 (m, 1H), 9.38 (s, 0.6 H), 8.46-8.33 (m, 1H), 8.23-8.07 (comp, 4H), 7.97-7.77 (comp, 4 H), 7.53 (s, 0.4 H), 7.14-7.13 (m, 1H), 5.85-5.80 (m, 1H), 5.03-4.97 (m, 1H), 4.87-4.73 (m, 2H), 3.99 (s, 3H), 3.98-3.69 (m, 4H), 3.09-2.95 (m, 2H), 1.59 (dd, J = 12.6, 6.8 Hz, 3H). |
| 103 | 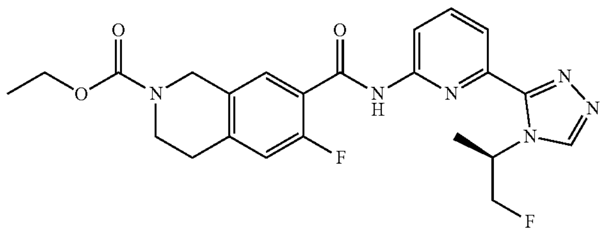 [SMILES: CCOC(=O)N1CCc2cc(F)c(C(=O)Nc3cccc(-c4nncn4[C@H](C)CF)n3)cc2C1] | 471 | |

TABLE 6-continued

| Example | Structure | LC-MS [M + H]+ unless otherwise noted | 1H-NMR |
|---|---|---|---|
| 104 | 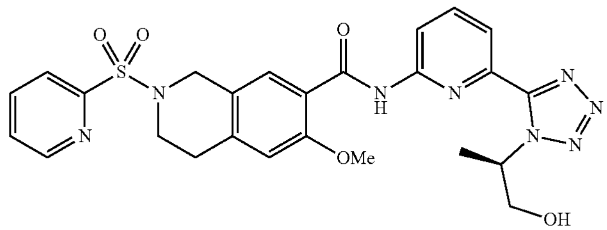 [SMILES: COc1cc2c(cc1C(=O)Nc1cccc(-c3nnnn3[C@H](C)CO)n1)CN(S(=O)(=O)c1ccccn1)CC2] | 551 | 1H NMR (400 MHz, DMSO-d6) δ 10.70 (s, 1H), 8.71 (ddd, J = 4.7, 1.8, 0.9 Hz, 1H), 8.40 (dd, J = 8.4, 0.9 Hz, 1H), 8.14-8.10 (comp, 2H), 8.00 (dt, J = 7.9, 1.0 Hz, 1H), 7.95 (dd, J = 7.6, 0.9 Hz, 1H), 7.72-7.65 (comp, 2H), 7.05 (s, 1H), 5.84-5.78 (m, 1H), 5.00 (t, J = 5.6 Hz, 1H), 4.46 (s, 2H), 3.95 (s, 3H), 3.89-3.72 (m, 2H), 3.57 (t, J = 5.9 Hz, 2H), 2.93 (t, J = 5.9 Hz, 2H), 1.59 (d, J = 6.8 Hz, 3H). |
| 105 | 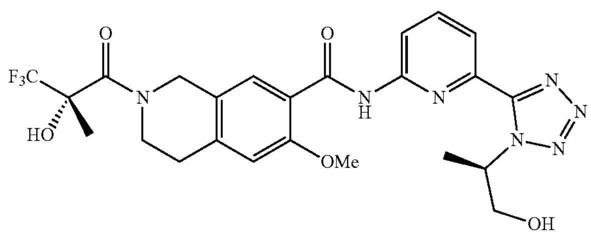 [SMILES: COc1cc2c(cc1C(=O)Nc1cccc(-c3nnnn3[C@H](C)CO)n1)CN(C(=O)[C@](C)(O)C(F)(F)F)CC2] | 550 | 1H NMR (400 MHz, DMSO-d6) δ 10.73 (s, 1H), 8.42 (dd, J = 8.4, 0.9 Hz, 1H), 8.18-8.08 (m, 1H), 7.95 (dd, J = 7.6, 0.9 Hz, 1H), 7.76-7.67 (m, 1H), 7.20 (br s, 1H), 7.11 (s, 1H), 5.86-5.76 (m, 1H), 5.09 (br s, 1H), 5.01 (t, J = 5.6 Hz, 1H), 4.64 (br s, 1H), 4.11 (br s, 1H), 3.99 (s, 3H), 3.89-3.67 (comp, 3H), 2.96-2.89 (m, 2H), 1.60 (d, J = 6.8 Hz, 3H). |
| 106 | 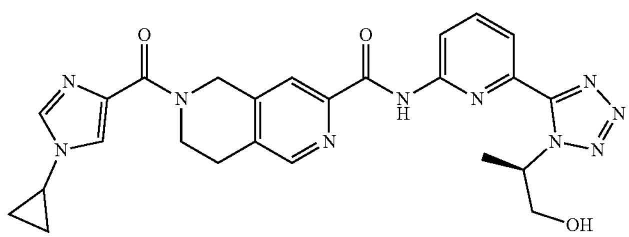 [SMILES: C[C@H](CO)n1nnnc1-c1cccc(NC(=O)c2cc3c(cn2)CCN(C(=O)c2cn(C4CC4)cn2)C3)n1] | 515 | 1H NMR (400 MHz, Chloroform-d) δ 10.48 (s, 1H), 8.44 (s, 1H), 8.37 (br s, 1H), 8.14-8.03 (comp, 2H), 7.97 (t, J = 8.0 Hz, 1H), 7.65 (d, J = 1.4 Hz, 1H), 7.56 (d, J = 1.5 Hz, 1H), 5.96-5.80 (m, 1H), 5.58 (br s, 1H), 4.96 (br s, 1H), 4.51 (br s, 1H), 4.24-4.09 (m, 2H), 4.02 (br s, 1H), 3.45-3.34 (m, 1H), 3.07 (br s, 2H), 1.70 (d, J = 6.8 Hz, 3H), 1.15-0.96 (comp, 4H). |
| 107 | 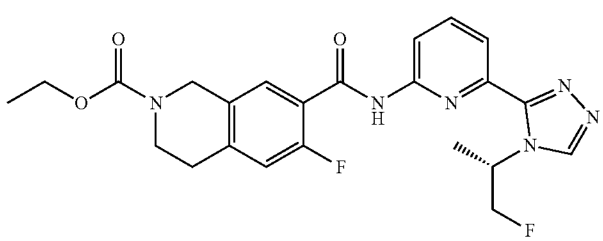 [SMILES: CCOC(=O)N1CCc2cc(F)c(C(=O)Nc3cccc(-c4nncn4[C@@H](C)CF)n3)cc2C1] | 471 | |
| 108 | 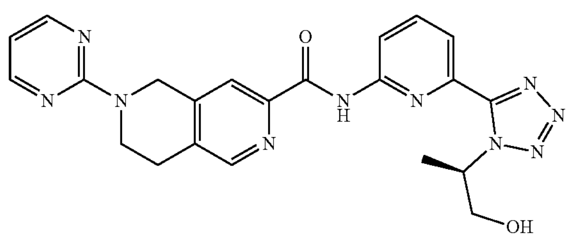 [SMILES: C[C@H](CO)n1nnnc1-c1cccc(NC(=O)c2cc3c(cn2)CCN(c2ncccn2)C3)n1] | 459 | 1H NMR (400 MHz, Chloroform-d) δ 10.53 (s, 1H), 8.49 (s, 1H), 8.43-8.39 (comp, 3H), 8.18 (s, 1H), 8.11 (dd, J = 7.6, 1.0 Hz, 1H), 8.00 (t, J = 8.0 Hz, 1H), 6.61 (t, J = 4.8 Hz, 1H), 5.87 (h, J = 6.5 Hz, 1H), 5.08 (s, 2H), 4.20 (t, J = 5.8 Hz, 2H), 4.16 (d, J = 6.0 Hz, 2H), 3.06 (t, J = 5.8 Hz, 2H), 1.71 (d, J = 6.8 Hz, 3H). |

TABLE 6-continued

| Example | Structure | LC-MS [M + H]+ unless otherwise noted | ¹H-NMR |
|---|---|---|---|
| 109 | 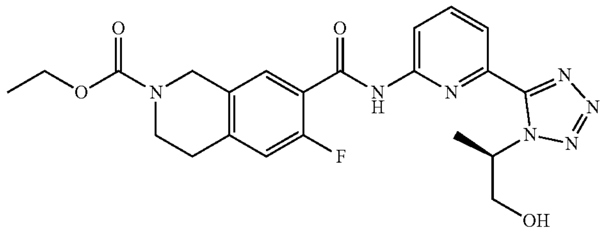 [SMILES: CCOC(=O)N1CCc2cc(F)c(C(=O)Nc3cccc(-c4nnnn4[C@H](C)CO)n3)cc2C1] | 470 | |
| 110 | 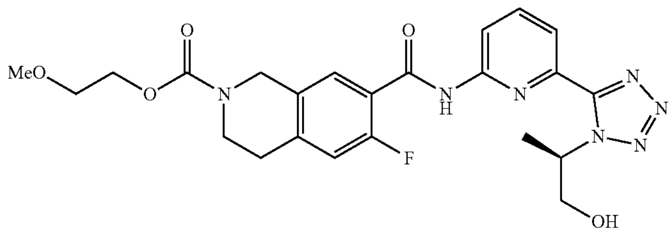 [SMILES: COCCOC(=O)N1CCc2cc(F)c(C(=O)Nc3cccc(-c4nnnn4[C@H](C)CO)n3)cc2C1] | 500 | |
| 111 | 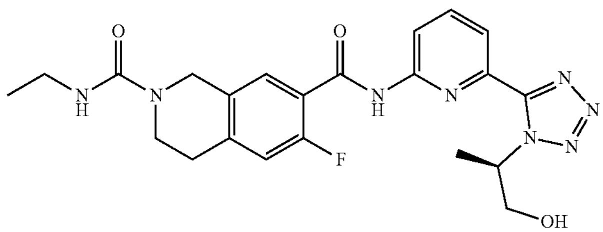 [SMILES: CCNC(=O)N1CCc2cc(F)c(C(=O)Nc3cccc(-c4nnnn4[C@H](C)CO)n3)cc2C1] | 469 | |
| 112 | 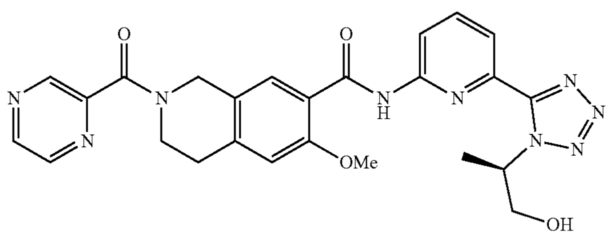 [SMILES: COc1cc2c(cc1C(=O)Nc1cccc(-c3nnnn3[C@H](C)CO)n1)CN(C(=O)c1cnccn1)CC2] | 516 | ¹H NMR (400 MHz, DMSO-d₆) (rotamers) δ 10.75 (s, 0.6 H), 10.71 (s, 0.4 H), 8.91 (d, J = 1.5 Hz, 0.6 H), 8.86 (d, J = 1.5 Hz, 0.4 H), 8.79 (d, J = 2.6 Hz, 0.6H), 8.78 (d, J = 2.6 Hz, 0.4H), 8.73-8.71 (m, 1H), 8.44 (d, J = 8.3 Hz, 0.6H), 8.37 (d, J = 8.4 Hz, 0.4H), 8.16-8.09 (m, 1H), 7.95 (td, J = 7.8, 0.9 Hz, 1H), 7.82 (s, 0.6H), 7.59 (s, 0.4H), 7.15 (s, 0.4H), 7.12 (s, 0.6H), 5.85-5.77 (m, 1H), 5.00 (q, J = 5.4 Hz, 1H), 4.85 (s, 1.2H), 4.70 (s, 0.8H), 3.99 (s, 3H), 3.94-3.62 (comp, 4H), 3.02 (t, J = 6.1 Hz, 1H), 2.97 (t, J = 5.8 Hz, 1H), 1.59 (dd, J = 6.7, 5.5 Hz, 3H). |
| 113 | 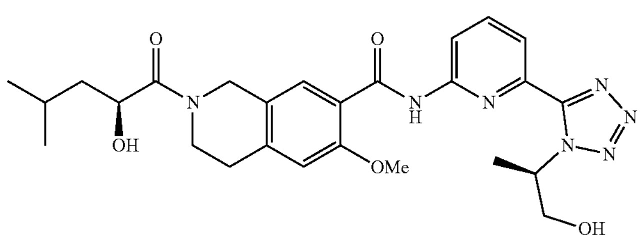 [SMILES: COc1cc2c(cc1C(=O)Nc1cccc(-c3nnnn3[C@H](C)CO)n1)CN(C(=O)[C@@H](O)CC(C)C)CC2] | 524 | ¹H NMR (400 MHz, DMSO-d₆) δ 10.73 (s, 1H), 8.42 (d, J = 8.4 Hz, 1H), 8.13 (t, J = 8.0 Hz, 1H), 7.95 (d, J = 7.6 Hz, 1H), 7.75 (d, J = 12.2 Hz, 1H), 7.11 (s, 1H), 5.88-5.76 (m, 1H), 5.01 (t, J = 5.6 Hz, 1H), 4.88 (dd, J = 41.8, 7.3 Hz, 1H), 4.81-4.54 (m, 2H), 4.46-4.38 (m, 1H), 3.98 (d, J = 3.8 Hz, 3H), 3.90-3.73 (m, 3H), 2.97-2.93 (m, 1H), 2.89-2.84 (m, 1H), 1.83-1.71 (m, 1H), 1.59 (d, J = 6.8 Hz, 3H), 1.51-1.31 (m, 2H), 0.98-0.82 (m, 6H). |

TABLE 6-continued

| Example | Structure | LC-MS [M + H]+ unless otherwise noted | ¹H-NMR |
|---|---|---|---|
| 114 | 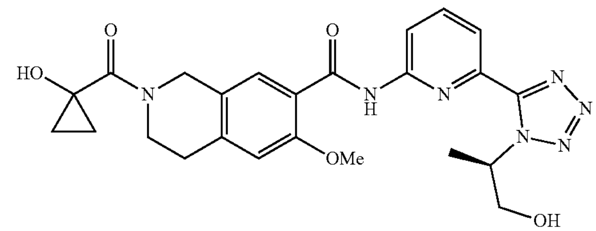 [SMILES: COc1cc2c(cc1C(=O)Nc1cccc(-c3nnnn3[C@H](C)CO)n1)CN(C(=O)C1(O)CC1)CC2] | 494 | ¹H NMR (400 MHz, DMSO-d₆) δ 10.74 (s, 1H), 8.42 (dd, J = 8.4, 0.9 Hz, 1H), 8.13 (t, J = 8.0 Hz, 1H), 7.95 (dd, J = 7.6, 0.9 Hz, 1H), 7.73 (s, 1H), 7.11 (s, 1H), 6.38 (s, 1H), 5.88-5.76 (m, 1H), 5.01 (t, J = 5.6 Hz, 1H), 4.79-4.53 (m, 2H), 3.99 (s, 3H), 3.89-3.72 (m, 2H), 2.93-2.88 (m, 2H), 1.60 (d, J = 6.8 Hz, 3H), 0.96-0.94 (m, 2H), 0.86-0.80 (m, 2H). |
| 115 | 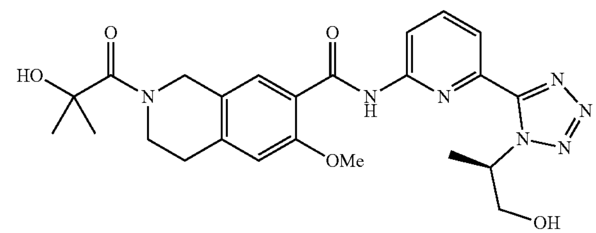 [SMILES: COc1cc2c(cc1C(=O)Nc1cccc(-c3nnnn3[C@H](C)CO)n1)CN(C(=O)C(C)(C)O)CC2] | 496 | ¹H NMR (400 MHz, DMSO-d₆) δ 10.73 (s, 1H), 8.42 (dd, J = 8.4, 0.9 Hz, 1H), 8.17-8.09 (m, 1H), 7.95 (dd, J = 7.6, 0.9 Hz, 1H), 7.71 (s, 1H), 7.09 (s, 1H), 5.85-5.78 (m, 1H), 5.49 (s, 1H), 5.01 (t, J = 5.6 Hz, 1H), 4.63-4.53 (m, 1H), 4.17-4.12 (m, 1H), 3.98 (s, 3H), 3.89-3.73 (m, 2H), 2.91 (br s, 2H), 1.60 (d, J = 6.7 Hz, 3H), 1.34 (s, 6H). |
| 116 | 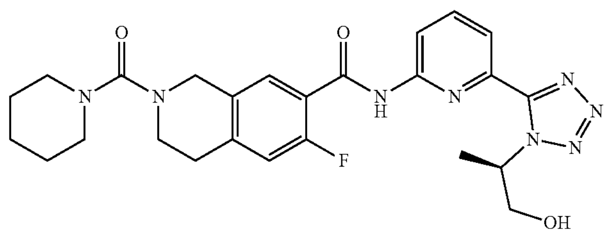 [SMILES: C[C@H](CO)n1nnnc1-c1cccc(NC(=O)c2cc3c(cc2F)CCN(C(=O)N2CCCCC2)C3)n1] | 509 | |
| 117 | 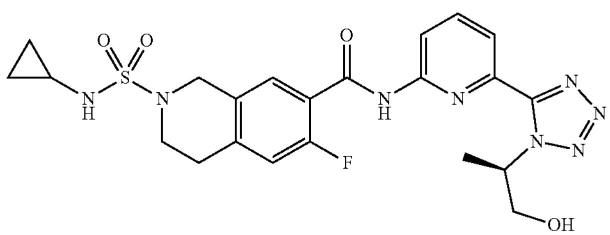 [SMILES: C[C@H](CO)n1nnnc1-c1cccc(NC(=O)c2cc3c(cc2F)CCN(S(=O)(=O)NC2CC2)C3)n1] | 517 | |
| 118 | 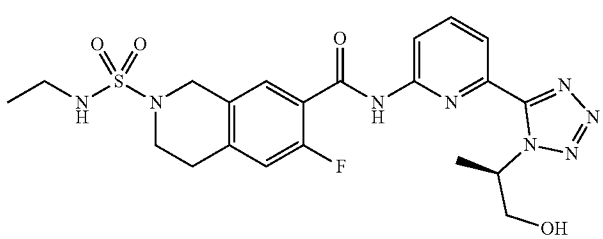 [SMILES: CCNS(=O)(=O)N1CCc2cc(F)c(C(=O)Nc3cccc(-c4nnnn4[C@H](C)CO)n3)cc2C1] | 505 | |
| 119 | 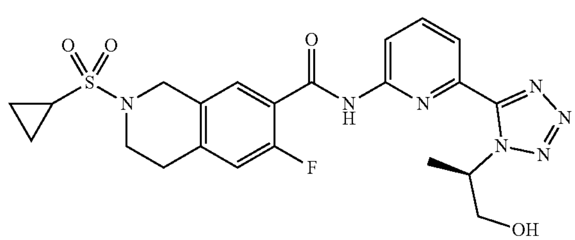 [SMILES: C[C@H](CO)n1nnnc1-c1cccc(NC(=O)c2cc3c(cc2F)CCN(S(=O)(=O)C2CC2)C3)n1] | 502 | |

TABLE 6-continued

| Example | Structure | LC-MS [M + H]+ unless otherwise noted | 1H-NMR |
|---------|-----------|----------------------------------------|--------|
| 120 | 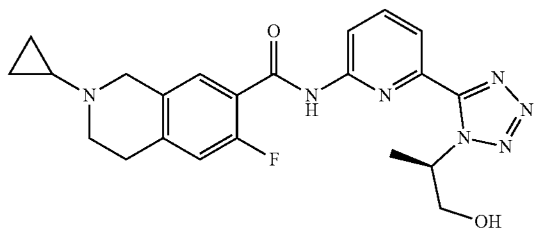 [SMILES: C[C@H](CO)n1nnnc1-c1cccc(NC(=O)c2cc3c(cc2F)CCN(C2CC2)C3)n1] | 438 | |
| 121 | 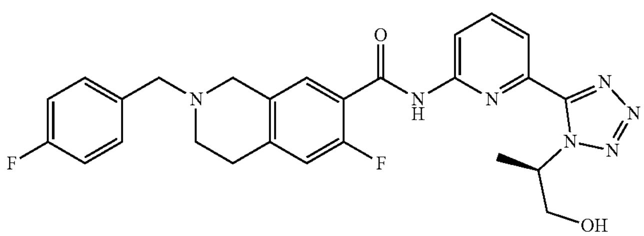 [SMILES: C[C@H](CO)n1nnnc1-c1cccc(NC(=O)c2cc3c(cc2F)CCN(Cc2ccc(F)cc2)C3)n1] | 506 | |
| 122 | 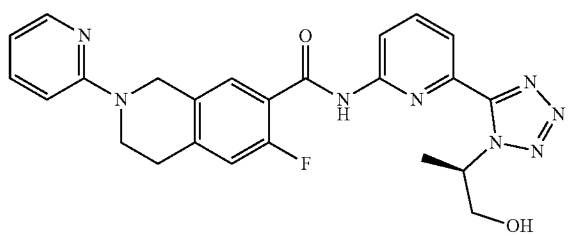 [SMILES: C[C@H](CO)n1nnnc1-c1cccc(NC(=O)c2cc3c(cc2F)CCN(c2ccccn2)C3)n1] | 475 | |
| 123 | 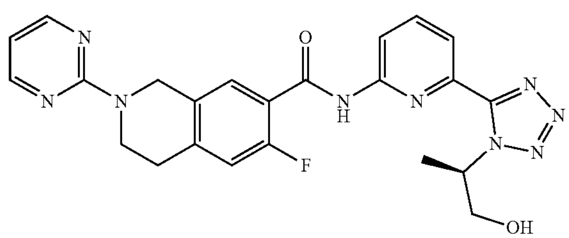 [SMILES: C[C@H](CO)n1nnnc1-c1cccc(NC(=O)c2cc3c(cc2F)CCN(c2ncccn2)C3)n1] | 476 | |
| 124 | 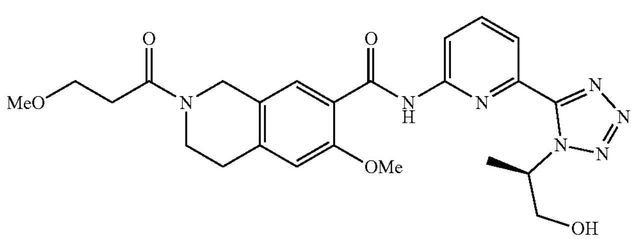 [SMILES: COCCC(=O)N1CCc2cc(OC)c(C(=O)Nc3cccc(-c4nnnn4[C@H](C)CO)n3)cc2C1] | 496 | 1H NMR (400 MHz, DMSO-d6) (rotamers) δ 10.73 (s, 1H), 8.42 (d, J = 8.5 Hz, 1H), 8.18-8.09 (m, 1H), 7.95 (d, J = 7.6 Hz, 1H), 7.78 (s, 0.4H), 7.72 (s, 0.6H), 7.11 (s, 1H), 5.83-5.78 (m, 1H), 5.01 (q, J = 5.4 Hz, 1H), 4.69 (s, 0.8H), 4.61 (s, 1.2H), 3.98 (d, J = 4.6 Hz, 3H), 3.84-3.77 (m, 2H), 3.72-3.67 (m, 2H), 3.58 (td, J = 6.5, 2.4 Hz, 2H), 3.22 (d, J = 5.9 Hz, 3H), 2.94 (t, J = 5.8 Hz, 1H), 2.85 (t, J = 6.0 Hz, 1H), 2.67 (t, J = 6.5 Hz, 2H), 1.59 (dd, J = 6.8, 1.4 Hz, 3H). |

TABLE 6-continued

| Example | Structure | LC-MS [M + H]+ unless otherwise noted | 1H-NMR |
|---|---|---|---|
| 125 | 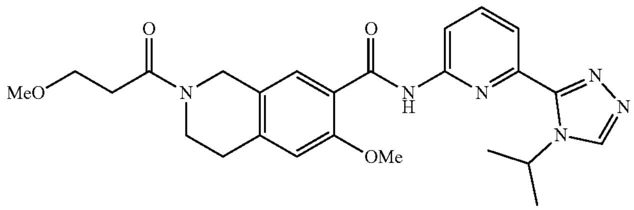 [SMILES: COCCC(=O)N1CCc2cc(OC)c(C(=O)Nc3cccc(-c4nncn4C(C)C)n3)cc2C1] | 479 | 1H NMR (400 MHz, DMSO-d6) (rotamers) δ 10.60 (d, J = 2.6 Hz, 1H), 8.90 (d, J = 1.1 Hz, 1H), 8.36-8.30 (m, 1H), 8.03 (td, J = 8.0, 2.1 Hz, 1H), 7.90-7.84 (m, 1H), 7.81 (s, 0.4H), 7.75 (s, 0.6H), 7.11 (s, 1H), 5.53-5.47 (m, 1H), 4.69 (s, 0.8H), 4.61 (s, 1.2zH), 3.98 (d, J = 3.6 Hz, 3H), 3.72-3.66 (m, 2H), 3.60-3.56 (m, 2H), 3.22 (d, J = 6.0 Hz, 3H), 2.93 (t, J = 5.9 Hz, 1.2H), 2.84 (t, J = 5.9 Hz, 0.8H), 2.67 (t, J = 6.5 Hz, 2H), 1.52 (dd, J = 6.7, 1.7 Hz, 6H). |
| 126 | 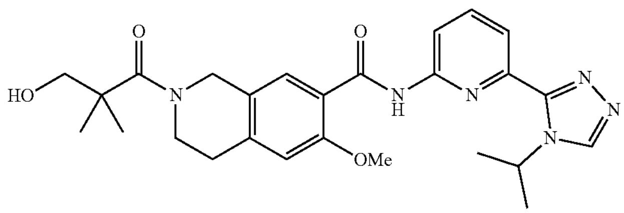 [SMILES: COc1cc2c(cc1C(=O)Nc1cccc(-c3nncn3C(C)C)n1)CN(C(=O)C(C)(C)CO)CC2] | 493 | 1H NMR (400 MHz, DMSO-d6) δ 10.60 (s, 1H), 8.90 (s, 1H), 8.32 (dd, J = 8.3, 0.9 Hz, 1H), 8.03 (t, J = 8.0 Hz, 1H), 7.87 (dd, J = 7.7, 0.9 Hz, 1H), 7.81 (s, 1H), 7.09 (s, 1H), 5.50 (hept, J = 6.7 Hz, 1H), 4.71 (s, 2H), 4.58 (t, J = 5.8 Hz, 1H), 3.97 (s, 3H), 3.78 (t, J = 5.9 Hz, 2H), 3.46 (d, J = 5.9 Hz, 2H), 2.89 (t, J = 5.8 Hz, 2H), 1.52 (d, J = 6.7 Hz, 6H), 1.19 (s, 6H). |
| 127 | 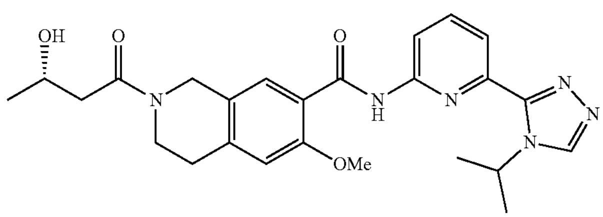 [SMILES: COc1cc2c(cc1C(=O)Nc1cccc(-c3nncn3C(C)C)n1)CN(C(=O)C[C@H](C)O)CC2] | 479 | 1H NMR (400 MHz, DMSO-d6) (rotamers) δ 10.60 (d, J = 2.4 Hz, 1H), 8.90 (d, J = 1.0 Hz, 1H), 8.37-8.31 (m, 1H), 8.03 (td, J = 8.0, 2.3 Hz, 1H), 7.87 (ddd, J = 7.6, 1.8, 0.9 Hz, 1H), 7.81 (s, 0.4H), 7.75 (s, 0.6H), 7.11 (d, J = 1.7 Hz, 1H), 5.50 (p, J = 6.6 Hz, 1H), 4.80-4.53 (comp, 3H), 4.07-4.00 (m, 1H), 3.97 (d, J = 3.4 Hz, 3H), 3.73-3.65 (m, 2H), 2.94 (t, J = 5.9 Hz, 1.2H), 2.84 (t, J = 6.0 Hz, 0.8H), 2.60 (d, J = 7.2 Hz, 0.4H), 2.56 (d, J = 7.3 Hz, 0.6H), 2.45-2.38 (m, 1H), 1.52 (dd, J = 6.7, 1.6 Hz, 6H), 1.11 (dd, J = 7.9, 6.2 Hz, 3H). |
| 128 | 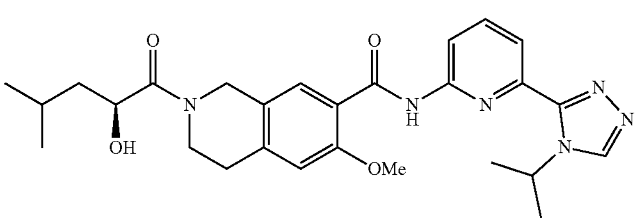 [SMILES: COc1cc2c(cc1C(=O)Nc1cccc(-c3nncn3C(C)C)n1)CN(C(=O)[C@@H](O)CC(C)C)CC2] | 507 | 1H NMR (400 MHz, DMSO-d) (rotamers) δ 10.60 (s, 1H), 8.90 (s, 1H), 8.32 (dd, J = 8.3, 0.9 Hz, 1H), 8.03 (t, J = 8.0 Hz, 1H), 7.87 (dd, J = 7.6, 0.9 Hz, 1H), 7.78 (d, J = 11.6 Hz, 1H), 7.11 (s, 1H), 5.50 (p, J = 6.7 Hz, 1H), 4.93 (d, J = 7.3 Hz, 0.6H), 4.86-4.51 (comp, 2.4H), 4.43-4.38 (m, 1H), 3.98 (d, J = 2.8 Hz, 3H), 3.78-3.75 (m, 1.6H), 3.71-3.56 (m, 0.4H), 2.95 (br s, 1H), 2.86 (t, J = 6.1 Hz, 1H), 1.77 (br s, 1H), 1.52 (d, J = 6.7 Hz, 6H), 1.47-1.31 (m, 1H), 1.26 (t, J = 6.1 Hz, 1H), 0.94-0.81 (m, 6H). |

TABLE 6-continued

| Example | Structure | LC-MS [M + H]+ unless otherwise noted | 1H-NMR |
|---|---|---|---|
| 129 | 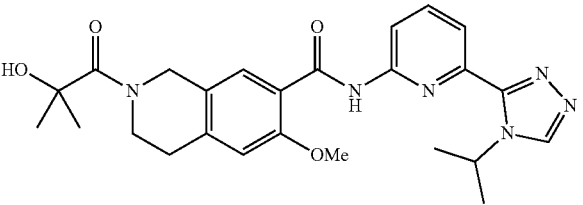 [SMILES: COc1cc2c(cc1C(=O)Nc1cccc(-c3nncn3C(C)C)n1)CN(C(=O)C(C)(C)O)CC2] | 479 | 1H NMR (400 MHz, DMSO-d6) δ 10.60 (s, 1H), 8.90 (s, 1H), 8.33 (dd, J = 8.3, 0.9 Hz, 1H), 8.03 (t, J = 8.0 Hz, 1H), 7.87 (dd, J = 7.7, 1.0 Hz, 1H), 7.75 (s, 1H), 7.09 (s, 1H), 5.55-5.44 (m, 2H), 5.20-5.08 (m, 1H), 4.64-4.56 (m, 1H), 4.23-4.13 (m, 1H), 3.98 (s, 3H), 3.80-3.71 (m, 1H), 2.91 (br s, 2H), 1.52 (d, J = 6.7 Hz, 6H), 1.34 (s, 6H). |
| 130 | 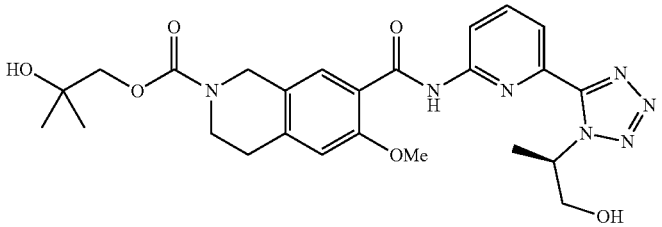 [SMILES: COc1cc2c(cc1C(=O)Nc1cccc(-c3nnnn3[C@H](C)CO)n1)CN(C(=O)OCC(C)(C)O)CC2] | 526 | 1H NMR (400 MHz, DMSO-d6) δ 10.74 (s, 1H), 8.42 (dd, J = 8.4, 0.9 Hz, 1H), 8.13 (t, J = 8.0 Hz, 1H), 7.95 (dd, J = 7.6, 0.9 Hz, 1H), 7.74 (s, 1H), 7.11 (s, 1H), 5.85-5.79 (m, 1H), 5.05-4.95 (m, 1H), 4.66-4.54 (m, 2H), 3.98 (s, 3H), 3.86-3.76 (comp, 4H), 3.68-3.62 (m, 2H), 2.89 (br s, 2H), 1.59 (d, J = 6.8 Hz, 3H), 1.13 (s, 6H). |
| 131 | 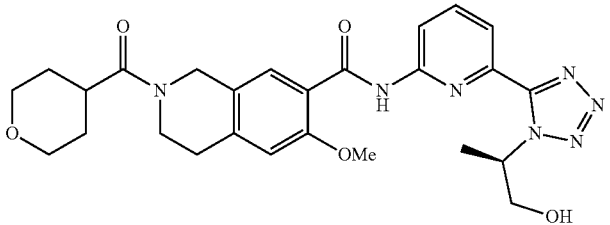 [SMILES: COc1cc2c(cc1C(=O)Nc1cccc(-c3nnnn3[C@H](C)CO)n1)CN(C(=O)C1CCOCC1)CC2] | 523 | 1H NMR (400 MHz, DMSO-d6) δ 10.73 (s, 1H), 8.42 (dd, J = 8.4, 0.9 Hz, 1H), 8.18-8.09 (m, 1H), 7.95 (dd, J = 7.6, 0.9 Hz, 1H), 7.73 (s, 1H), 7.07 (s, 1H), 5.87-5.77 (m, 1H), 5.01 (t, J = 5.6 Hz, 1H), 4.40 (s, 2H), 3.98 (s, 3H), 3.91-3.76 (m, 2H), 3.61 (t, J = 4.7 Hz, 4H), 3.45 (t, J = 5.8 Hz, 2H), 3.18 (t, J = 4.7 Hz, 4H), 2.91 (t, J = 5.8 Hz, 2H), 1.60 (d, J = 6.9 Hz, 3H). |
| 132 | 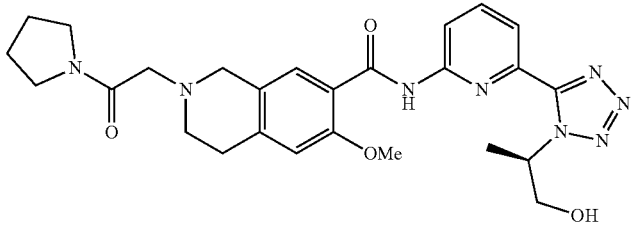 [SMILES: COc1cc2c(cc1C(=O)Nc1cccc(-c3nnnn3[C@H](C)CO)n1)CN(CC(=O)N1CCCC1)CC2] | 521 | 1H NMR (400 MHz, Chloroform-d) δ 10.63 (s, 1H), 8.55 (dd, J = 7.7, 1.7 Hz, 1H), 8.05-7.92 (comp, 3H), 6.79 (s, 1H), 5.64 (h, J = 6.6 Hz, 1H), 4.17-4.10 (m, 2H), 4.07 (s, 3H), 3.87-3.77 (mj, 2H), 3.52 (t, J = 6.8 Hz, 4H), 3.39 (s, 2H), 3.09-2.89 (m, 5H), 2.00-1.93 (m, 2H), 1.90-1.84 (m, 2H), 1.72 (d, J = 6.8 Hz, 3H). |
| 133 | 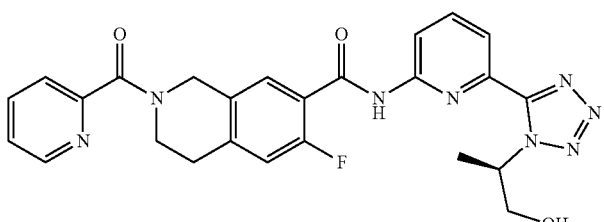 | 503 | |

TABLE 6-continued

| Example | Structure | LC-MS [M + H]+ unless otherwise noted | 1H-NMR |
|---|---|---|---|
| 134 | 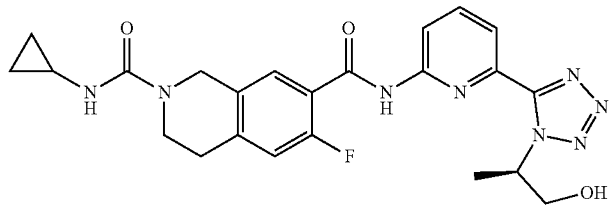 [SMILES: C[C@H](CO)n1nnnc1-c1cccc(NC(=O)c2cc3c(cc2F)CCN(C(=O)NC2CC2)C3)n1] | 481 | |
| 135 | 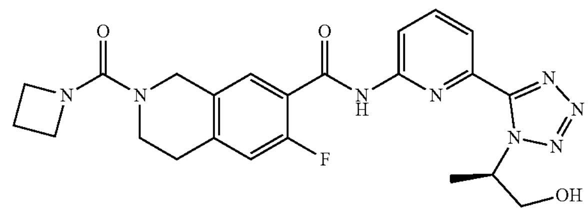 [SMILES: C[C@H](CO)n1nnnc1-c1cccc(NC(=O)c2cc3c(cc2F)CCN(C(=O)N2CCC2)C3)n1] | 481 | |
| 136 | 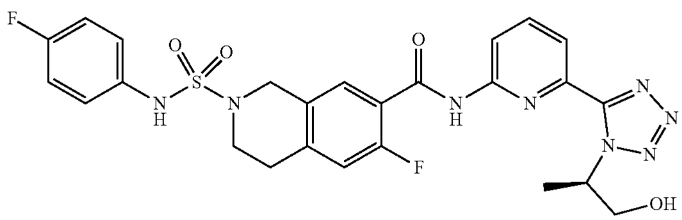 [SMILES: C[C@H](CO)n1nnnc1-c1cccc(NC(=O)c2cc3c(cc2F)CCN(S(=O)(=O)Nc2ccc(F)cc2)C3)n1] | 571 | |
| 137 | 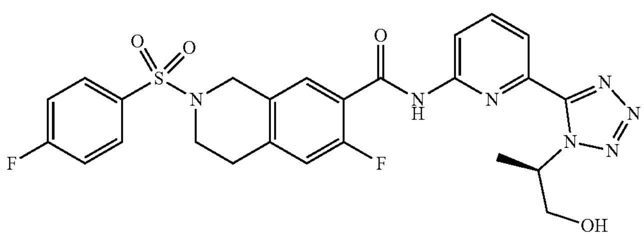 [SMILES: C[C@H](CO)n1nnnc1-c1cccc(NC(=O)c2cc3c(cc2F)CCN(S(=O)(=O)c2ccc(F)cc2)C3)n1] | 556 | |
| 138 | 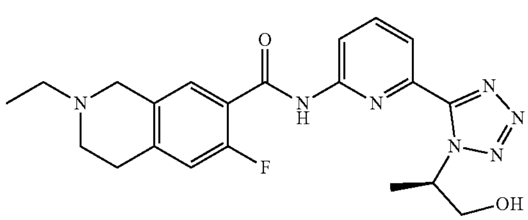 [SMILES: CCN1CCc2cc(F)c(C(=O)Nc3cccc(-c4nnnn4[C@H](C)CO)n3)cc2C1] | 426 | |
| 139 | 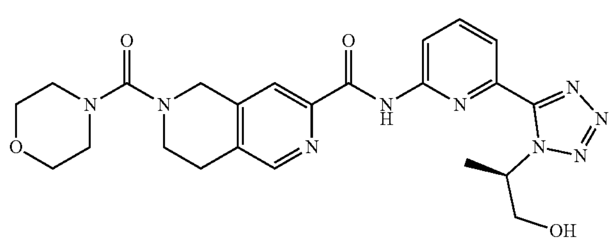 [SMILES: C[C@H](CO)n1nnnc1-c1cccc(NC(=O)c2cc3c(cn2)CCN(C(=O)N2CCOCC2)C3)n1] | 494 | 1H NMR (400 MHz, Chloroform-d) δ 10.46 (s, 1H), 8.40 (s, 1H), 8.35 (d, J = 8.2 Hz, 1H), 8.04-8.02 (comp, 2H), 7.94 (t, J = 7.9 Hz, 1H), 5.98-5.82 (m, 1H), 4.55 (s, 2H), 4.14 (qd, J = 11.8, 6.2 Hz, 2H), 3.72 (t, J = 4.7 Hz, 4H), 3.58 (t, J = 5.7 Hz, 2H), 3.33 (t, J = 4.7 Hz, 4H), 3.01 (t, J = 5.8 Hz, 2H), 1.67 (d, J = 6.8 Hz, 3H). |

TABLE 6-continued

| Example | Structure | LC-MS [M + H]+ unless otherwise noted | ¹H-NMR |
|---|---|---|---|
| 140 | 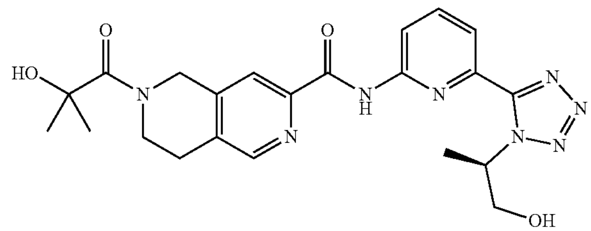 [SMILES: C[C@H](CO)n1nnnc1-c1cccc(NC(=O)c2cc3c(cn2)CCN(C(=O)C(C)(C)O)C3)n1] | 467 | ¹H NMR (400 MHz, DMSO-d₆) δ 10.77 (s, 1H), 8.60 (s, 1H), 8.42 (dd, J = 8.4, 0.9 Hz, 1H), 8.16 (t, J = 8.0 Hz, 1H), 8.09 (s, 1H), 7.97 (dd, J = 7.6, 0.9 Hz, 1H), 5.90-5.75 (m, 1H), 5.55 (s, 1H), 5.29 (br s, 1H), 4.99 (t, J = 5.7 Hz, 1H), 4.79 (br s, 1H), 4.17 (br s, 1H), 3.84-3.71 (m, 2H), 3.60 (br s, 1 H), 2.96 (br s, 2H), 1.59 (d, J = 6.8 Hz, 3H), 1.35 (s, 6H). |
| 141 | 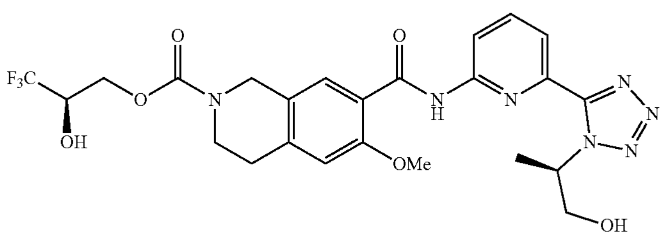 [SMILES: COc1cc2c(cc1C(=O)Nc1cccc(-c3nnnn3[C@H](C)CO)n1)CN(C(=O)OC[C@@H](O)C(F)(F)F)CC2] | 566 | ¹H NMR (400 MHz, DMSO-d₆) δ 10.73 (s, 1H), 8.42 (dd, J = 8.3, 0.9 Hz, 1H), 8.13 (t, J = 8.0 Hz, 1H), 7.95 (dd, J = 7.6, 0.9 Hz, 1H), 7.72 (d, J = 9.2 Hz, 1H), 7.11 (s, 1H), 6.59 (d, J = 6.2 Hz, 1H), 5.87-5.77 (m, 1H), 5.01 (t, J = 5.6 Hz, 1H), 4.64-4.55 (m, 2H), 4.38-4.21 (comp, 2H), 4.14 (dd, J = 11.5, 5.7 Hz, 1H), 3.98 (s, 3H), 3.92-3.72 (m, 2H), 3.63 (br s, 2H), 2.89 (t, J = 6.0 Hz, 2H), 1.59 (d, J = 6.8 Hz, 3H). |
| 142 | 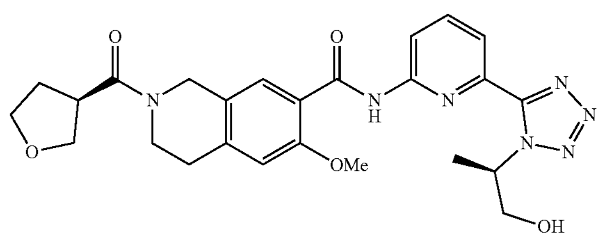 [SMILES: COc1cc2c(cc1C(=O)Nc1cccc(-c3nnnn3[C@H](C)CO)n1)CN(C(=O)[C@@H]1CCOC1)CC2] | 508 | ¹H NMR (400 MHz, DMSO-d₆) (rotamers) δ 10.73 (s, 1H), 8.46-8.37 (m, 1H), 8.13 (td, J = 8.0, 2.7 Hz, 1H), 7.95 (d, J = 7.5 Hz, 1H), 7.81 (s, 0.5H), 7.73 (s, 0.5H), 7.11 (d, J = 3.4 Hz, 1H), 5.85-5.78 (m, 1H), 5.01 (td, J = 5.6, 2.7 Hz, 1H), 4.83-4.68 (m, 1H), 4.63 (s, 1H), 3.98 (d, J = 4.2 Hz, 3H), 3.96-3.55 (comp, 5H), 3.51-3.42 (m, 1H), 2.94 (t, J = 5.9 Hz, 1H), 2.86 (t, J = 6.1 Hz, 1H), 2.10-1.95 (m, 2H), 1.63-1.56 (m, 3H), 1.27-1.22 (m, 2H). |
| 143 | 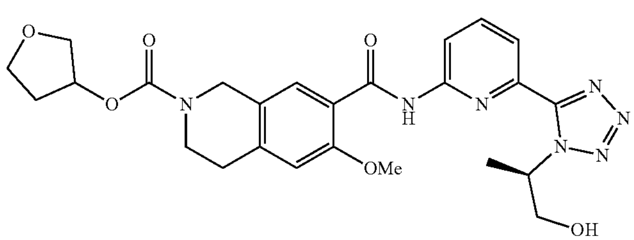 [SMILES: COc1cc2c(cc1C(=O)Nc1cccc(-c3nnnn3[C@H](C)CO)n1)CN(C(=O)OC1CCOC1)CC2] | 524 | ¹H NMR (400 MHz, DMSO-d₆) (mixture of diastereomers) δ 10.73 (s, 1H), 8.42 (d, J = 8.4 Hz, 1H), 8.13 (t, J = 8.0 Hz, 1H), 7.95 (dd, J = 7.6, 0.9 Hz, 1H), 7.73 (s, 1H), 7.10 (s, 1H), 5.84-5.78 (m, 1H), 5.20-5.15 (m, 1H), 5.01 (t, J = 5.6 Hz, 1H), 4.56 (br s, 2H), 3.98 (s, 3H), 3.90-3.67 (comp, 6H), 3.61 (t, J = 5.9 Hz, 2H), 2.88 (t, J = 5.9 Hz, 2H), 2.17-2.08 (m, 1H), 2.02-1.83 (m, 1H), 1.59 (d, J = 6.8 Hz, 3H). |

TABLE 6-continued

| Example | Structure | LC-MS [M + H]+ unless otherwise noted | 1H-NMR |
| --- | --- | --- | --- |
| 144 | 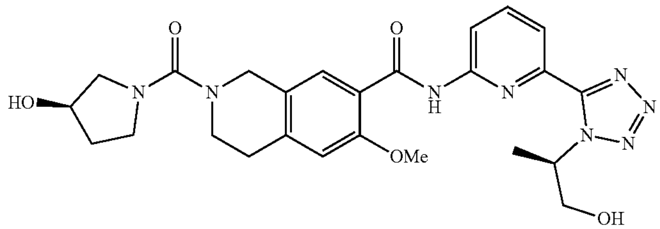 [SMILES: COc1cc2c(cc1C(=O)Nc1cccc(-c3nnnn3[C@H](C)CO)n1)CN(C(=O)N1CC[C@@H](O)C1)CC2] | 523 | 1H NMR (400 MHz, Chloroform-d) δ 10.61 (s, 1H), 8.54 (dd, J = 7.5, 1.8 Hz, 1H), 7.98 (dd, J = 9.2, 7.4 Hz, 3H), 6.80 (s, 1H), 5.65 (h, J = 6.7 Hz, 1H), 4.48 (s, 3H), 4.13 (t, J = 5.4 Hz, 2H), 4.08 (s, 3H), 3.83 (t, J = 5.8 Hz, 1H), 3.77-3.60 (comp, 3H), 3.54-3.35 (comp, 3H), 3.10-2.96 (m, 1H), 2.90 (dt, J = 16.8, 5.4 Hz, 1H), 2.04-1.91 (m, 3H), 1.72 (d, J = 6.8 Hz, 3H). |
| 145 | 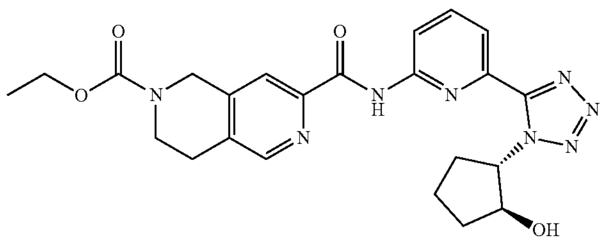 [SMILES: CCOC(=O)N1CCc2cnc(C(=O)Nc3cccc(-c4nnnn4[C@H]4CCC[C@@H]4O)n3)cc2C1] | 479 | |
| 146 | 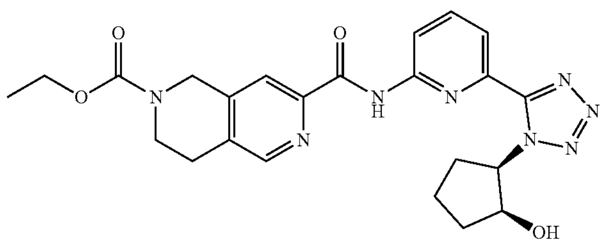 [SMILES: CCOC(=O)N1CCc2cnc(C(=O)Nc3cccc(-c4nnnn4[C@@H]4CCC[C@@H]4O)n3)cc2C1] | 479 | |
| 147 | 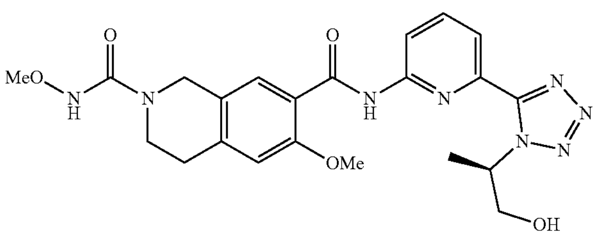 [SMILES: CONC(=O)N1CCc2cc(OC)c(C(=O)Nc3cccc(-c4nnnn4[C@H](C)CO)n3)cc2C1] | 483 | 1H NMR (400 MHz, Chloroform-d) δ 10.59 (s, 1H), 8.54 (dd, J = 7.1, 2.3 Hz, 1H), 8.04 (s, 1H), 8.02-7.94 (m, 2H), 7.29 (s, 1H), 6.83 (s, 1H), 5.74-5.53 (m, 1H), 4.55 (s, 2H), 4.16-4.12 (m, 2H), 4.09 (s, 3H), 3.75 (s, 3H), 3.69 (t, J = 5.8 Hz, 2H), 2.94 (t, J = 5.9 Hz, 2H), 1.72 (d, J = 6.8 Hz, 3H). |
| 148 | 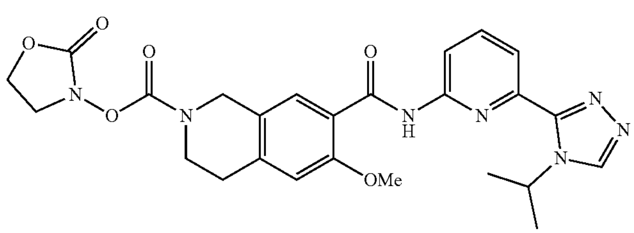 [SMILES: COc1cc2c(cc1C(=O)Nc1cccc(-c3nncn3C(C)C)n1)CN(C(=O)ON1CCOC1=O)CC2] | 520 | 1H NMR (400 MHz, DMSO-d6) (rotamers) δ 10.61 (d, J = 4.1 Hz, 1H), 8.90 (d, J = 1.7 Hz, 1H), 8.33 (dd, J = 8.3, 3.6 Hz, 1H), 8.03 (td, J = 7.9, 3.0 Hz, 1H), 7.87 (dd, J = 7.6, 2.3 Hz, 1H), 7.82 (s, 0.5H), 7.77 (s, 0.5H), 7.14 (s, 1H), 5.59-5.44 (m, 1H), 4.67 (s, 1H), 4.62 (s, 1H), 4.30 (t, J = 8.0 Hz, 2H), 4.19 (s, 2H)f, 3.98 (d, J = 4.8 Hz, 3H), 3.68 (q, J = 6.3 Hz, 2H), 3.58 (dd, J = 8.9, 7.1 Hz, 2H), 2.97 (t, J = 5.8 Hz, 1H), 2.88 (t, J = 6.0 Hz, 1H), 1.52 (dd, J = 6.8, 2.7 Hz, 6H). |

TABLE 6-continued

| Example | Structure | LC-MS [M + H]+ unless otherwise noted | ¹H-NMR |
|---|---|---|---|
| 149 | 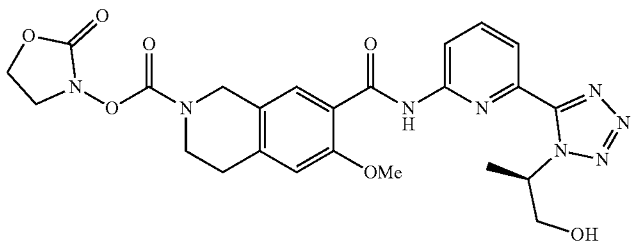 [SMILES: COc1cc2c(cc1C(=O)Nc1cccc(-c3nnnn3[C@H](C)CO)n1)CN(C(=O)ON1CCOC1=O)CC2] | 537 | ¹H NMR (400 MHz, DMSO-d₆) (rotamers) δ 10.74 (d, J = 3.5 Hz, 1H), 8.42 (dd, J = 8.4, 3.5 Hz, 1H), 8.13 (td, J = 8.0, 3.1 Hz, 1H), 7.96 (dd, J = 7.6, 2.6 Hz, 1H), 7.79 (s, 0H), 7.74 (s, 1H), 7.14 (s, 1H), 5.85-5.77 (m, 1H), 5.01 (q, J = 5.5 Hz, 1H), 4.67 (s, 1H), 4.62 (s, 1H), 4.30 (t, J = 8.0 Hz, 2H), 4.19 (s, 2H), 3.99 (d, J = 6.1 Hz, 3H), 3.87-3.76 (m, 2H), 3.71-3.65 (m, 2H), 3.58 (t, J = 8.0 Hz, 2H), 2.98 (t, J = 5.8 Hz, 1H), 2.89 (t, J = 5.9 Hz, 1H), 1.60 (dd, J = 6.8, 2.5 Hz, 3H). |
| 150 | 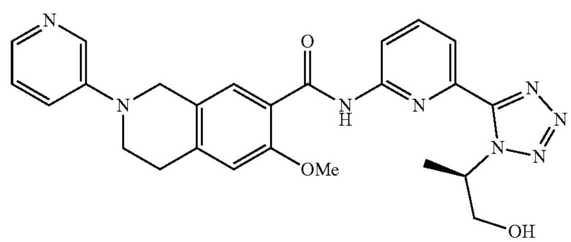 [SMILES: COc1cc2c(cc1C(=O)Nc1cccc(-c3nnnn3[C@H](C)CO)n1)CN(c1cccnc1)CC2] | 487 | ¹H NMR (400 MHz, Chloroform-d) δ 10.64 (s, 1H), 8.58 (dd, J = 7.3, 2.1 Hz, 1H), 8.40 (d, J = 2.9 Hz, 1H), 8.13 (s, 1H), 8.12-8.08 (m, 1H), 8.05-7.94 (comp, 2H), 7.24-7.18 (comp, 2H), 6.86 (s, 1H), 5.67-5.62 (m, 1H), 4.46 (s, 2H), 4.14 (d, J = 6.3 Hz, 2H), 4.11 (s, 3H), 3.64 (t, J = 5.9 Hz, 2H), 3.07 (t, J = 5.8 Hz, 2H), 1.73 (d, J = 6.9 Hz, 3H). |
| 151 | 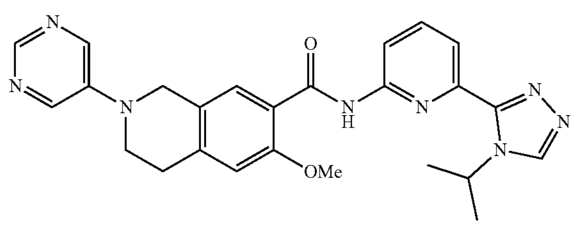 [SMILES: COc1cc2c(cc1C(=O)Nc1cccc(-c3nncn3C(C)C)n1)CN(c1cncnc1)CC2] | 471 | ¹H NMR (500 MHz, Chloroform-d) δ 10.40 (s, 1H), 8.70 (s, 1H), 8.50-8.47 (m, 1H), 8.43 (s, 2H), 8.37 (s, 1H), 8.15 (s, 1H), 8.00 (dd, J = 7.8, 0.9 Hz, 1H), 7.90 (t, J = 8.0 Hz, 1H), 6.86 (s, 1H), 5.54 (p, J = 6.8 Hz, 1H), 4.49 (s, 2H), 4.05 (s, 3H), 3.65 (t, J = 5.8 Hz, 2H), 3.07 (t, J = 5.8 Hz, 2H), 1.62 (d, J = 6.8 Hz, 6H). |
| 152 | 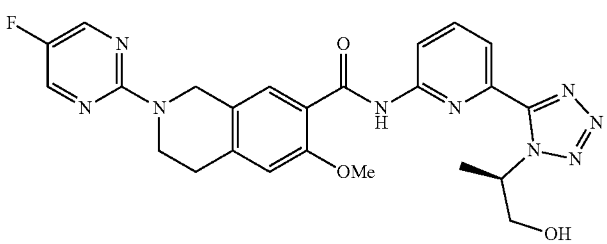 [SMILES: COc1cc2c(cc1C(=O)Nc1cccc(-c3nnnn3[C@H](C)CO)n1)CN(c1ncc(F)cn1)CC2] | 506 | ¹H NMR (400 MHz, DMSO-d₆) δ 10.74 (s, 1H), 8.51 (d, J = 0.8 Hz, 2H), 8.43 (d, J = 8.4 Hz, 1H), 8.13 (t, J = 8.0 Hz, 1H), 7.95 (dd, J = 7.6, 0.9 Hz, 1H), 7.77 (s, 1H), 7.12 (s, 1H), 5.84-5.79 (m, 1H), 5.00 (t, J = 5.6 Hz, 1H), 4.84 (s, 2H), 3.99-3.95 (comp, 5H), 3.91-3.74 (m, 2H), 2.96 (t, J = 5.8 Hz, 2H), 1.59 (d, J = 6.8 Hz, 3H). |
| 153 | 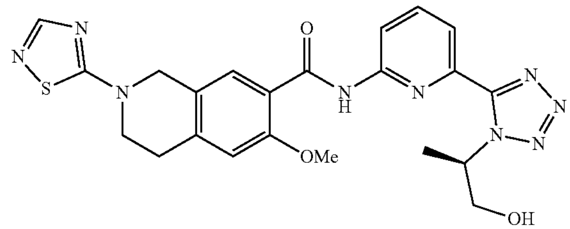 [SMILES: COc1cc2c(cc1C(=O)Nc1cccc(-c3nnnn3[C@H](C)CO)n1)CN(c1ncns1)CC2] | 494 | |

TABLE 6-continued

| Example | Structure | LC-MS [M + H]+ unless otherwise noted | 1H-NMR |
|---|---|---|---|
| 154 | (structure) | 506 | 1H NMR (400 MHz, DMSO-$d_6$) δ 10.74 (s, 1H), 8.43 (dd, J = 8.4, 1.0 Hz, 1H), 8.19 (dd, J = 8.5, 1.3 Hz, 1H), 8.13 (t, J = 8.0 Hz, 1H), 7.98 (dd, J = 2.3, 1.4 Hz, 1H), 7.95 (dd, J = 7.6, 0.9 Hz, 1H), 7.81 (s, 1H), 7.14 (s, 1H), 5.86-5.76 (m, 1H), 5.01 (t, J = 5.6 Hz, 1H), 4.71 (s, 2H), 3.99 (s, 3H), 3.92-3.71 (comp, 4H), 3.00 (t, J = 5.9 Hz, 2H), 1.60 (d, J = 6.8 Hz, 3H). |

Assay
HTRF® KinEASE™ Assay

ASK1 was purchased from Thermofisher (Catalogue #PV4011), ATP was purchased from Sigma (Catalogue #A7699), HTRF® KinEASE™ Assay System was obtained from Cisbio (Bedford, Mass.). ½ Area plate was purchased from Perkin Elmer (Catalogue ##6005560). HTRF® KinEASE™-STK is a generic method for measuring serine/threonine kinase activities using a time-resolved fluorescence resonance energy transfer (TR-FRET) immunoassay. The $IC_{50}$ value for each compound was determined in the presence of compound (various concentration from 0 to 10 µM) and a fixed amount of ATP and peptide substrates. The test compound, 1 µM STK3 peptide substrate, and 5 µM of ASK1 kinase are incubated with kinase reaction buffer containing 50 mM HEPES Ph 7.5, 0.01% BRIJ-35, 10 mM $MgCl_2$, and 1 mM EGTA for 30 minutes. 100 µM ATP is added to start kinase reaction and incubated for 3 hours. The STK3-antibody labeled with $Eu^{3+}$-Cryptate and 125 nM streptavidin-XL665 are mixed in a single addition with stop reagents provided by the Cisbio kit used to stop the kinase reaction. Fluorescence is detected using an Envision Multilabeled 2014 reader from PerkinElmer. The Fluorescence is measured at 615 nm (Cryptate) and 665 nm (XL665) and a ratio of 665 nm/615 nm is calculated for each well. The resulting TR-FRET is proportional to the phosphorylation level. Staurosporine was used as the positive control. $IC_{50}$ was determined by Xlfit 5.3.

By using above method, the inhibition of ASK1 was evaluated for the compounds of Formula (I). The results are shown in Table 7. Example numbers correspond to those in Table 5. $IC_{50}$ ranges are as follows: A=$IC_{50}$<1.25 nM; B=1.25 nM<$IC_{50}$<10 nM; C=10 nM<$IC_{50}$<100 nM; D=100 nM<$IC_{50}$<1 µM; E=$IC_{50}$>1 µM

TABLE 7

| Example | IC50 | Example | IC50 |
|---|---|---|---|
| 1 | B | 2 | C |
| 3 | C | 4 | B |
| 5 | C | 6 | C |
| 7 | B | 8 | B |
| 9 | B | 10 | B |
| 11 | B | 12 | A |
| 13 | B | 14 | A |
| 15 | A | 16 | B |
| 17 | B | 18 | A |
| 19 | A | 20 | A |
| 21 | B | 22 | A |
| 23 | A | 24 | B |
| 25 | B | 26 | A |
| 27 | A | 28 | A |
| 29 | A | 30 | A |
| 31 | A | 32 | A |
| 33 | A | 34 | B |
| 35 | A | 36 | A |
| 37 | B | 38 | C |
| 39 | A | 40 | B |
| 41 | B | 42 | A |
| 43 | A | 44 | A |
| 45 | A | 46 | A |
| 47 | B | 48 | B |
| 49 | B | 50 | B |
| 51 | B | 52 | A |
| 53 | B | 54 | B |
| 55 | A | 56 | A |
| 57 | A | 58 | B |
| 59 | A | 60 | A |
| 61 | A | 62 | B |
| 63 | B | 64 | B |
| 65 | B | 66 | A |
| 67 | B | 68 | A |
| 69 | A | 70 | A |
| 71 | A | 72 | A |
| 73 | A | 74 | A |
| 75 | A | 76 | A |
| 77 | A | 78 | A |
| 79 | A | 80 | B |
| 81 | B | 82 | B |
| 83 | B | 84 | B |
| 85 | B | 86 | B |
| 87 | B | 88 | A |
| 89 | A | 90 | A |
| 91 | A | 92 | A |
| 93 | B | 94 | B |
| 95 | — | 96 | A |
| 97 | A | 98 | B |
| 98 | B | 99 | C |
| 99 | C | 100 | B |
| 100 | B | 101 | A |
| 101 | A | 102 | B |
| 102 | B | 103 | B |
| 103 | B | 104 | A |
| 104 | A | 105 | A |
| 105 | A | 106 | B |
| 106 | B | 107 | B |
| 107 | B | 108 | B |
| 108 | B | 109 | B |
| 109 | B | 110 | C |
| 110 | C | 111 | B |

TABLE 7-continued

| Example | IC$_{50}$ | Example | IC$_{50}$ |
|---|---|---|---|
| 111 | B | 112 | A |
| 112 | A | 113 | A |
| 113 | A | 114 | A |
| 114 | A | 115 | A |
| 115 | A | 116 | B |
| 116 | B | 117 | C |
| 117 | C | 118 | B |
| 118 | B | 119 | C |
| 119 | C | 120 | C |
| 120 | C | 121 | C |
| 121 | C | 122 | B |
| 122 | B | 123 | B |
| 123 | B | 124 | A |
| 124 | A | 125 | A |
| 125 | A | 126 | A |
| 126 | A | 127 | A |
| 127 | A | 128 | A |
| 128 | A | 129 | A |
| 129 | A | 130 | A |
| 130 | A | 131 | A |
| 131 | A | 132 | A |
| 132 | A | 133 | C |
| 133 | C | 134 | B |
| 134 | B | 135 | B |
| 135 | B | 136 | C |
| 136 | C | 137 | C |
| 137 | C | 138 | D |
| 138 | D | 139 | B |
| 139 | B | 140 | B |
| 140 | B | 141 | A |
| 141 | A | 142 | A |
| 142 | A | 143 | B |
| 143 | B | 144 | A |
| 144 | A | 145 | C |
| 145 | C | 146 | C |
| 146 | C | 147 | A |
| 147 | A | 148 | A |
| 148 | A | 149 | A |
| 149 | A | 150 | A |
| 150 | A | 151 | A |
| 151 | A | 152 | B |
| 152 | B | 153 | B |
| 153 | B | 154 | B |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound selected from the compounds set forth below or a pharmaceutically acceptable salt thereof:

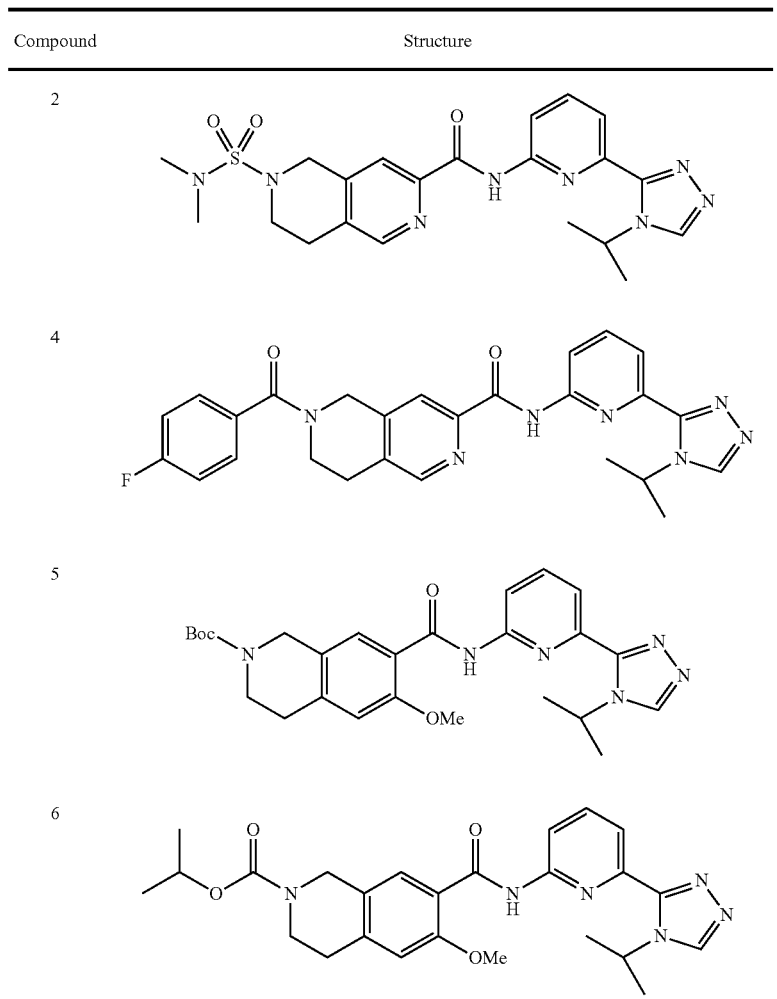

| Compound | Structure |
|---|---|
| 2 | 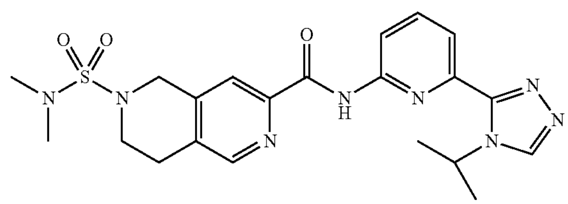 [SMILES: CC(C)n1cnnc1-c1cccc(NC(=O)c2cc3c(cn2)CCN(S(=O)(=O)N(C)C)C3)n1] |
| 4 | 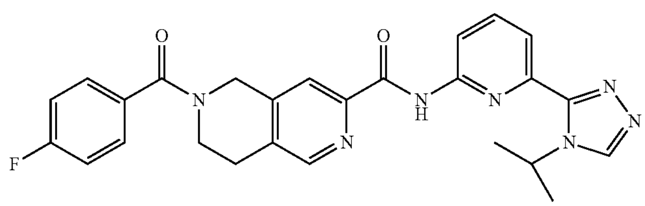 [SMILES: CC(C)n1cnnc1-c1cccc(NC(=O)c2cc3c(cn2)CCN(C(=O)c2ccc(F)cc2)C3)n1] |
| 5 | 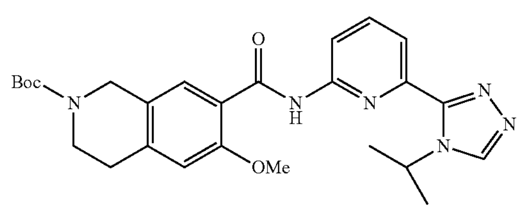 [SMILES: COc1cc2c(cc1C(=O)Nc1cccc(-c3nncn3C(C)C)n1)CN(C(=O)OC(C)(C)C)CC2] |
| 6 | 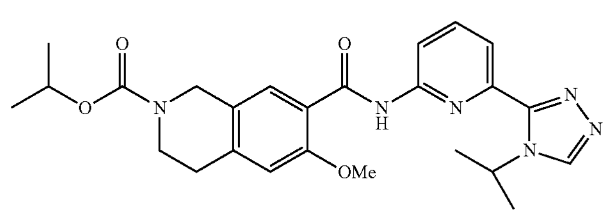 [SMILES: COc1cc2c(cc1C(=O)Nc1cccc(-c3nncn3C(C)C)n1)CN(C(=O)OC(C)C)CC2] |

-continued

| Compound | Structure |
|---|---|
| 7 | 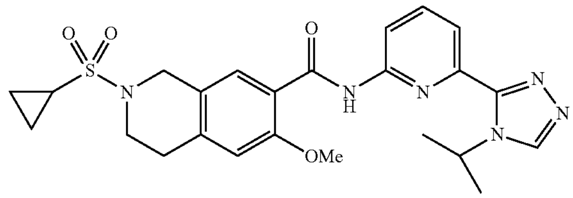 [SMILES: COc1cc2c(cc1C(=O)Nc1cccc(-c3nncn3C(C)C)n1)CN(S(=O)(=O)C1CC1)CC2] |
| 8 | 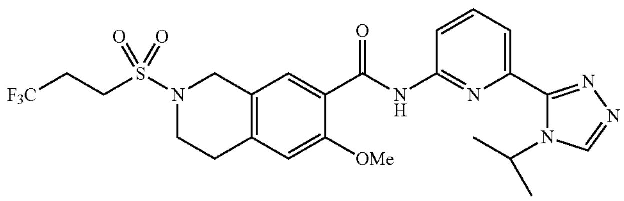 [SMILES: COc1cc2c(cc1C(=O)Nc1cccc(-c3nncn3C(C)C)n1)CN(S(=O)(=O)CCC(F)(F)F)CC2] |
| 9 | 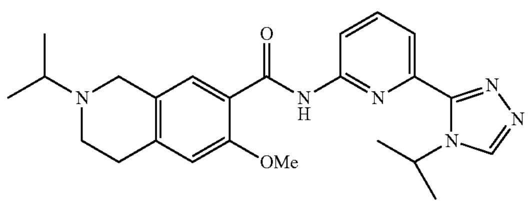 [SMILES: COc1cc2c(cc1C(=O)Nc1cccc(-c3nncn3C(C)C)n1)CN(C(C)C)CC2] |
| 10 | 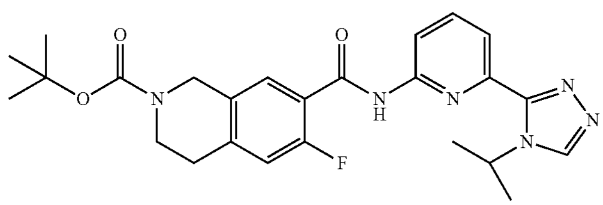 [SMILES: CC(C)n1cnnc1-c1cccc(NC(=O)c2cc3c(cc2F)CCN(C(=O)OC(C)(C)C)C3)n1] |
| 11 | 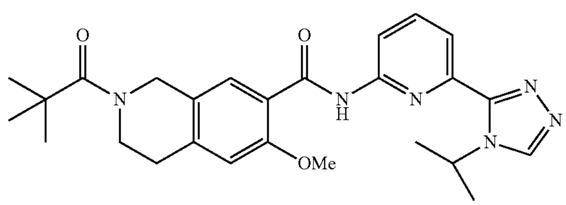 [SMILES: COc1cc2c(cc1C(=O)Nc1cccc(-c3nncn3C(C)C)n1)CN(C(=O)C(C)(C)C)CC2] |
| 12 | 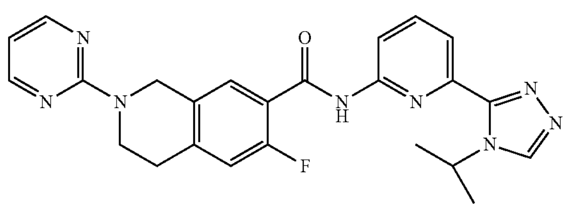 [SMILES: CC(C)n1cnnc1-c1cccc(NC(=O)c2cc3c(cc2F)CCN(c2ncccn2)C3)n1] |
| 13 | 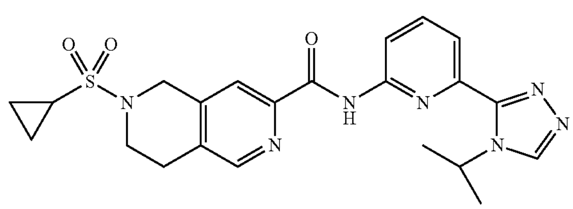 [SMILES: CC(C)n1cnnc1-c1cccc(NC(=O)c2cc3c(cn2)CCN(S(=O)(=O)C2CC2)C3)n1] |

-continued
| Compound | Structure |
|---|---|
| 14 | 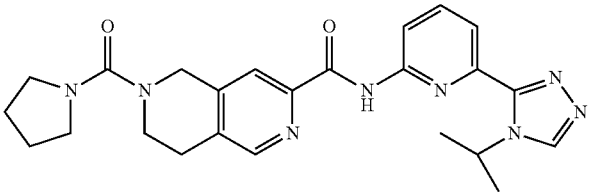 [SMILES: CC(C)n1cnnc1-c1cccc(NC(=O)c2cc3c(cn2)CCN(C(=O)N2CCCC2)C3)n1] |
| 15 | 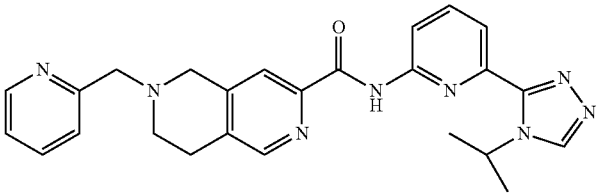 [SMILES: CC(C)n1cnnc1-c1cccc(NC(=O)c2cc3c(cn2)CCN(Cc2ccccn2)C3)n1] |
| 16 | 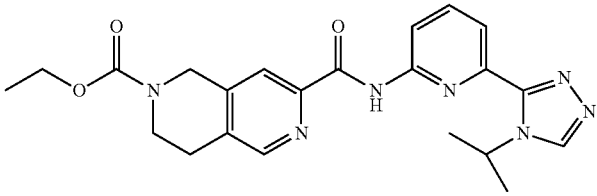 [SMILES: CCOC(=O)N1CCc2cnc(C(=O)Nc3cccc(-c4nncn4C(C)C)n3)cc2C1] |
| 17 | 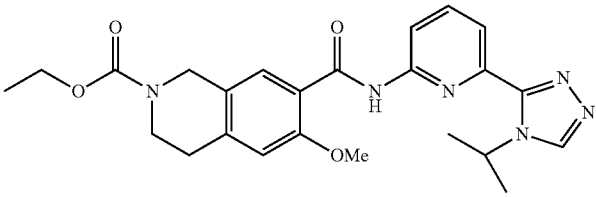 |
| 18 | 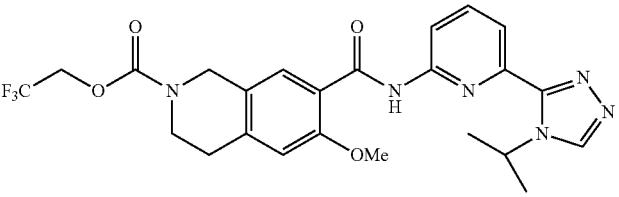 [SMILES: COc1cc2c(cc1C(=O)Nc1cccc(-c3nncn3C(C)C)n1)CN(C(=O)OCC(F)(F)F)CC2] |
| 19 | 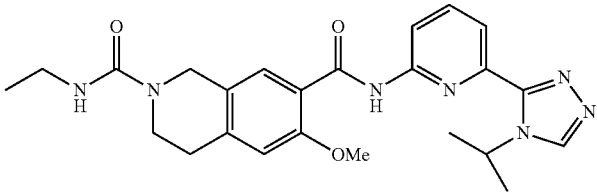 [SMILES: CCNC(=O)N1CCc2cc(OC)c(C(=O)Nc3cccc(-c4nncn4C(C)C)n3)cc2C1] |
| 20 | 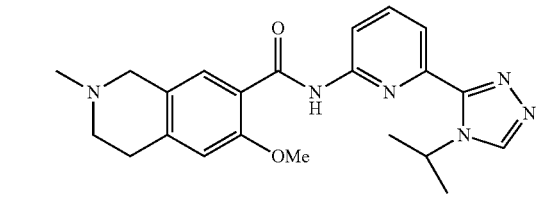 |

-continued
| Compound | Structure |
|---|---|
| 21 | 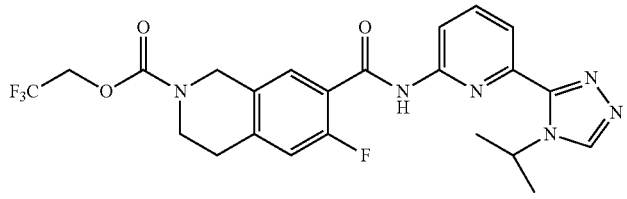 [SMILES: CC(C)n1cnnc1-c1cccc(NC(=O)c2cc3c(cc2F)CCN(C(=O)OCC(F)(F)F)C3)n1] |
| 22 | 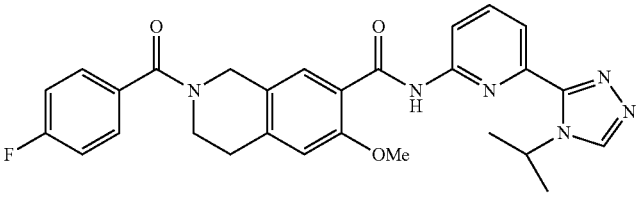 [SMILES: COc1cc2c(cc1C(=O)Nc1cccc(-c3nncn3C(C)C)n1)CN(C(=O)c1ccc(F)cc1)CC2] |
| 23 | 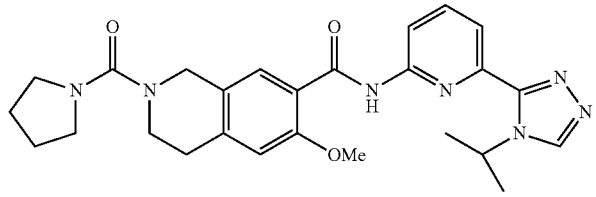 [SMILES: COc1cc2c(cc1C(=O)Nc1cccc(-c3nncn3C(C)C)n1)CN(C(=O)N1CCCC1)CC2] |
| 24 | 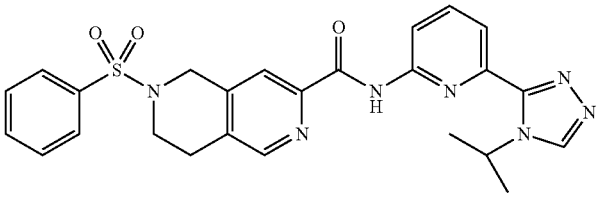 [SMILES: CC(C)n1cnnc1-c1cccc(NC(=O)c2cc3c(cn2)CCN(S(=O)(=O)c2ccccc2)C3)n1] |
| 25 | 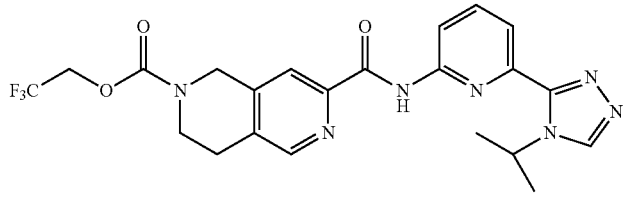 [SMILES: CC(C)n1cnnc1-c1cccc(NC(=O)c2cc3c(cn2)CCN(C(=O)OCC(F)(F)F)C3)n1] |
| 26 | 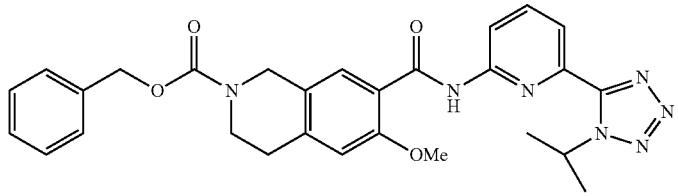 [SMILES: COc1cc2c(cc1C(=O)Nc1cccc(-c3nnnn3C(C)C)n1)CN(C(=O)OCc1ccccc1)CC2] |
| 27 | 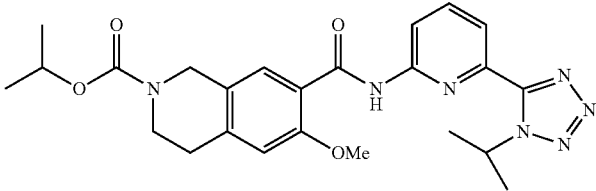 |

-continued

| Compound | Structure |
|---|---|
| 28 | 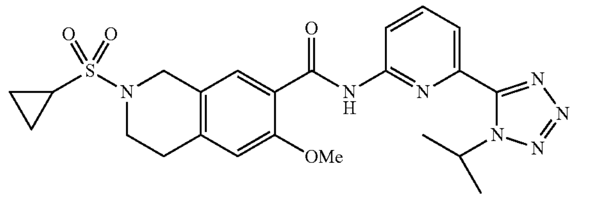 [SMILES: COc1cc2c(cc1C(=O)Nc1cccc(-c3nnnn3C(C)C)n1)CN(S(=O)(=O)C1CC1)CC2] |
| 29 | 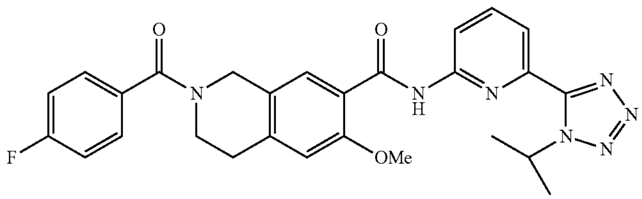 [SMILES: COc1cc2c(cc1C(=O)Nc1cccc(-c3nnnn3C(C)C)n1)CN(C(=O)c1ccc(F)cc1)CC2] |
| 30 | 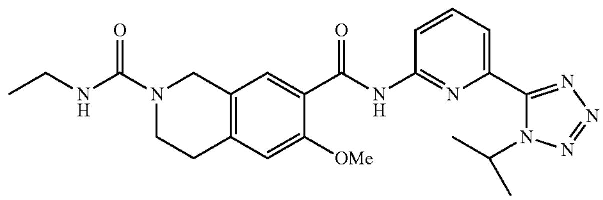 [SMILES: CCNC(=O)N1CCc2cc(OC)c(C(=O)Nc3cccc(-c4nnnn4C(C)C)n3)cc2C1] |
| 31 | 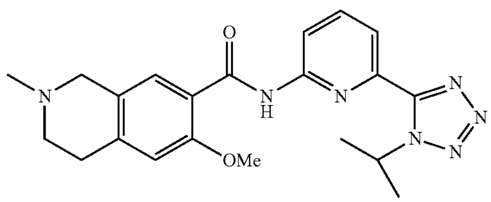 [SMILES: COc1cc2c(cc1C(=O)Nc1cccc(-c3nnnn3C(C)C)n1)CN(C)CC2] |
| 32 | 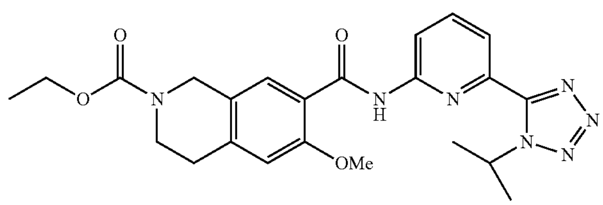 [SMILES: CCOC(=O)N1CCc2cc(OC)c(C(=O)Nc3cccc(-c4nnnn4C(C)C)n3)cc2C1] |
| 33 | 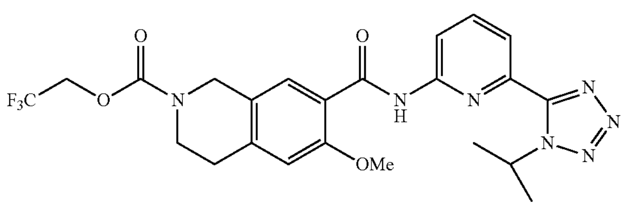 [SMILES: COc1cc2c(cc1C(=O)Nc1cccc(-c3nnnn3C(C)C)n1)CN(C(=O)OCC(F)(F)F)CC2] |
| 34 | 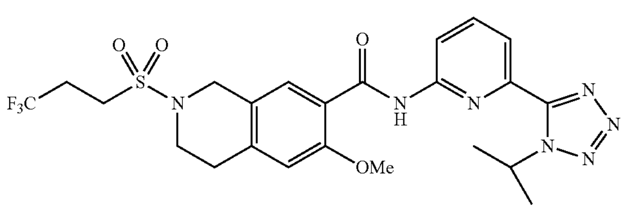 [SMILES: COc1cc2c(cc1C(=O)Nc1cccc(-c3nnnn3C(C)C)n1)CN(S(=O)(=O)CCC(F)(F)F)CC2] |

-continued

| Compound | Structure |
|---|---|
| 35 | 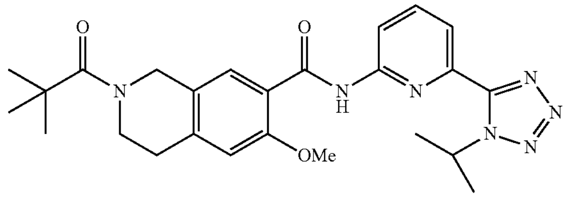 [SMILES: COc1cc2c(cc1C(=O)Nc1cccc(-c3nnnn3C(C)C)n1)CN(C(=O)C(C)(C)C)CC2] |
| 36 | 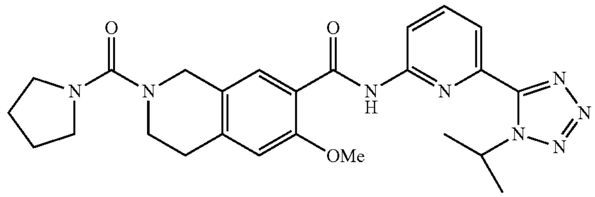 [SMILES: COc1cc2c(cc1C(=O)Nc1cccc(-c3nnnn3C(C)C)n1)CN(C(=O)N1CCCC1)CC2] |
| 37 | 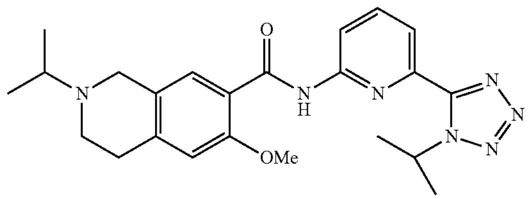 [SMILES: COc1cc2c(cc1C(=O)Nc1cccc(-c3nnnn3C(C)C)n1)CN(C(C)C)CC2] |
| 38 | 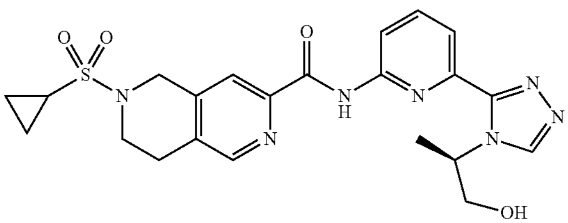 [SMILES: C[C@H](CO)n1cnnc1-c1cccc(NC(=O)c2cc3c(cn2)CCN(S(=O)(=O)C2CC2)C3)n1] |
| 39 | 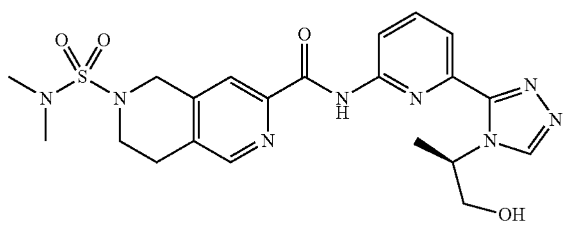 [SMILES: C[C@H](CO)n1cnnc1-c1cccc(NC(=O)c2cc3c(cn2)CCN(S(=O)(=O)N(C)C)C3)n1] |
| 40 | 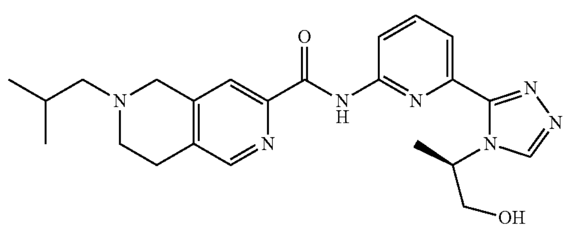 [SMILES: CC(C)CN1CCc2cnc(C(=O)Nc3cccc(-c4nncn4[C@H](C)CO)n3)cc2C1] |
| 41 | 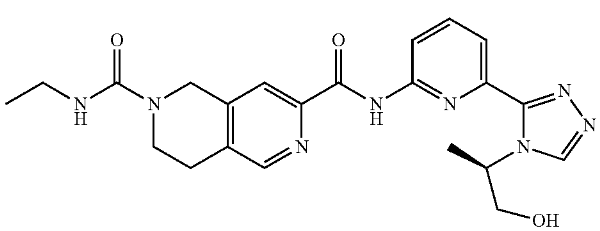 |

-continued
| Compound | Structure |
|---|---|
| 42 | 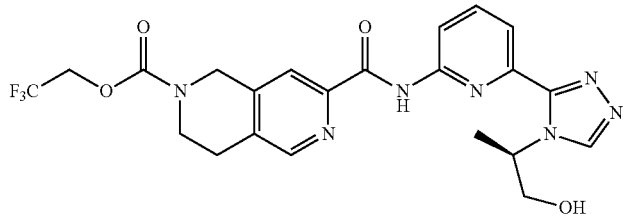 [SMILES: C[C@H](CO)n1cnnc1-c1cccc(NC(=O)c2cc3c(cn2)CCN(C(=O)OCC(F)(F)F)C3)n1] |
| 43 | 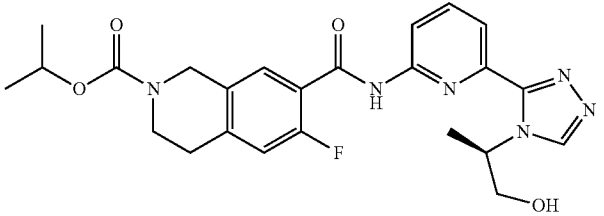 [SMILES: CC(C)OC(=O)N1CCc2cc(F)c(C(=O)Nc3cccc(-c4nncn4[C@H](C)CO)n3)cc2C1] |
| 44 | 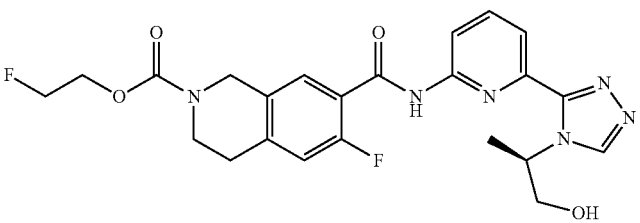 [SMILES: C[C@H](CO)n1cnnc1-c1cccc(NC(=O)c2cc3c(cc2F)CCN(C(=O)OCCF)C3)n1] |
| 45 | 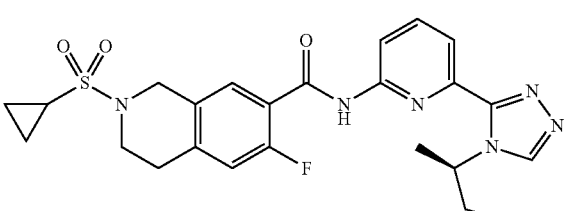 |
| 46 | 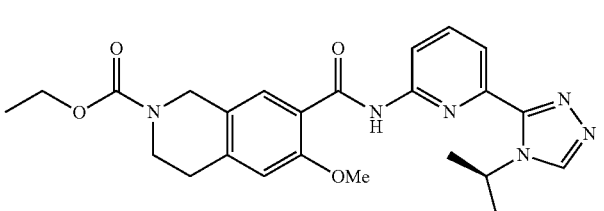 |
| 47 | 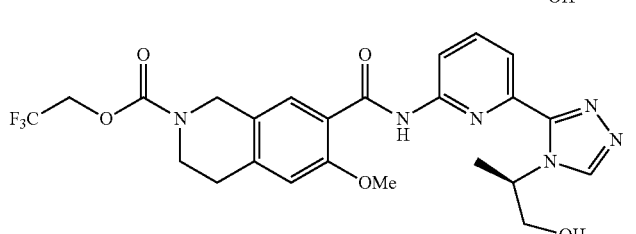 |
| 48 | 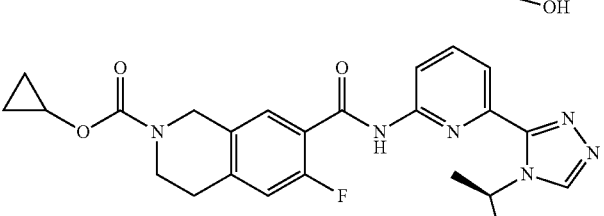 |

-continued
| Compound | Structure |
|---|---|
| 49 | 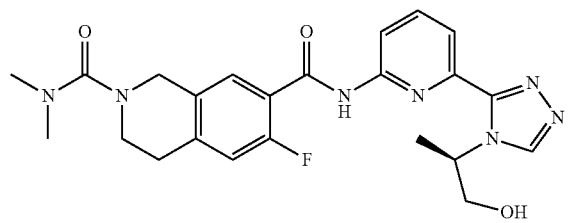 [SMILES: C[C@H](CO)n1cnnc1-c1cccc(NC(=O)c2cc3c(cc2F)CCN(C(=O)N(C)C)C3)n1] |
| 50 | 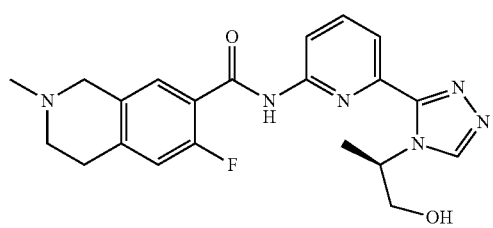 [SMILES: C[C@H](CO)n1cnnc1-c1cccc(NC(=O)c2cc3c(cc2F)CCN(C)C3)n1] |
| 51 | 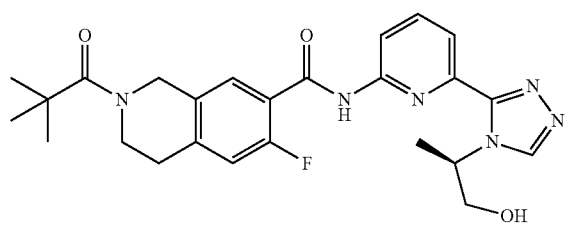 [SMILES: C[C@H](CO)n1cnnc1-c1cccc(NC(=O)c2cc3c(cc2F)CCN(C(=O)C(C)(C)C)C3)n1] |
| 52 | 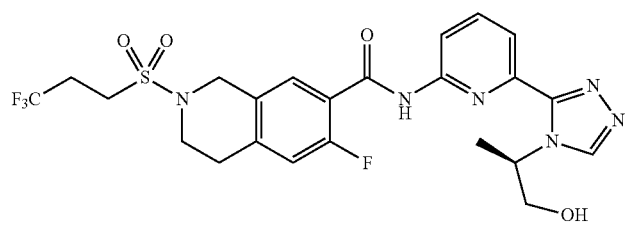 [SMILES: C[C@H](CO)n1cnnc1-c1cccc(NC(=O)c2cc3c(cc2F)CCN(S(=O)(=O)CCC(F)(F)F)C3)n1] |
| 53 | 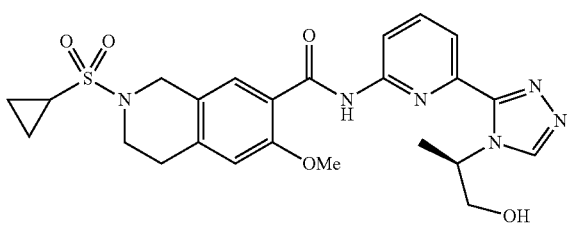 |
| 54 | 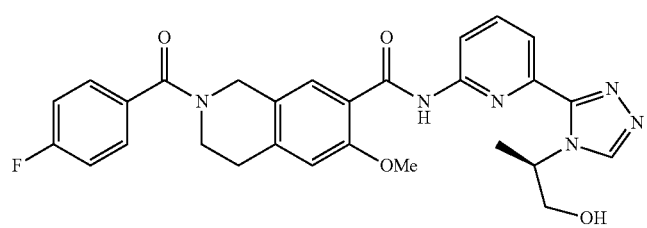 [SMILES: COc1cc2c(cc1C(=O)Nc1cccc(-c3nncn3[C@H](C)CO)n1)CN(C(=O)c1ccc(F)cc1)CC2] |

-continued

| Compound | Structure |
|---|---|
| 55 | 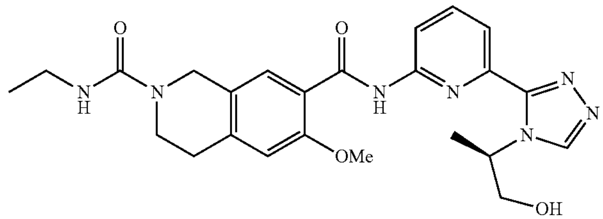 |
| 56 | 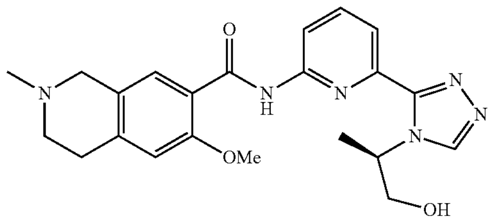 [SMILES: COc1cc2c(cc1C(=O)Nc1cccc(-c3nncn3[C@H](C)CO)n1)CN(C)CC2] |
| 57 | 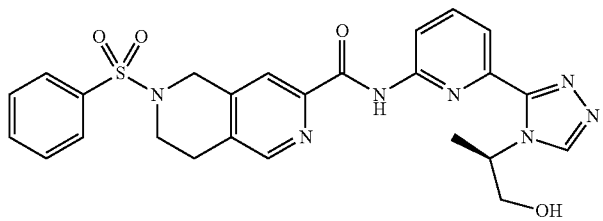 [SMILES: C[C@H](CO)n1cnnc1-c1cccc(NC(=O)c2cc3c(cn2)CCN(S(=O)(=O)c2ccccc2)C3)n1] |
| 58 | 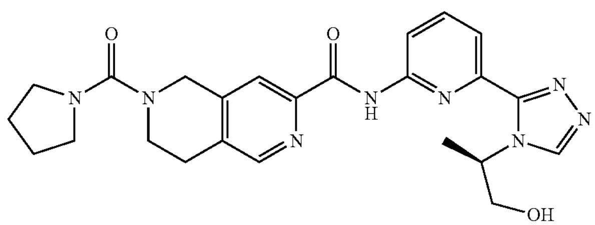 [SMILES: C[C@H](CO)n1cnnc1-c1cccc(NC(=O)c2cc3c(cn2)CCN(C(=O)N2CCCC2)C3)n1] |
| 59 | 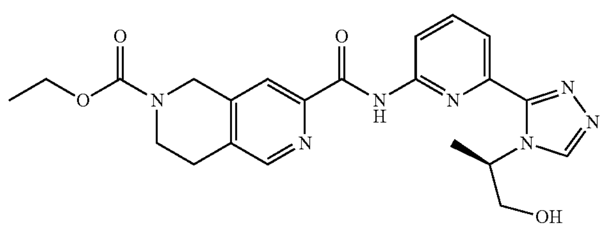 [SMILES: CCOC(=O)N1CCc2cnc(C(=O)Nc3cccc(-c4nncn4[C@H](C)CO)n3)cc2C1] |
| 60 | 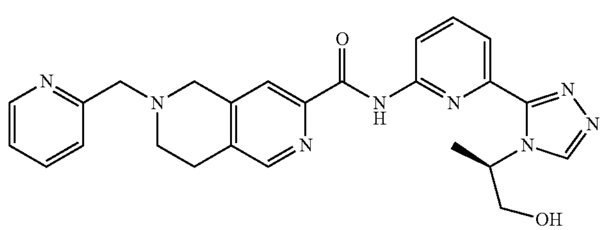 [SMILES: C[C@H](CO)n1cnnc1-c1cccc(NC(=O)c2cc3c(cn2)CCN(Cc2ccccn2)C3)n1] |
| 61 | 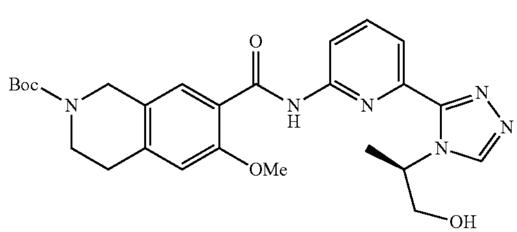 [SMILES: COc1cc2c(cc1C(=O)Nc1cccc(-c3nncn3[C@H](C)CO)n1)CN(C(=O)OC(C)(C)C)CC2] |

-continued
| Compound | Structure |
|---|---|
| 62 | 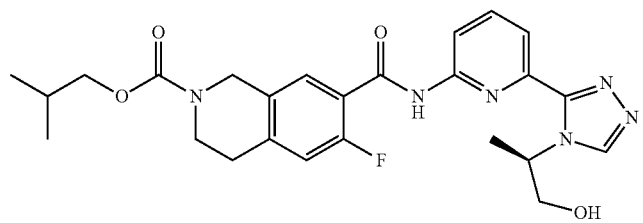 [SMILES: CC(C)COC(=O)N1CCc2cc(F)c(C(=O)Nc3cccc(-c4nncn4[C@H](C)CO)n3)cc2C1] |
| 63 | 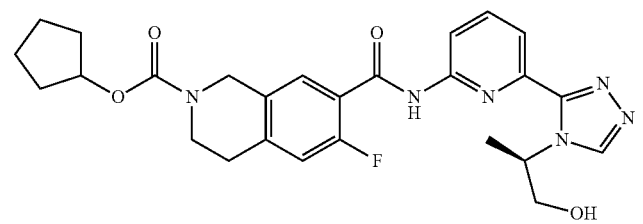 [SMILES: C[C@H](CO)n1cnnc1-c1cccc(NC(=O)c2cc3c(cc2F)CCN(C(=O)OC2CCCC2)C3)n1] |
| 64 | 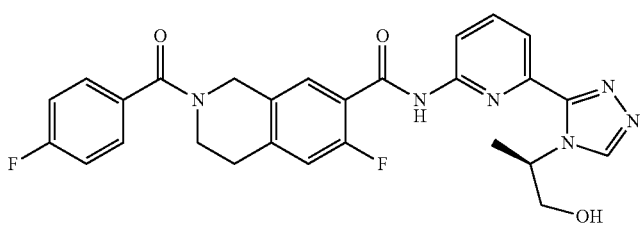 [SMILES: C[C@H](CO)n1cnnc1-c1cccc(NC(=O)c2cc3c(cc2F)CCN(C(=O)c2ccc(F)cc2)C3)n1] |
| 65 | 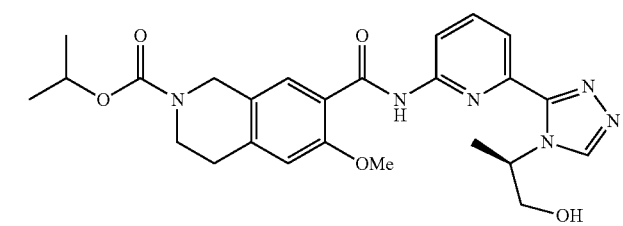 [SMILES: COc1cc2c(cc1C(=O)Nc1cccc(-c3nncn3[C@H](C)CO)n1)CN(C(=O)OC(C)C)CC2] |
| 66 | 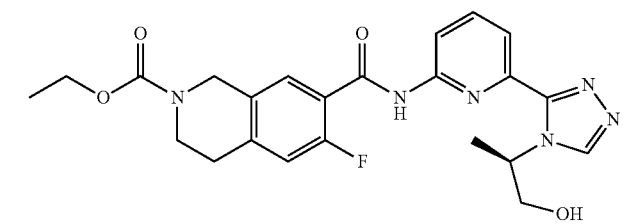 [SMILES: CCOC(=O)N1CCc2cc(F)c(C(=O)Nc3cccc(-c4nncn4[C@H](C)CO)n3)cc2C1] |
| 67 | 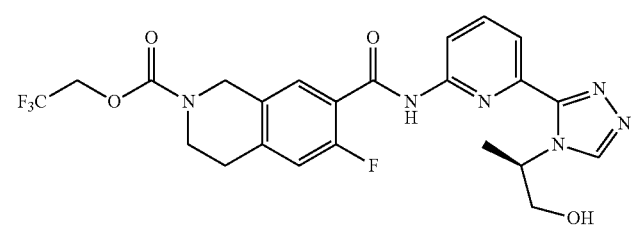 [SMILES: C[C@H](CO)n1cnnc1-c1cccc(NC(=O)c2cc3c(cc2F)CCN(C(=O)OCC(F)(F)F)C3)n1] |

-continued

| Compound | Structure |
|---|---|
| 68 | 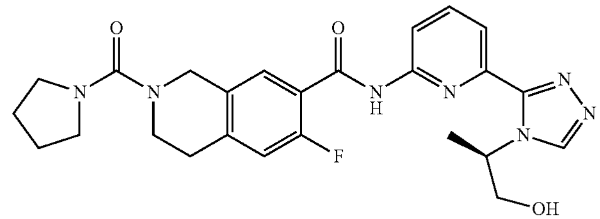 [SMILES: C[C@H](CO)n1cnnc1-c1cccc(NC(=O)c2cc3c(cc2F)CCN(C(=O)N2CCCC2)C3)n1] |
| 69 | 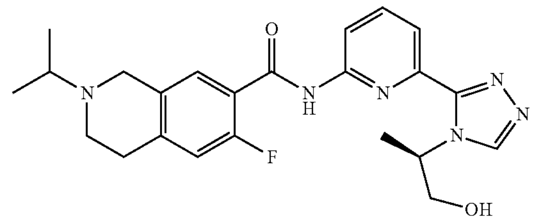 [SMILES: CC(C)N1CCc2cc(F)c(C(=O)Nc3cccc(-c4nncn4[C@H](C)CO)n3)cc2C1] |
| 70 | 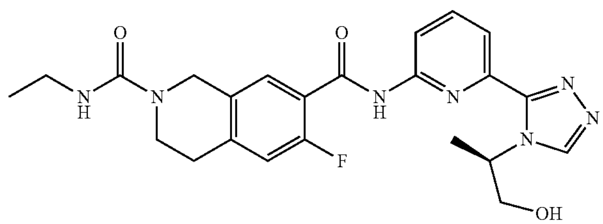 [SMILES: CCNC(=O)N1CCc2cc(F)c(C(=O)Nc3cccc(-c4nncn4[C@H](C)CO)n3)cc2C1] |
| 71 | 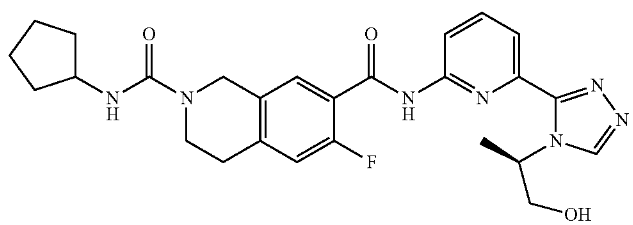 [SMILES: C[C@H](CO)n1cnnc1-c1cccc(NC(=O)c2cc3c(cc2F)CCN(C(=O)NC2CCCC2)C3)n1] |
| 72 | 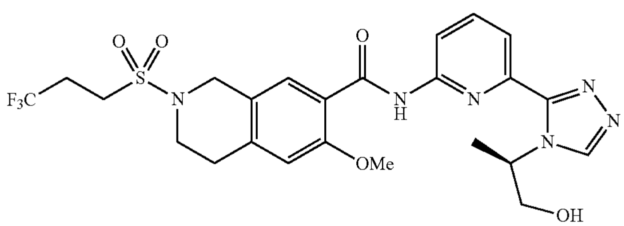 [SMILES: COc1cc2c(cc1C(=O)Nc1cccc(-c3nncn3[C@H](C)CO)n1)CN(S(=O)(=O)CCC(F)(F)F)CC2] |
| 73 | 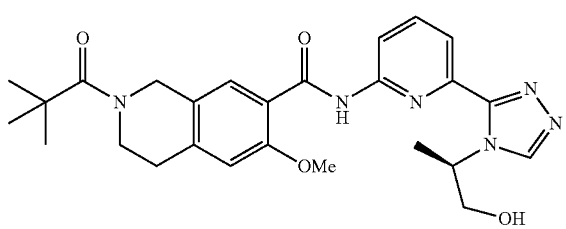 [SMILES: COc1cc2c(cc1C(=O)Nc1cccc(-c3nncn3[C@H](C)CO)n1)CN(C(=O)C(C)(C)C)CC2] |
| 74 | 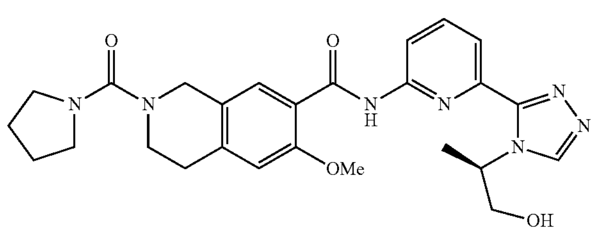 [SMILES: COc1cc2c(cc1C(=O)Nc1cccc(-c3nncn3[C@H](C)CO)n1)CN(C(=O)N1CCCC1)CC2] |

| Compound | Structure |
|---|---|
| 75 | 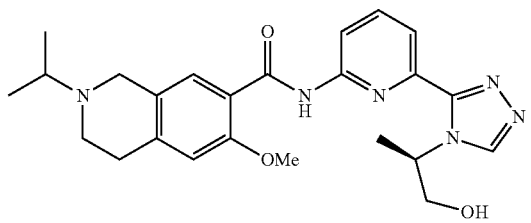 [SMILES: COc1cc2c(cc1C(=O)Nc1cccc(-c3nncn3[C@H](C)CO)n1)CN(C(C)C)CC2] |
| 76 | 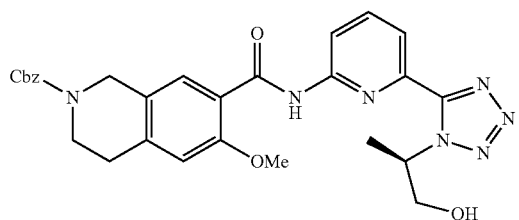 [SMILES: COc1cc2c(cc1C(=O)Nc1cccc(-c3nnnn3[C@H](C)CO)n1)CN(C(=O)OCc1ccccc1)CC2] |
| 77 | 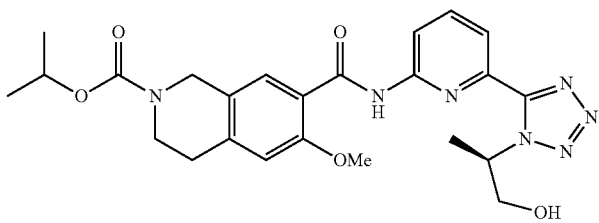 [SMILES: COc1cc2c(cc1C(=O)Nc1cccc(-c3nnnn3[C@H](C)CO)n1)CN(C(=O)OC(C)C)CC2] |
| 78 | 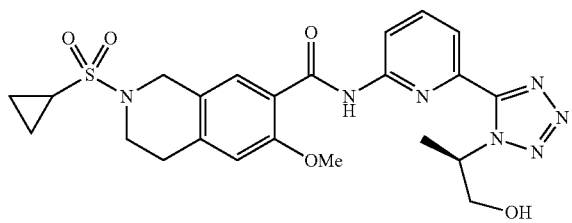 [SMILES: COc1cc2c(cc1C(=O)Nc1cccc(-c3nnnn3[C@H](C)CO)n1)CN(S(=O)(=O)C1CC1)CC2] |
| 79 | 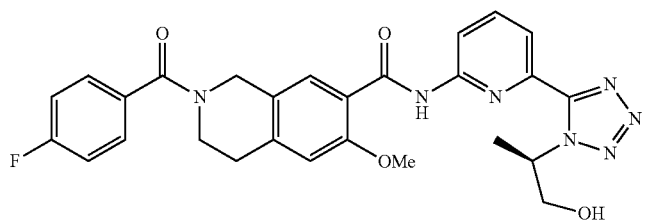 [SMILES: COc1cc2c(cc1C(=O)Nc1cccc(-c3nnnn3[C@H](C)CO)n1)CN(C(=O)c1ccc(F)cc1)CC2] |
| 80 | 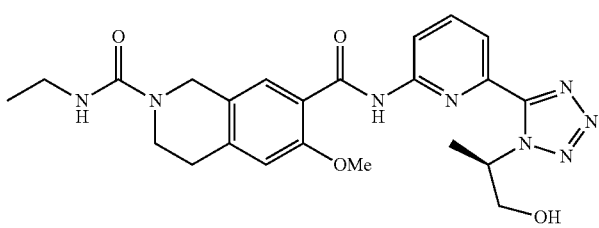 [SMILES: CCNC(=O)N1CCc2cc(OC)c(C(=O)Nc3cccc(-c4nnnn4[C@H](C)CO)n3)cc2C1] |

-continued
| Compound | Structure |
|---|---|
| 81 | 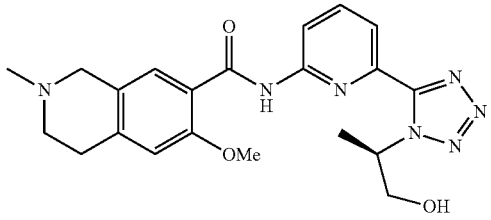 |
| 82 | 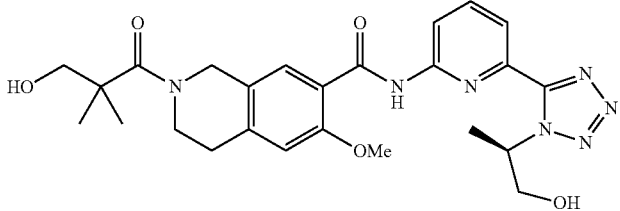 [SMILES: COc1cc2c(cc1C(=O)Nc1cccc(-c3nnnn3[C@H](C)CO)n1)CN(C(=O)C(C)(C)CO)CC2] |
| 83 | 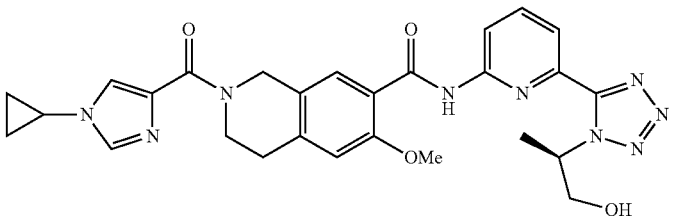 [SMILES: COc1cc2c(cc1C(=O)Nc1cccc(-c3nnnn3[C@H](C)CO)n1)CN(C(=O)c1cn(C3CC3)cn1)CC2] |
| 84 | 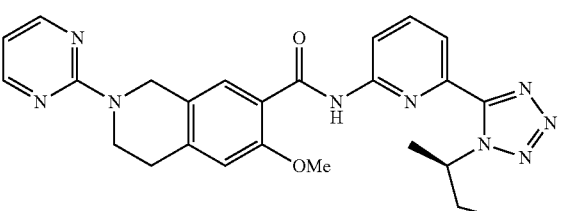 |
| 85 | 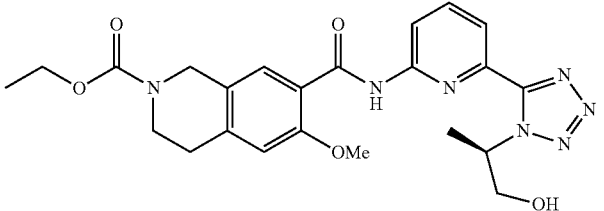 [SMILES: CCOC(=O)N1CCc2cc(OC)c(C(=O)Nc3cccc(-c4nnnn4[C@H](C)CO)n3)cc2C1] |
| 86 | 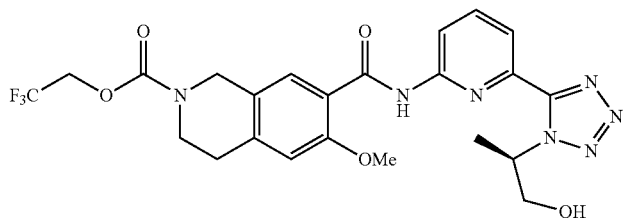 [SMILES: COc1cc2c(cc1C(=O)Nc1cccc(-c3nnnn3[C@H](C)CO)n1)CN(C(=O)OCC(F)(F)F)CC2] |
| 87 | 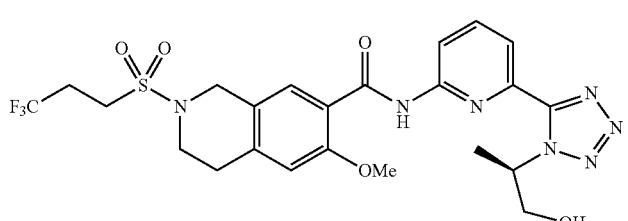 |

| Compound | Structure |
|---|---|
| 88 | 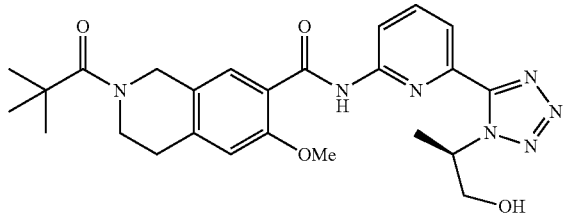 |
| 89 | 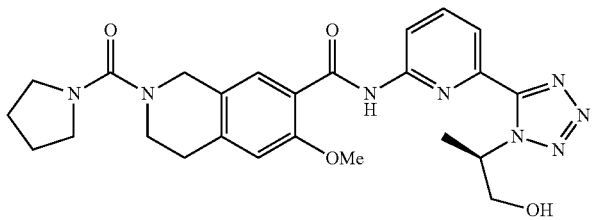 |
| 90 | 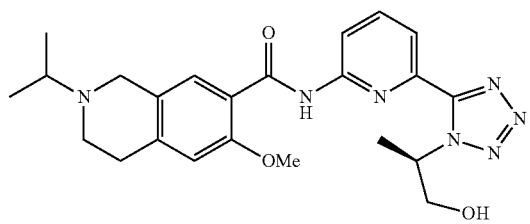 [SMILES: COc1cc2c(cc1C(=O)Nc1cccc(-c3nnnn3[C@H](C)CO)n1)CN(C(C)C)CC2] |
| 91 | 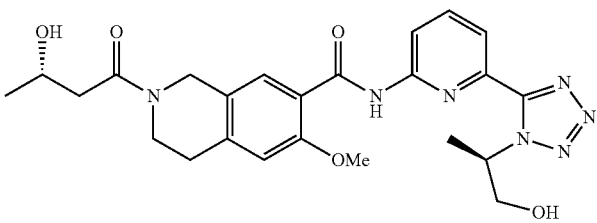 [SMILES: COc1cc2c(cc1C(=O)Nc1cccc(-c3nnnn3[C@H](C)CO)n1)CN(C(=O)C[C@H](C)O)CC2] |
| 92 | 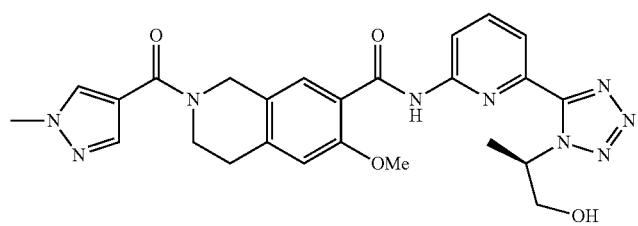 [SMILES: COc1cc2c(cc1C(=O)Nc1cccc(-c3nnnn3[C@H](C)CO)n1)CN(C(=O)c1cnn(C)c1)CC2] |
| 93 | 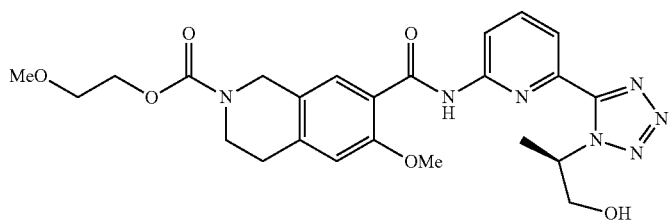 [SMILES: COCCOC(=O)N1CCc2cc(OC)c(C(=O)Nc3cccc(-c4nnnn4[C@H](C)CO)n3)cc2C1] |

-continued

| Compound | Structure |
|---|---|
| 94 | 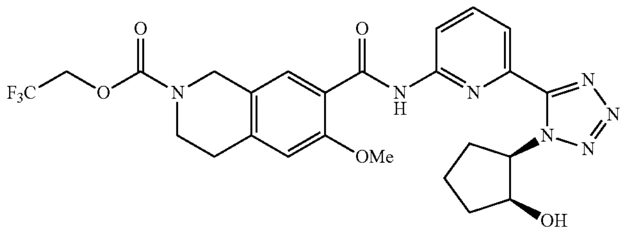 [SMILES: COc1cc2c(cc1C(=O)Nc1cccc(-c3nnnn3[C@@H]3CCC[C@@H]3O)n1)CN(C(=O)OCC(F)(F)F)CC2] |
| 95 | 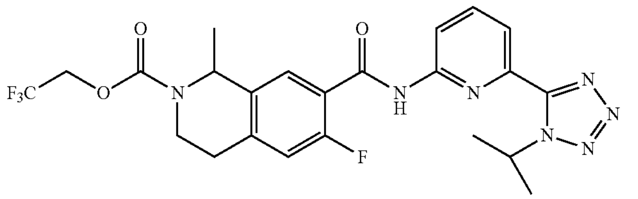 [SMILES: CC1c2cc(C(=O)Nc3cccc(-c4nnnn4C(C)C)n3)c(F)cc2CCN1C(=O)OCC(F)(F)F] |
| 96 | 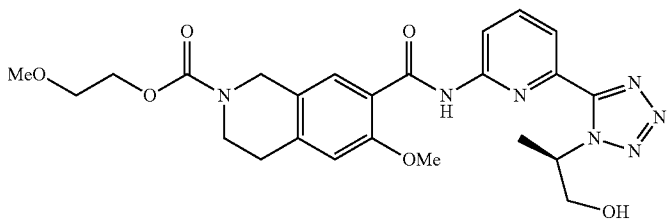 [SMILES: COCCOC(=O)N1CCc2cc(OC)c(C(=O)Nc3cccc(-c4nnnn4[C@H](C)CO)n3)cc2C1] |
| 97 | 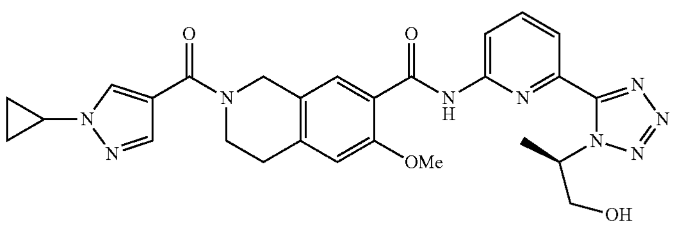 [SMILES: COc1cc2c(cc1C(=O)Nc1cccc(-c3nnnn3[C@H](C)CO)n1)CN(C(=O)c1cnn(C3CC3)c1)CC2] |
| 98 | 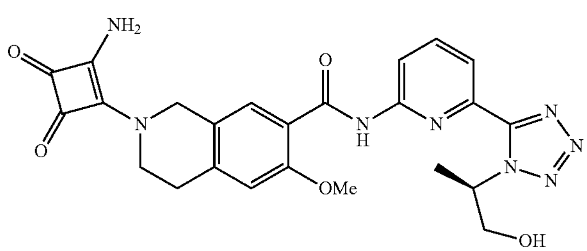 [SMILES: COc1cc2c(cc1C(=O)Nc1cccc(-c3nnnn3[C@H](C)CO)n1)CN(c1c(N)c(=O)c1=O)CC2] |
| 99 | 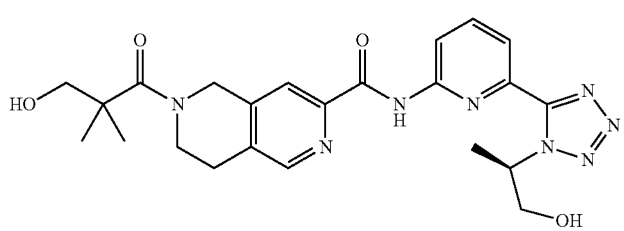 [SMILES: C[C@H](CO)n1nnnc1-c1cccc(NC(=O)c2cc3c(cn2)CCN(C(=O)C(C)(C)CO)C3)n1] |
| 100 | 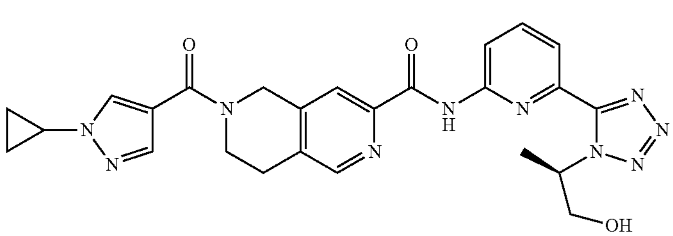 [SMILES: C[C@H](CO)n1nnnc1-c1cccc(NC(=O)c2cc3c(cn2)CCN(C(=O)c2cnn(C4CC4)c2)C3)n1] |

-continued

| Compound | Structure |
|---|---|
| 101 | 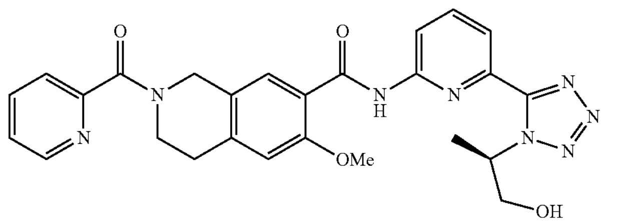 [SMILES: COc1cc2c(cc1C(=O)Nc1cccc(-c3nnnn3[C@H](C)CO)n1)CN(C(=O)c1ccccn1)CC2] |
| 102 | 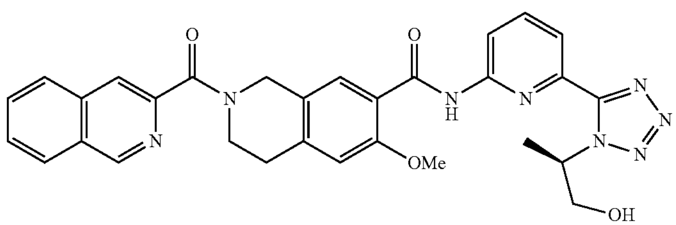 [SMILES: COc1cc2c(cc1C(=O)Nc1cccc(-c3nnnn3[C@H](C)CO)n1)CN(C(=O)c1cc3ccccc3cn1)CC2] |
| 103 | 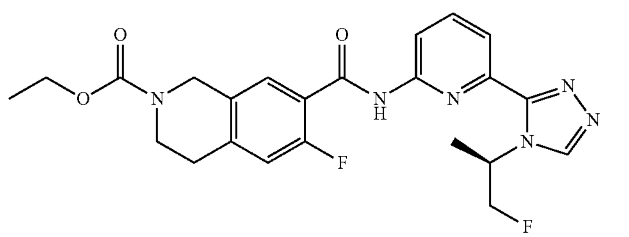 [SMILES: CCOC(=O)N1CCc2cc(F)c(C(=O)Nc3cccc(-c4nncn4[C@H](C)CF)n3)cc2C1] |
| 104 | 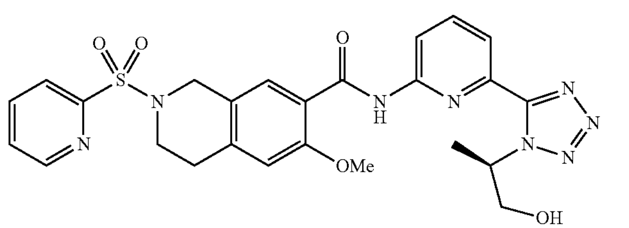 [SMILES: COc1cc2c(cc1C(=O)Nc1cccc(-c3nnnn3[C@H](C)CO)n1)CN(S(=O)(=O)c1ccccn1)CC2] |
| 105 | 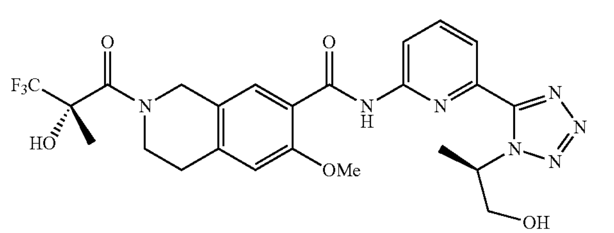 [SMILES: COc1cc2c(cc1C(=O)Nc1cccc(-c3nnnn3[C@H](C)CO)n1)CN(C(=O)[C@](C)(O)C(F)(F)F)CC2] |
| 106 | 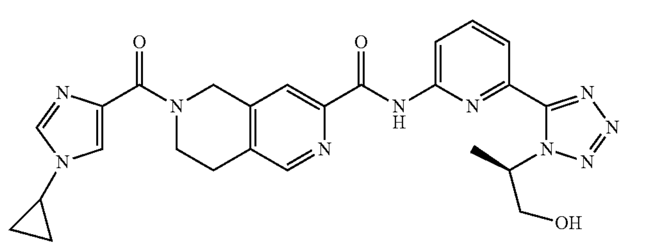 [SMILES: C[C@H](CO)n1nnnc1-c1cccc(NC(=O)c2cc3c(cn2)CCN(C(=O)c2cn(C4CC4)cn2)C3)n1] |

-continued
| Compound | Structure |
|---|---|
| 107 | 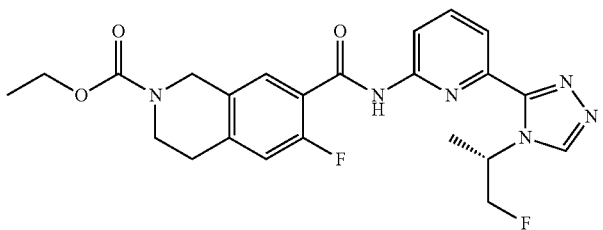 [SMILES: CCOC(=O)N1CCc2cc(F)c(C(=O)Nc3cccc(-c4nncn4[C@@H](C)CF)n3)cc2C1] |
| 108 | 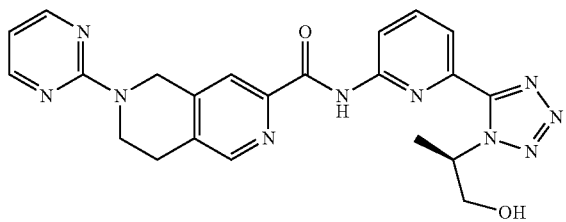 [SMILES: C[C@H](CO)n1nnnc1-c1cccc(NC(=O)c2cc3c(cn2)CCN(c2ncccn2)C3)n1] |
| 109 | 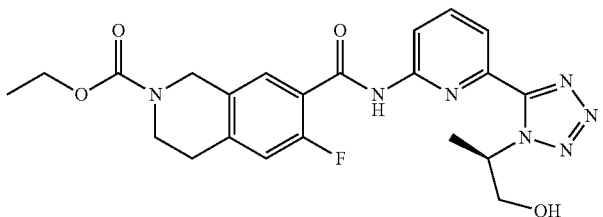 [SMILES: CCOC(=O)N1CCc2cc(F)c(C(=O)Nc3cccc(-c4nnnn4[C@H](C)CO)n3)cc2C1] |
| 110 | 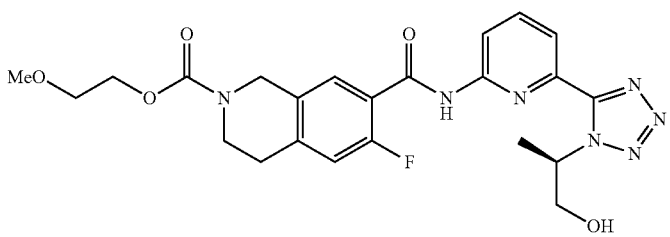 [SMILES: COCCOC(=O)N1CCc2cc(F)c(C(=O)Nc3cccc(-c4nnnn4[C@H](C)CO)n3)cc2C1] |
| 111 | 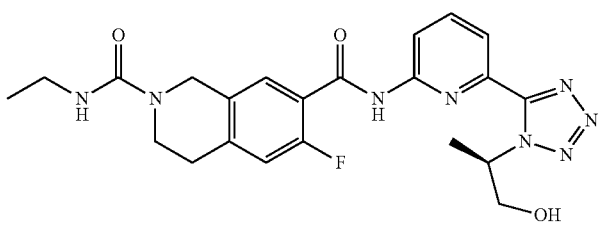 [SMILES: CCNC(=O)N1CCc2cc(F)c(C(=O)Nc3cccc(-c4nnnn4[C@H](C)CO)n3)cc2C1] |
| 112 | 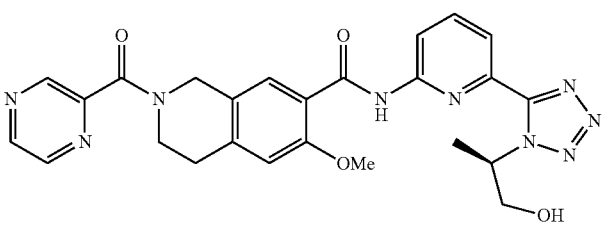 [SMILES: COc1cc2c(cc1C(=O)Nc1cccc(-c3nnnn3[C@H](C)CO)n1)CN(C(=O)c1cnccn1)CC2] |

-continued

| Compound | Structure |
|---|---|
| 113 | 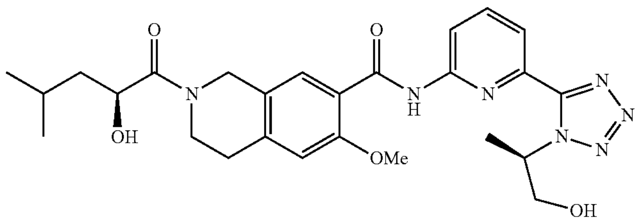 [SMILES: COc1cc2c(cc1C(=O)Nc1cccc(-c3nnnn3[C@H](C)CO)n1)CN(C(=O)[C@@H](O)CC(C)C)CC2] |
| 114 | 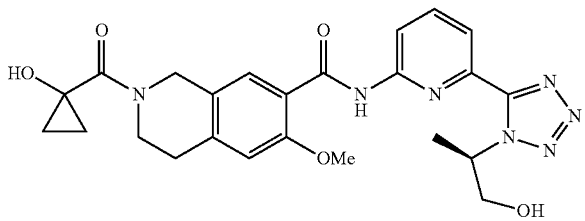 [SMILES: COc1cc2c(cc1C(=O)Nc1cccc(-c3nnnn3[C@H](C)CO)n1)CN(C(=O)C1(O)CC1)CC2] |
| 115 | 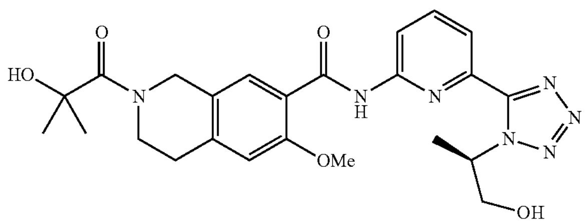 [SMILES: COc1cc2c(cc1C(=O)Nc1cccc(-c3nnnn3[C@H](C)CO)n1)CN(C(=O)C(C)(C)O)CC2] |
| 116 | 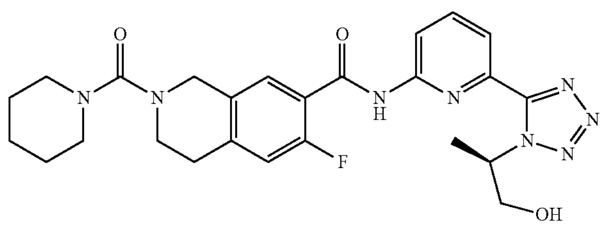 [SMILES: C[C@H](CO)n1nnnc1-c1cccc(NC(=O)c2cc3c(cc2F)CCN(C(=O)N2CCCCC2)C3)n1] |
| 117 | 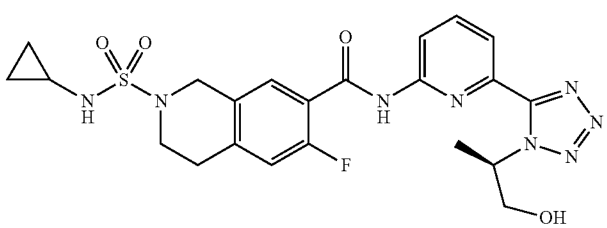 [SMILES: C[C@H](CO)n1nnnc1-c1cccc(NC(=O)c2cc3c(cc2F)CCN(S(=O)(=O)NC2CC2)C3)n1] |
| 118 | 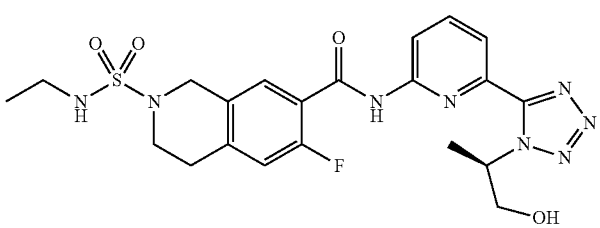 [SMILES: CCNS(=O)(=O)N1CCc2cc(F)c(C(=O)Nc3cccc(-c4nnnn4[C@H](C)CO)n3)cc2C1] |
| 119 | 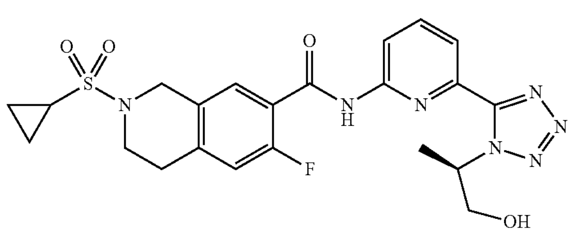 [SMILES: C[C@H](CO)n1nnnc1-c1cccc(NC(=O)c2cc3c(cc2F)CCN(S(=O)(=O)C2CC2)C3)n1] |

-continued
| Compound | Structure |
|---|---|
| 120 | 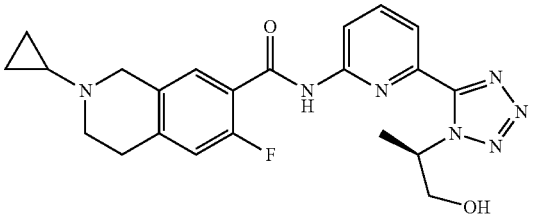 [SMILES: C[C@H](CO)n1nnnc1-c1cccc(NC(=O)c2cc3c(cc2F)CCN(C2CC2)C3)n1] |
| 121 | 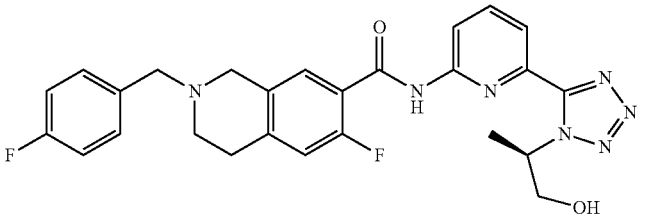 [SMILES: C[C@H](CO)n1nnnc1-c1cccc(NC(=O)c2cc3c(cc2F)CCN(Cc2ccc(F)cc2)C3)n1] |
| 122 | 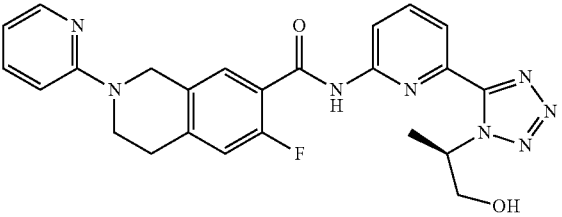 [SMILES: C[C@H](CO)n1nnnc1-c1cccc(NC(=O)c2cc3c(cc2F)CCN(c2ccccn2)C3)n1] |
| 123 | 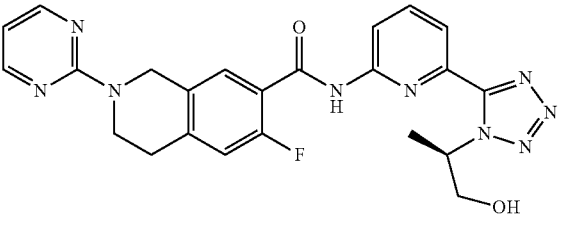 [SMILES: C[C@H](CO)n1nnnc1-c1cccc(NC(=O)c2cc3c(cc2F)CCN(c2ncccn2)C3)n1] |
| 124 | 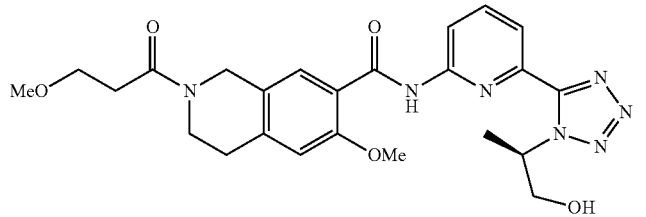 [SMILES: COCCC(=O)N1CCc2cc(OC)c(C(=O)Nc3cccc(-c4nnnn4[C@H](C)CO)n3)cc2C1] |
| 125 | 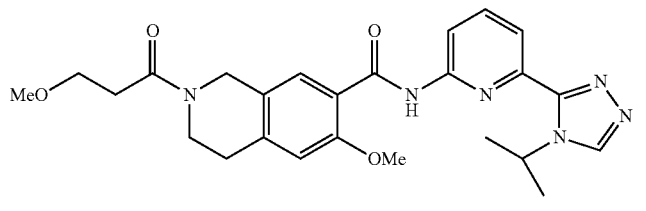 [SMILES: COCCC(=O)N1CCc2cc(OC)c(C(=O)Nc3cccc(-c4nncn4C(C)C)n3)cc2C1] |
| 126 | 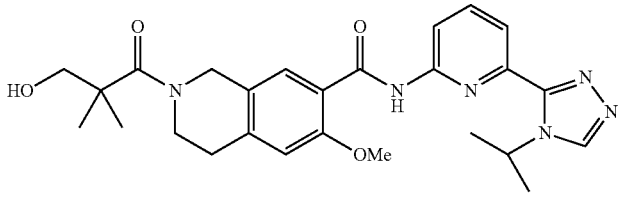 [SMILES: COc1cc2c(cc1C(=O)Nc1cccc(-c3nncn3C(C)C)n1)CN(C(=O)C(C)(C)CO)CC2] |

-continued

| Compound | Structure |
|---|---|
| 127 | 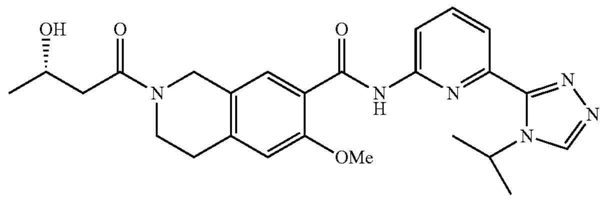 [SMILES: COc1cc2c(cc1C(=O)Nc1cccc(-c3nncn3C(C)C)n1)CN(C(=O)C[C@H](C)O)CC2] |
| 128 | 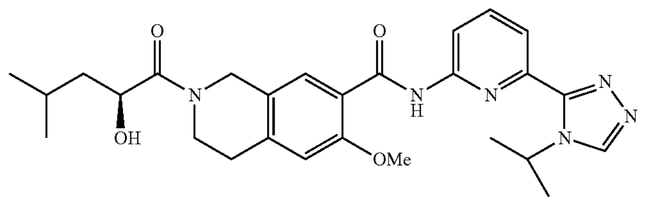 [SMILES: COc1cc2c(cc1C(=O)Nc1cccc(-c3nncn3C(C)C)n1)CN(C(=O)[C@@H](O)CC(C)C)CC2] |
| 129 | 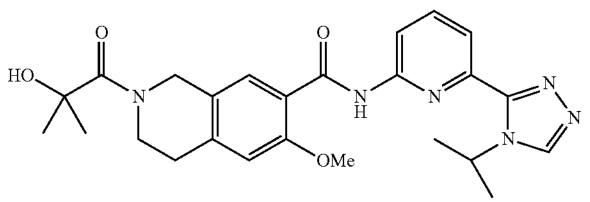 [SMILES: COc1cc2c(cc1C(=O)Nc1cccc(-c3nncn3C(C)C)n1)CN(C(=O)C(C)(C)O)CC2] |
| 130 | 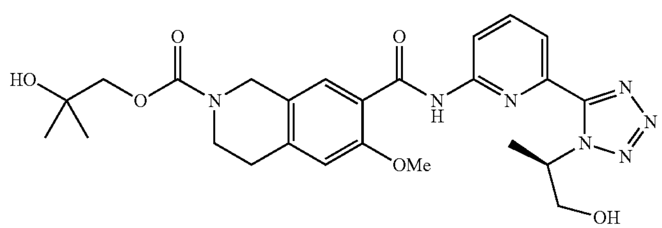 [SMILES: COc1cc2c(cc1C(=O)Nc1cccc(-c3nnnn3[C@H](C)CO)n1)CN(C(=O)OCC(C)(C)O)CC2] |
| 131 | 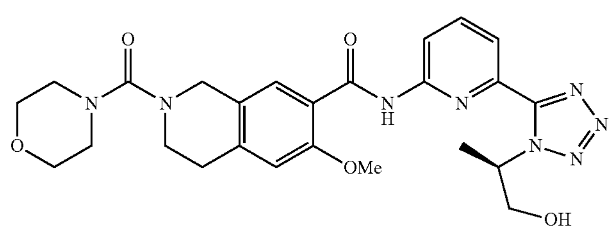 [SMILES: COc1cc2c(cc1C(=O)Nc1cccc(-c3nnnn3[C@H](C)CO)n1)CN(C(=O)N1CCOCC1)CC2] |
| 132 | 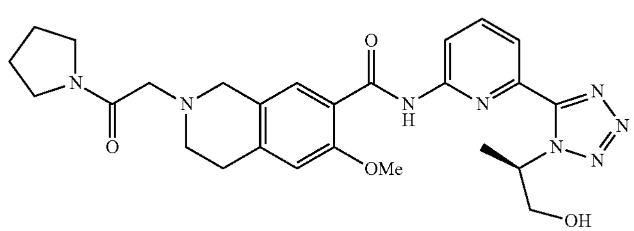 [SMILES: COc1cc2c(cc1C(=O)Nc1cccc(-c3nnnn3[C@H](C)CO)n1)CN(CC(=O)N1CCCC1)CC2] |
| 133 | 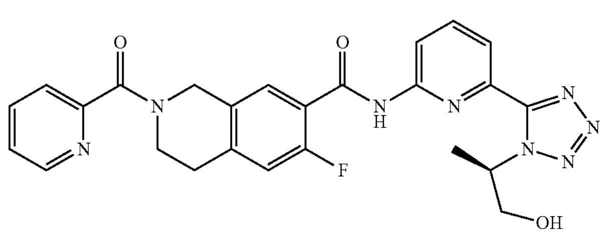 [SMILES: C[C@H](CO)n1nnnc1-c1cccc(NC(=O)c2cc3c(cc2F)CCN(C(=O)c2ccccn2)C3)n1] |

| Compound | Structure |
|---|---|
| 134 | 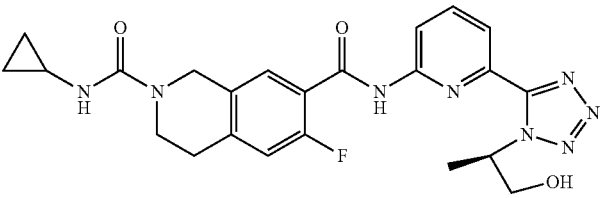 [SMILES: C[C@H](CO)n1nnnc1-c1cccc(NC(=O)c2cc3c(cc2F)CCN(C(=O)NC2CC2)C3)n1] |
| 135 | 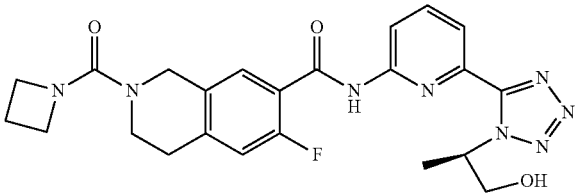 [SMILES: C[C@H](CO)n1nnnc1-c1cccc(NC(=O)c2cc3c(cc2F)CCN(C(=O)N2CCC2)C3)n1] |
| 136 | 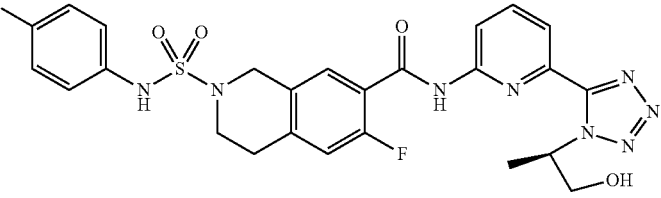 |
| 137 | 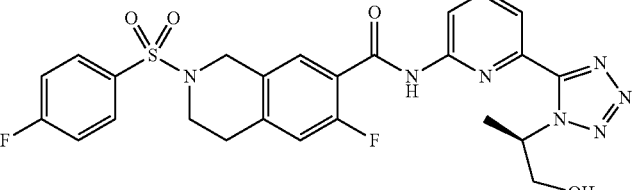 |
| 138 | 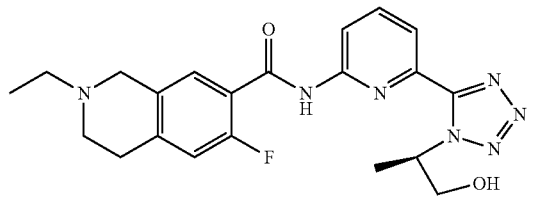 [SMILES: CCN1CCc2cc(F)c(C(=O)Nc3cccc(-c4nnnn4[C@H](C)CO)n3)cc2C1] |
| 139 | 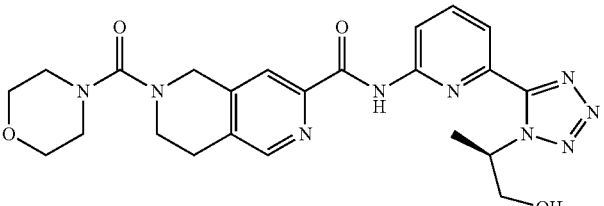 |
| 140 | 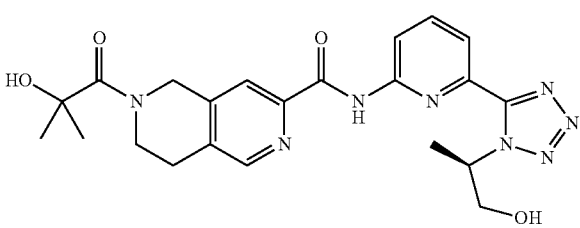 [SMILES: C[C@H](CO)n1nnnc1-c1cccc(NC(=O)c2cc3c(cn2)CCN(C(=O)C(C)(C)O)C3)n1] |

-continued

| Compound | Structure |
|---|---|
| 141 | 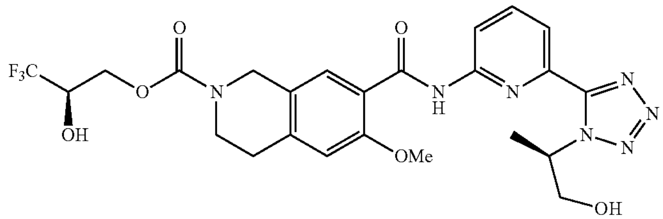 [SMILES: COc1cc2c(cc1C(=O)Nc1cccc(-c3nnnn3[C@H](C)CO)n1)CN(C(=O)OC[C@@H](O)C(F)(F)F)CC2] |
| 142 | 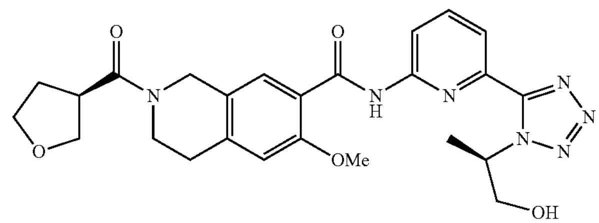 [SMILES: COc1cc2c(cc1C(=O)Nc1cccc(-c3nnnn3[C@H](C)CO)n1)CN(C(=O)[C@@H]1CCOC1)CC2] |
| 143 | 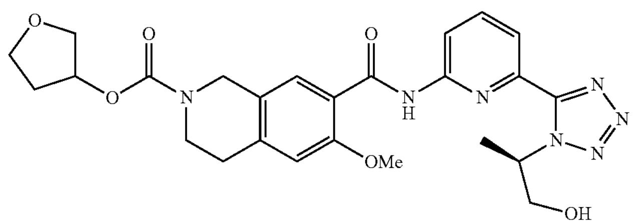 [SMILES: COc1cc2c(cc1C(=O)Nc1cccc(-c3nnnn3[C@H](C)CO)n1)CN(C(=O)OC1CCOC1)CC2] |
| 144 | 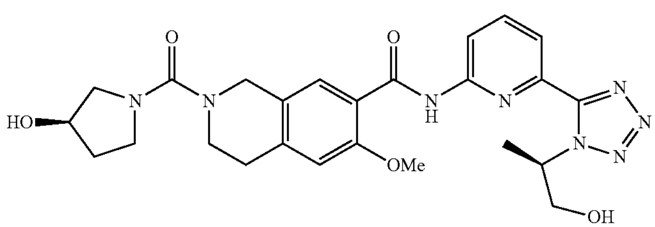 [SMILES: COc1cc2c(cc1C(=O)Nc1cccc(-c3nnnn3[C@H](C)CO)n1)CN(C(=O)N1CC[C@@H](O)C1)CC2] |
| 145 | 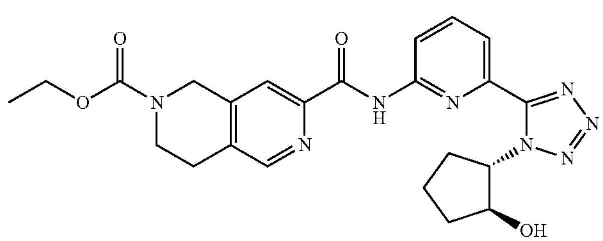 [SMILES: CCOC(=O)N1CCc2cnc(C(=O)Nc3cccc(-c4nnnn4[C@H]4CCC[C@@H]4O)n3)cc2C1] |
| 146 | 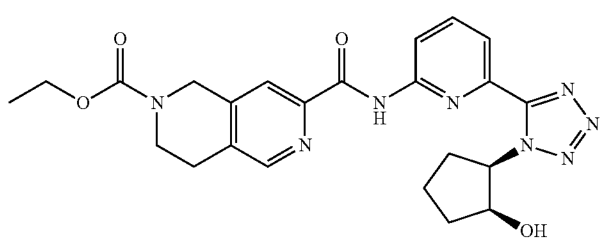 [SMILES: CCOC(=O)N1CCc2cnc(C(=O)Nc3cccc(-c4nnnn4[C@@H]4CCC[C@@H]4O)n3)cc2C1] |

| Compound | Structure |
|---|---|
| 147 | 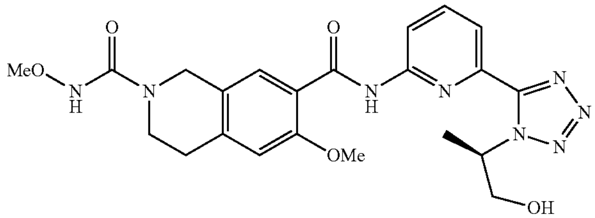 [SMILES: CONC(=O)N1CCc2cc(OC)c(C(=O)Nc3cccc(-c4nnnn4[C@H](C)CO)n3)cc2C1] |
| 148 | 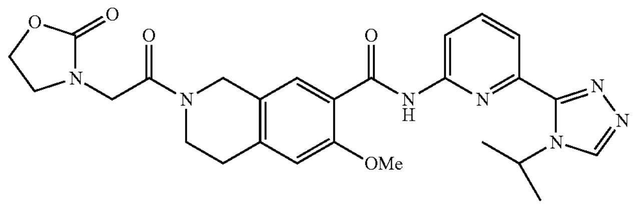 [SMILES: COc1cc2c(cc1C(=O)Nc1cccc(-c3nncn3C(C)C)n1)CN(C(=O)CN1CCOC1=O)CC2] |
| 149 | 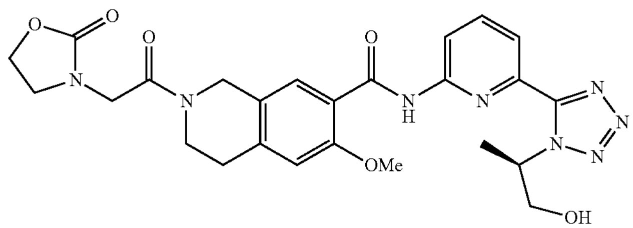 [SMILES: COc1cc2c(cc1C(=O)Nc1cccc(-c3nnnn3[C@H](C)CO)n1)CN(C(=O)CN1CCOC1=O)CC2] |
| 150 | 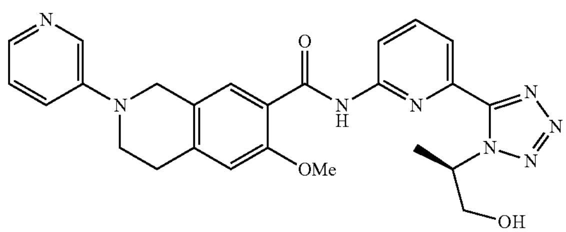 [SMILES: COc1cc2c(cc1C(=O)Nc1cccc(-c3nnnn3[C@H](C)CO)n1)CN(c1cccnc1)CC2] |
| 151 | 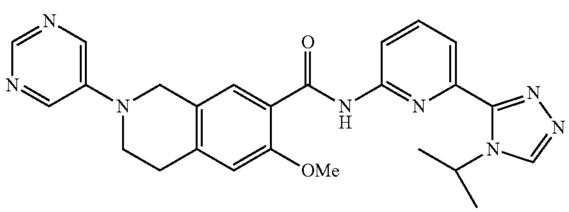 [SMILES: COc1cc2c(cc1C(=O)Nc1cccc(-c3nncn3C(C)C)n1)CN(c1cncnc1)CC2] |
| 152 | 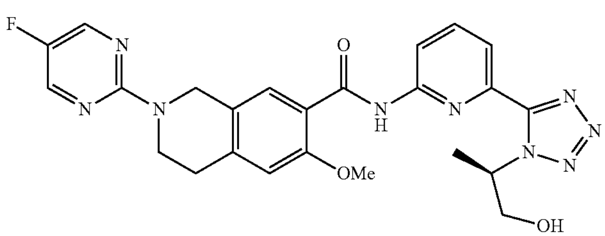 [SMILES: COc1cc2c(cc1C(=O)Nc1cccc(-c3nnnn3[C@H](C)CO)n1)CN(c1ncc(F)cn1)CC2] |
| 153 | 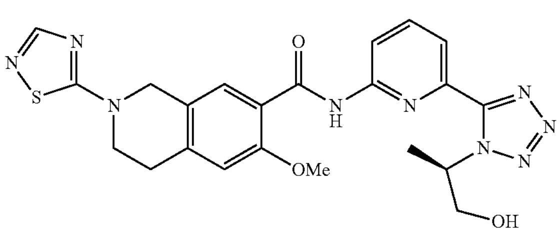 [SMILES: COc1cc2c(cc1C(=O)Nc1cccc(-c3nnnn3[C@H](C)CO)n1)CN(c1ncns1)CC2] |

| Compound | Structure |
|---|---|
| 154 | (chemical structure) |

2. A pharmaceutical composition comprising a compound according to claim 1 and a pharmaceutically acceptable excipient or carrier.

3. A method for treating an ASK-1 mediated disease or condition in a subject in need thereof, comprising administering to the subject a therapeutically effective amount of a compound of claim 1.

4. The method according to claim 3, wherein the ASK-1 mediated disease or condition is selected from the group consisting of an autoimmune disorder, a neurodegenerative disorder, an inflammatory disease, chronic kidney disease, renal disease, cardiovascular disease, a metabolic disease, or an acute or chronic liver disease.

5. The method according to claim 4, wherein the ASK-1 mediated disease or condition is a chronic liver disease selected from the group consisting of primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency.

6. The method according to claim 4, wherein the ASK-1 mediated disease or condition is a renal disease selected from the group consisting of diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease.

7. The method according to claim 4, wherein the ASK-1 mediated disease or condition is a cardiovascular disease selected from the group consisting of atherosclerosis, arteriosclerosis, reperfusion/ischemia in stroke, cardiac hypertrophy, respiratory diseases, heart attacks, myocardial ischemia.

8. The method according to claim 4, wherein the ASK-1 mediated disease or condition is a metabolic disease selected from the group consisting of insulin resistance, Type I and Type II diabetes, and obesity.

9. The method according to claim 4, wherein the ASK-1 mediated disease or condition is a chronic kidney disease selected from the group consisting of polycystic kidney disease, pyelonephritis, kidney fibrosis and glomerulonephritis.

10. A method for treating a disease selected from the group consisting of glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, multiple sclerosis, or Sjoegren's syndrome in a subject in need thereof, comprising administering to the subject a therapeutically effective amount of a compound according to claim 1.

11. A method for treating a disease selected from the group consisting of ischemia/reperfusion in stroke, heart attacks, myocardial ischemia, organ hypoxia, vascular hyperplasia, cardiac hypertrophy, hepatic ischemia, congestive heart failure, pathologic immune responses such as that caused by T cell activation, and thrombin-induced platelet aggregation in a subject in need thereof, comprising administering to the subject a therapeutically effective amount of a compound according to claim 1.

12. A method for treating a disease selected from the group consisting of osteoporosis, osteoarthritis and multiple myeloma-related bone disorder in a subject in need thereof, comprising administering to the subject a therapeutically effective amount of a compound according to claim 1.

13. A method for treating a disease selected from the group consisting of Alzheimer's disease, Parkinson's disease, amyotrophic lateral sclerosis (ALS), epilepsy, seizures, Huntington's disease, polyglutamine diseases, traumatic brain injury, ischemic and hemorrhaging stroke, cerebral ischemias or neurodegenerative disease, including apoptosis-driven neurodegenerative disease, caused by traumatic injury, acute hypoxia, ischemia or glutamate neurotoxicity in a subject in need thereof, comprising administering to the subject a therapeutically effective amount of a compound according to claim 1.

* * * * *